(12) United States Patent
Jun et al.

(10) Patent No.: US 10,290,820 B2
(45) Date of Patent: *May 14, 2019

(54) AMINE-BASED COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Mi-Eun Jun, Yongin (KR); Sang-Hyun Han, Yongin (KR); Young-Kook Kim, Yongin (KR); Seok-Hwan Hwang, Yongin (KR); Sam-Il Kho, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 228 days.

This patent is subject to a terminal disclaimer.

(21) Appl. No.: 14/572,701

(22) Filed: Dec. 16, 2014

(65) Prior Publication Data

US 2015/0364705 A1 Dec. 17, 2015

(30) Foreign Application Priority Data

Jun. 13, 2014 (KR) .................. 10-2014-0072299

(51) Int. Cl.
*H01L 51/00* (2006.01)
*C07D 213/74* (2006.01)
(Continued)

(52) U.S. Cl.
CPC ........ *H01L 51/0094* (2013.01); *C07C 211/54* (2013.01); *C07C 211/56* (2013.01);
(Continued)

(58) Field of Classification Search
None
See application file for complete search history.

(56) References Cited

U.S. PATENT DOCUMENTS 7,233,019 B2  6/2007  Ionkin et al.
9,136,480 B2 * 9/2015  Kim ...................... H01L 51/006
(Continued)

FOREIGN PATENT DOCUMENTS

CN  103187531 A  * 7/2013  ............. H01L 51/50
JP  2013-063931  4/2013
(Continued)

OTHER PUBLICATIONS

Machine English translation of Yong et al. (CN 103187531 A). Oct. 20, 2016.*
(Continued)

*Primary Examiner* — Jay Yang
(74) *Attorney, Agent, or Firm* — Lewis Roca Rothgerber Christie LLP

(57) ABSTRACT

An amine-based compound is represented by Formula 1.

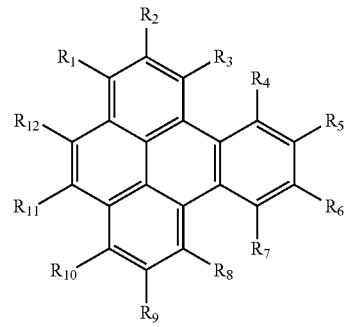

Where, in Formula 1, at least one of $R_1$, $R_3$, $R_8$, and $R_{10}$ is a group represented by Formula 2.

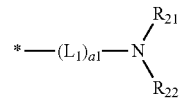

Where, in Formula 2, a1 is selected from 0, 1, 2 and 3. The remaining substituents of Formulae 1 and 2 are as described herein. An organic light-emitting device (OLED) includes the amine-based compound represented by Formula 1.

15 Claims, 1 Drawing Sheet

(51) Int. Cl.
*C07C 255/58* (2006.01)
*C07D 215/38* (2006.01)
*C07D 333/76* (2006.01)
*C07C 211/54* (2006.01)
*C07C 211/56* (2006.01)
*C07C 211/58* (2006.01)
*C07C 211/61* (2006.01)
*C07D 307/91* (2006.01)
*C07F 7/08* (2006.01)
*C09B 57/00* (2006.01)
*C09B 23/14* (2006.01)
*C09B 57/02* (2006.01)
*C09B 57/10* (2006.01)
*C09B 1/00* (2006.01)
*C09B 3/00* (2006.01)
*H01L 51/50* (2006.01)

(52) U.S. Cl.
CPC .......... *C07C 211/58* (2013.01); *C07C 211/61* (2013.01); *C07C 255/58* (2013.01); *C07D 213/74* (2013.01); *C07D 215/38* (2013.01); *C07D 307/91* (2013.01); *C07D 333/76* (2013.01); *C07F 7/081* (2013.01); *C07F 7/0816* (2013.01); *C09B 1/00* (2013.01); *C09B 3/00* (2013.01); *C09B 23/148* (2013.01); *C09B 57/00* (2013.01); *C09B 57/001* (2013.01); *C09B 57/008* (2013.01); *C09B 57/02* (2013.01); *C09B 57/10* (2013.01); *H01L 51/006* (2013.01); *H01L 51/0055* (2013.01); *C07B 2200/05* (2013.01); *C07C 2601/14* (2017.05); *C07C 2603/18* (2017.05); *C07C 2603/26* (2017.05); *C07C 2603/52* (2017.05); *H01L 51/0058* (2013.01); *H01L 51/0065* (2013.01); *H01L 51/5012* (2013.01)

(56) References Cited

U.S. PATENT DOCUMENTS

| | | |
|---|---|---|
| 2005/0156164 A1 | 7/2005 | Sotoyama |
| 2009/0102373 A1 | 4/2009 | Hayoz et al. |
| 2010/0225229 A1* | 9/2010 | Hosoda .................. B82Y 20/00 313/504 |
| 2011/0095282 A1 | 4/2011 | Pflumm et al. |
| 2011/0156014 A1 | 6/2011 | Kim et al. |
| 2012/0181922 A1 | 7/2012 | Kawamura et al. |
| 2012/0214993 A1 | 8/2012 | Aihara et al. |
| 2012/0326133 A1 | 12/2012 | Kim et al. |
| 2013/0079517 A1 | 3/2013 | Schafer et al. |
| 2014/0367656 A1* | 12/2014 | Kim ...................... H01L 51/006 257/40 |

FOREIGN PATENT DOCUMENTS

| | | |
|---|---|---|
| KR | 10-2005-0084912 | 8/2005 |
| KR | 10-2005-0109513 | 11/2005 |
| KR | 10-2006-0006760 | 1/2006 |
| KR | 10-2010-0024340 | 3/2010 |
| KR | 10-2010-0073954 | 7/2010 |
| KR | 10-2012-0117622 | 10/2012 |
| KR | 10-2012-0117675 | 10/2012 |
| KR | 10-2012-0117692 | 10/2012 |
| KR | 10-2013-0000230 | 1/2013 |
| WO | WO 2011/021689 A1 | 2/2011 |

OTHER PUBLICATIONS

U.S. Office Action dated Dec. 4, 2014, issued in U.S. Appl. No. 14/164,312 (18 pages).

* cited by examiner

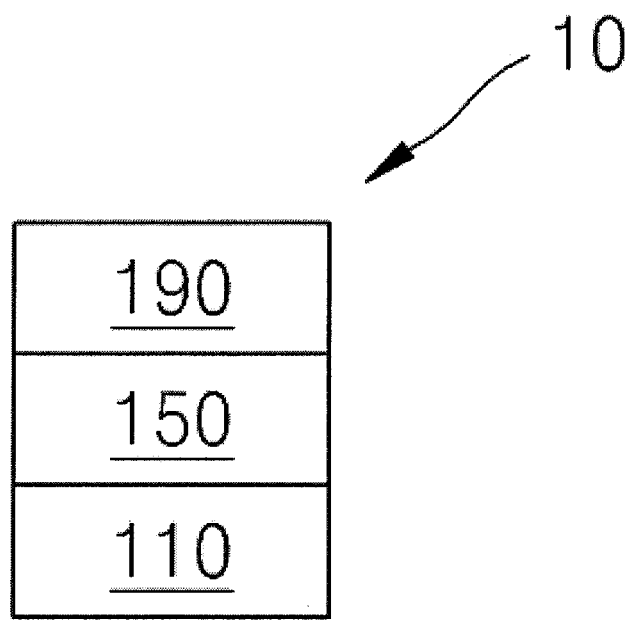

AMINE-BASED COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2014-0072299, filed on Jun. 13, 2014, in the Korean Intellectual Property Office, the entire content of which is incorporated herein by reference.

BACKGROUND

1. Field

One or more embodiments of the present disclosure relate to an amine-based compound and an organic light-emitting device including the same.

2. Description of the Related Art

Organic light-emitting devices (OLEDs) are self-emitting devices that have features, such as wide viewing angles, high contrast ratios, quick response times, high brightness, and excellent driving voltage characteristics. In addition, OLEDs can produce multicolored images.

An OLED may include a first electrode disposed on a substrate, and a hole transport region, an emission layer, an electron transport region, and a second electrode sequentially formed on the first electrode. Holes injected from the first electrode are transported to the emission layer through the hole transport region, and electrons injected from the second electrode are transported to the emission layer through the electron transport region. Carriers, such as the holes and electrons, recombine in the emission layer to generate excitons. When the excitons drop (or relax) from an excited state to a ground state, light is emitted.

SUMMARY

One or more embodiments of the present disclosure include an amine-based compound and an organic light-emitting device (OLED) including the same.

Additional aspects of embodiments will be set forth in part in the description which follows and, in part, will be apparent from the description, or may be learned by practice of the presented embodiments.

According to one or more embodiments of the present disclosure, an amine-based compound is represented by Formula 1:

Formula 1

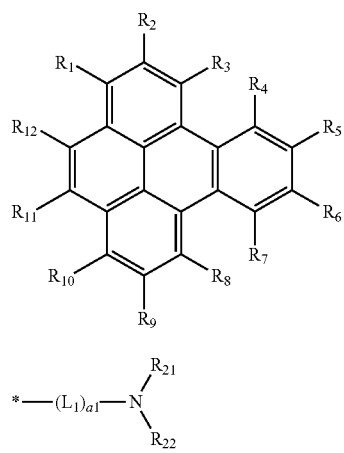

Formula 2 where, in Formulae 1 and 2, $L_1$ is selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic hetero-condensed polycyclic group;

a1 is selected from 0, 1, 2 and 3;

$R_1$, $R_3$, $R_8$, and $R_{10}$ are each independently selected from a group represented by Formula 2, a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic hetero-condensed polycyclic group, —$N(Q_1)(Q_2)$, —$Si(Q_3)(Q_4)(Q_5)$ and —$B(Q_6)(Q_7)$;

at least one of $R_1$, $R_3$, $R_8$, and $R_{10}$ is a group represented by Formula 2;

$R_2$, $R_4$ to $R_7$, $R_9$, $R_{11}$, and $R_{12}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic hetero-condensed polycyclic group, —$N(Q_1)(Q_2)$, —$Si(Q_3)(Q_4)(Q_5)$, and —$B(C)_6)(Q_7)$;

$R_{21}$ and $R_{22}$ are each independently selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic hetero-condensed polycyclic group;

at least one substituent of the substituted $C_3$-$C_{10}$ cycloalkylene group, substituted $C_3$-$C_{10}$ heterocycloalkylene group, substituted $C_3$-$C_{10}$ cycloalkenylene group, substituted $C_3$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_3$-$C_{10}$ heterocycloalkyl group, substituted $C_3$-$C_{10}$ cycloalkenyl group, substituted $C_3$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic hetero-condensed polycyclic group is selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy;

a $C_1$-$C_{60}$ alkyl group, a $C_2$-$C_{60}$ alkenyl group, a $C_2$-$C_{60}$ alkynyl group, and a $C_1$-$C_{60}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy, a $C_6$-$C_{60}$ arylthio, a $C_1$-$C_{60}$ heteroaryl group, a monovalent non-aromatic condensed polycyclic group, a monovalent non-aromatic hetero-condensed polycyclic group, $-N(Q_{11})(Q_{12})$, $-Si(Q_{13})(Q_{14})(Q_{15})$, and $-B(Q_{16})(Q_{17})$;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$a alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic hetero-condensed polycyclic group, $-N(Q_{21})(Q_{22})$, $-Si(Q_{23})(Q_{24})(Q_{25})$, and $-B(Q_{26})(Q_{27})$; and $-N(Q_{31})(Q_{32})$, $-Si(Q_{33})(Q_{34})(Q_{35})$, and $-B(Q_{36})(Q_{37})$, where $Q_1$ to $Q_7$, $Q_{11}$ to $Q_{17}$, $Q_{21}$ to $Q_{27}$, and $Q_{31}$ to $Q_{37}$ are each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic hetero-condensed polycyclic group.

According to one or more embodiments of the present disclosure, an organic light-emitting device (OLED) includes a first electrode; a second electrode facing the first electrode; and an organic layer between the first electrode and the second electrode and including an emission layer, where the organic layer includes the amine-based compound.

BRIEF DESCRIPTION OF THE DRAWING

These and/or other aspects will become apparent and more readily appreciated from the following description, taken in conjunction with the accompanying drawing, which is a schematic cross-sectional view of a structure of an organic light-emitting device (OLED) according to an embodiment of the present disclosure.

DETAILED DESCRIPTION

Reference will now be made to embodiments of the present disclosure, examples of which are illustrated in the accompanying drawing, where like reference numerals refer to like elements throughout. In this regard, the present embodiments may have different forms and should not be construed as being limited to the descriptions set forth herein. Accordingly, the embodiments are described below, by referring to the figures, merely to explain aspects of the present description. As used herein, the term "and/or" includes any and all combinations of one or more of the associated listed items. Expressions such as "at least one of," when preceding a list of elements, modify the entire list of elements and do not modify the individual elements of the list. As used herein, the terms "use," "using," and "used" may have the same meaning as the terms "utilize," "utilizing," and "utilized," respectively.

Like reference numerals in the accompanying drawing denote like elements, and thus their description will not be repeated.

As used herein, the singular forms "a," "an," and "the" are intended to include the plural forms as well, unless the context clearly indicates otherwise.

It will be further understood that the terms "comprises" and/or "comprising" used herein specify the presence of the stated features or components, but do not preclude the presence or addition of one or more other features or components.

It will be understood that when a layer, region, or component is referred to as being "on" or "formed on" another layer, region, or component, it can be directly or indirectly on or formed on the other layer, region, or component. For example, intervening layers, regions, or components may be present.

Sizes of components in the accompanying drawing may be exaggerated for convenience of explanation. Because sizes and thicknesses of the components in the accompanying drawing may be arbitrarily illustrated for convenience of explanation, the following embodiments are not limited thereto.

An embodiment of an amine-based compound is represented by Formula 1, where at least one of $R_1$, $R_3$, $R_8$, and $R_{10}$ in Formula 1 is a group represented by Formula 2:

Formula 1

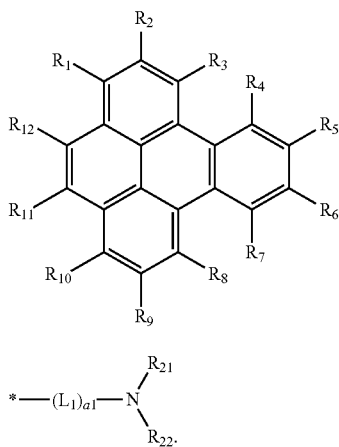

Formula 2

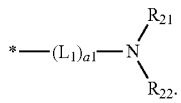

The embodiment of the amine-based compound represented by Formula 1 includes a substituent that includes at least one group represented by Formula 2. In Formula 2, * represents a binding site at a carbon atom of Formula 1. For example, in Formula 2, * is a binding site at a benzopyrene ring of Formula 1.

In Formula 2, $L_1$ may be selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_1$-$C_{60}$ heteroarylene group (e.g., a substituted or unsubstituted $C_2$-$C_{60}$ heteroarylene group), a substituted or unsubstituted divalent non-aromatic condensed polycyclic group, and a substituted or unsubstituted divalent non-aromatic hetero-condensed polycyclic group, where at least one substituent of the substituted $C_3$-$C_{10}$ cycloalkylene group, substituted $C_3$-$C_{10}$ heterocycloalkylene group, substituted $C_3$-$C_{10}$ cycloalkenylene group, substituted $C_3$-$C_{10}$ heterocycloalkenylene group, substituted $C_6$-$C_{60}$ arylene group, substituted $C_1$-$C_{60}$ heteroarylene group (e.g., a substituted $C_2$-$C_{60}$ heteroarylene group), substituted divalent non-aromatic condensed polycyclic group, and substituted divalent non-aromatic hetero-condensed polycyclic group is selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy;

a $C_1$-$C_{60}$ alkyl group, a $C_2$-$C_{60}$ alkenyl group, a $C_2$-$C_{60}$ alkynyl group, and a $C_1$-$C_{60}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy, a $C_6$-$C_{60}$ arylthio, a $C_1$-$C_{60}$ heteroaryl group (e.g., a $C_2$-$C_{60}$ heteroaryl group), a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), where $Q_{11}$ to $Q_{17}$, $Q_{21}$ to $Q_{27}$, and $Q_{31}$ to $Q_{37}$ are each independently selected from, a $C_1$-$C_{60}$alkyl group, a $C_6$-$C_{60}$aryl group, a $C_1$-$C_{60}$heteroaryl group (e.g., a $C_2$-$C_{60}$ heteroaryl group), a monovalent non-aromatic condensed polycyclic group, and a monovalent non-aromatic hetero-condensed polycyclic group.

In one embodiment, in Formula 2, $L_1$ may be selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenyiene group, a benzocarbazolylene group, a dibenzocarbazolylene group, a thiadiazolylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, and an imidazopyridinylene group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group, but $L_1$ is not limited thereto.

In another embodiment, in Formula 2, $L_1$ may be a group selected from Formulae 3-1 to 3-30, but $L_1$ is not limited thereto:

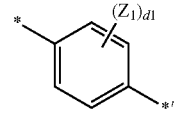

3-1

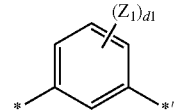

3-2

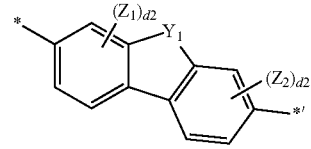

3-3

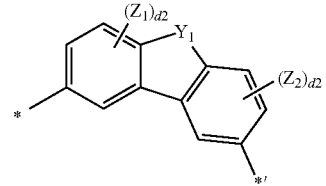

3-4

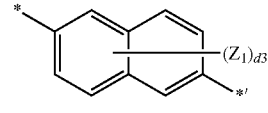

3-5

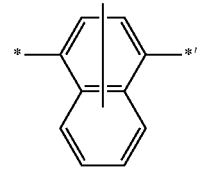

3-6

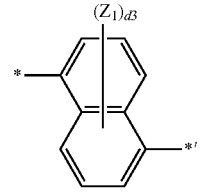

3-7

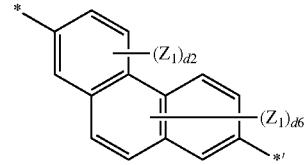

3-8

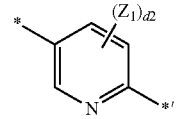

3-9

-continued
3-9 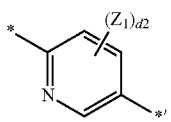
3-10 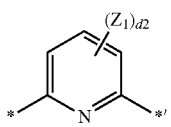
3-11 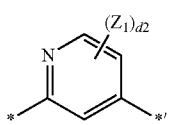
3-12 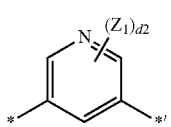
3-13 
3-14 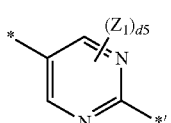
3-15 
3-16 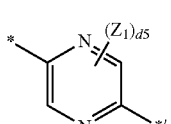
3-17 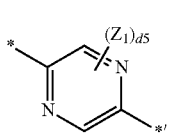
3-18 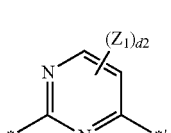
3-19 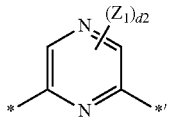
3-20 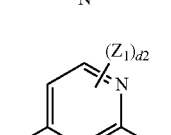
-continued
3-21 
3-22 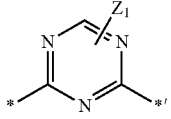
3-23 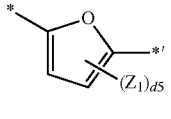
3-24 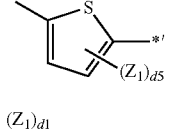
3-25 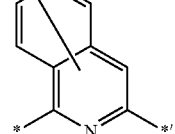
3-26 
3-27 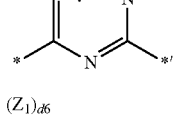
3-28 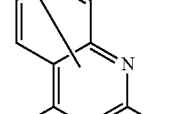
3-29 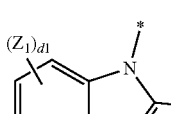
3-30 
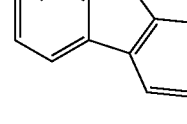
In Formulae 3-1 to 3-30,
$Y_1$ is O, S, $C(Z_3)(Z_4)$, $N(Z_5)$, or $Si(Z_6)(Z_7)$;
$Z_1$ to $Z_7$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$alkyl group, a $C_1$-$C_{20}$alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 is an integer selected from 1 to 4;

d2 is an integer selected from 1 to 3;

d3 is an integer selected from 1 to 6;

d4 is an integer selected from 1 to 8;

d5 is an integer of 0 or 1;

d6 is an integer selected from 1 to 5; and

* and *' each independently represent a binding site at a neighboring atom.

In another embodiment, in Formula 2, $L_1$ may be a group selected from Formulae 4-1 to 4-21, but $L_1$ is not limited thereto:

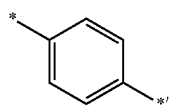

4-1

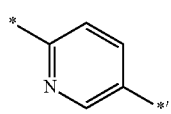

4-2

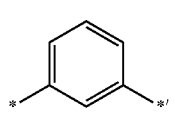

4-3

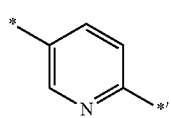

4-4

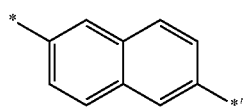

4-5

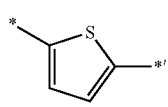

4-6

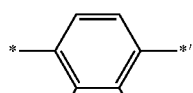

4-7

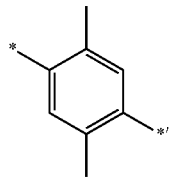

4-8

-continued

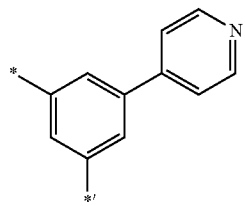

4-9

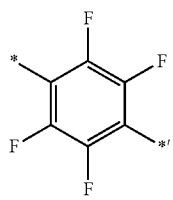

4-10

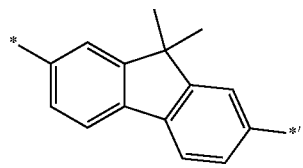

4-11

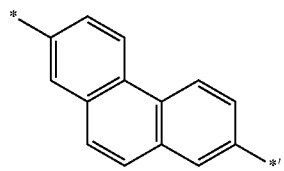

4-12

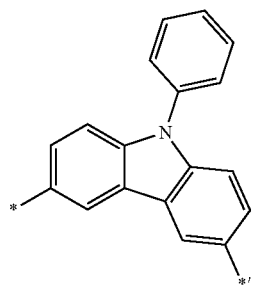

4-13

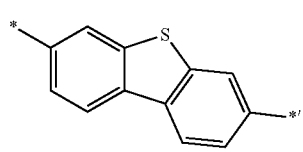

4-14

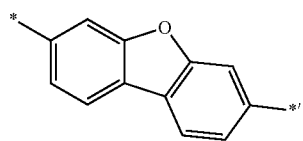

4-15

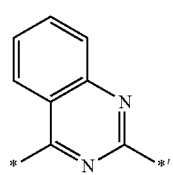

4-16

-continued

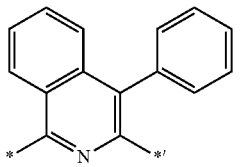
4-17

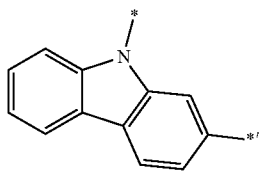
4-18

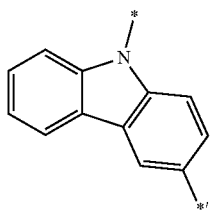
4-19

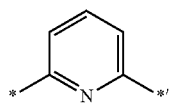
4-20

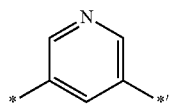
4-21

In Formulae 4-1 to 4-21,

* and *' each independently represent a binding site at a neighboring atom.

In Formula 2, a1 may be an integer selected from 0, 1, 2, and 3. For example, in Formula 2, a1 may be an integer of 0 or 1, but a1 is not limited thereto. In Formula 2, when a1 is 0, $(L_1)_{a1}$ is a single bond. When a1 is 2 or greater, a plurality of $L_1$s may be identical to or different from each other.

In Formula 1, $R_1$, $R_3$, $R_8$, and $R_{10}$ may be each independently selected from the group represented by Formula 2, a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group (e.g., a substituted or unsubstituted $C_2$-$C_{60}$ heteroaryl group), a substituted or unsubstituted monovalent non-aromatic condensed polycyclic group, a substituted or unsubstituted monovalent non-aromatic hetero-condensed polycyclic group, —$N(Q_1)(Q_2)$, —$Si(Q_3)(Q_4)(Q_5)$, and —$B(Q_6)(Q_7)$;

at least one of $R_1$, $R_3$, $R_8$, and $R_{10}$ is a group represented by Formula 2;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_3$-$C_{10}$ heterocycloalkyl group, substituted $C_3$-$C_{10}$ cycloalkenyl group, substituted $C_3$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group (e.g., substituted $C_2$-$C_{60}$ heteroaryl group), substituted monovalent non-aromatic condensed polycyclic group, and substituted monovalent non-aromatic hetero-condensed polycyclic group is selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy;

a $C_1$-$C_{60}$ alkyl group, a $C_2$-$C_{60}$ alkenyl group, a $C_2$-$C_{60}$ alkynyl group, and a $C_1$-$C_{60}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy, a $C_6$-$C_{60}$ arylthio, a $C_1$-$C_{60}$ heteroaryl group (e.g., a $C_2$-$C_{60}$ heteroaryl group), a monovalent non-aromatic condensed polycyclic group, a monovalent non-aromatic hetero-condensed polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, a monovalent non-aromatic hetero-condensed polycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, where $Q_1$ to $Q_7$, $Q_{11}$ to $Q_{17}$, $Q_{21}$ to $Q_{27}$, and $Q_{31}$ to $Q_{37}$ are each independently selected from a $C_1$-$C_{60}$ alkyl group, a $C_6$-$C_{60}$ aryl group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group.

In some embodiments, in Formula 1, $R_1$, $R_3$, $R_8$, and $R_{10}$ are each independently selected from the group represented by Formula 2, a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), where $Q_3$ to $Q_5$ are each independently selected from a $C_1$-$C_{20}$ alkyl group, a phenyl group, and a naphthyl group; and at least one of $R_1$, $R_3$, $R_8$, and $R_{10}$ is the group represented by Formula 2, but $R_1$, $R_3$, $R_8$, and $R_{10}$ are not limited thereto.

In some embodiments, the amine-based compound may have one or two groups represented by Formula 2, but the amine-based compound is not limited thereto.

In some embodiments, in Formula 1, $R_1$, $R_3$, $R_8$, or $R_{10}$ may be represented by Formula 2, but Formula 1 is not limited thereto.

In some embodiments, in Formula 1, $R_3$ and $R_{10}$ may be each independently the group represented by Formula 2; $R_3$ and $R_8$ may be each independently the group represented by Formula 2; $R_1$ and $R_{10}$ may be each independently the group represented by Formula 2; $R_1$ and $R_8$ may be each independently the group represented by Formula 2; $R_1$ and $R_3$ may be each independently the group represented by Formula 2; and $R_3$ and $R_{10}$ may be each independently the group represented by Formula 2, but $R_1$, $R_3$, $R_8$, and $R_{10}$ are not limited thereto.

In Formula 1, $R_2$, $R_4$ to $R_7$, $R_9$, $R_{11}$, and $R_{12}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group (e.g., a substituted or unsubstituted $C_2$-$C_{60}$ heteroaryl group), a substituted or unsubstituted monovalent non-aromatic condensed polycyclic group, a substituted or unsubstituted monovalent non-aromatic hetero-condensed polycyclic group, and —N($Q_1$)($Q_2$), —Si($Q_3$)($Q_4$)($Q_5$), and —B($Q_6$)($Q_7$), where:

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_3$-$C_{10}$ heterocycloalkyl group, substituted $C_3$-$C_{10}$ cycloalkenyl group, substituted $C_3$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group (e.g., substituted $C_2$-$C_{60}$ heteroaryl group), substituted monovalent non-aromatic condensed polycyclic group, and substituted monovalent non-aromatic hetero-condensed polycyclic group is selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy;

a $C_1$-$C_{60}$ alkyl group, a $C_2$-$C_{60}$ alkenyl group, a $C_2$-$C_{60}$ alkynyl group, and a $C_1$-$C_{60}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy, a $C_6$-$C_{60}$ arylthio, a $C_1$-$C_{60}$ heteroaryl group (e.g., a $C_2$-$C_{60}$ heteroaryl group), a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), where $Q_1$ to $Q_7$, $Q_{11}$ to $Q_{17}$, $Q_{21}$ to $Q_{27}$ and $Q_{31}$ to $Q_{37}$ are each independently selected from a $C_1$-$C_{60}$ alkyl group, a $C_6$-$C_{60}$ aryl group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group.

In some embodiments, in Formula 1, $R_2$, $R_4$ to $R_7$, $R_9$, $R_{11}$, and $R_{12}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), where $Q_3$ to $Q_5$ are each independently selected from a $C_1$-$C_{20}$ alkyl group, a phenyl group, and a naphthyl group, but $R_2$, $R_4$ to $R_7$, $R_9$, $R_{11}$, and $R_{12}$ are not limited thereto.

In Formula 2, $R_{21}$ and $R_{22}$ may be each independently selected from a substituted or unsubstituted $C_6$-$C_{60}$ aryl group, a substituted or unsubstituted $C_1$-$C_{60}$ heteroaryl group (e.g., a substituted or unsubstituted $C_2$-$C_{60}$ heteroaryl group), a substituted or unsubstituted monovalent non-aromatic condensed polycyclic group, and a substituted or unsubstituted monovalent non-aromatic hetero-condensed polycyclic group, where at least one substituent of the substituted $C_6$-$C_{60}$ aryl group, substituted $C_1$-$C_{60}$ heteroaryl group (e.g., substituted $C_2$-$C_{60}$ heteroaryl group), substituted monovalent non-aromatic condensed polycyclic group, and substituted monovalent non-aromatic hetero-condensed polycyclic group may be selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy;

a $C_1$-$C_{60}$ alkyl group, a $C_2$-$C_{60}$ alkenyl group, a $C_2$-$C_{60}$ alkynyl group, and a $C_1$-$C_{60}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy, a $C_6$-$C_{60}$ arylthio, a $C_1$-$C_{60}$ heteroaryl group (e.g., a $C_2$-$C_{60}$ heteroaryl group), a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), where $Q_{11}$ to $Q_{17}$, $Q_{21}$ to $Q_{27}$, and $Q_{31}$ to $Q_{37}$ are each independently selected from a $C_1$-$C_{60}$ alkyl group, a $C_6$-$C_{60}$ aryl group, a $C_1$-$C_{60}$ heteroaryl group (e.g., a $C_2$-$C_{60}$ heteroaryl group), a monovalent non-aromatic condensed polycyclic group, and a monovalent non-aromatic hetero-condensed polycyclic group.

In some embodiments, in Formula 2, $R_{21}$ and $R_{22}$ are each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazoly group, an oxadiazolyl group, a triazinyl group, a dibenzofuranyl group, a dibenzothiophenyl group, a dibenzosilolyl group, a benzocarbazolyl group, and a dibenzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{23}$)($Q_{24}$)($Q_{25}$), a $C_1$-$C_{20}$ alkyl group substituted with a halogen atom, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, where:

$Q_{23}$ to $Q_{25}$ are each independently selected from a $C_1$-$C_{20}$ alkyl group, a phenyl group, a naphthyl group, and a pyridinyl group, but $R_{21}$ and $R_{22}$ are not limited thereto.

In some embodiments, in Formula 2, $R_{21}$ and $R_{22}$ are each independently selected from:

a phenyl group, a naphthyl group, a fluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, a quinolinyl group, an isoquinolinyl group, a phenanthridinyl group, an acridinyl group, a phenanthrolinyl group, a benzimidazolyl group, a benzofuranyl group, a benzothiophenyl group, a benzoxazolyl group, a triazolyl group, a tetrazolyl group, a triazinyl group, a dibenzofuranyl group, a dibenzothiophenyl group, and a dibenzosilolyl group; and a phenyl group, a naphthyl group, a fluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, a quinolinyl group, an isoquinolinyl group, a phenanthridinyl group, an acridinyl group, a phenanthrolinyl group, a benzimidazolyl group, a benzofuranyl group, a benzothiophenyl group, a benzoxazolyl group, a triazolyl group, a tetrazolyl group, a triazinyl group, a dibenzofuranyl group, a dibenzothiophenyl group, and a dibenzosilolyl group, each substituted with at least one selected from a deuterium atom, a halogen atom, a cyano group, a nitro group, a methyl group, an ethyl group, an n-propyl group, a tert-butyl group, a methoxy group, an ethoxy group, a tert-butoxy group, —Si(CH$_3$)$_3$, —Si(Ph)$_3$, —CF$_3$, a phenyl group, a naphthyl group, a fluorenyl group, a phenanthrenyl group, an anthracenyl group, a triphenylenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a naphthyridinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group and a dibenzothiophenyl group, but $R_{21}$ and $R_{22}$ are not limited thereto.

In some embodiments, in Formula 2, $R_{21}$ and $R_{22}$ may be each independently a group selected from Formulae 5-1 to 5-52, but $R_{21}$ and $R_{22}$ are not limited thereto:

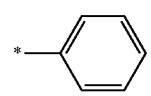

5-1

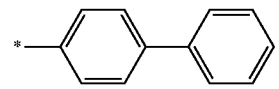

5-2

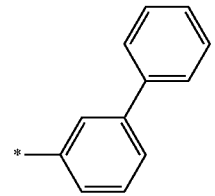

5-3

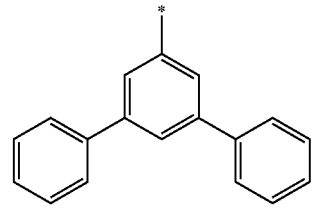

5-4

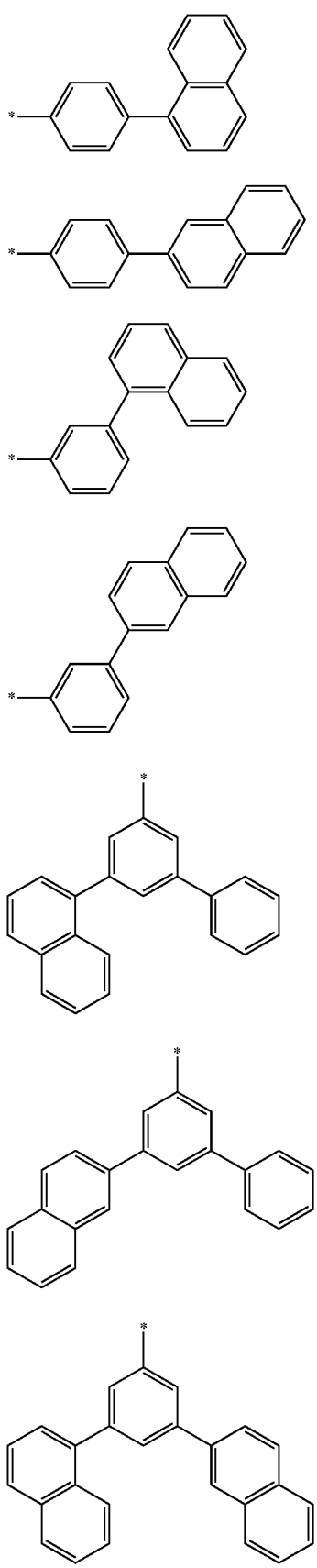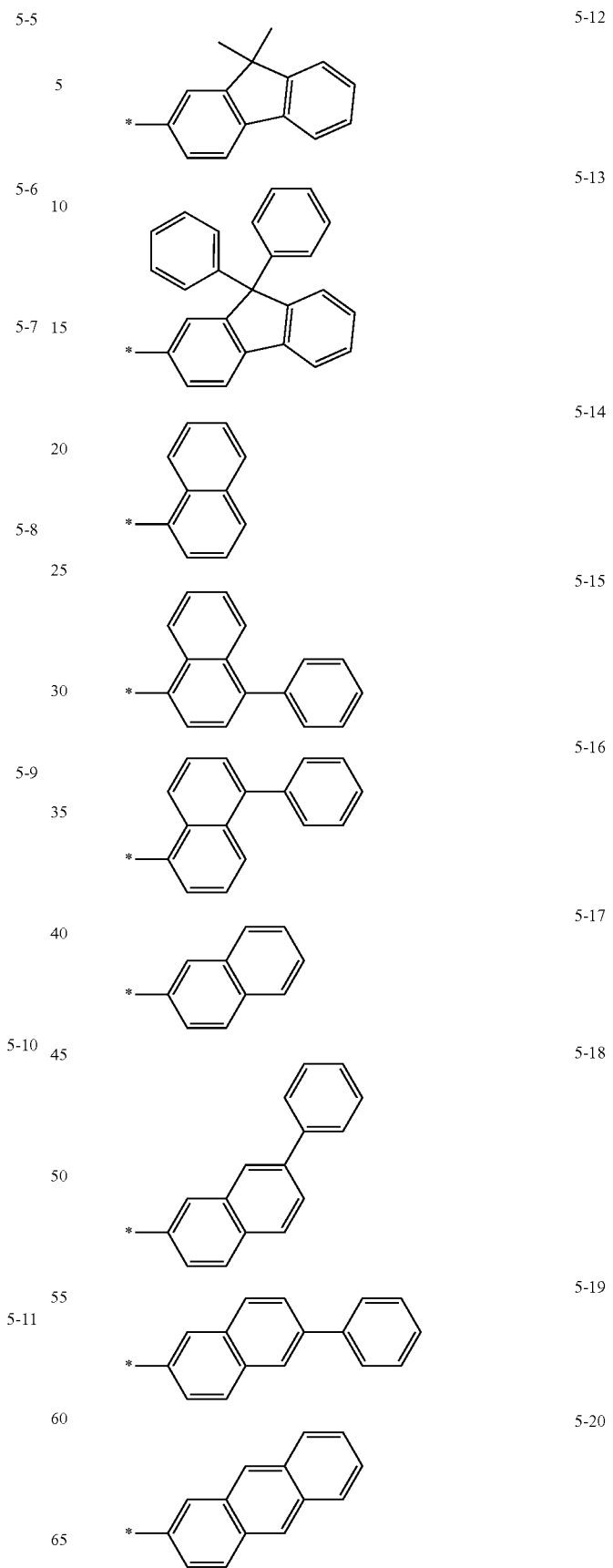

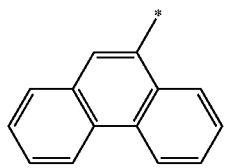
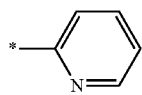
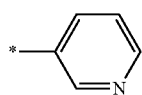
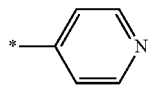
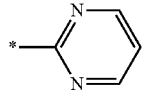
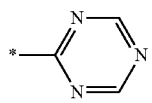
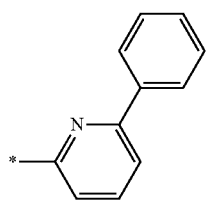
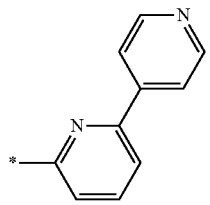
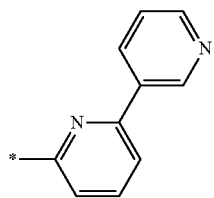
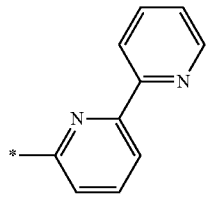
5-21
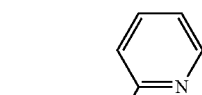
5-22
5-23
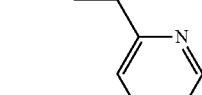
5-24
5-25
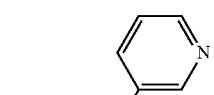
5-26
5-27
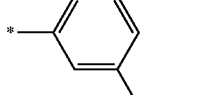
5-28
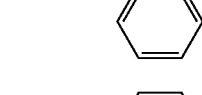
5-29
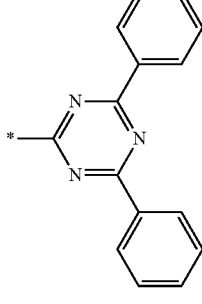
5-30
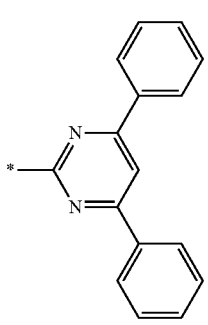
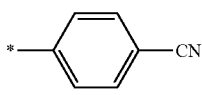
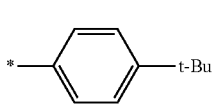

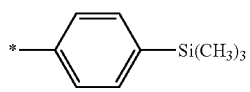
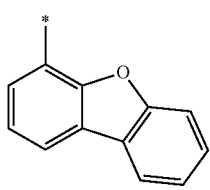
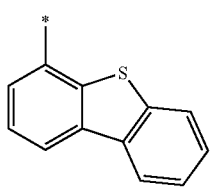
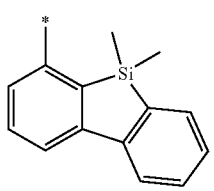
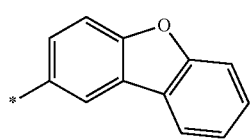
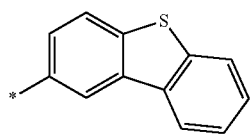
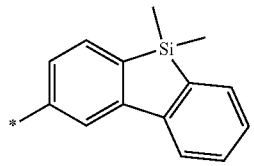
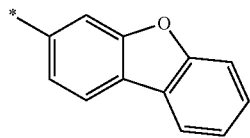
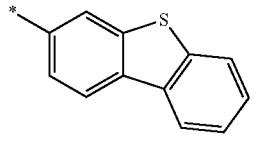
5-38
5-39
5-40
5-41
5-42
5-43
5-44
5-45
5-46
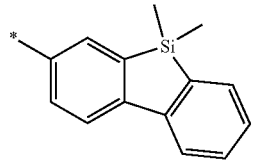  5-47
  5-48
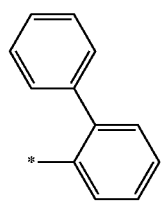
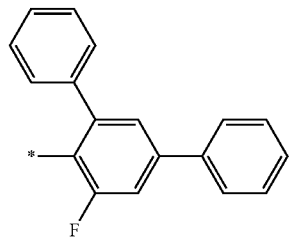  5-49
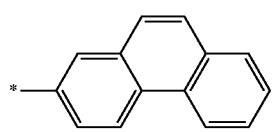  5-50
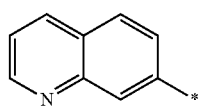  5-51
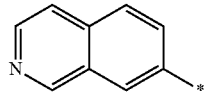  5-52
In Formulae 5-1 to 5-52, * represents a binding site at a neighboring atom.
In one embodiment, the amine-based compound represented by Formula 1 may be represented by Formula 1A:
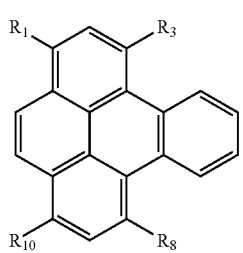
Formula 1A
In Formula 1A,
$R_1$, $R_3$, $R_8$, and $R_{10}$ are as defined above in the present specification.

In another embodiment, the amine-based compound is represented by

Formula 1A, where, in Formula 1A, $R_1$ is the group represented by Formula 2; and $R_3$, $R_8$, and $R_{10}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), where $Q_3$ to $Q_5$ are each independently selected from a $C_1$-$C_{20}$ alkyl group, a phenyl group, and a naphthyl group, but the amine-based compound is not limited thereto:

In another embodiment, the amine-based compound is represented by Formula 1A, where, in Formula 1A, $R_1$ and $R_{10}$ are each independently the group represented by Formula 2; and $R_3$ and $R_8$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), where $Q_3$ to $Q_5$ are each independently selected from a $C_1$-$C_{20}$ alkyl group, a phenyl group, and a naphthyl group, but the amine-based compound is not limited thereto.

In another embodiment, the amine-based compound may be represented by Formula 1A, where, in Formula 1A, $R_1$ and $R_8$ may be each independently a group represented by Formula 2; and $R_3$ and $R_{10}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), where $Q_3$ to $Q_5$ are each independently selected from a $C_1$-$C_{20}$ alkyl group, a phenyl group, and a naphthyl group, but the amine-based compound is not limited thereto.

In another embodiment, the amine-based compound may be represented by Formula 1A, where, in Formula 1A, $R_3$ may be a group represented by Formula 2; and $R_1$, $R_8$, and $R_{10}$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), where $Q_3$ to $Q_5$ may be each independently selected from a $C_1$-$C_{20}$ alkyl group, a phenyl group, and a naphthyl group, but the amine-based compound is not limited thereto.

In another embodiment, the amine-based compound may be represented by Formula 1A, $R_3$ and $R_8$ may be each independently a group represented by Formula 2; and $R_1$ and $R_{10}$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), where $Q_3$ to $Q_5$ are each independently selected from a $C_1$-$C_{20}$ alkyl group, a phenyl group, and a naphthyl group.

In another embodiment, the amine-based compound may be represented by Formula 1A, $R_3$ and $R_{10}$ may be each independently a group represented by Formula 2; and $R_1$ and $R_8$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), where $Q_3$ to $Q_5$ are each independently selected from a $C_1$-$C_{20}$ alkyl group, a phenyl group, and a naphthyl group, but the amine-based compound is not limited thereto.

In another embodiment, the amine-based compound may be represented by one selected from Compounds 1 to 153, but the amine-based compound is not limited thereto:

1
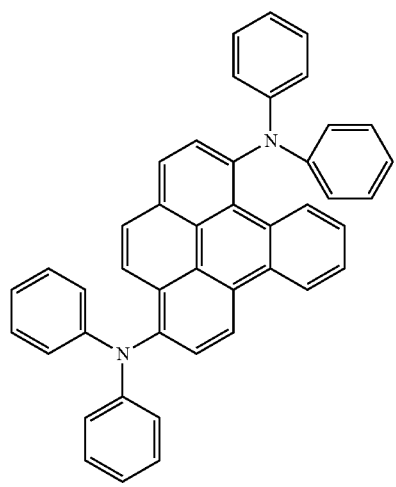
2
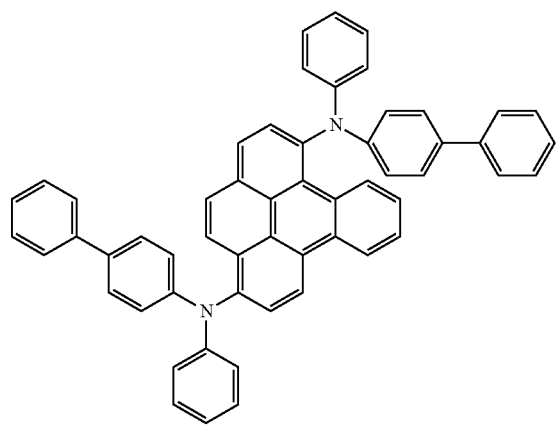
3
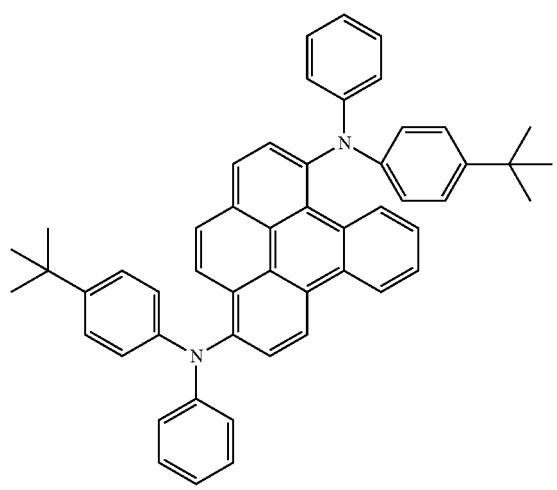
4
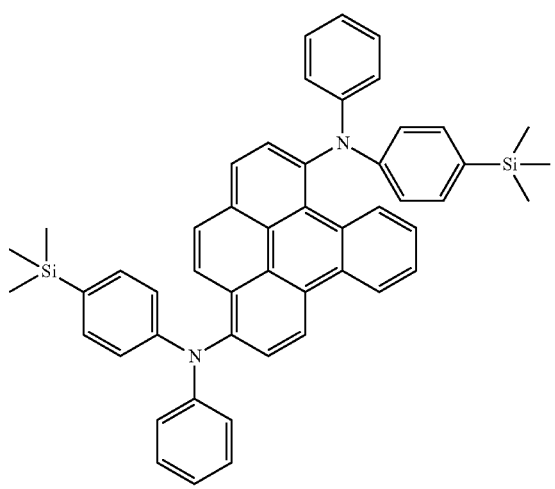
5
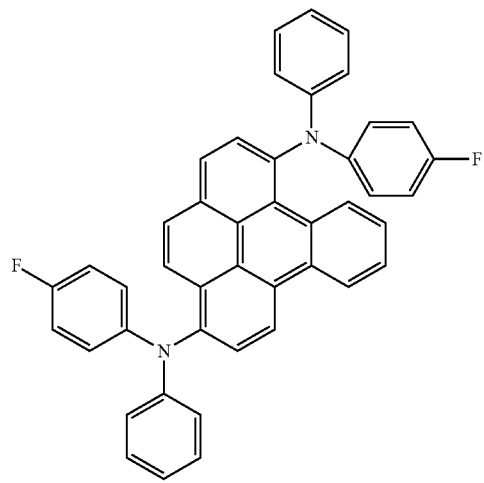
6
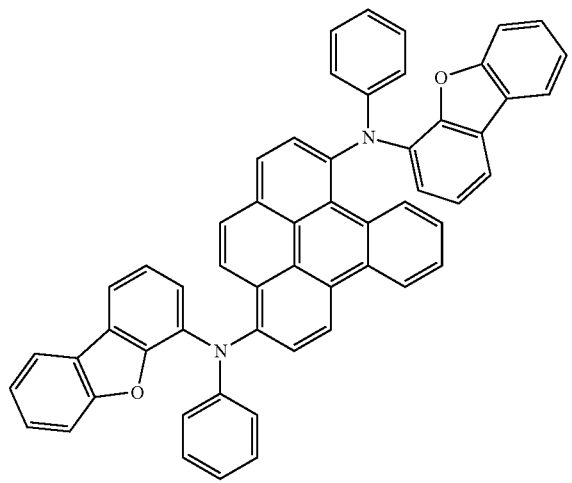

-continued
7
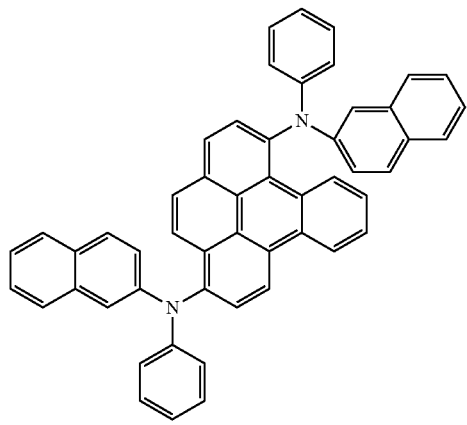
8
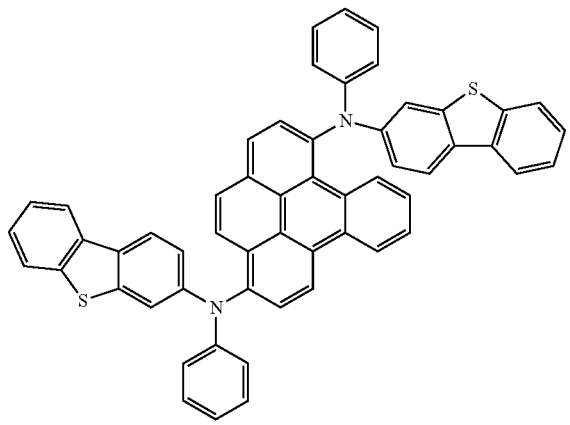
9
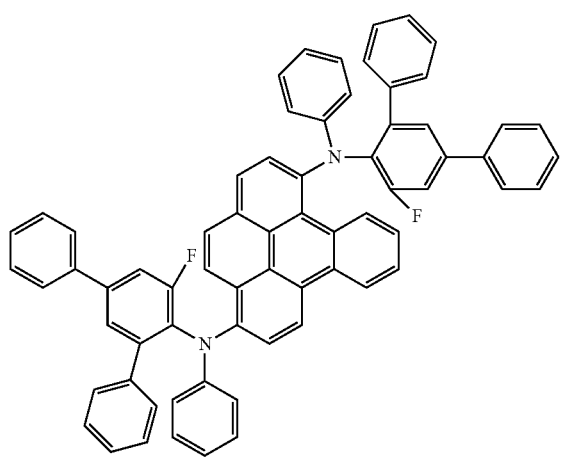
10
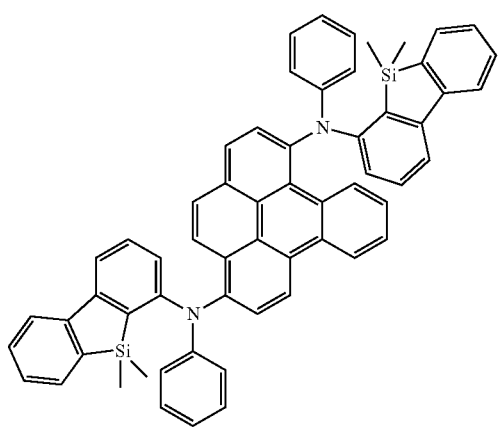
11
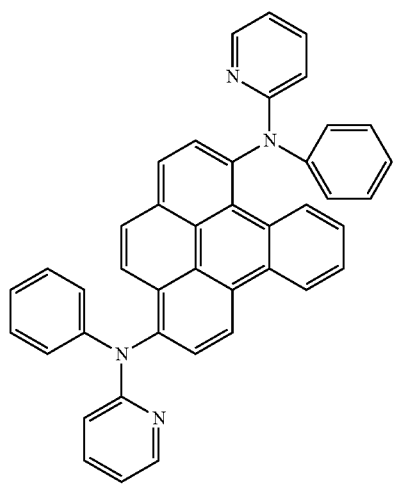
12
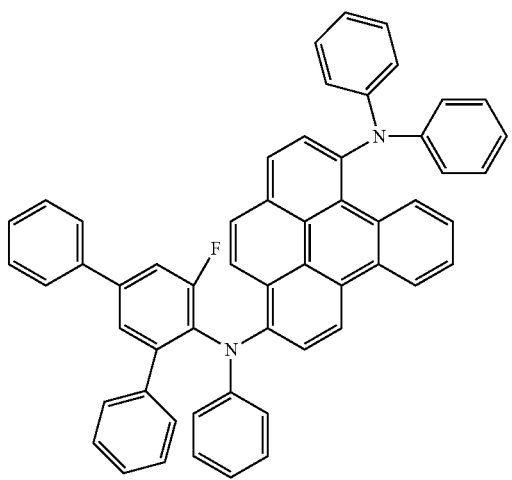

-continued
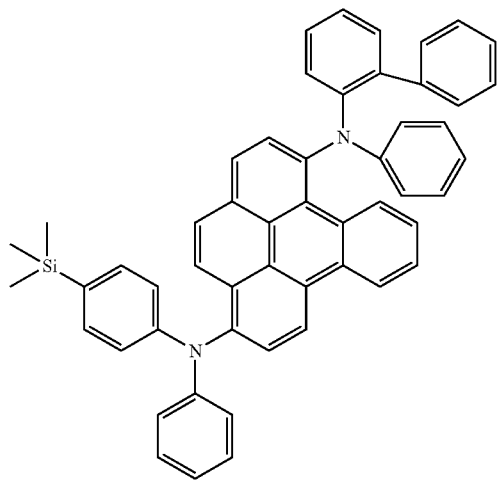
13
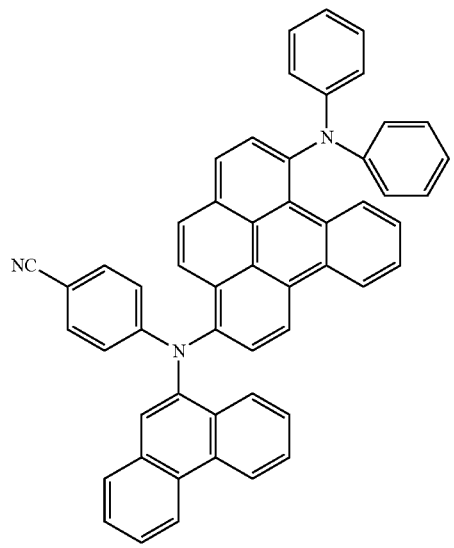
14
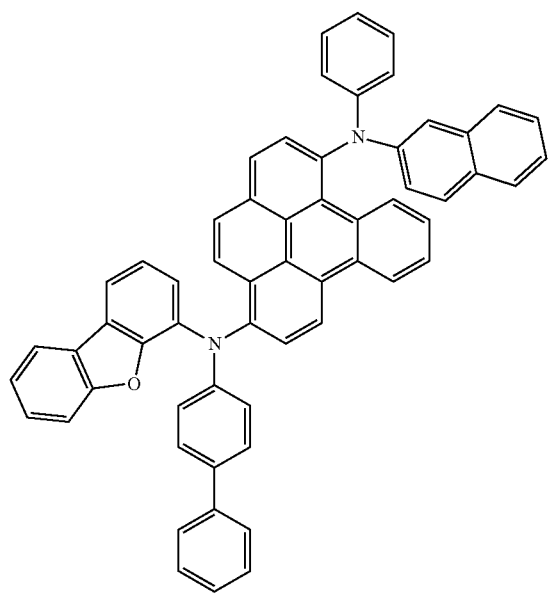
15
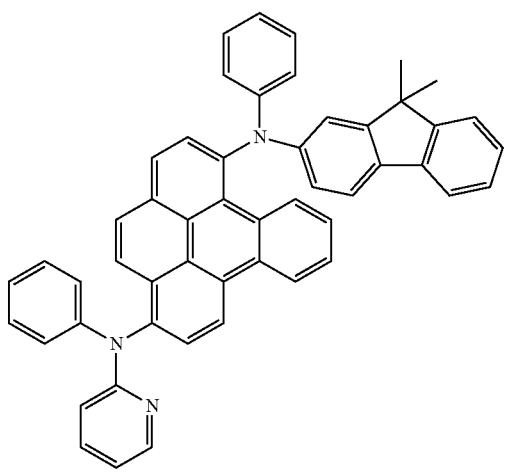
16
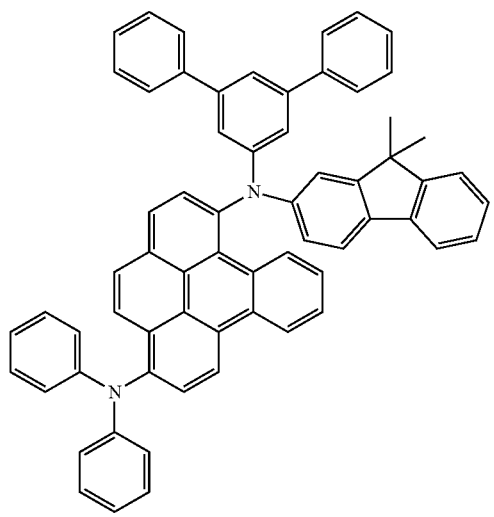
17
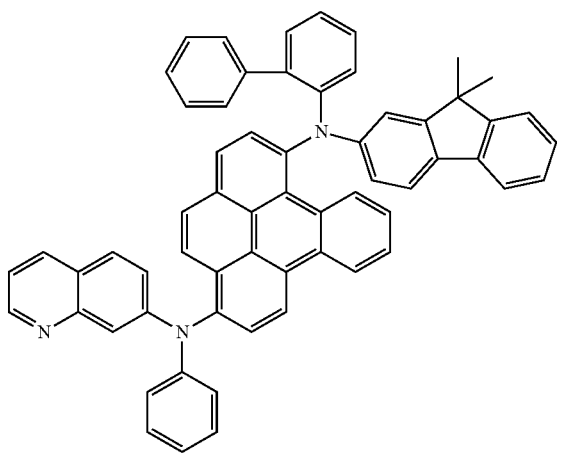
18

-continued
19
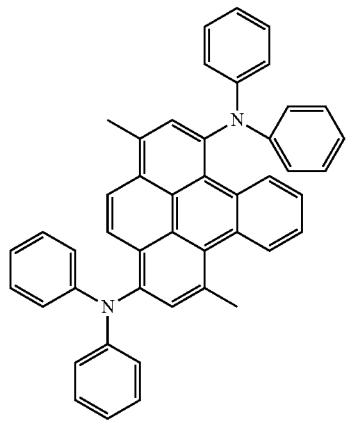
20
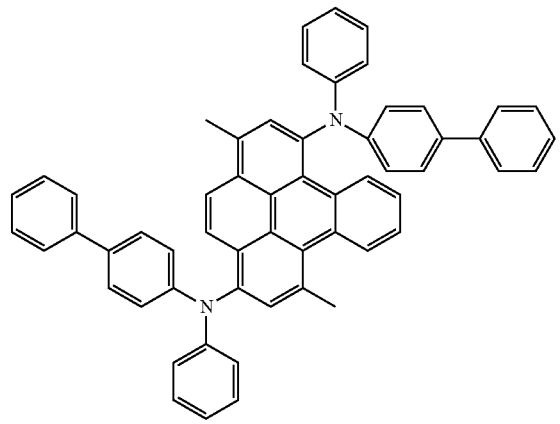
21
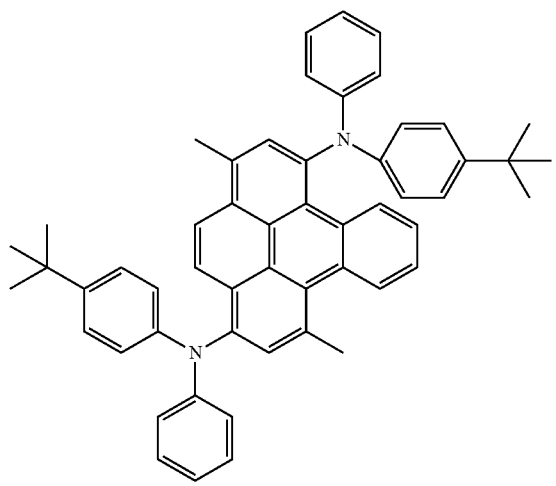
22
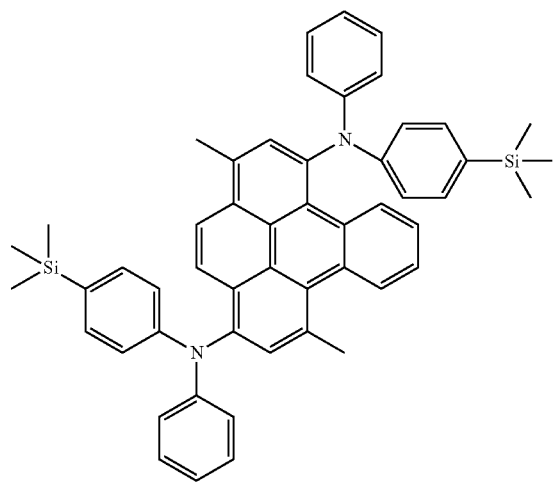
23
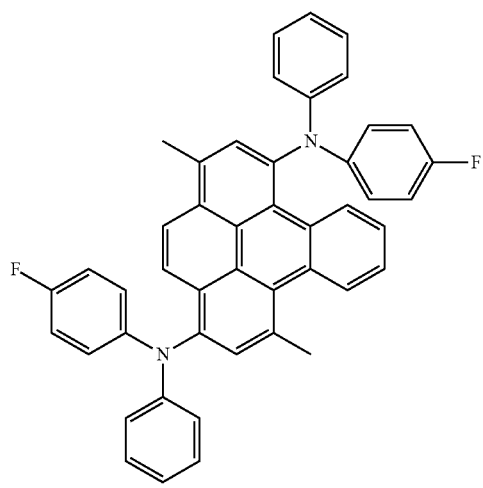
24
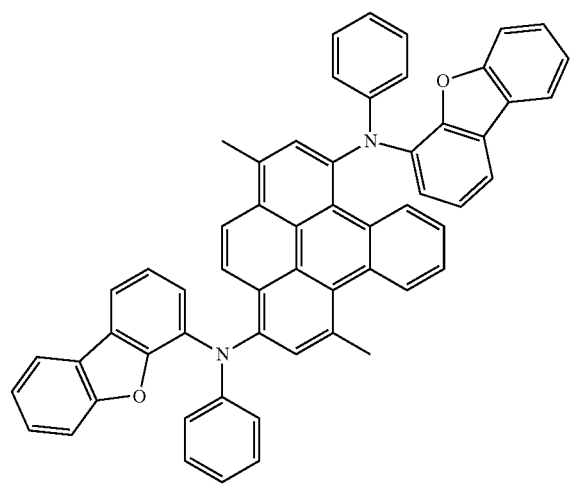

-continued
25
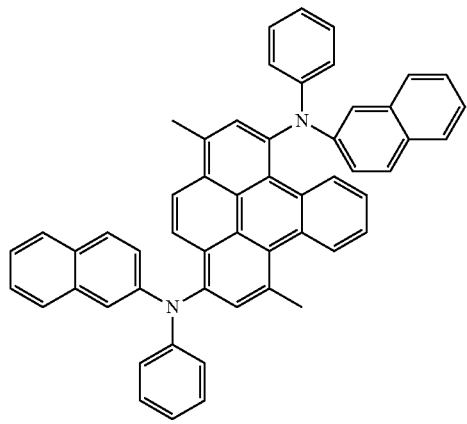
26
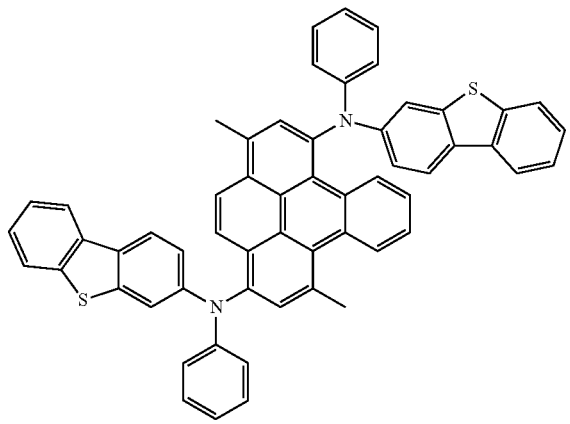
27
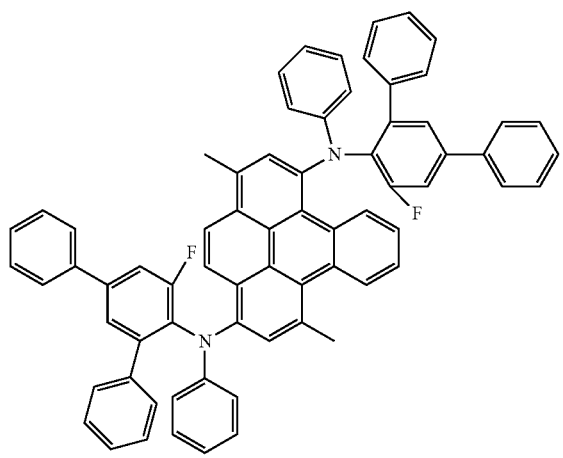
28
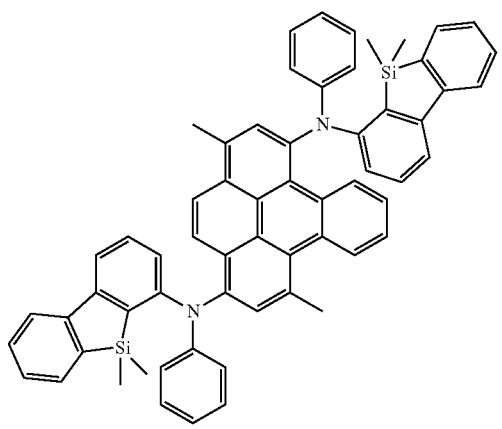
29
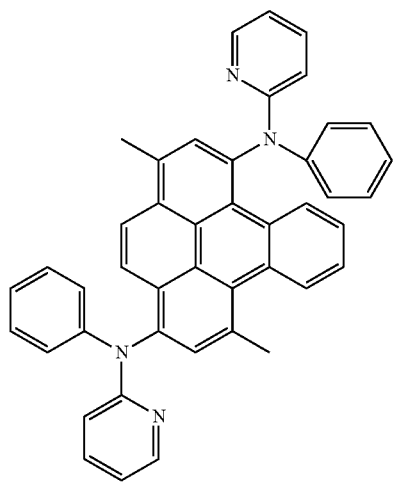
30
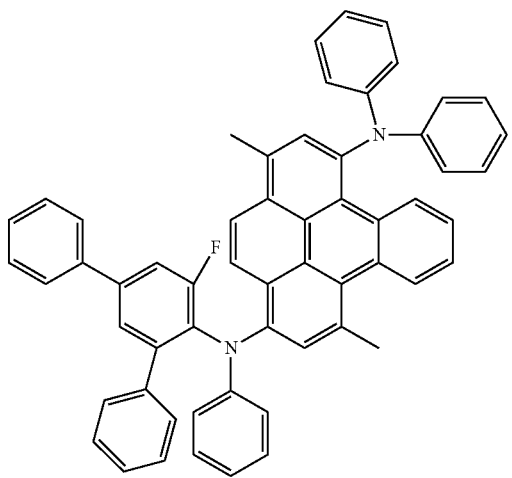

-continued
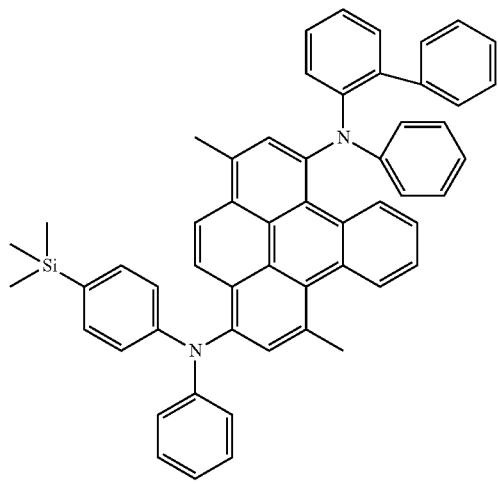
31
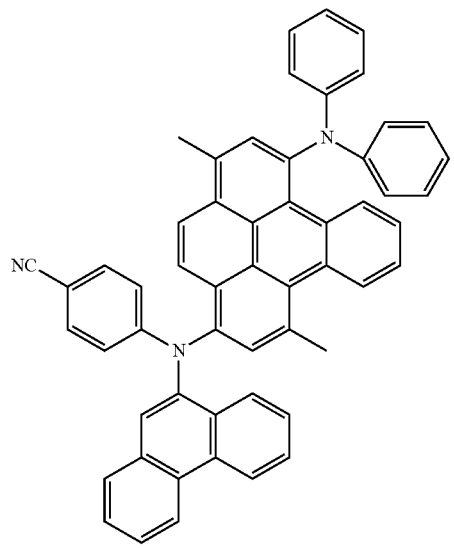
32
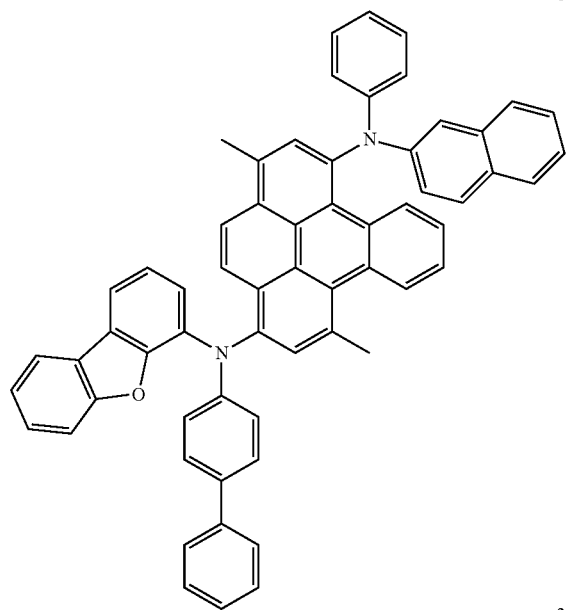
33
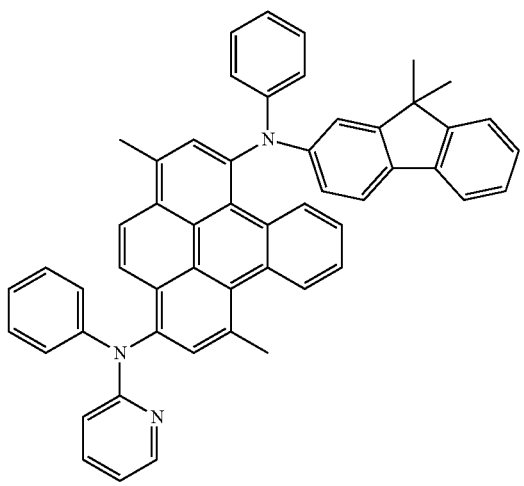
34
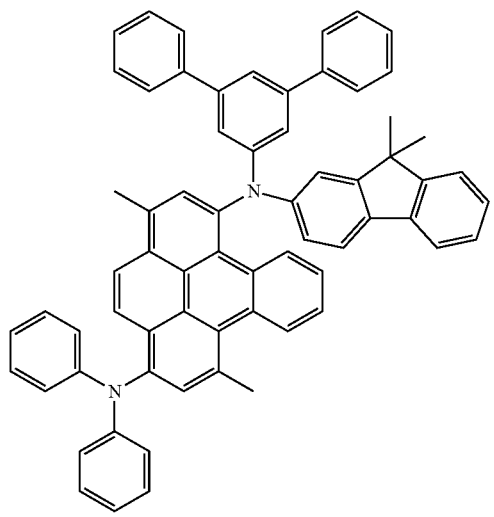
35
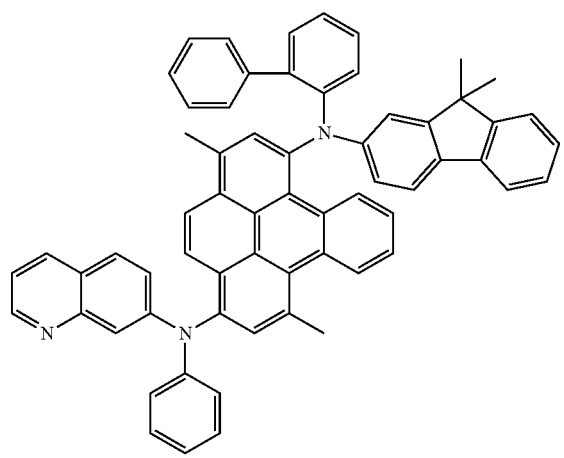
36

-continued
37
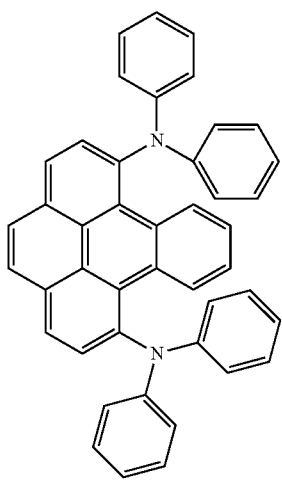
38
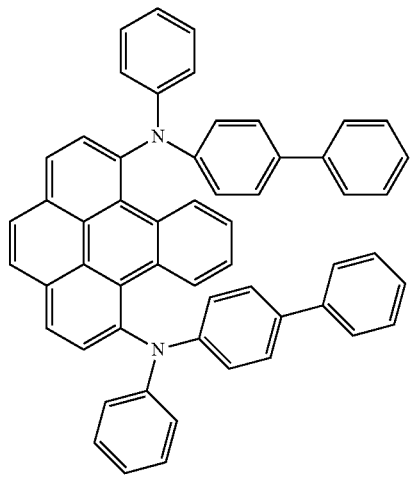
39
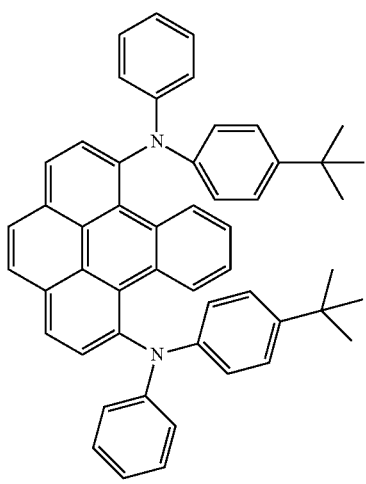
40
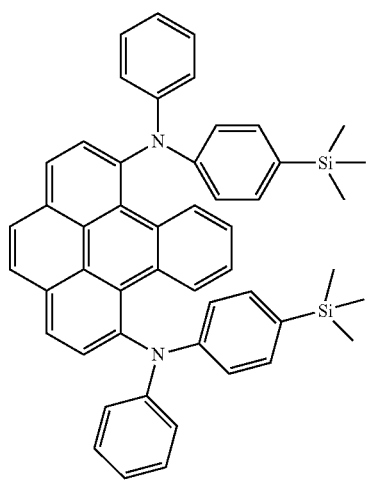
41
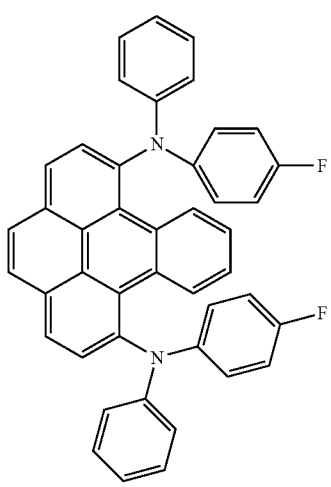
42
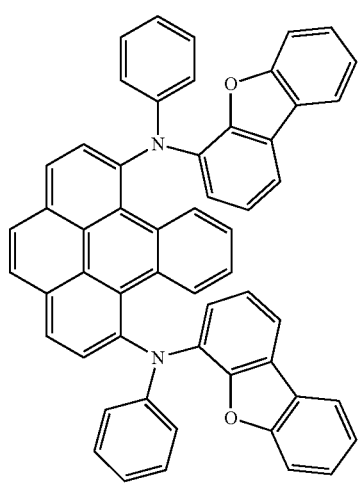

-continued
43
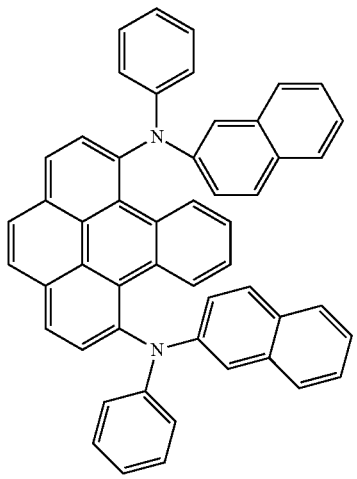
44
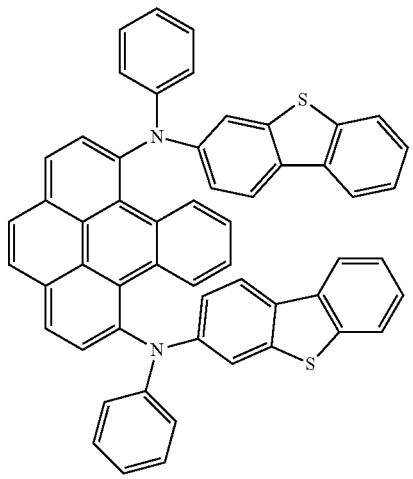
45
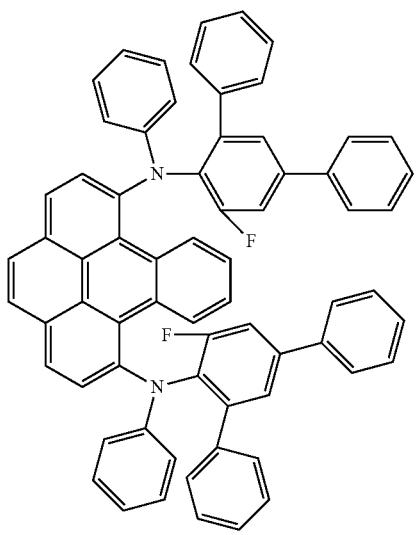
46
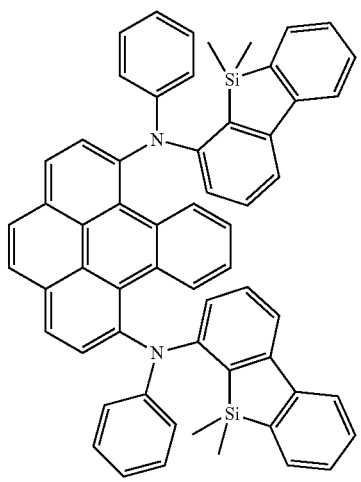
47
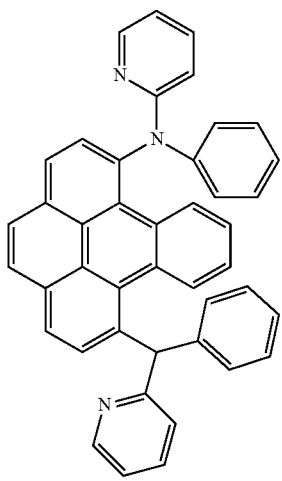
48
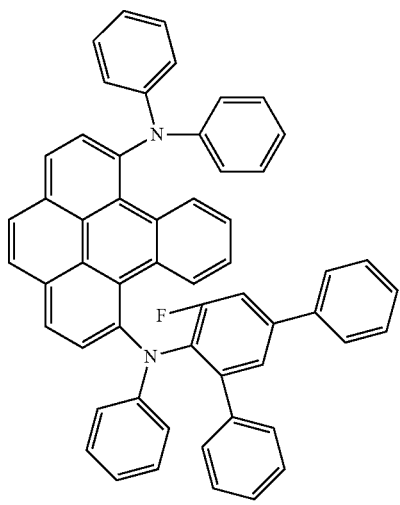

-continued
49
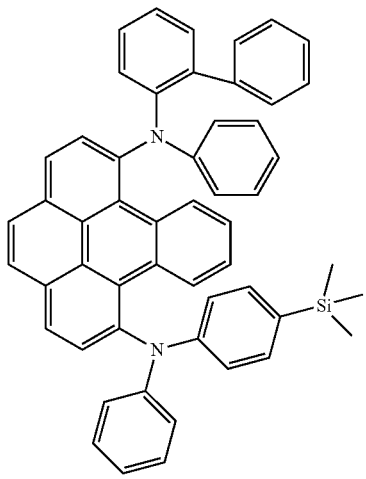
50
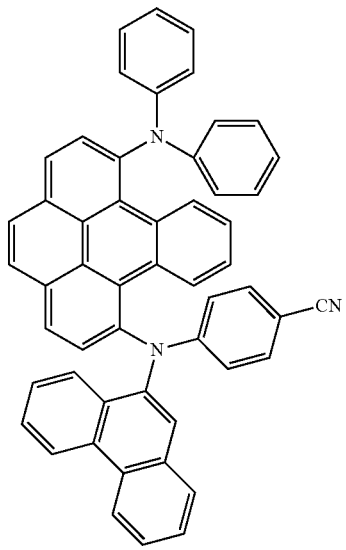
51
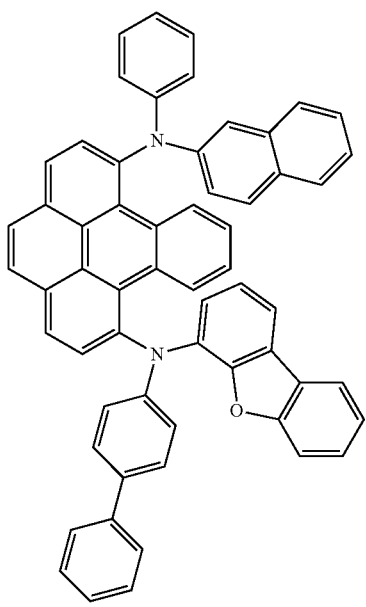
52
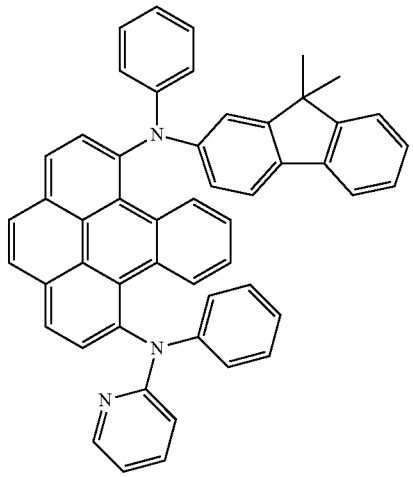
53
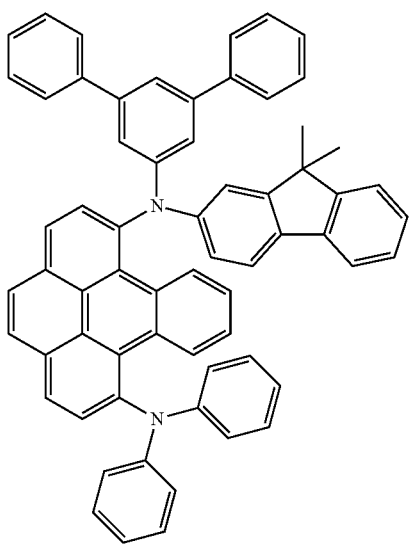
54
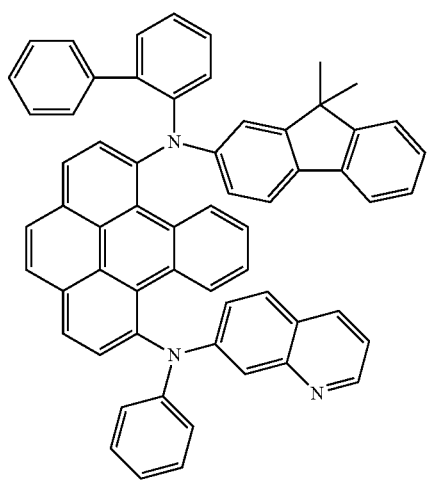

-continued
55
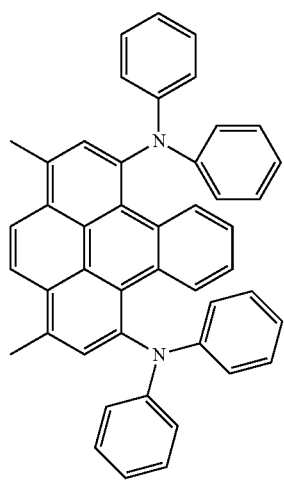
56
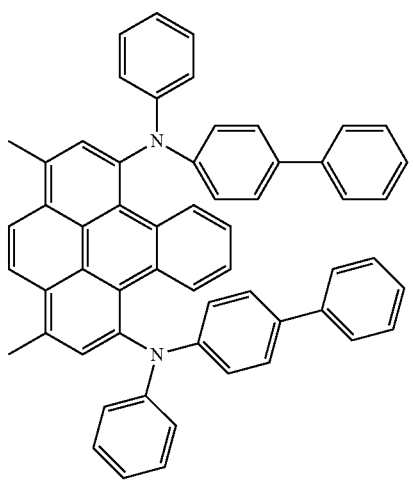
57
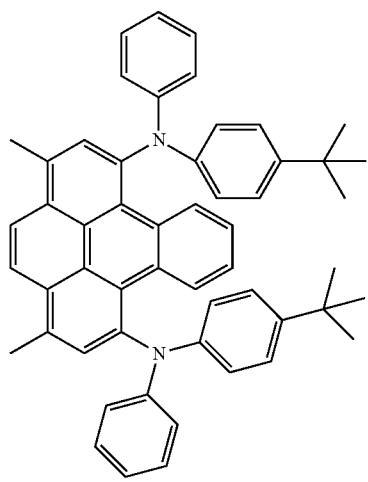
58
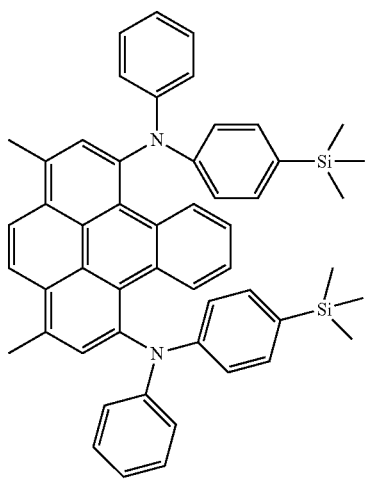
59
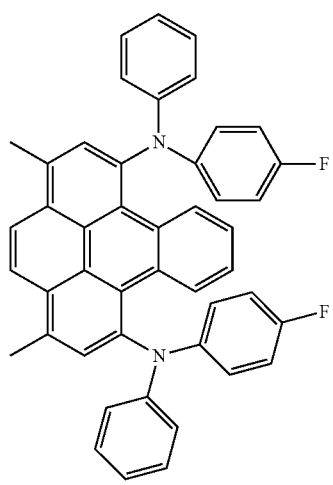
60
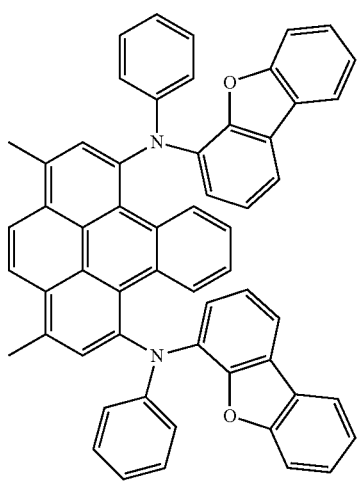

-continued
61
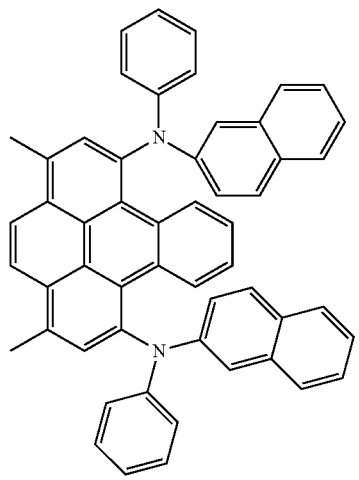
62
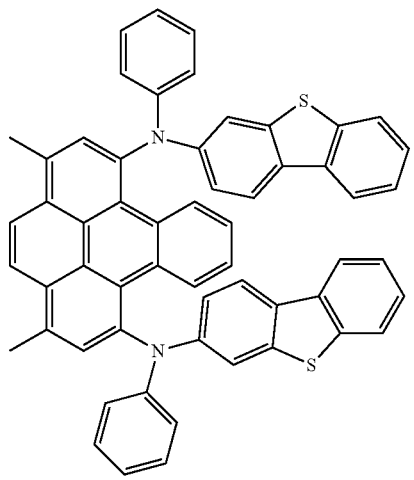
63
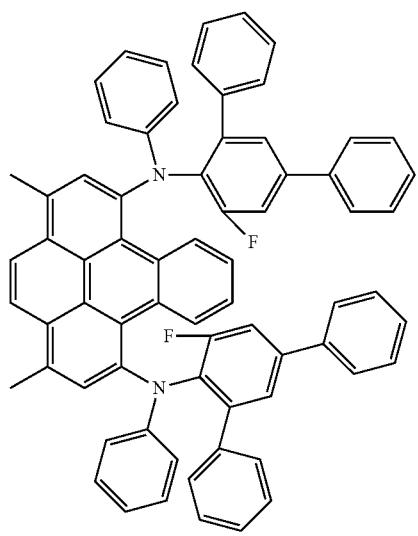
64
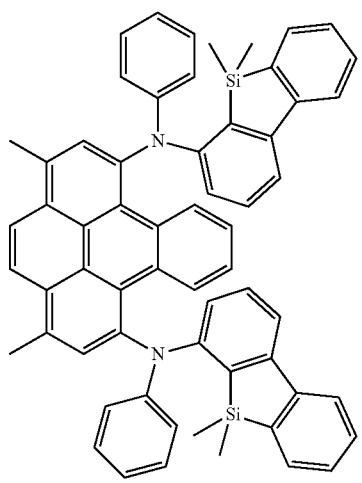
65
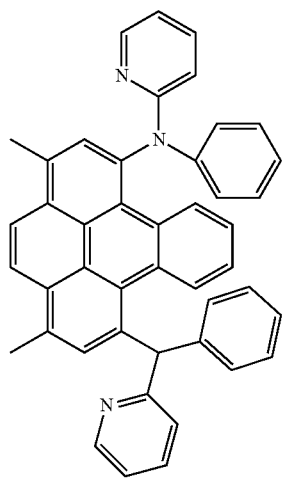
66
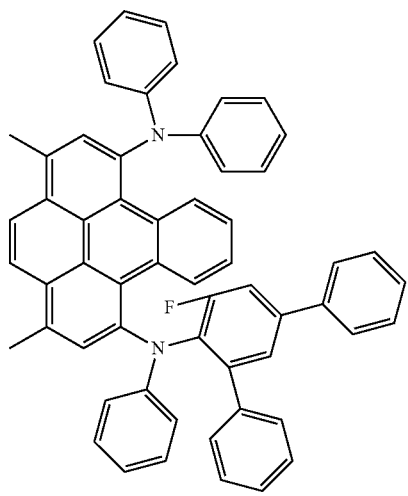

-continued
67
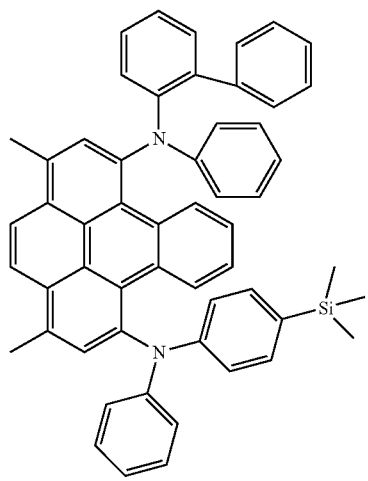
68
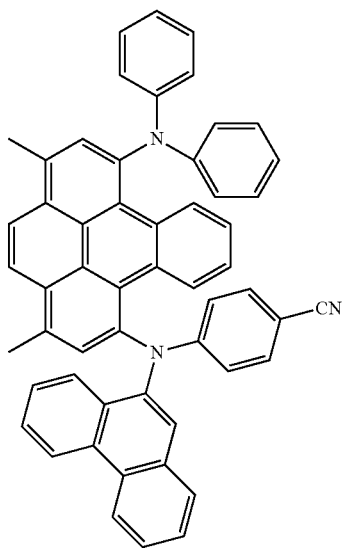
69
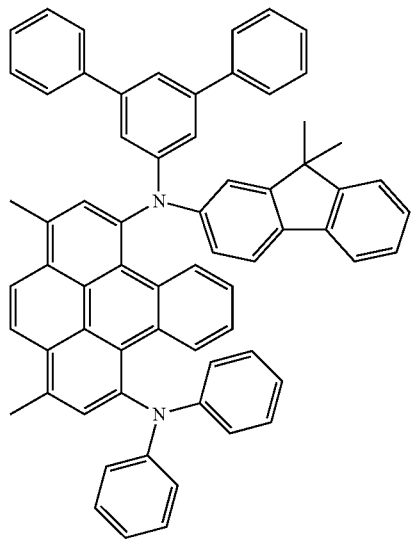
70
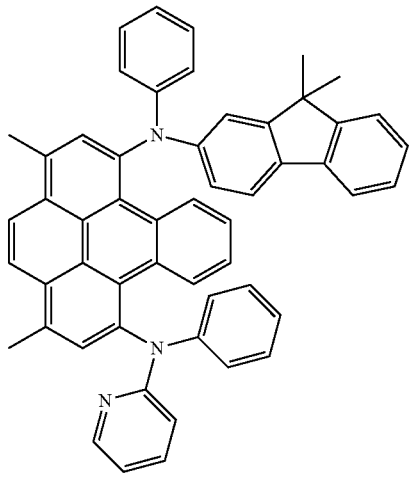
71
72
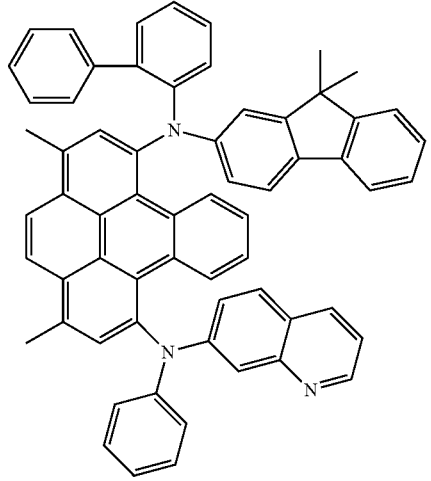

-continued
73
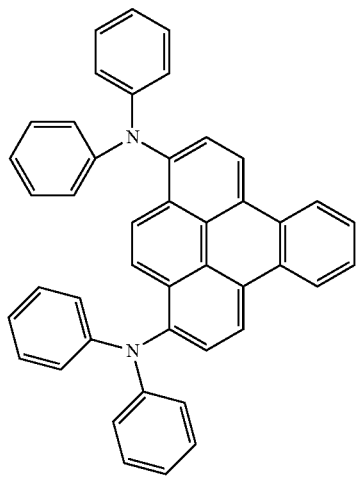
74
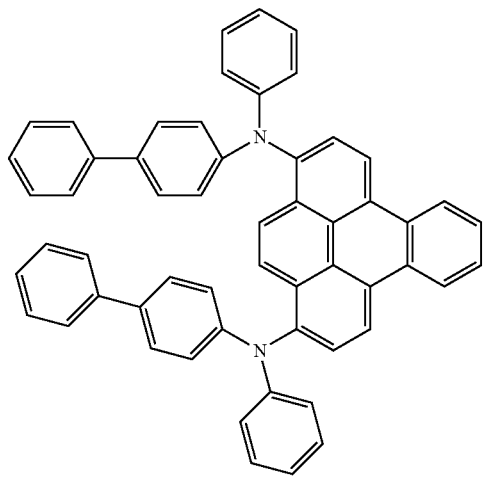
75
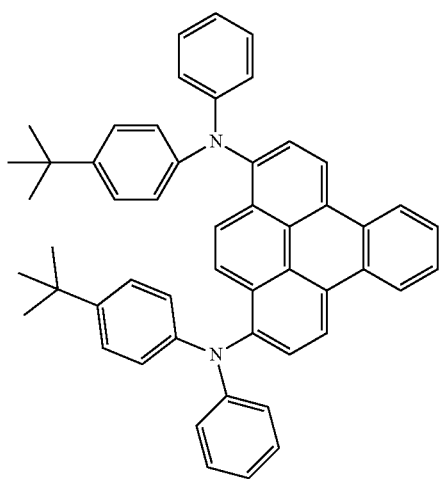
76
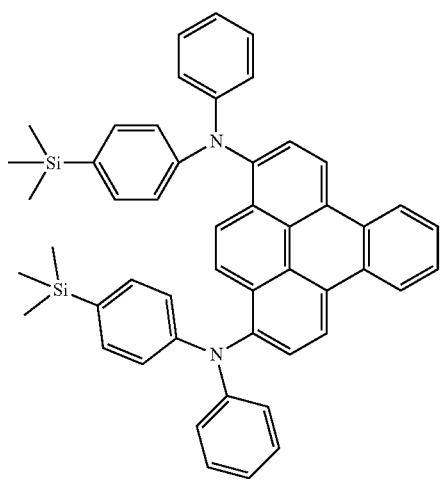
77
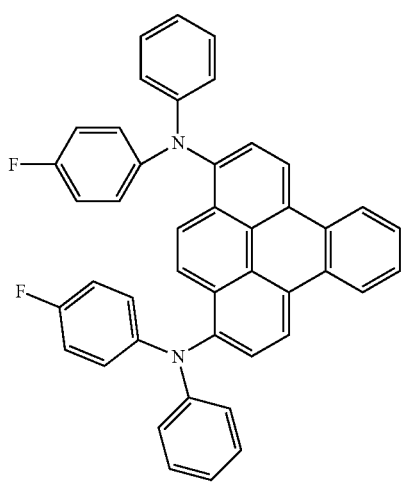
78
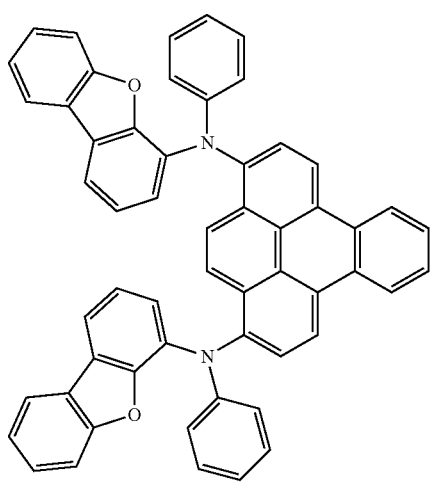

79
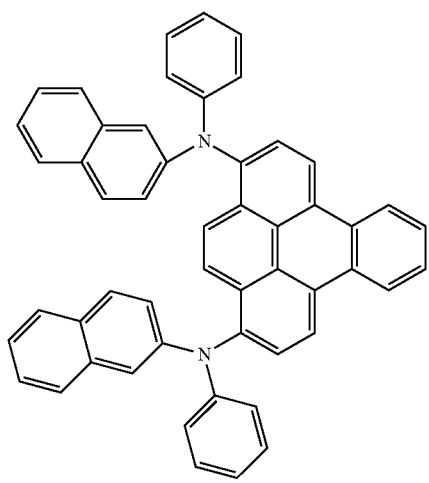
80
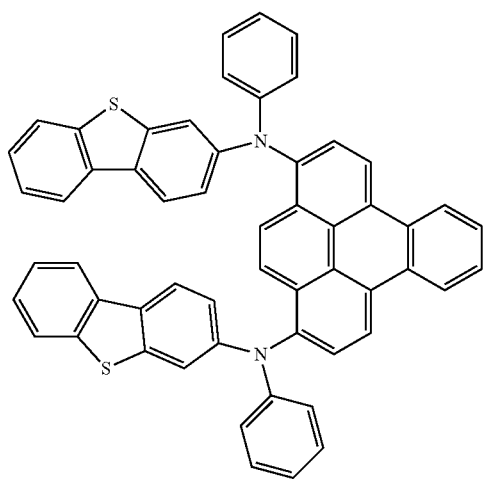
81
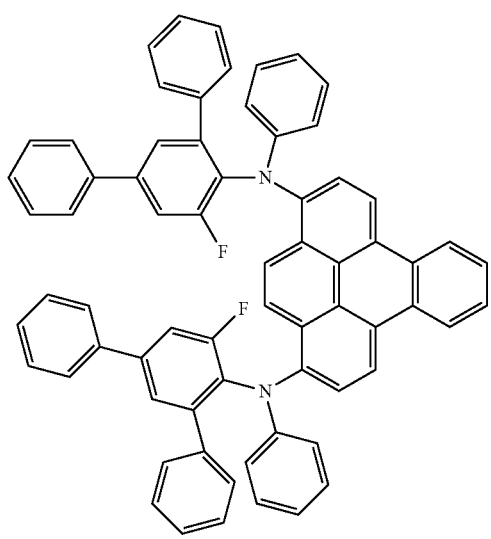
82
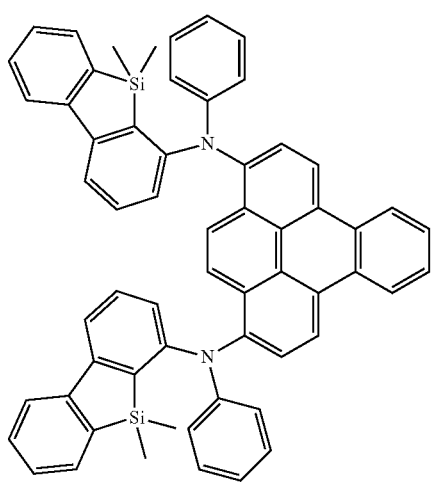
83
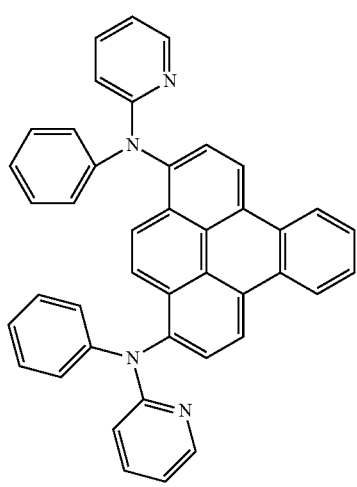
84
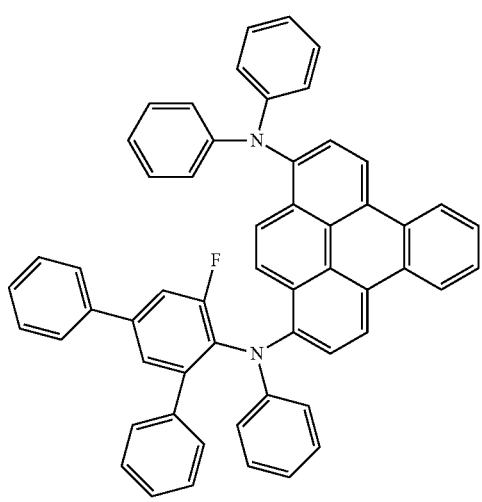

-continued
85
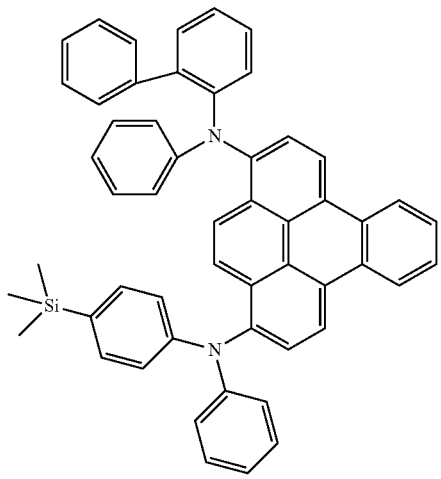
86
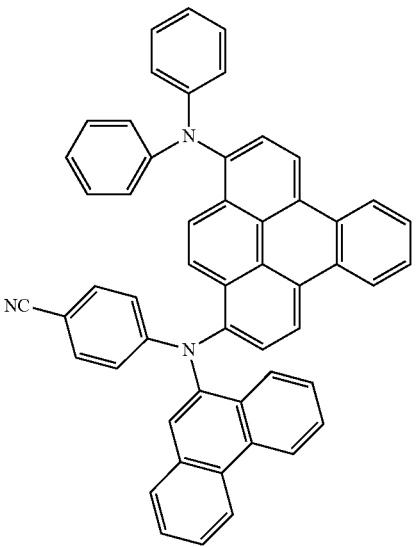
87
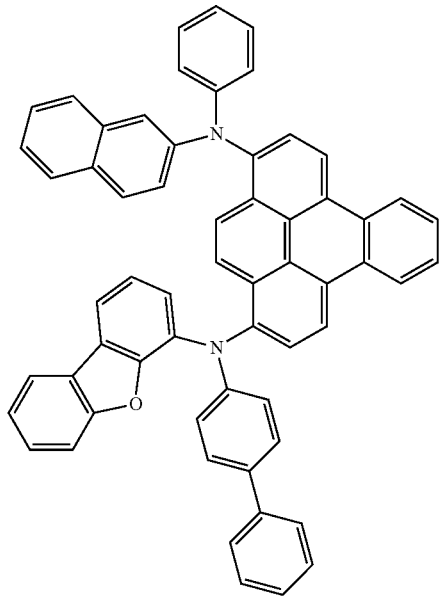
88
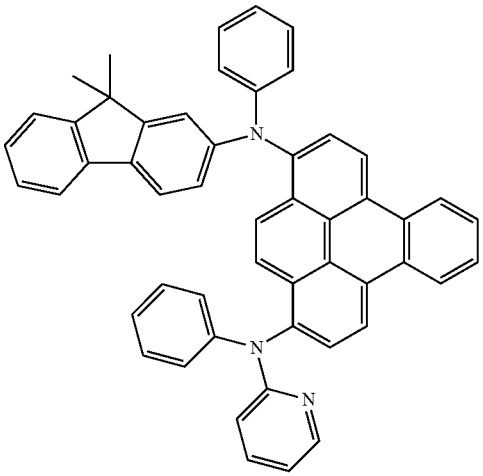
89
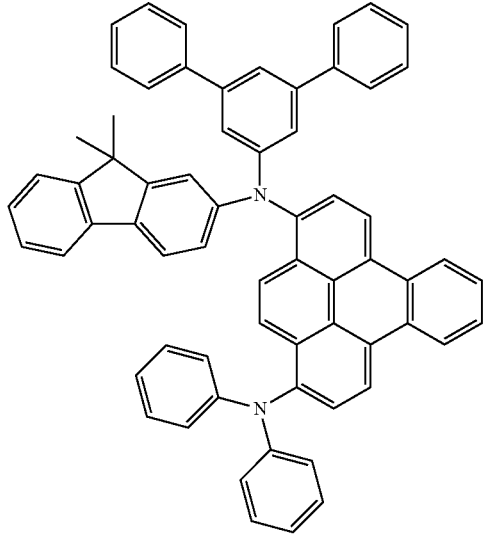
90
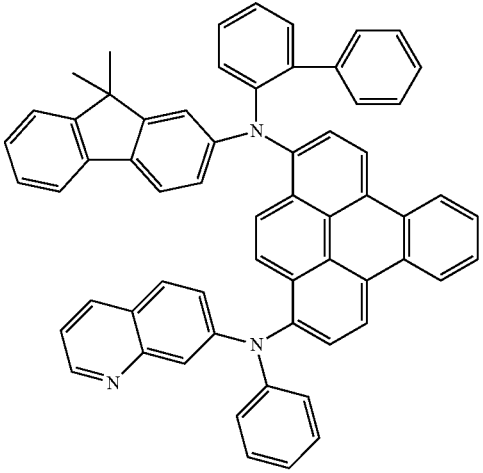

-continued
91 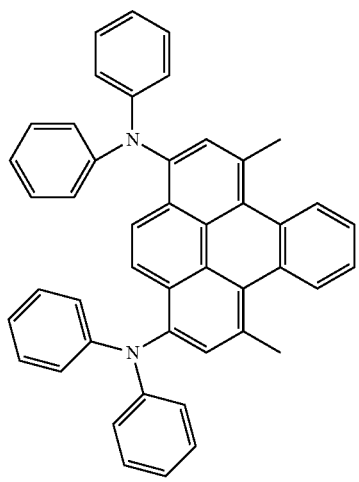
92 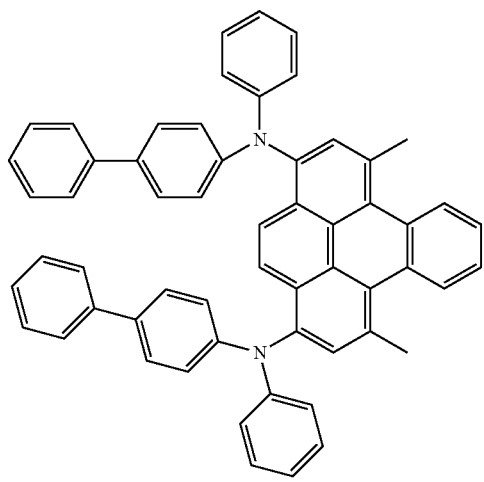
93 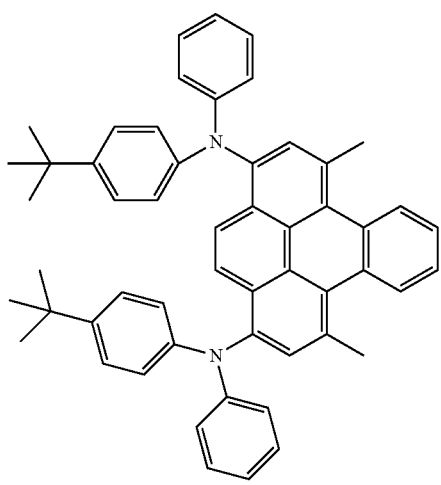
94 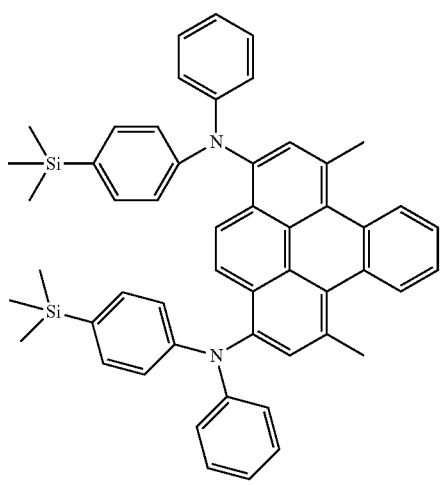
95 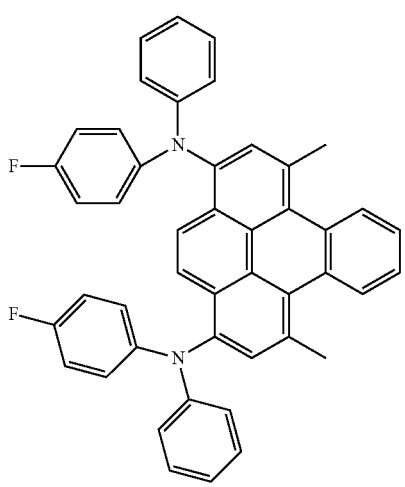
96 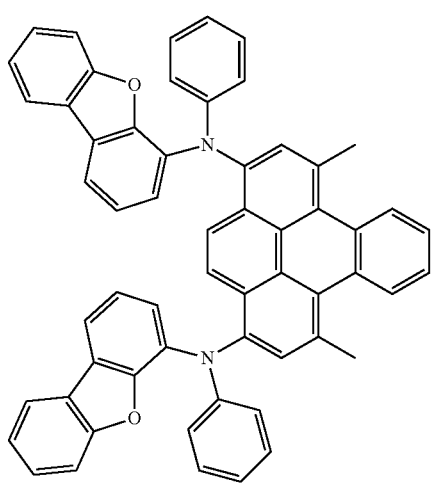

-continued
97
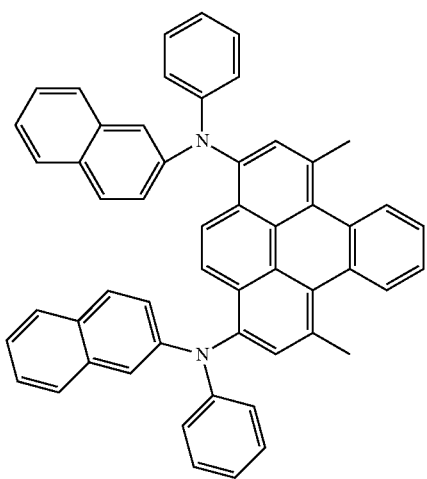
98
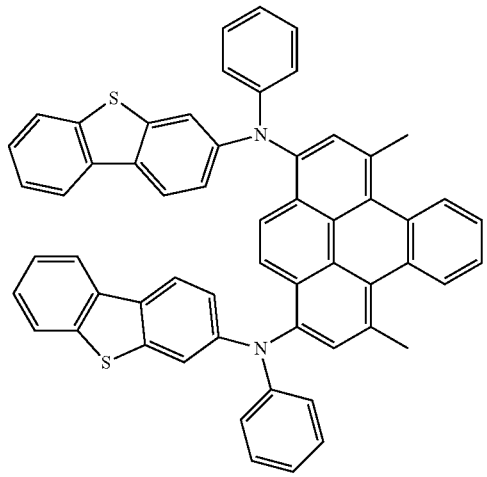
99
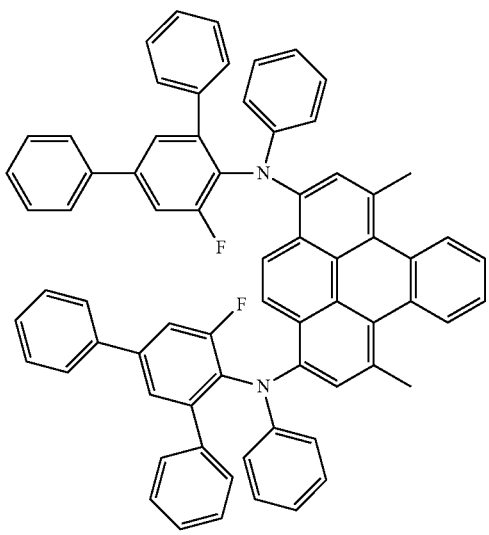
100
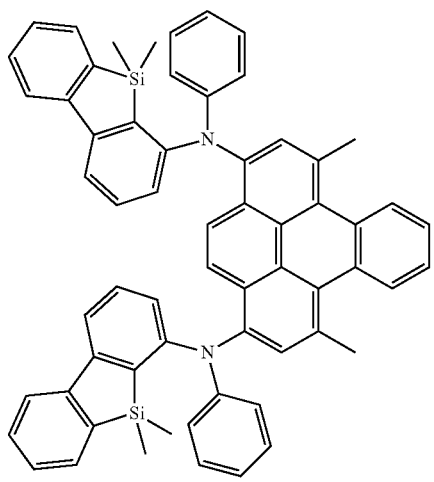
101
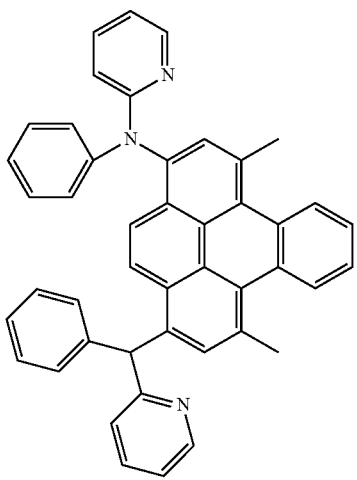
102
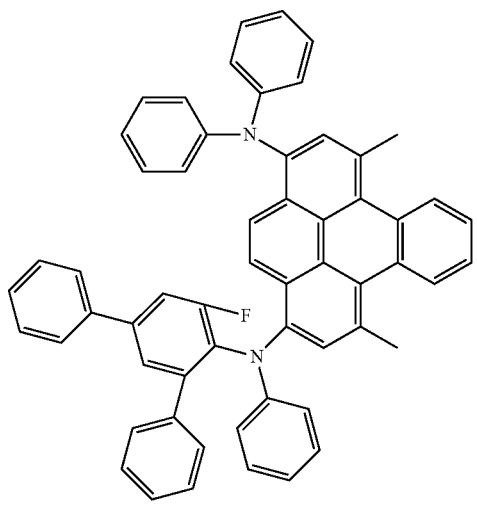

-continued
103 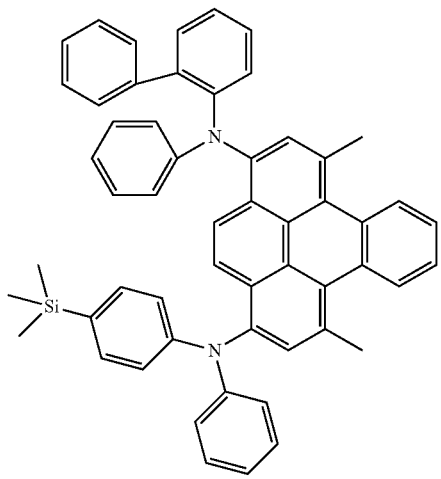
104 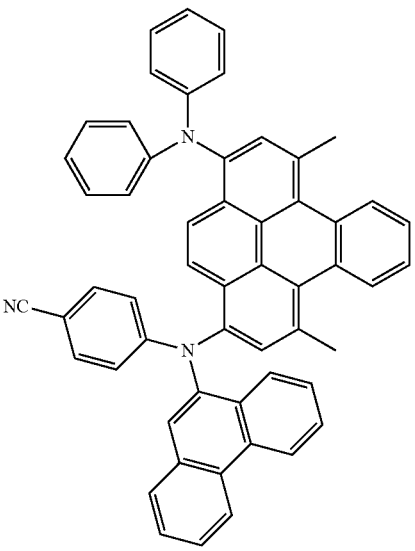
105 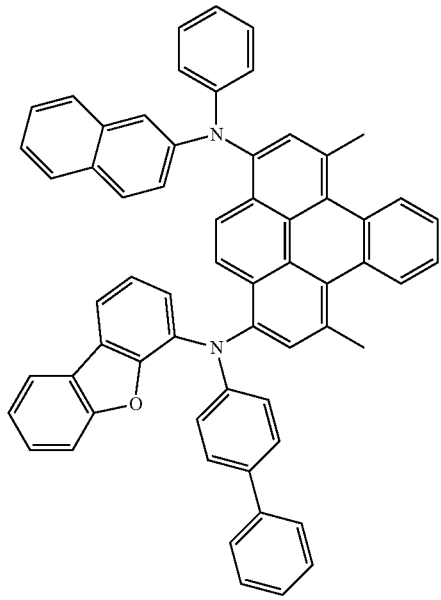
106 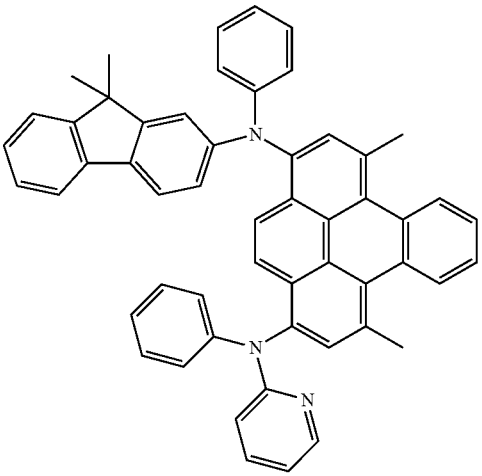
107 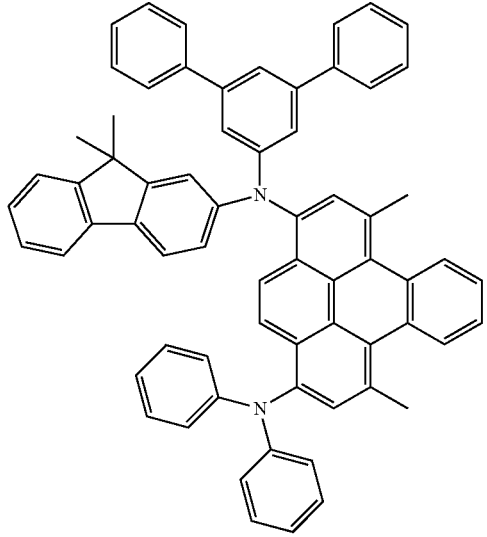
108 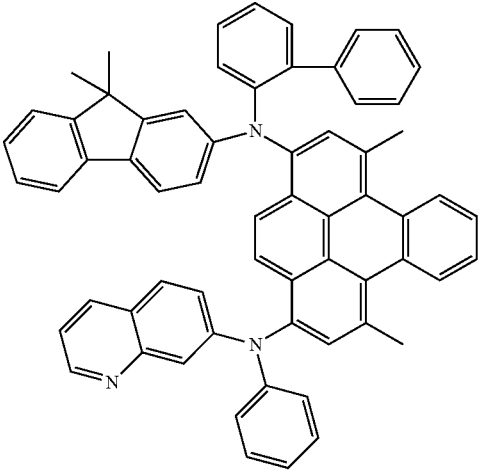

-continued
109 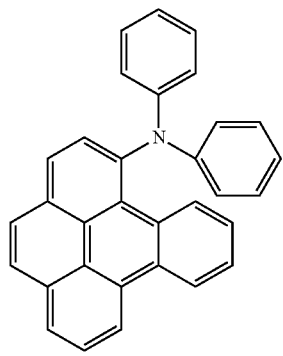 110 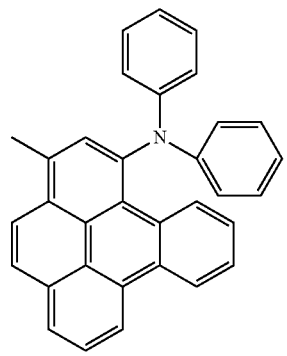
111 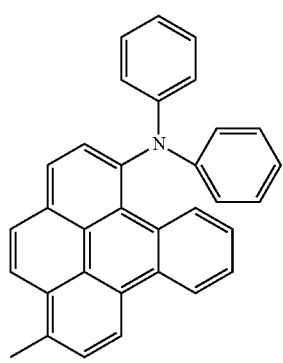 112 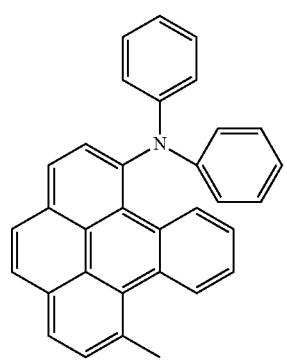
113 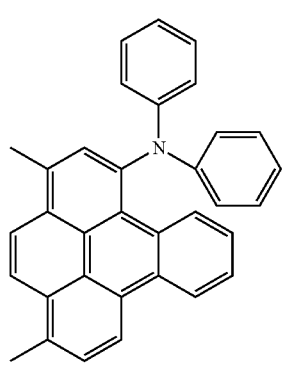 114 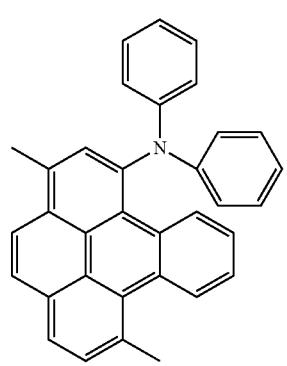
115 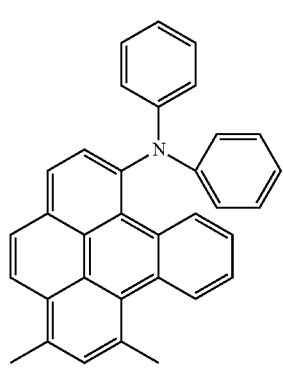 116 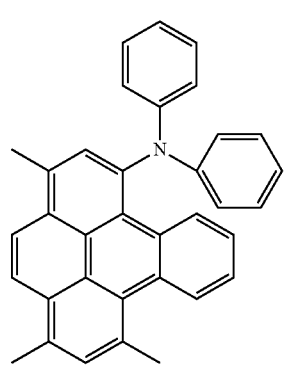

-continued
117
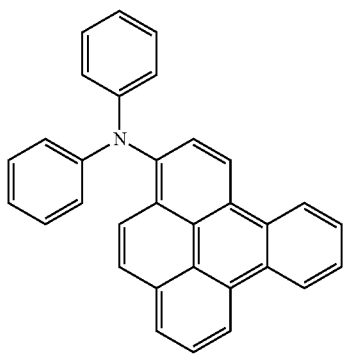
118
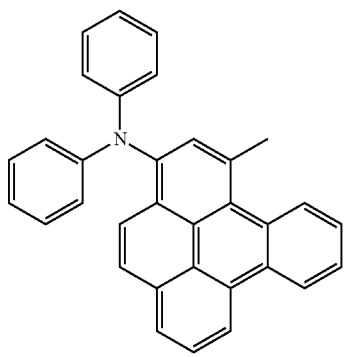
119
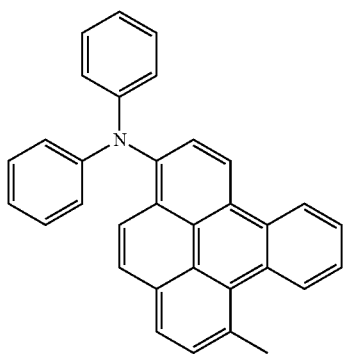
120
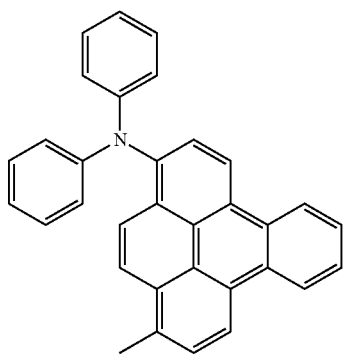
121
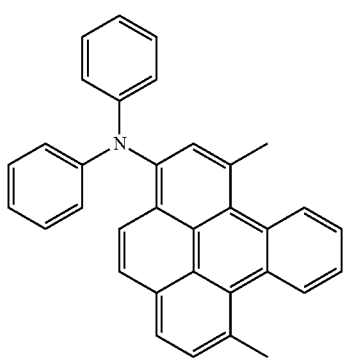
122
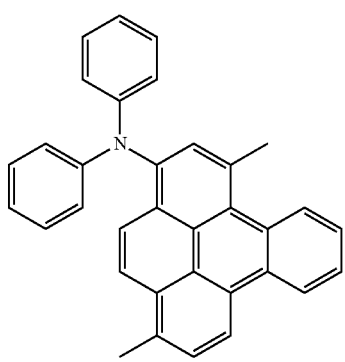
123
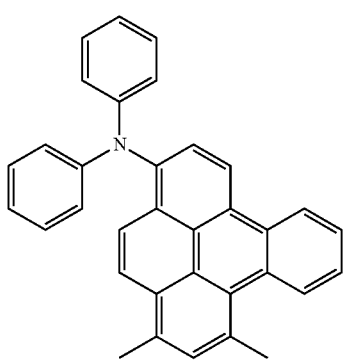
124
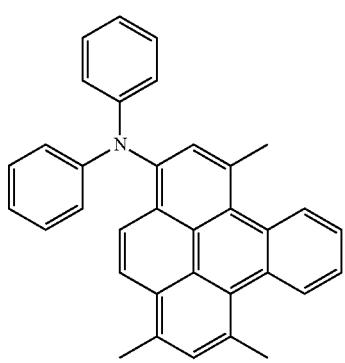

-continued
125
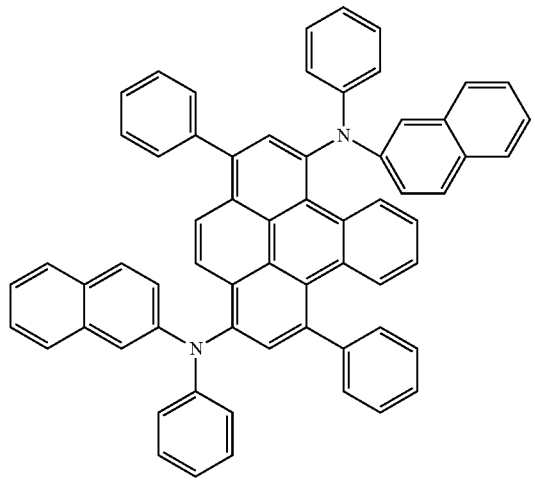
126
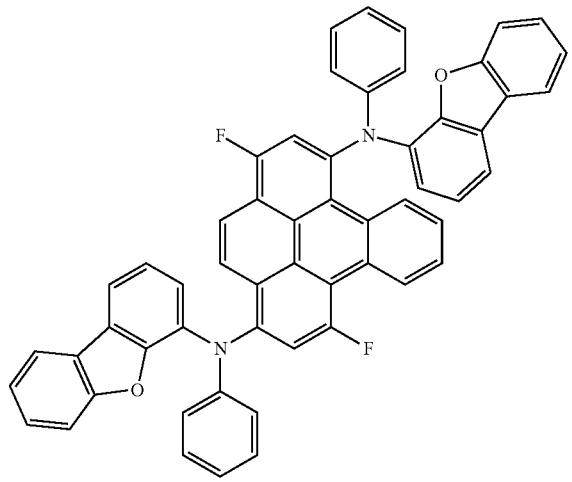
127
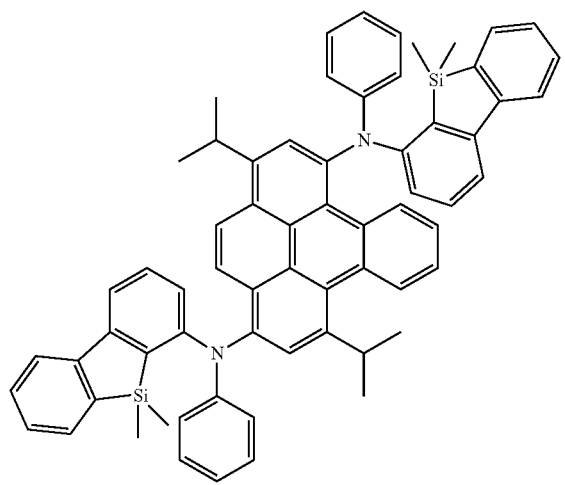
128
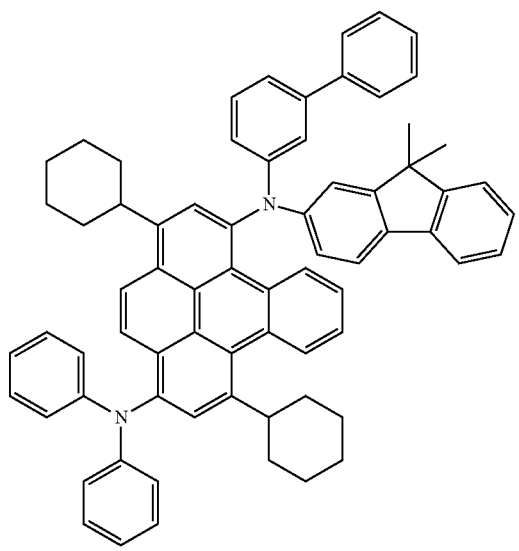
129
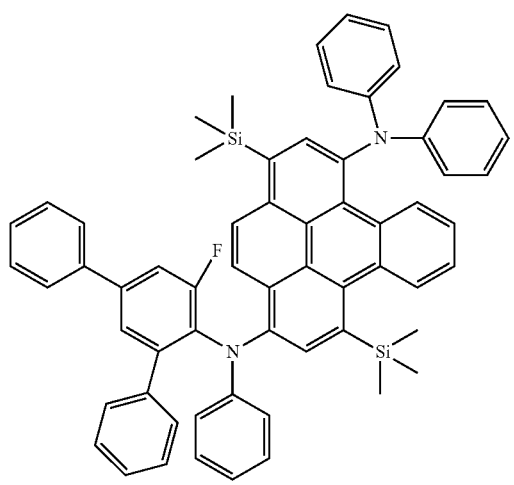
130
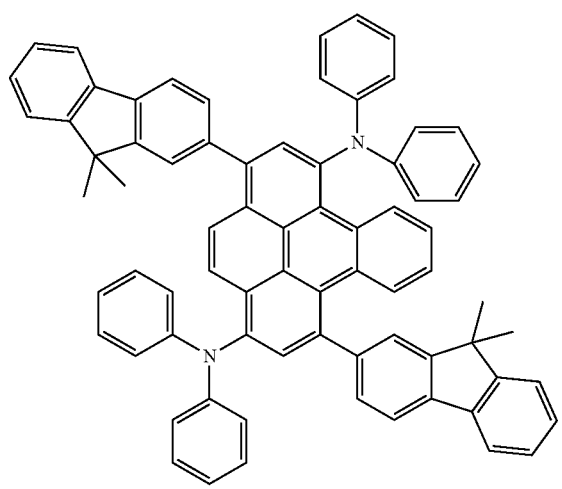

131
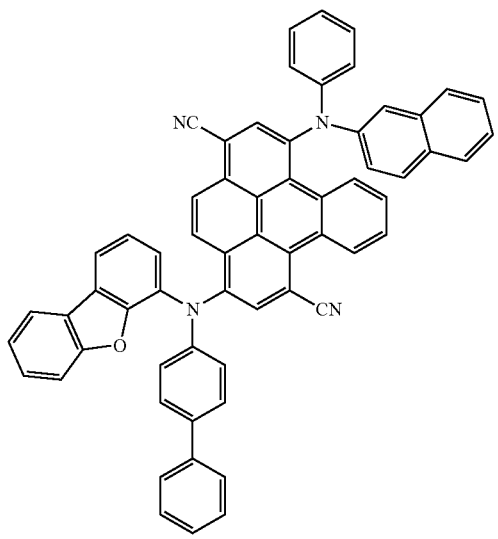
132
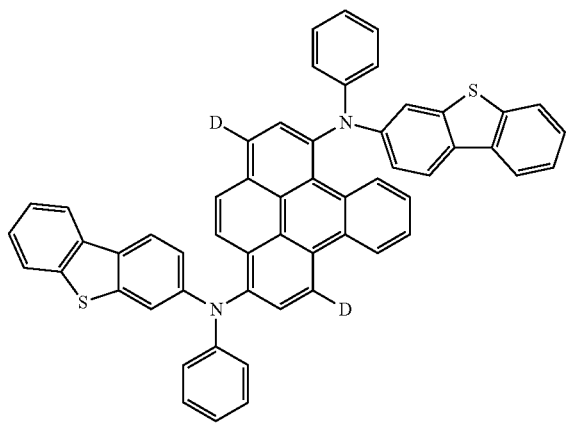
133
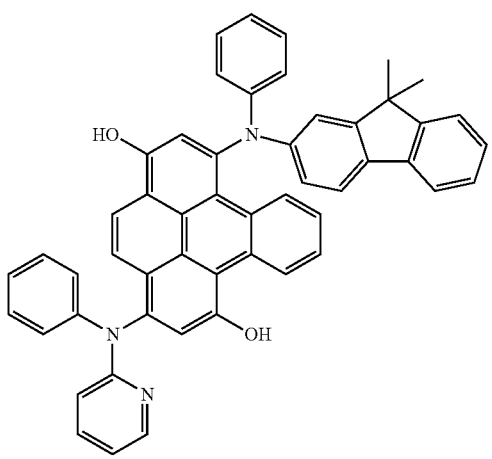
134
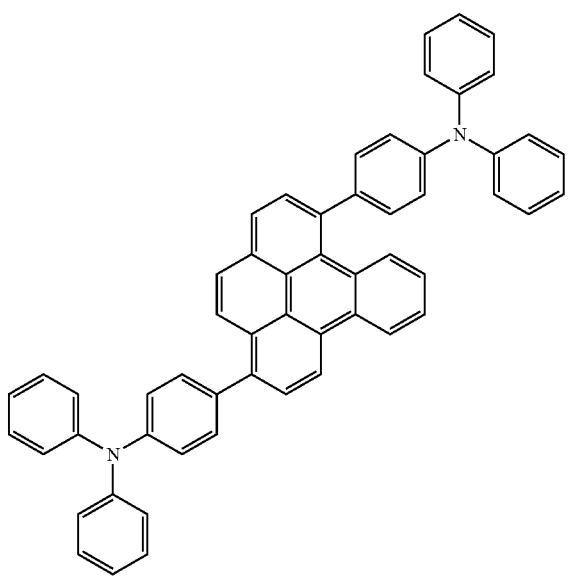

135
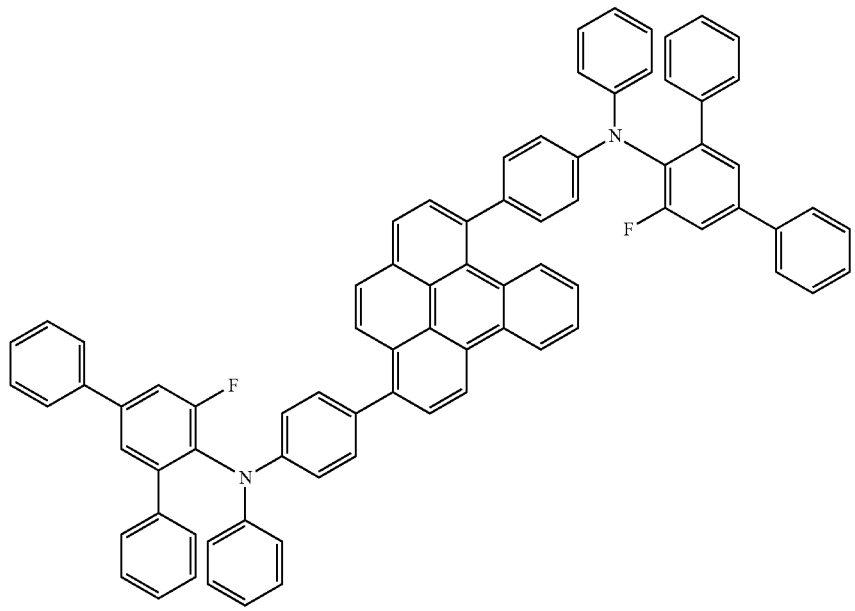
136
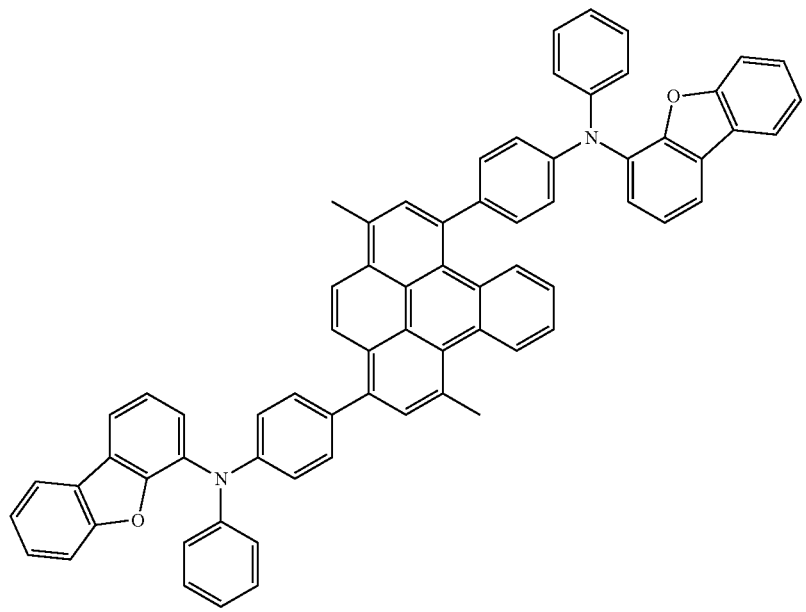

137
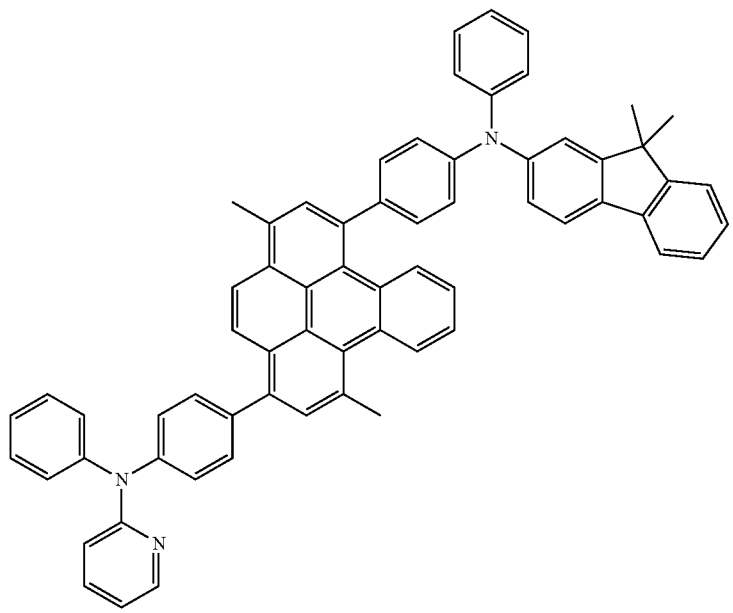
138
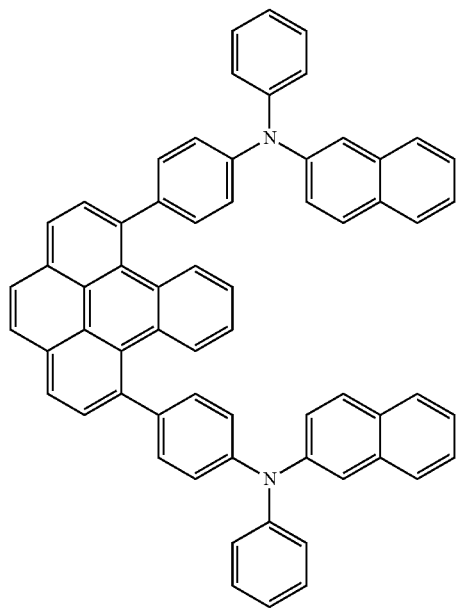
139
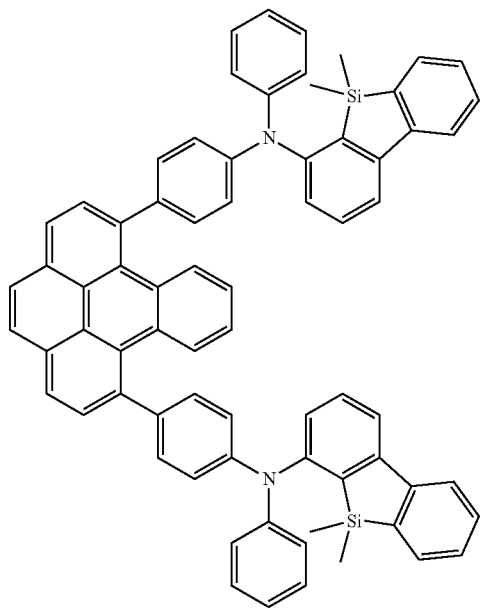

-continued
140
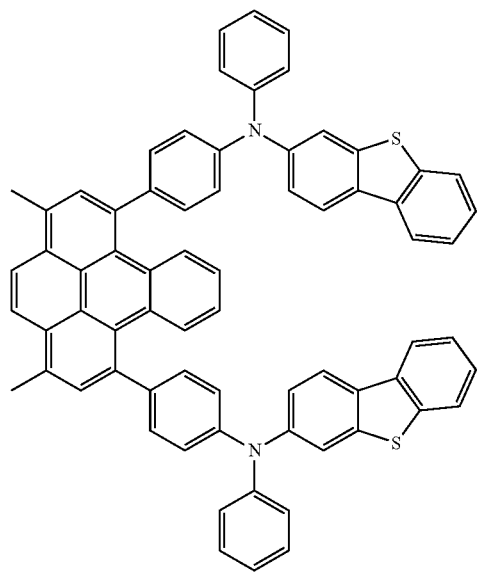
141
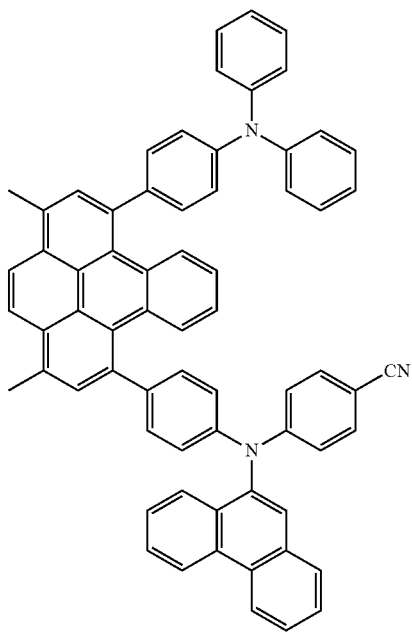
142
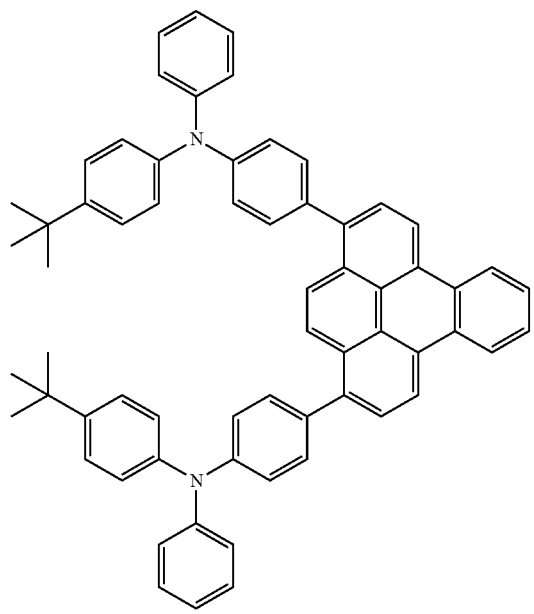
143
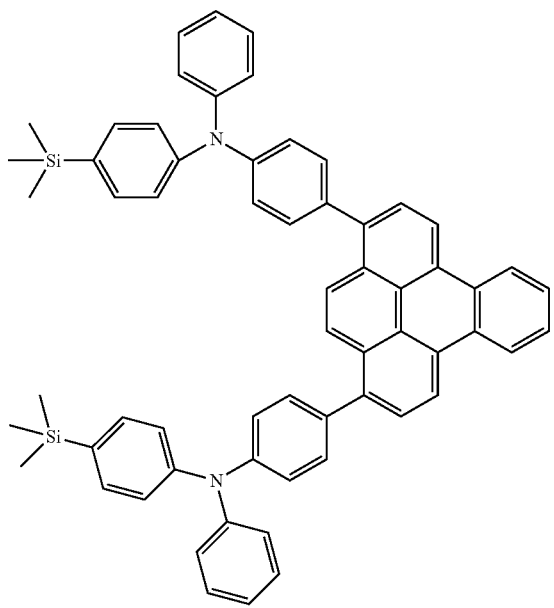

-continued
144
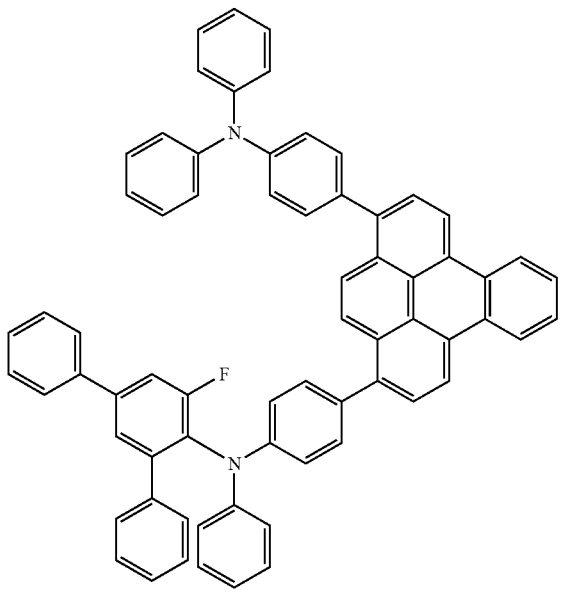
145
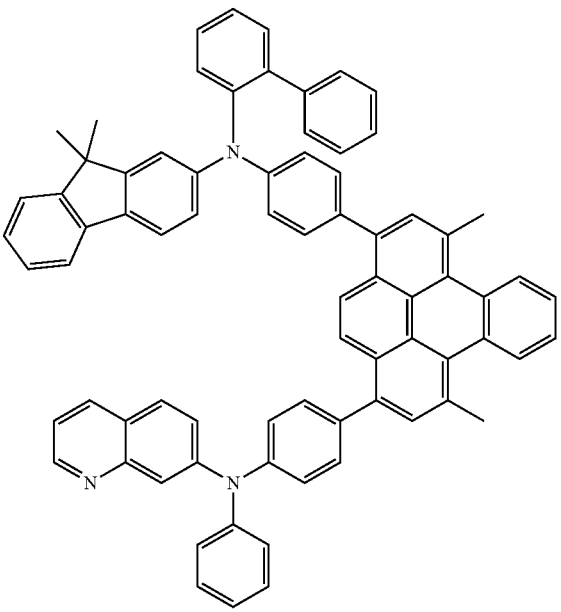
146
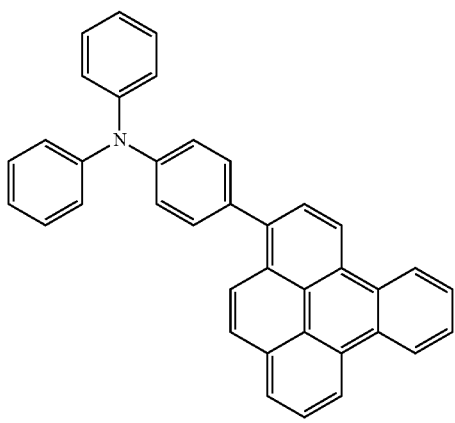
147
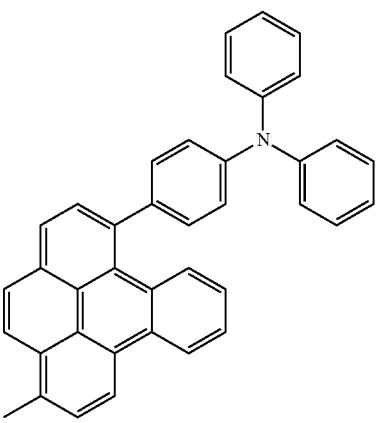
148
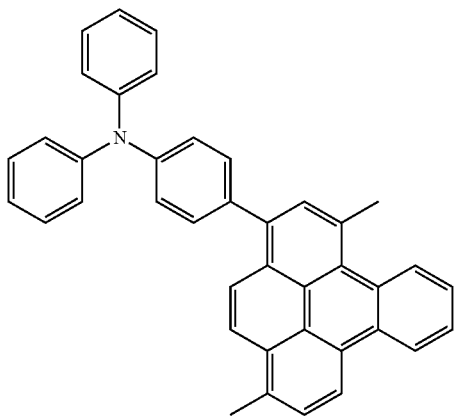
149
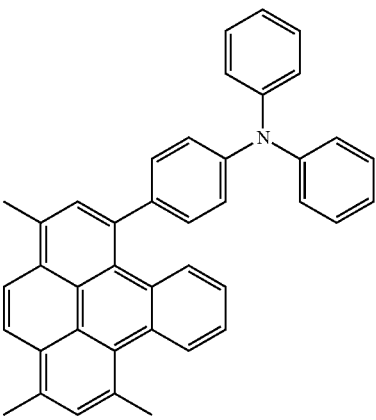

150
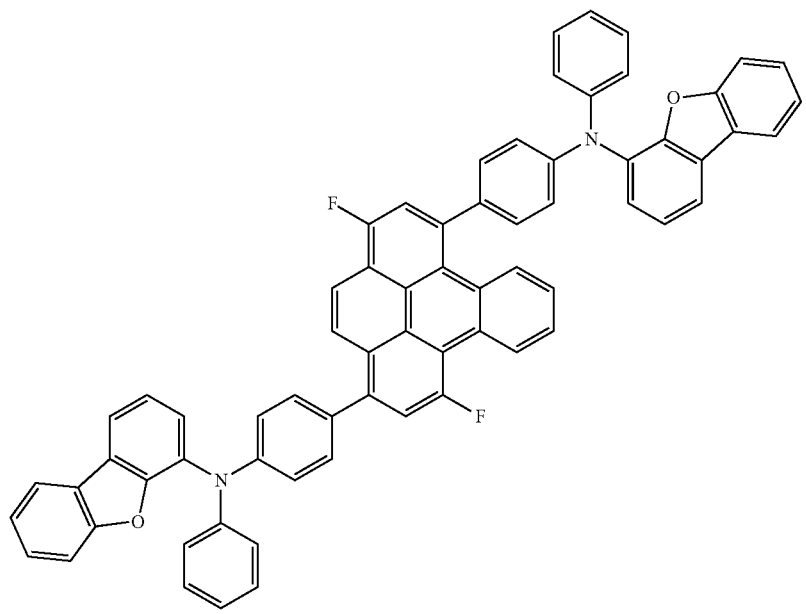
151
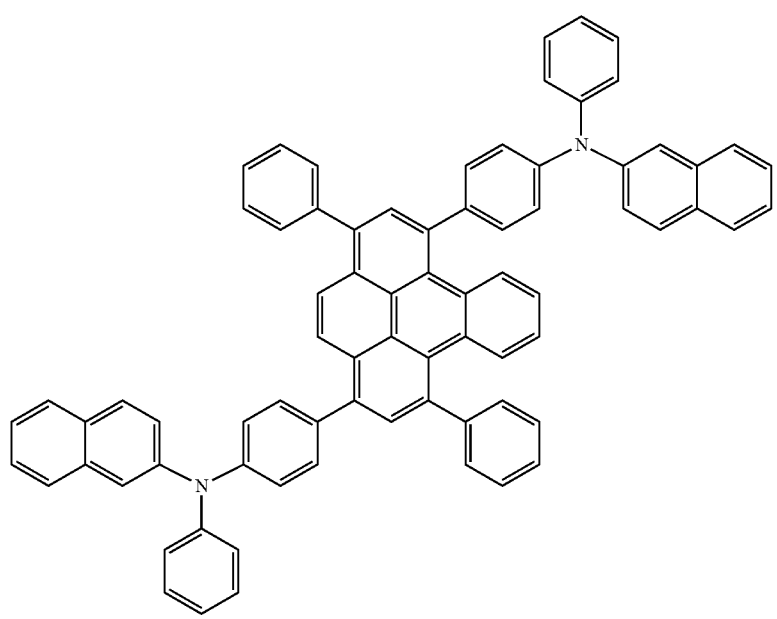

-continued

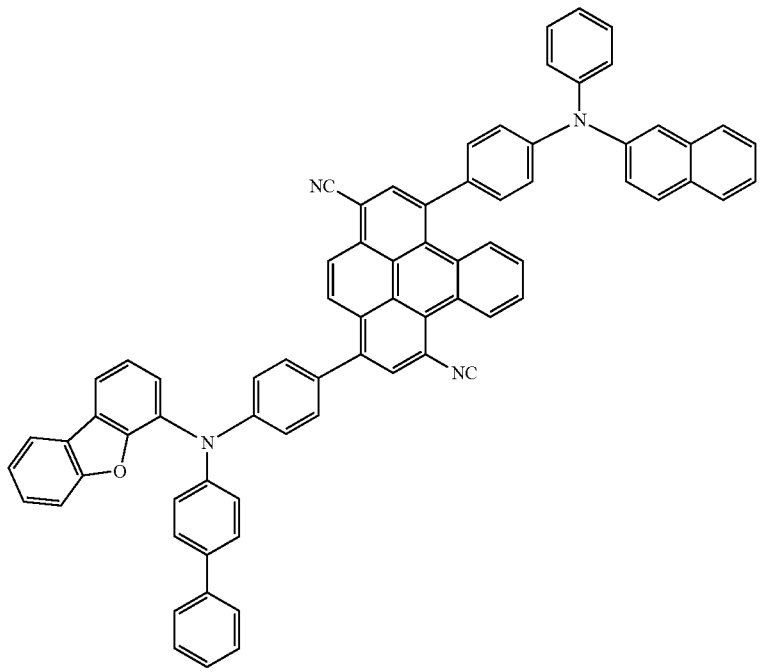

152

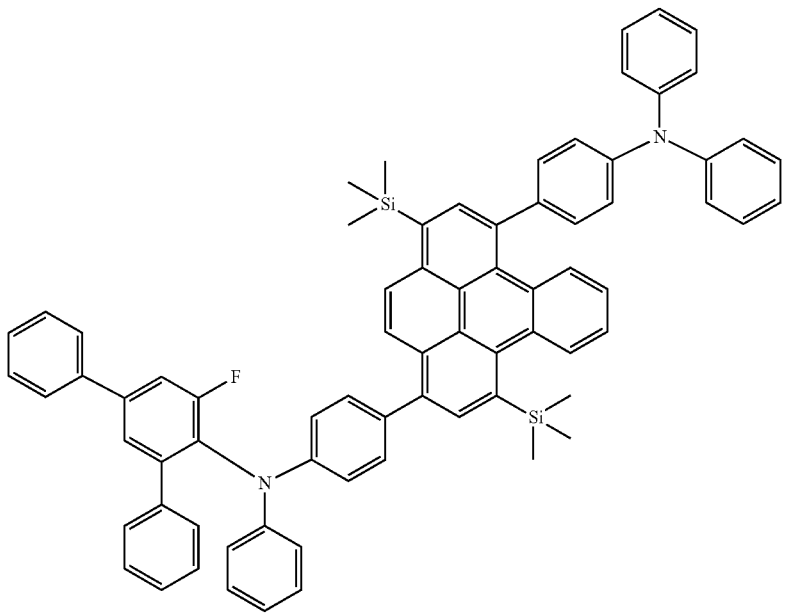

153

The amine-based compound represented by Formula 1 includes a benzopyrene core. The amine-based compound represented by Formula 1 may strongly emit blue fluorescent light as a result of having the benzopyrene core.

In general, an amine-based compound having a pyrene core is capable of being synthesized into an amine derivative having a symmetrical structure. However, the amine-based compound represented by Formula 1 may be capable of being synthesized into an amine derivative having an asymmetrical structure by including the benzopyrene core.

The amine-based compound represented by Formula 1 may have various suitable substituents and thus may have various suitable electrical characteristics and light-emitting characteristics.

Therefore, an OLED including the amine-based compound represented by Formula 1 may have a low driving voltage, a high efficiency, a high brightness, a long lifespan, and a high color purity.

The amine-based compound represented by Formula 1 may be synthesized by using any suitable organic synthesis method available in the art. The synthesis method for synthesizing the amine-based compound may be understood by (or be apparent to) one of ordinary skill in the art by referring to the examples described herein.

The amine-based compound represented by Formula 1 may be included between a pair of electrodes of an OLED. In some embodiments, the amine-based compound may be included in an emission layer (EML). Thus, in some embodiments, an OLED includes a first electrode, a second electrode facing the first electrode, and an organic layer that is disposed between the first electrode and the second electrode and includes an EML, where the organic layer includes the amine-based compound represented by Formula 1.

As used herein, the expression "(the organic layer) may include at least one amine-based compound of Formula 1" may be understood as meaning "(the organic layer) may include one amine-based compound represented by Formula 1 or at least two different compounds selected from amine-based compounds represented by Formula 1".

In some embodiments, the organic layer may only include Compound 1 as the amine-based compound. Here, Compound 1 may be included in the EML of the OLED. In some embodiments, the organic layer may include Compound 1 and Compound 2 as the amine-based compound. Here, Compound 1 and Compound 2 may be included in the same layer (e.g., both Compound 1 and Compound 2 may be included in an EML) or respectively included in two different layers (e.g., Compound 1 may be included in an EML and Compound 2 may be included in an electron transport layer (ETL)).

The organic layer may further include at least one of i) a hole transport region that is disposed between the first electrode and the EML and includes at least one of a hole injection layer (HIL), a hole transport layer (HTL), a buffer layer, and an electron blocking layer (EBL) and ii) an electron transport region that is disposed between the EML and the second electrode and includes at least one of a hole blocking layer (HBL), an electron transport layer (ETL), and an electron injection layer (EIL).

As used herein, the expression "organic layer" refers to a single layer and/or multiple layers disposed between a first electrode and a second electrode of an OLED. However, a material included in the "organic layer" is not limited to an organic material (e.g., the organic layer may include inorganic materials or compounds).

The accompanying drawing is a schematic cross-sectional view of an OLED 10 according to an embodiment of the present disclosure. The OLED 10 includes a first electrode 110, an organic layer 150, and a second electrode 190.

Hereinafter, a structure the OLED 10 and a method of manufacturing the OLED 10 according to an embodiment of the present disclosure will be described with reference to the accompanying drawing.

A substrate may be additionally disposed on a lower part of the first electrode 110 and/or on an upper part of the second electrode 190 as shown in the accompanying drawing. The substrate may be a glass substrate or a transparent plastic substrate having excellent mechanical strength, thermal stability, transparency, surface smoothness, ease of handling, and waterproofness.

The first electrode 110 may be formed by applying a first electrode material on the substrate by deposition or sputtering. When the first electrode 110 is an anode, the first electrode material may be selected from materials having a high work function to facilitate hole injection. The first electrode 110 may be a reflective electrode, a semitransparent electrode, or a transparent electrode. Examples of the first electrode material may include indium-tin oxide (ITO), indium-zinc oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode 110 may be formed as a semitransparent electrode or a reflective electrode.

The first electrode 110 may be formed as a single layer or have a multi-layered structure having at least two layers. For example, the first electrode 110 may have a three-layered structure, e.g., ITO/Ag/ITO, but the first electrode is not limited thereto.

The organic layer 150 is formed on the first electrode 110. The organic layer 150 includes an EML.

The organic layer 150 may further include a hole transport region disposed between the first electrode and the EML. The organic layer 150 may further include an electron transport region disposed between the EML and the second electrode.

The hole transport region may include at least one of a HIL, a HTL, a buffer layer, and an EBL, and the electron transport region may include at least one of a HBL, an ETL, and an EIL.

The hole transport region may have a structure of a single layer formed of one material, a single layer formed of multiple different materials, or multiple layers formed of multiple different materials.

For example, the hole transport region may have a structure of a single layer formed of multiple different materials or a structure of HIL/HTL, HIL/HTL/buffer layer, HIL/buffer layer, HTL/buffer layer, or HIL/HTL/EBL sequentially stacked on the first electrode 110, but the structure of the hole transport region is not limited thereto.

When the hole transport region includes the HIL, the HIL may be formed on the first electrode 110 by using various suitable methods such as vacuum deposition, spin coating, casting, Langmuir-Blodgett (LB) deposition, inkjet printing, laser printing, or laser induced thermal imaging (LITI).

When the HIL is formed by vacuum deposition, the deposition conditions may be selected from ranges of, for example, a deposition temperature of about 100° C. to about 500° C., a degree of vacuum of about $10^{-8}$ to about $10^{-3}$ torr, and a deposition speed of about 0.01 to about 100 Å/sec in consideration of a suitable (or desired) compound for an HIL (e.g., in consideration of the material used for the deposition) and a suitable (or desired) structure of the HIL.

When the HIL is formed by spin coating, the deposition conditions may be selected from ranges of, for example, a coating speed of about 2,000 rpm to about 5,000 rpm and a heat treatment temperature of about 80° C. to about 200° C. in consideration of a suitable (or desired) compound for an HIL (e.g., in consideration of the material used for the spin coating) and a suitable (or desired) structure of the HIL.

When the hole transport region includes the HTL, the HTL may be formed on the first electrode 110 or the HIL by using various suitable methods such as vacuum deposition, spin coating, casting, LB deposition, inkjet printing, laser printing, or LITI. When the HTL is formed by vacuum deposition and spin coating, the deposition conditions and the coating conditions of the HTL may be the same as the deposition conditions and the coating conditions described with respect to the HIL.

The hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine) (TCTA), polyaniline/Dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), polyaniline/poly(4-styrenesulfonate) (PANI/PSS), a compound represented by Formula 201, and a compound represented by Formula 202:

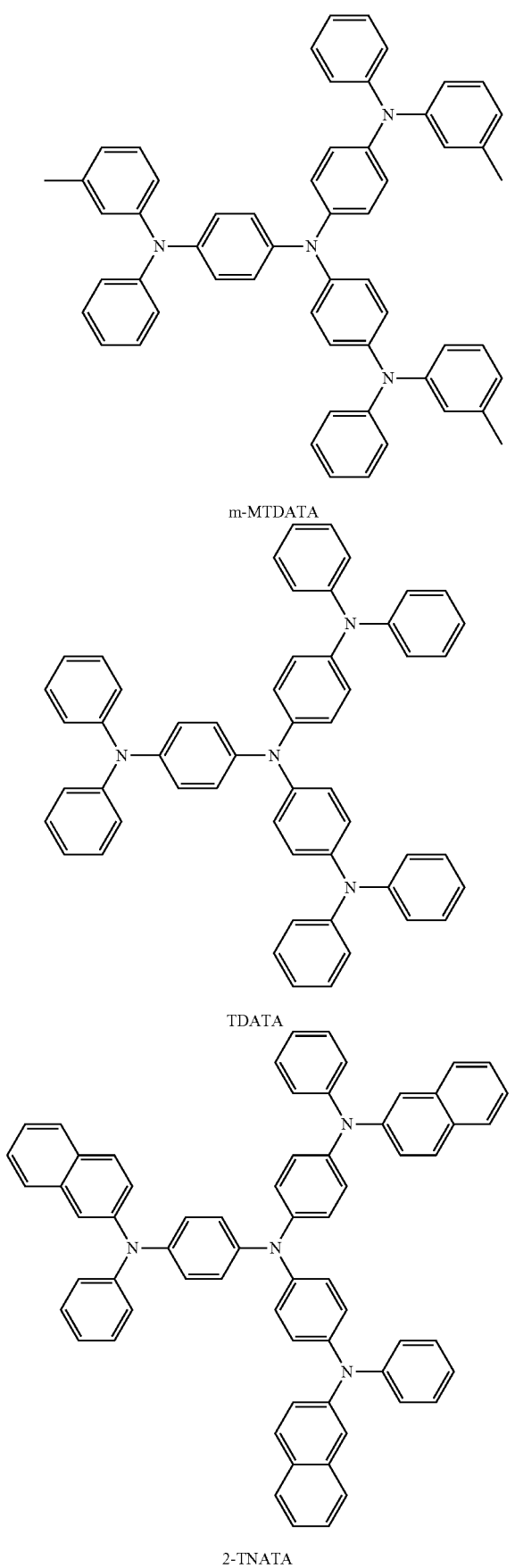
m-MTDATA
TDATA
2-TNATA
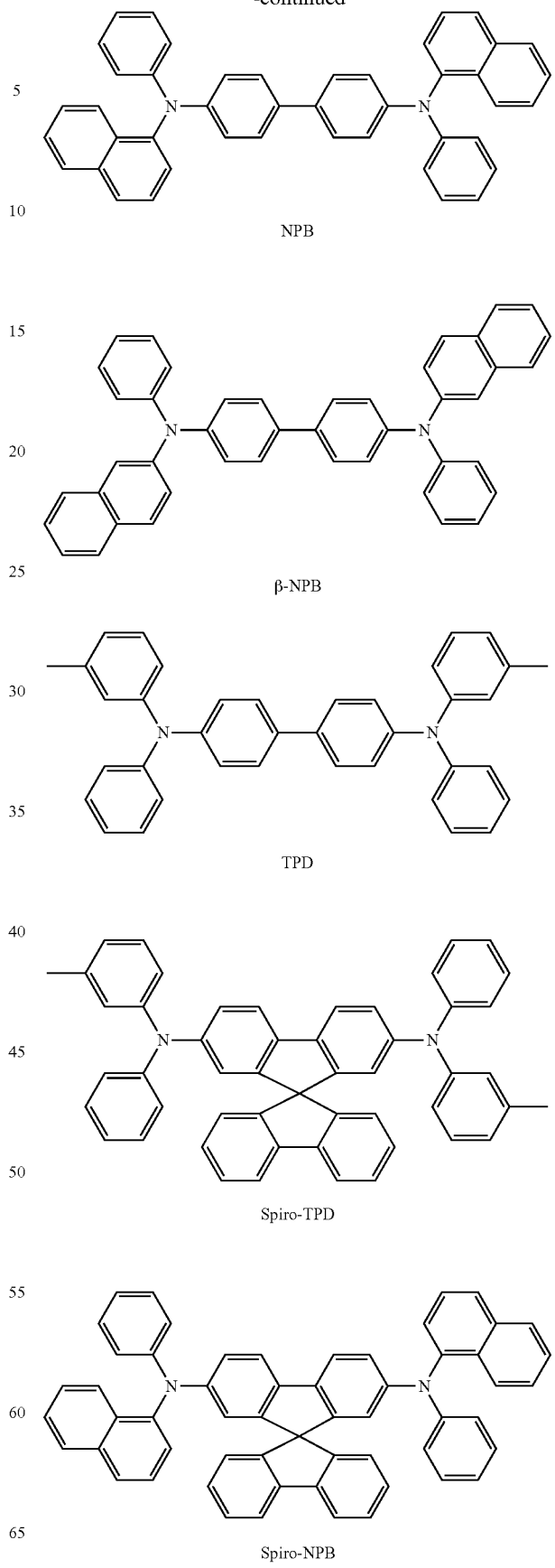
NPB
β-NPB
TPD
Spiro-TPD
Spiro-NPB

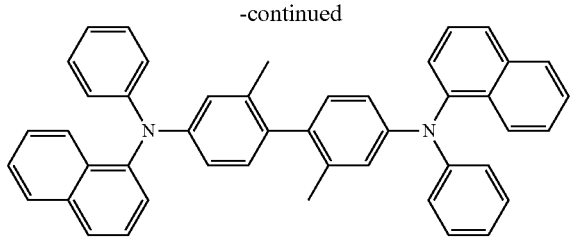

α-NPB

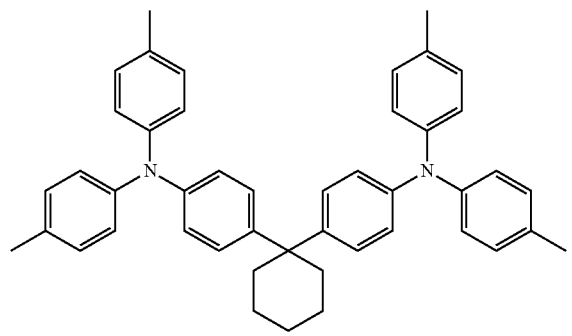

TAPC

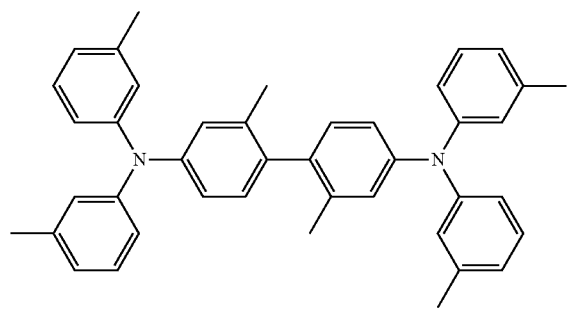

HMTPD

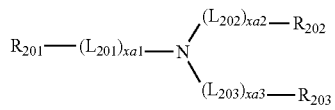

Formula 201

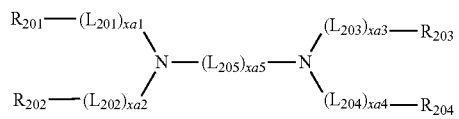

Formula 202

In Formulae 201 and 202, $L_{201}$ to $L_{205}$ are each independently as defined in the description of $L_1$ in the present specification;

xa1 to xa4 are each independently an integer selected from 0, 1, 2, and 3;

xa5 is an integer selected from 1, 2, 3, 4 and 5; and $R_{201}$ to $R_{204}$ are each independently as defined in the description of $R_{21}$ in the present specification.

In some embodiments, in Formulae 201 and 202, $L_{201}$ to $L_{205}$ are each independently selected from:

a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 are each independently an integer selected from 0, 1, and 2;

xa5 is an integer selected from 1, 2, and 3;

$R_{201}$ to $R_{204}$ are each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, but $R_{201}$ to $R_{204}$ are not limited thereto.

The compound represented by Formula 201 may be represented by Formula 201A:

Formula 201A

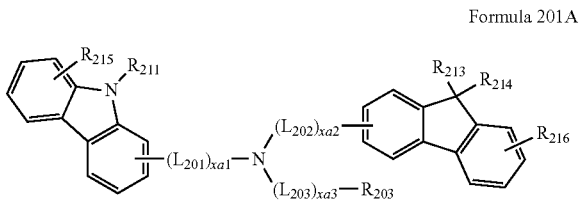

In some embodiments, the compound represented by Formula 201 may be represented by Formula 201A-1:

Formula 201A-1

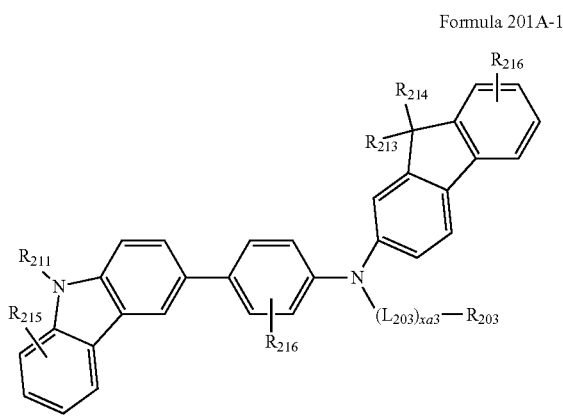

In some embodiments, the compound represented by Formula 202 may be represented by Formula 202A:

Formula 202A

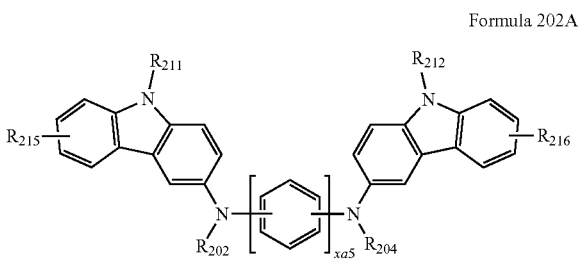

In Formulae 201A, 201A-1, and 202A, $L_{202}$ to $L_{203}$, xa1 to xa3, xa5, and $R_{202}$ to $R_{204}$ are as defined in the descriptions thereof in the present specification, where $R_{211}$ is as defined in the descriptions of $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arythio group, a $C_1$-$C_{60}$ heteroaryl group (e.g., a $C_2$-$C_{60}$ heteroaryl group), a monovalent non-aromatic condensed polycyclic group, and a monovalent non-aromatic heterocondensed polycyclic group.

In Formulae 201, 201A-1, and 202A, $L_{202}$ to $L_{203}$, xa1 to xa3, xa5, and $R_{202}$ to $R_{204}$ may be as defined in the present specification, $R_{211}$ may be as defined in $R_{203}$, and $R_{213}$ to $R_{216}$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), and a non-aromatic condensed polycyclic group.

For example, in Formulae 201A, 201A-1, and 202A, $L_{202}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently an integer of 0 or 1;

$R_{203}$ and $R_{211}$ and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:
a $C_1$-$C_{20}$ alkyl group and a $C_1$-$C_{20}$ alkoxy;
a $C_1$-$C_{20}$ alkyl group and a $C_1$-$C_{20}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from:
a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;
a $C_1$-$C_{20}$ alkyl group and a $C_1$-$C_{20}$ alkoxy;
a $C_1$-$C_{20}$ alkyl group and a $C_1$-$C_{20}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; where:

xa5 may be an integer of 1 or 2.

In Formulae 201A and 201A-1, $R_{213}$ and $R_{214}$ may link to each other (e.g., combine together) and form a saturated or unsaturated ring.

The compound represented by Formula 201 and the compound represented by Formula 202 may include Compounds HT1 to HT20 below, but are not limited thereto:

HT1

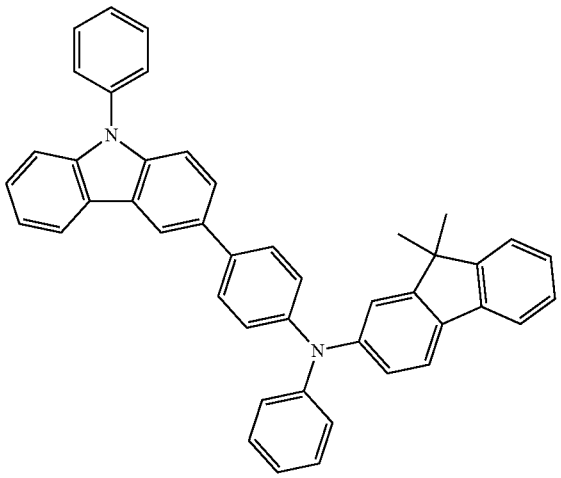

95
-continued
HT2
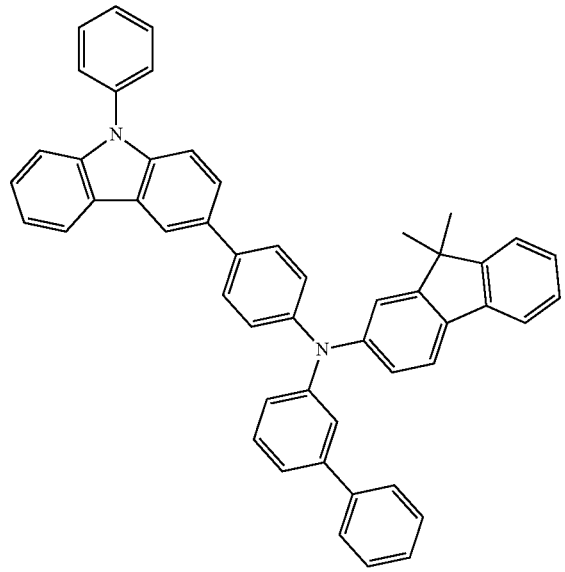
96
-continued
HT4
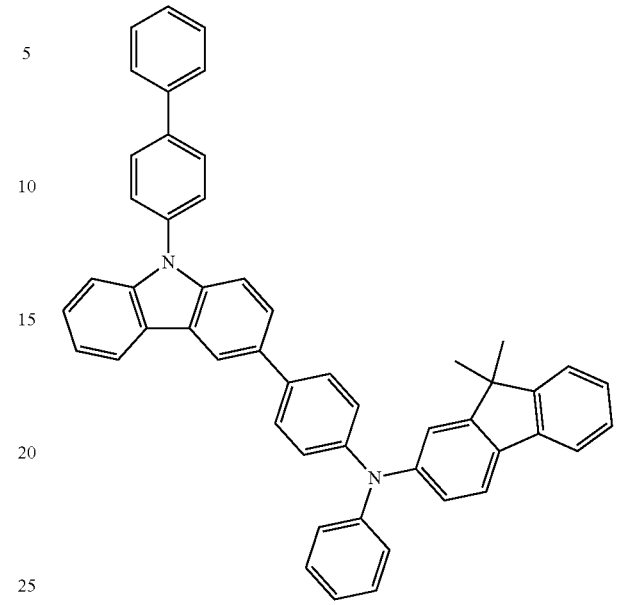
HT3
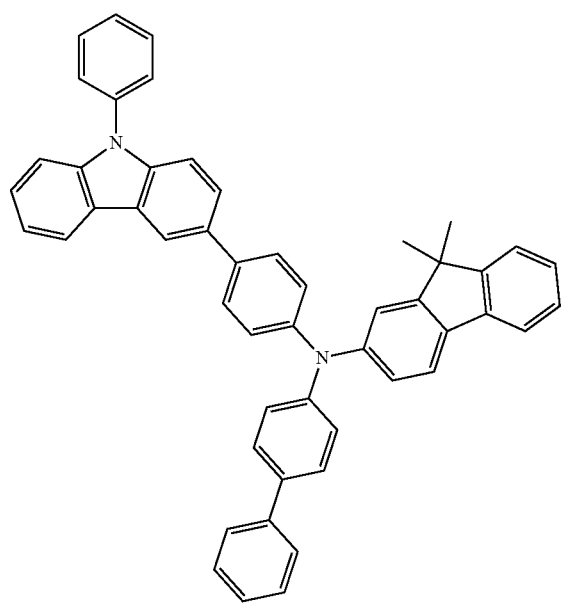
HT5
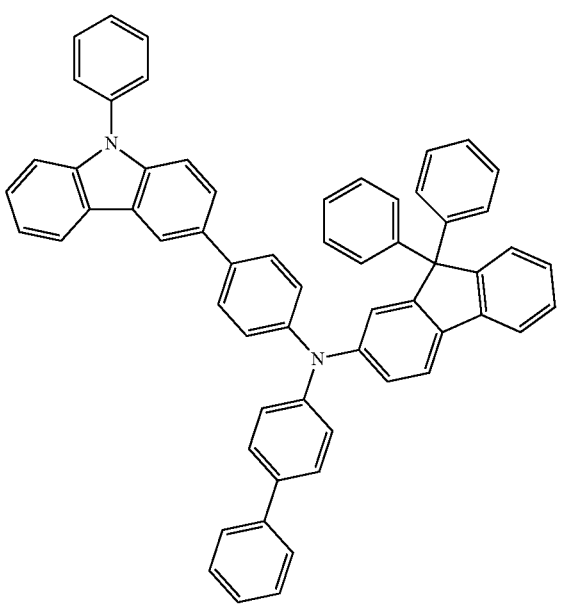

HT6
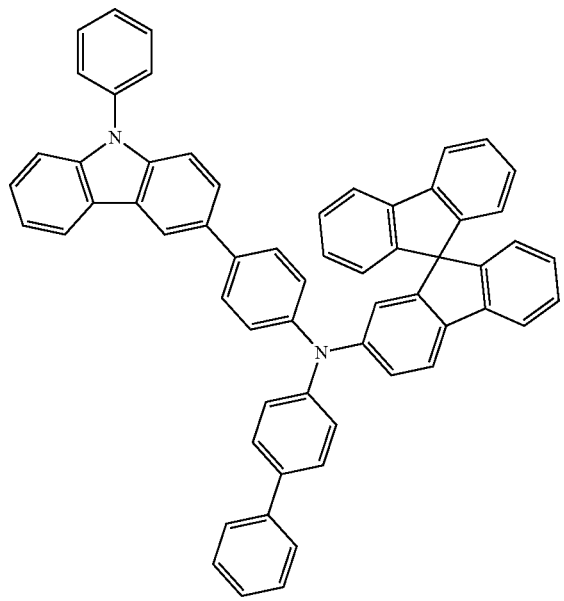
HT8
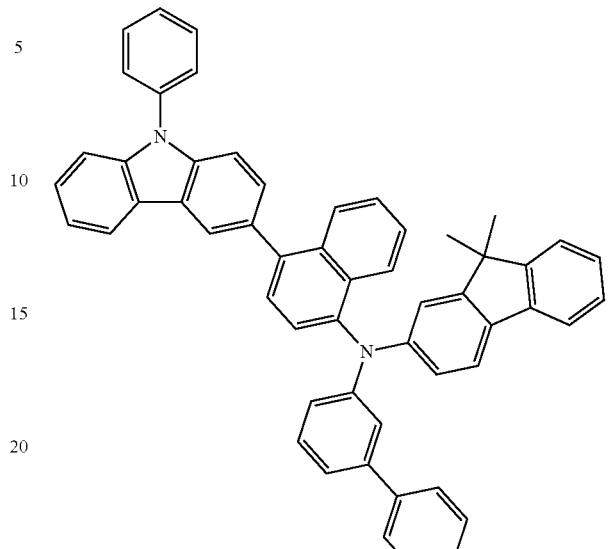
HT7
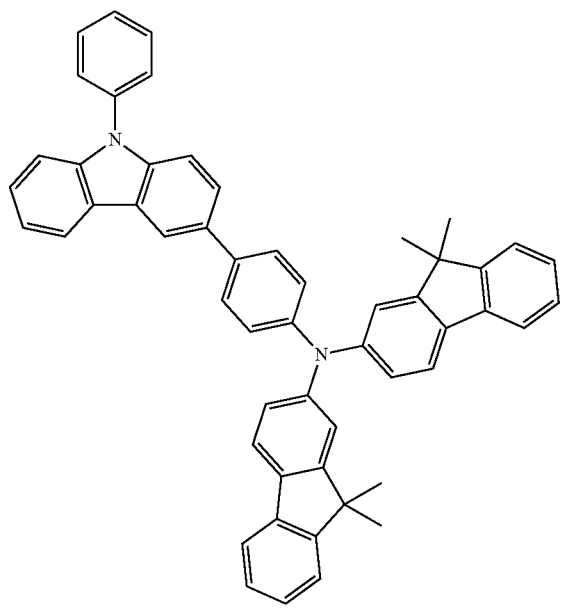
HT9
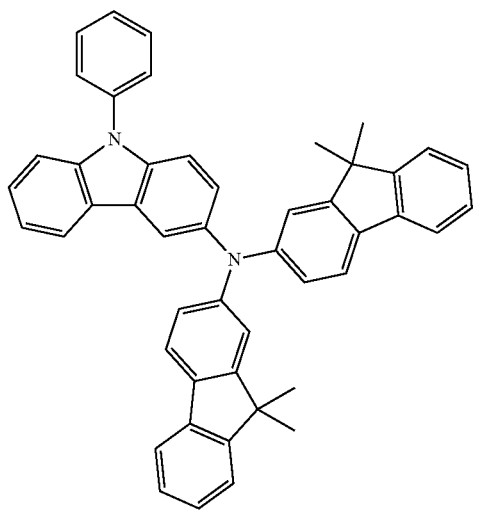

HT10
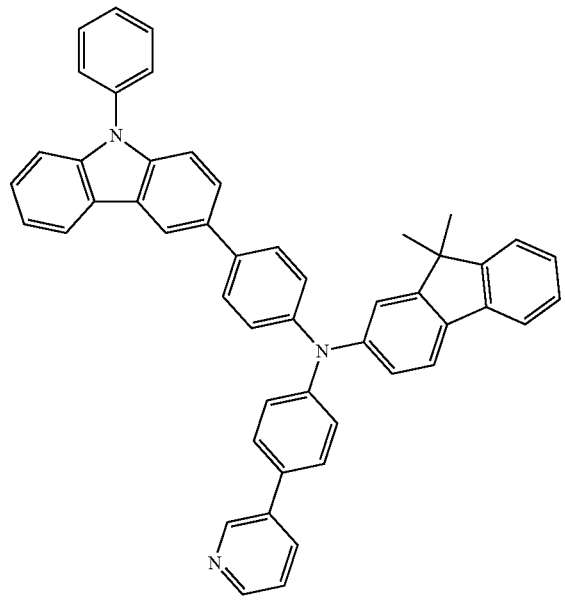
HT11
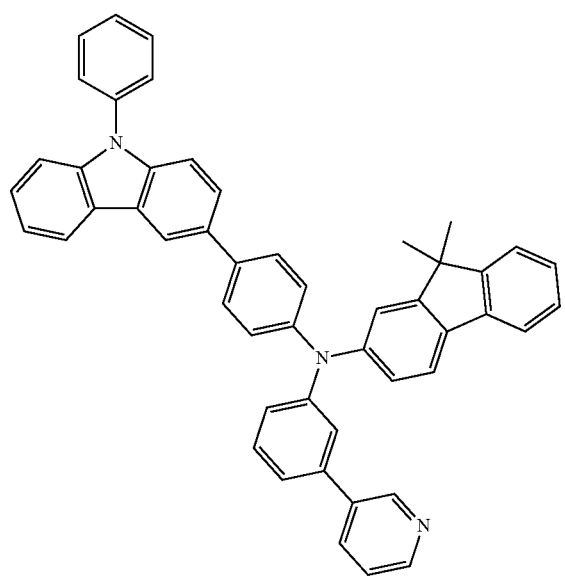
HT12
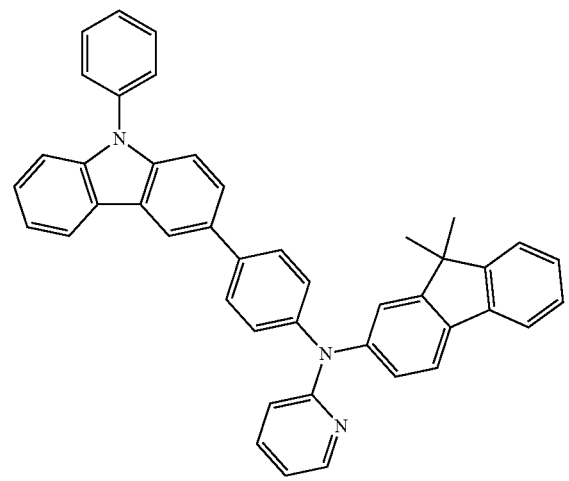
HT13
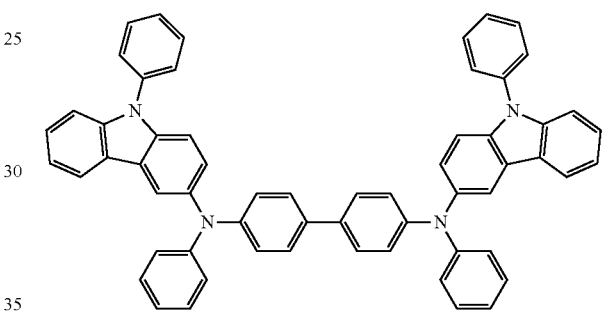
HT14
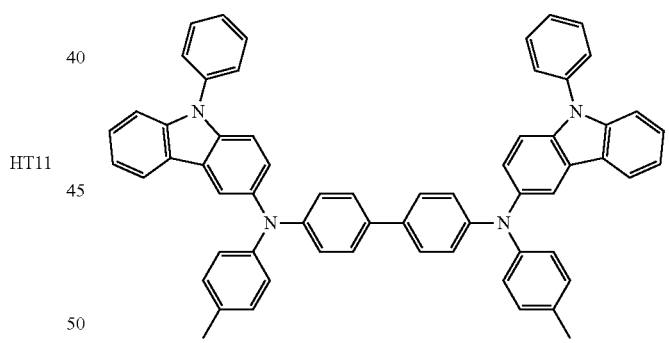
HT15
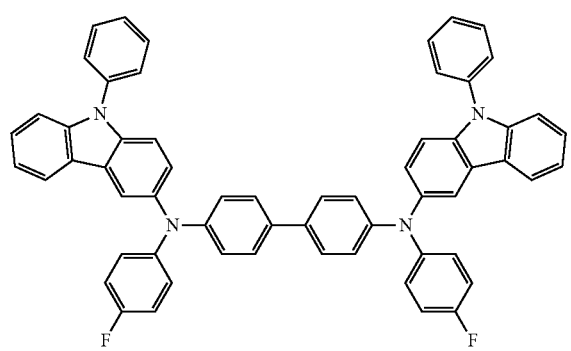

-continued

HT16

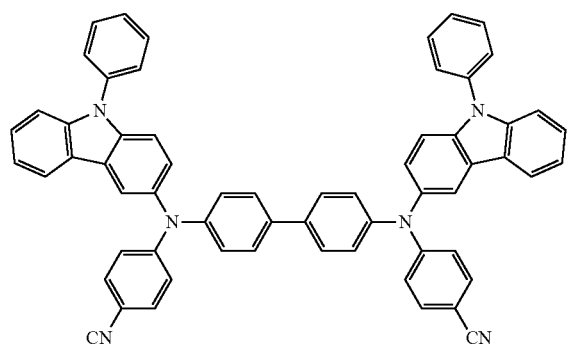

HT17

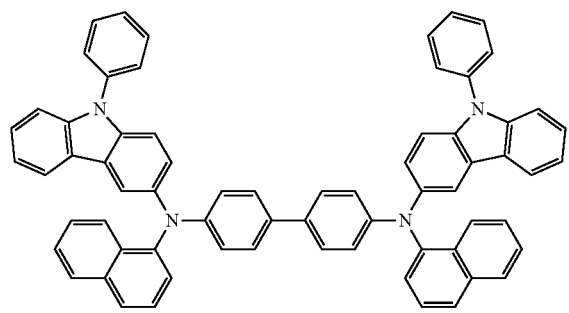

HT18

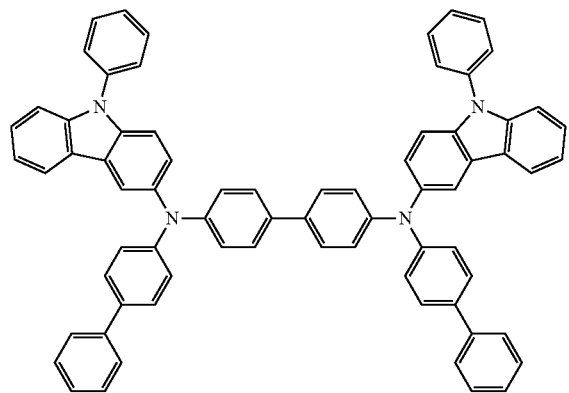

HT19

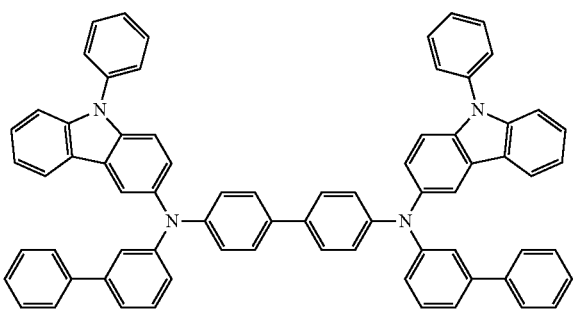

-continued

HT20

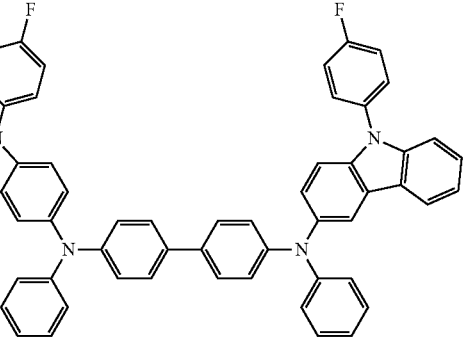

A thickness of the hole transport region may be in a range of about 100 Å to about 10,000 Å, for example, about 100 Å to about 1,000 Å. When the hole transport region includes both the HIL and the HTL, a thickness of the HIL may be in a range of about 100 Å to about 10,000 Å, for example, about 100 Å to about 1,000 Å, and a thickness of the HTL may be in a range of about 50 Å to about 2,000 Å, for example, about 100 Å to about 1,500 Å. When thicknesses of the hole transport region, the HIL, and the HTL are within any of the foregoing ranges, satisfactory hole transporting properties may be obtained without substantial increase in driving voltage.

The hole transport region may further include a charge-generating material in addition to the materials above to improve conductivity. The charge-generating material may be homogeneously or unhomogeneously (e.g., inhomogeneously or heterogeneously) dispersed in the hole transport region.

The charge-generating material may be, for example, a p-dopant. The p-dopant may be one of quinone derivative, metal oxide, and cyano group-containing compounds, but the p-dopant is not limited thereto. Examples of the p-dopant may include quinone derivative, such as a tetracyanoquinonedimethane (TCNQ) and 2,3,5,6-tetrafluoro-tetracyano-1,4-benzoquinondimethane (F4-TCNQ); metal oxides, such as a tungsten oxide and a molybdenum oxide; and Compound HT-D1 below, but the p-dopant is not limited thereto:

compound HT-D1

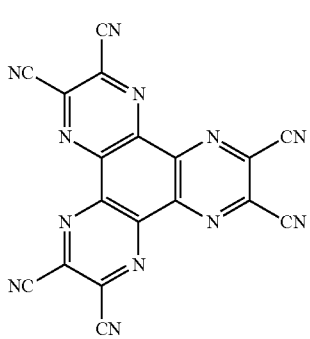

F4-TCNQ

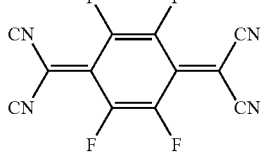

The hole transport region may further include at least one of a buffer layer or an EBL in addition to the HIL and the HTL. The buffer layer may increase light-emitting efficiency by compensating an optical resonance distance according the wavelength of light emitted from the EML. The buffer layer may include a material that may be included in the hole transport region. The EBL may block injection of electrons from the electron transport region.

The EML may be formed on the first electrode 110 or the hole transport region by using various suitable methods such as vacuum deposition, spin coating, casting, LB deposition, inkjet printing, laser printing, or LITI. When the EML is formed by vacuum deposition and spin coating, the deposition conditions and the coating conditions of the EML may be the same as the deposition conditions and the coating conditions described with respect to the HIL.

When the OLED 10 is a full-color OLED, the EML may be patterned as a red EML, a green EML, and a blue EML depending on a red pixel, a green pixel, and a blue pixel. Alternatively, the EML may have a multiple-layered structure, in which a red EML, a green EML, and a blue EML are stacked or a single-layered structure including all of a red light-emitting material, a green light-emitting material, and a blue light-emitting material mixed therein so as to emit white light. Alternatively, the EML may be a white light EML, and the OLED 10 may further include a color converting layer that converts the white light into light of a suitable (or desired) color or a color filter.

The EML may include a host or a dopant.

The host may include at least one of TPBi, TBADN, AND (also, referred to as "DNA"), CBP, CDBP, and TCP below:

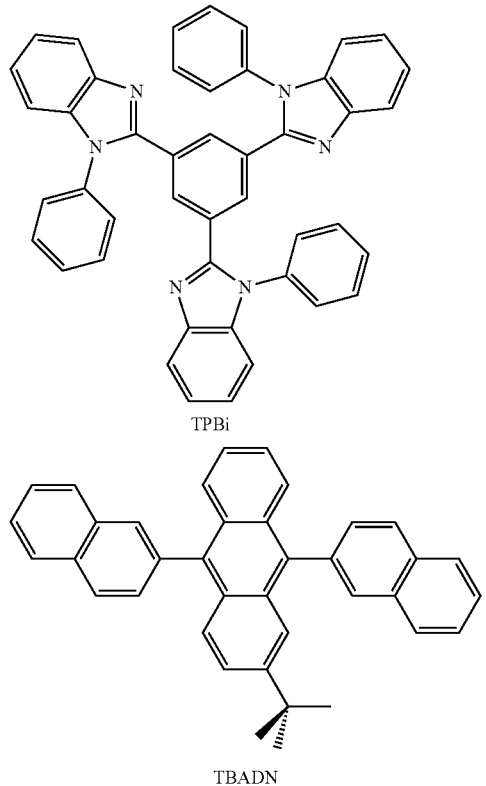

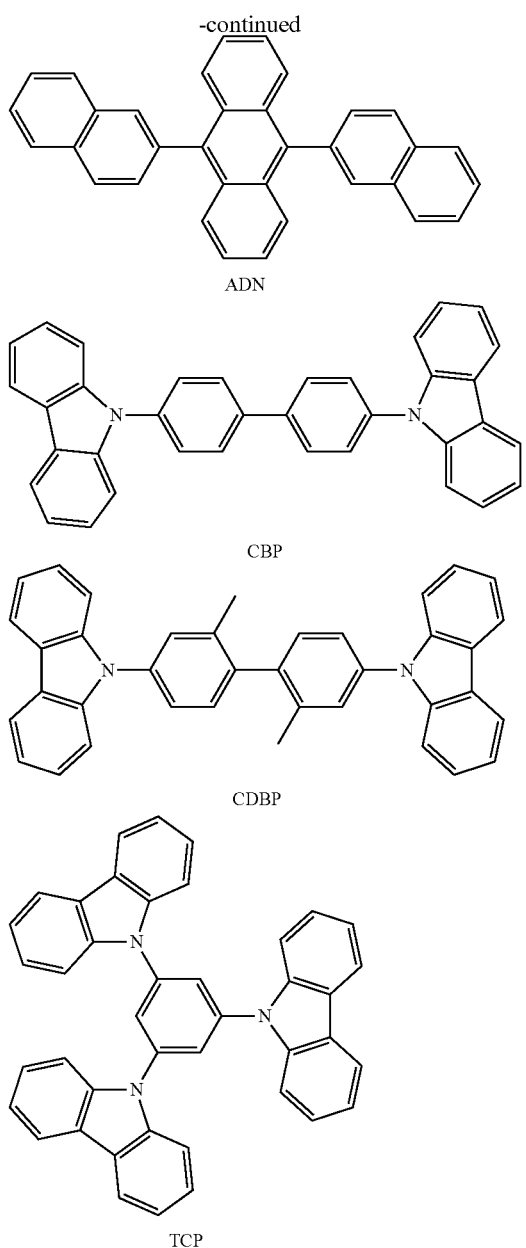

Also, the host may include a compound represented by Formula 301.

$$Ar_{301}\text{-}[(L_{301})_{xb1}\text{-}R_{301}]_{xb2} \qquad \text{Formula 301}$$

In Formula 301, $Ar_{301}$ is selected from:

a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group;

a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a non-aromatic condensed polycyclic group, and —Si($Q_{301}$)($Q_{302}$)($Q_{303}$), where $Q_{301}$ to $Q_{303}$ are each independently selected from a hydrogen atom, a $C_1$-$C_{60}$ alkyl group, a $C_2$-$C_{60}$ alkenyl group, a $C_6$-$C_{60}$ aryl group, and a $C_1$-$C_{60}$ heteroaryl group (e.g., a $C_2$-$C_{60}$ heteroaryl group);

$L_{301}$ is as defined in the description of $L_{201}$ in the present specification;

$R_{301}$ is selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 is an integer selected from 0, 1, 2, and 3; and xb2 is an integer selected from 1, 2, 3, and 4.

In some embodiments, in Formula 301, $L_{301}$ is selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ is selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but $L_{301}$ and $R_{301}$ are not limited thereto.

In some embodiments, the host may include a compound represented by Formula 301A:

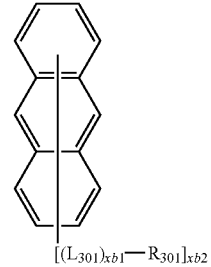

Formula 301A $[(L_{301})_{xb1}-R_{301}]_{xb2}$

The descriptions of the substituents in the compound represented by Formula 301A may be the same as the corresponding descriptions provided elsewhere in the present specification.
The compound represented by Formula 301 may include at least one of Compounds H1 to H42 below, but the compound represented by Formula 301 is not limited thereto:
H1
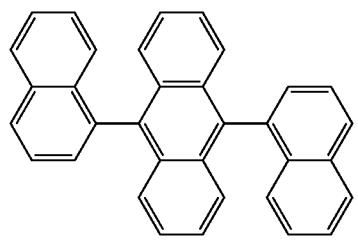
H2
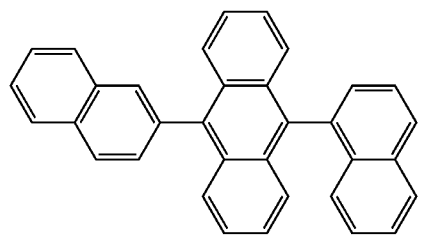
H3
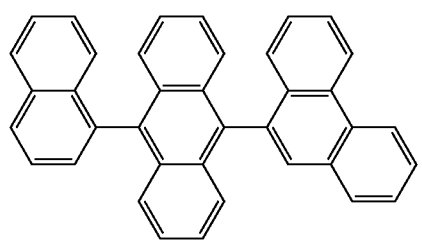
H4
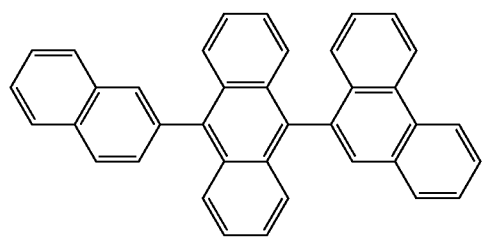
H5
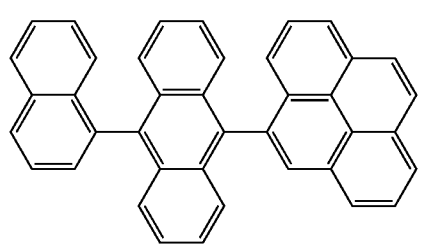
-continued
H6
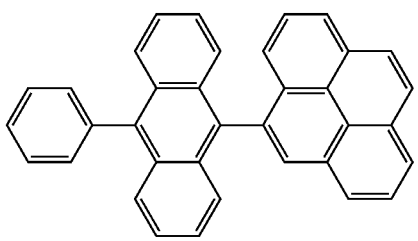
H7
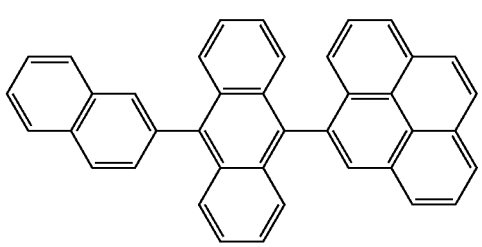
H8
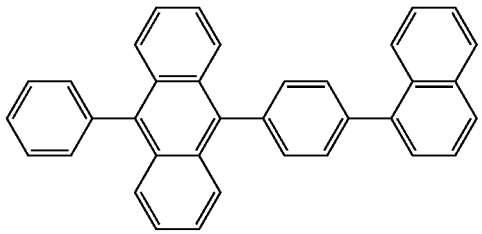
H9
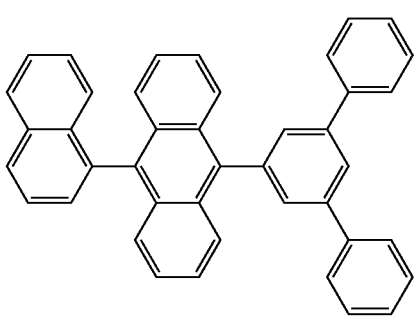
H10
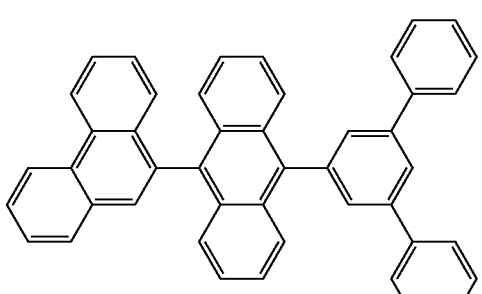
H11
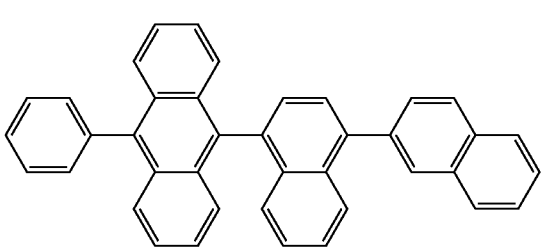

H12
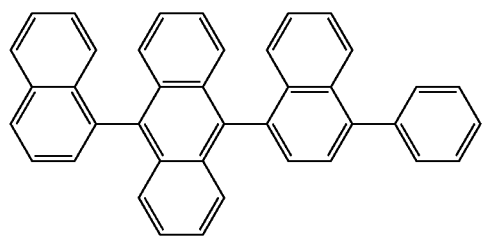
H13
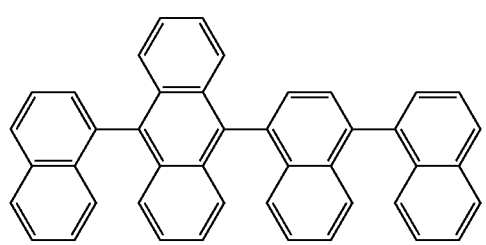
H14
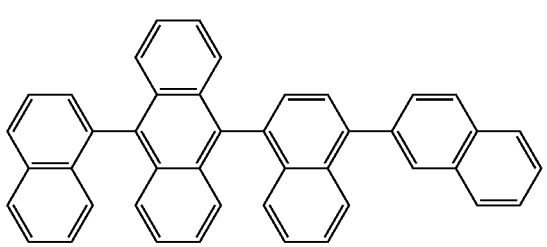
H15
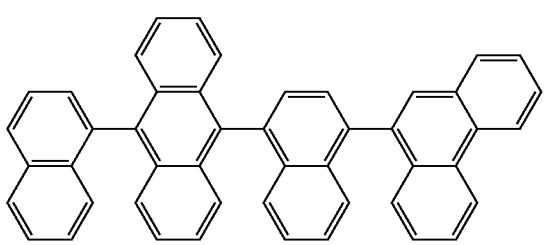
H16
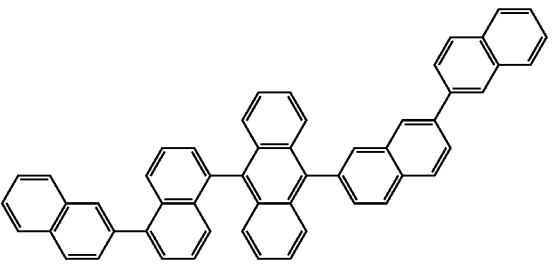
H17
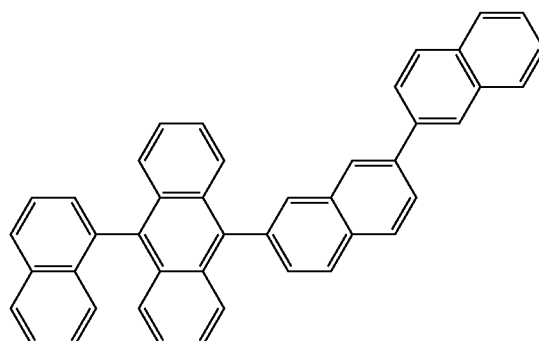
H18
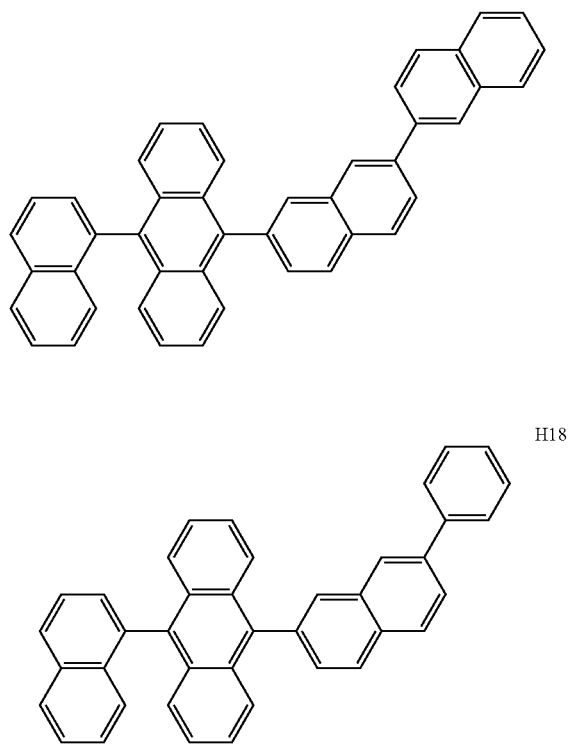
H19
H20
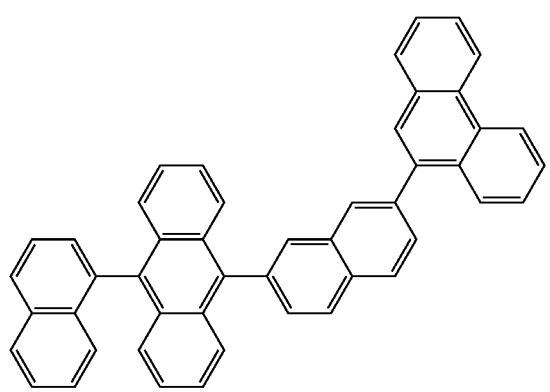

H21
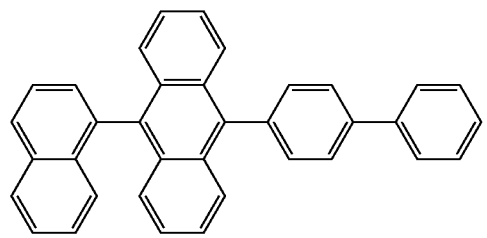
H22
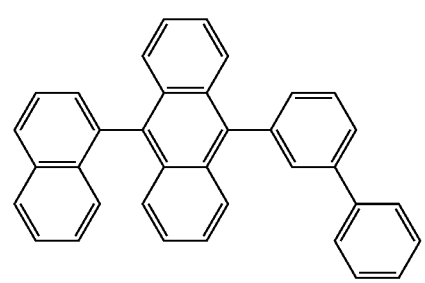
H23
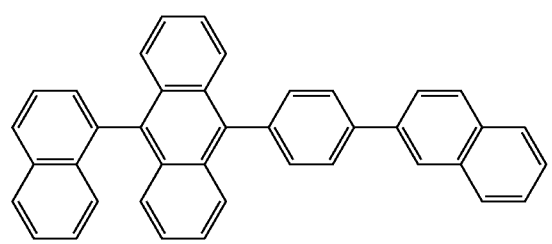
H24
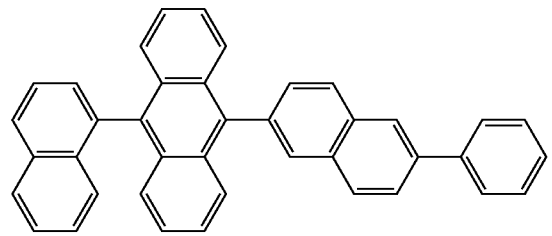
H25
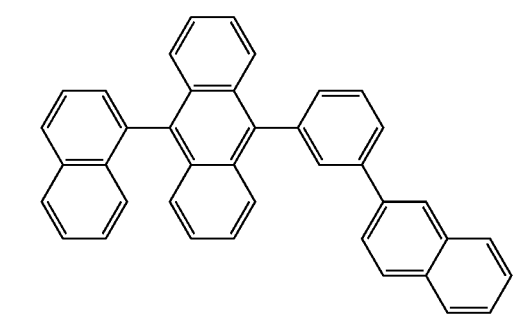
H26
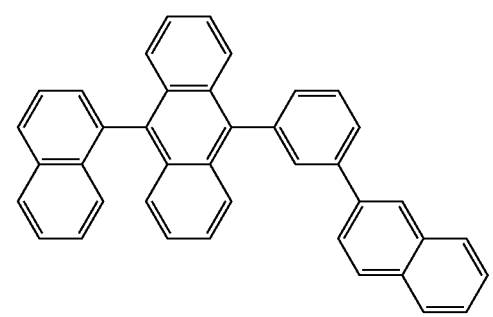
H27
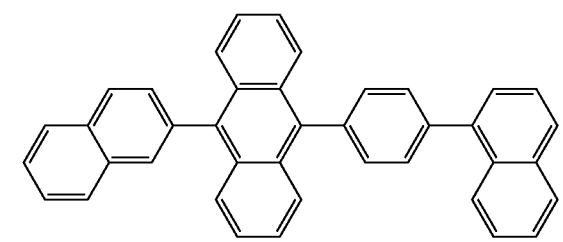
H28
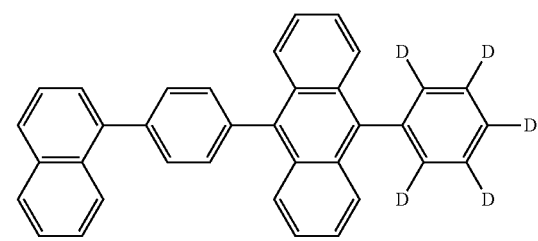
H29
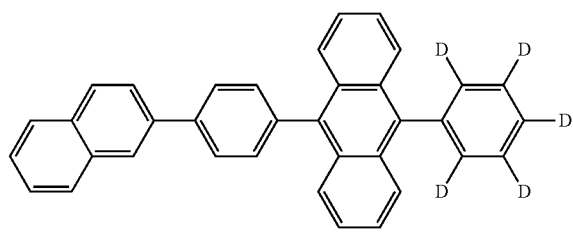
H30
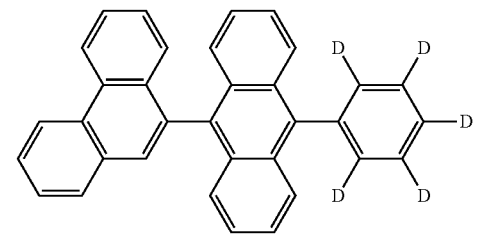
H31
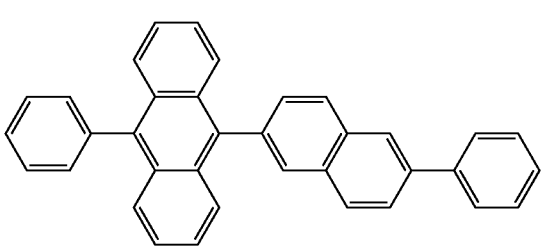

H32
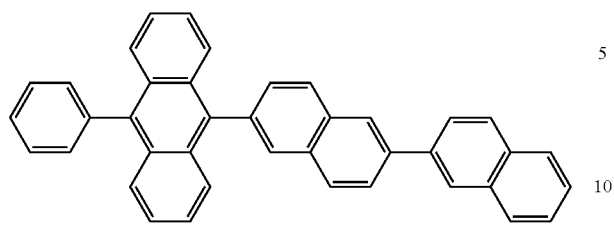
H33
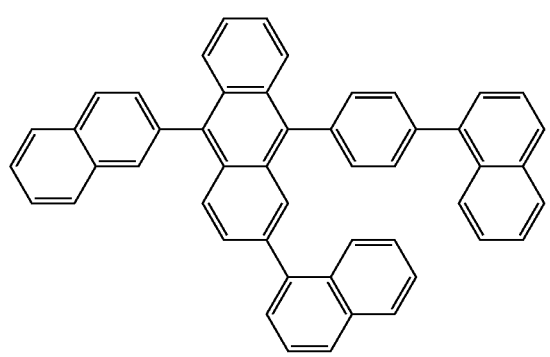
H34
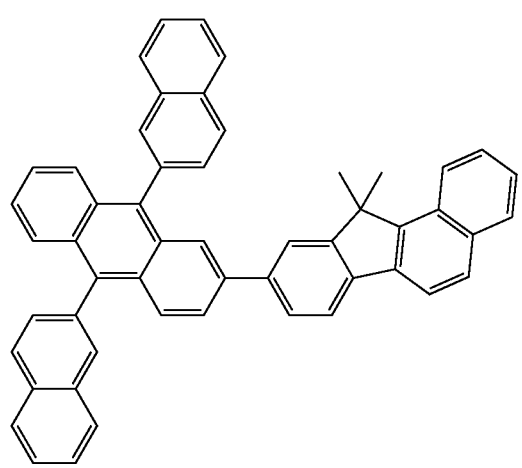
H35
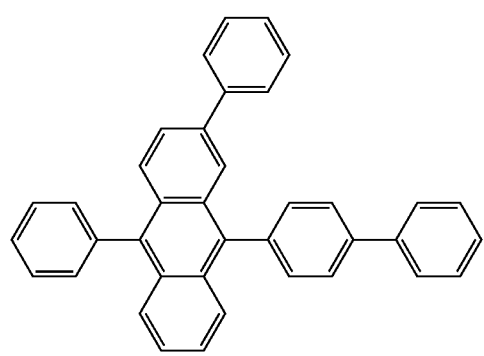
H36
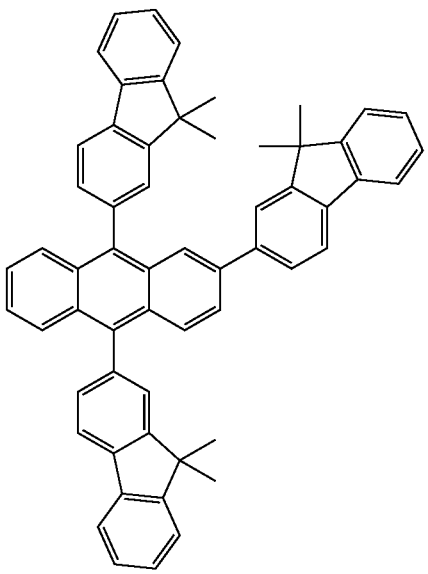
H37
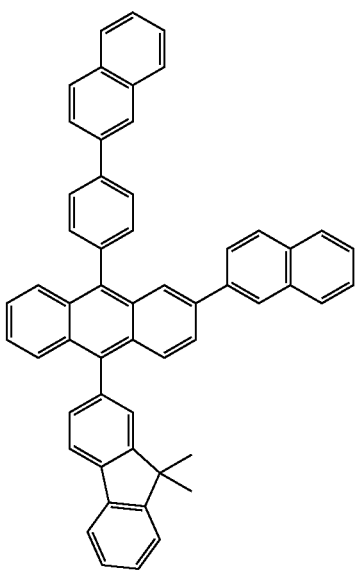
H38
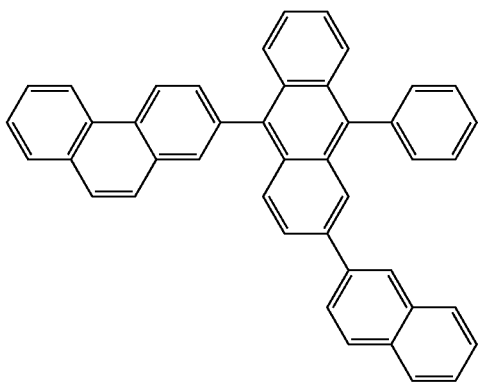

H39
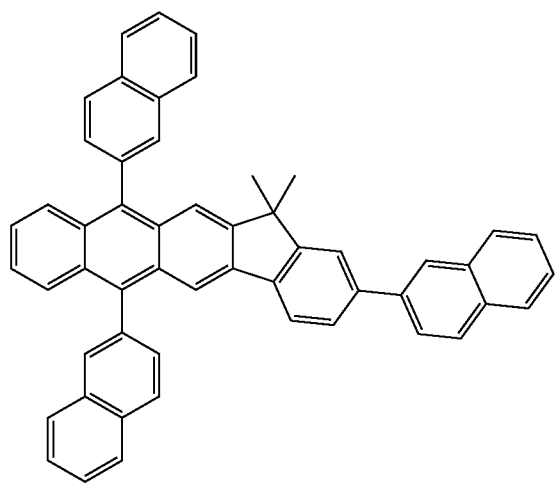
H42
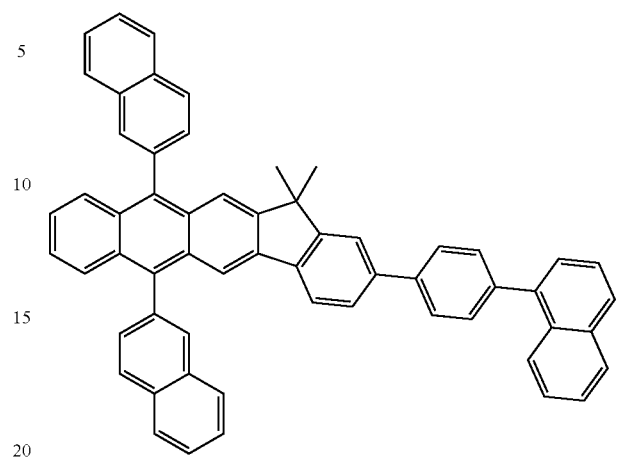
Also, the host may include at least one of Compounds H43 to H49 below, but the host is not limited thereto:
H40
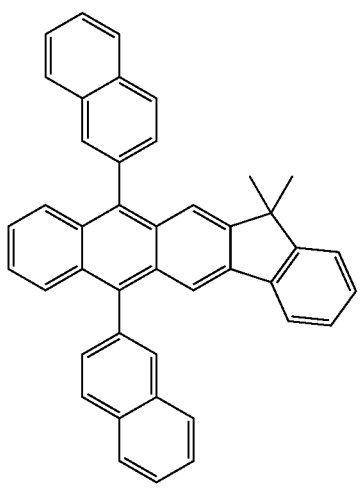
H43
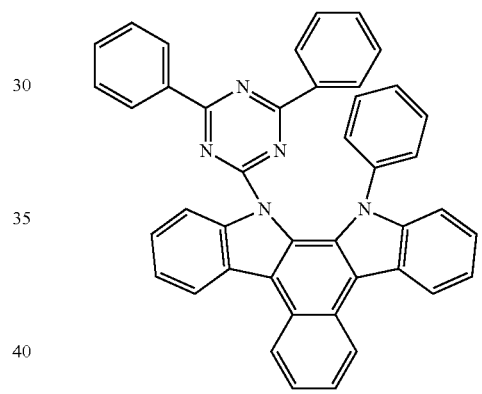
H41
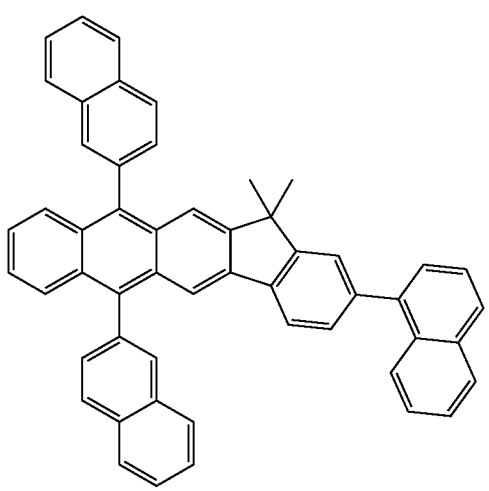
H44
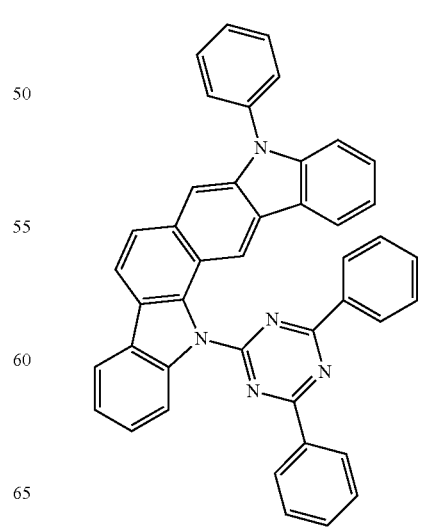

H45

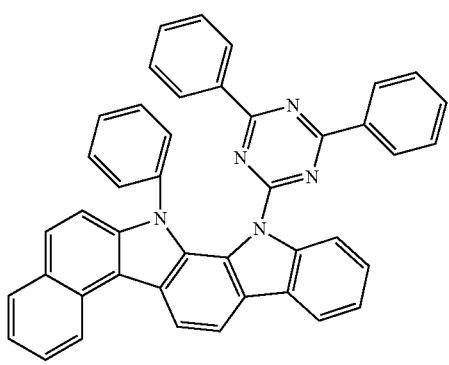

H46

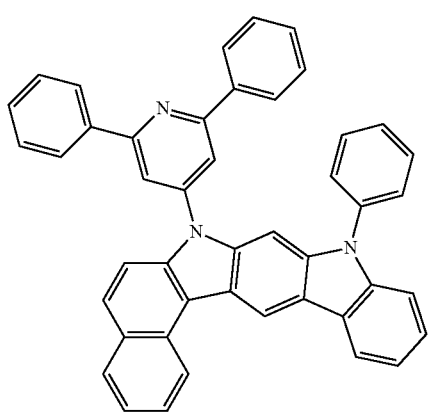

H47

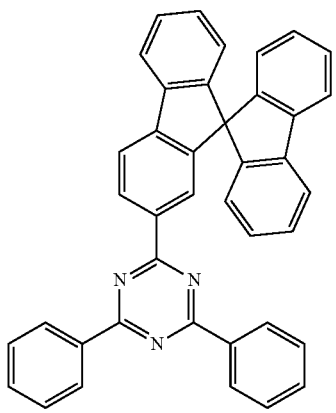

H48

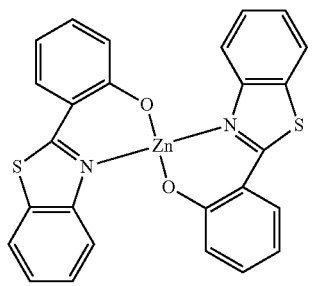

H49

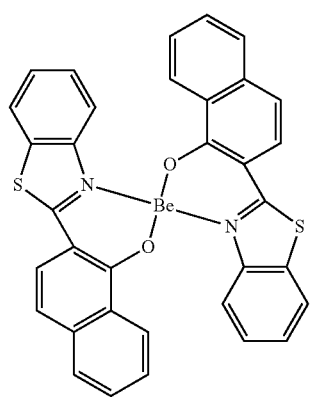

The dopant may include the amine-based compound represented by Formula 1. The dopant may further include at least one of a fluorescent dopant and a phosphorescent dopant in addition to the amine-based compound represented by Formula 1.

The phosphorescent dopant may include an organic metal complex represented by Formula 401 below:

Formula 401

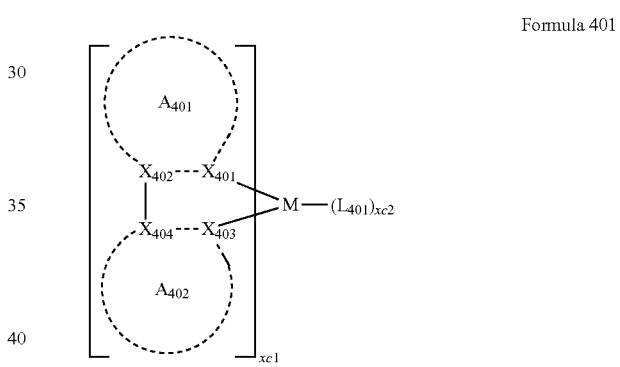

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen or carbon;

$A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy;

a $C_1$-$C_{60}$ alkyl group, a $C_2$-$C_{60}$ alkenyl group, a $C_2$-$C_{60}$ alkynyl group, and a $C_1$-$C_{60}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy, a $C_6$-$C_{60}$ arylthio, a $C_1$-$C_{60}$ heteroaryl group (e.g., a $C_2$-$C_{60}$ heteroaryl group), a non-aromatic condensed polycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), and a non-aromatic condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), and a non-aromatic condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a non-aromatic condensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), and where $Q_{401}$ to $Q_{407}$, $Q_{411}$ to $Q_{417}$, and $Q_{421}$ to $Q_{427}$ are the same as $Q_1$ to $Q_7$, $Q_{11}$ to $Q_{17}$, and $Q_{21}$ to $Q_{27}$ as described with respect to Formulae 1 and 2;

$L_{401}$ is an organic ligand;
xc1 is 1, 2, or 3; and
xc2 is 0, 1, 2, or 3.

$L_{401}$ may be any one selected from a monovalent, a divalent, or a trivalent organic ligand. For example, $L_{401}$ may be a halogen ligand (for example, Cl or F), a diketone ligand (for example, acetylacetonate, 1,3-diphenyl-1,3-propanedionate, 2,2,6,6-tetramethyl-3,5-heptanedionate, and hexafluoroacetonate), a carboxylic acid ligand (for example, picolinate, dimethyl-3-pyrazolecarboxylate, and benzoate), a carbon monoxide ligand, an isonitrile ligand, a cyano ligand, and a phosphorus ligand (for example, may be selected from phosphine and phosphite), but it is not limited thereto.

In Formula 401, when $A_{401}$ has two or more substituents, the two or more substituents of $A_{401}$ may be coupled to each other to form a saturated or an unsaturated ring.

In Formula 401, when $A_{402}$ has two or more substituents, the two or more substituents of $A_{402}$ may be coupled to each other to form a saturated or an unsaturated ring.

In Formula 401, when xc1 is two or greater, a plurality of ligands

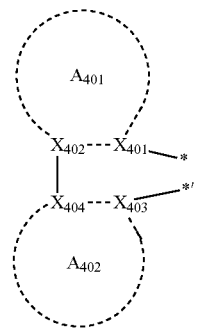

in Formula 401 may be the same or different. In Formula 401, when xc1 is two or greater, $A_{401}$ and $A_{402}$ may be respectively connected to $A_{401}$ and $A_{402}$ of a neighboring ligand either directly or via a linking group (for example, a $C_1$-$C_5$ alkylene group and —N(R')— (where, R' is a $C_1$-$C_{10}$ alkyl group or a $C_6$-$C_{20}$ aryl group) or —C(=O)—) disposed therebetween.

The phosphorescent dopant may include at least one selected from Compounds PD1 to PD74, but it is not limited thereto:

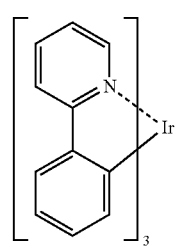

PD1

-continued
PD2
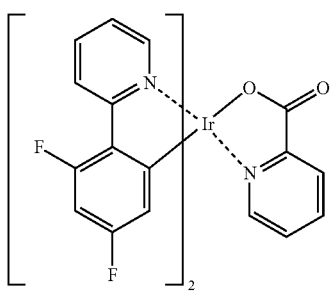
PD3
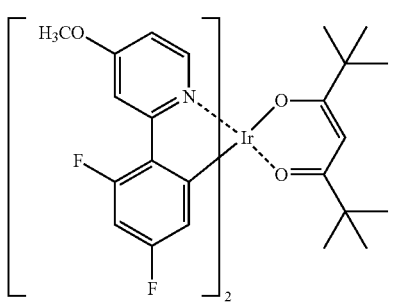
PD4
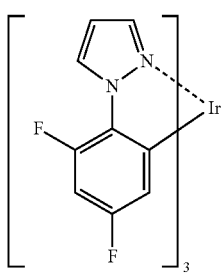
PD5
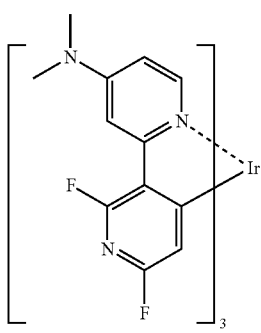
PD6
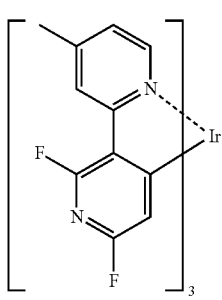
-continued
PD7
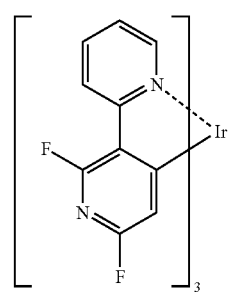
PD8
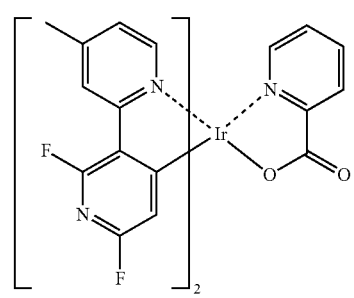
PD9
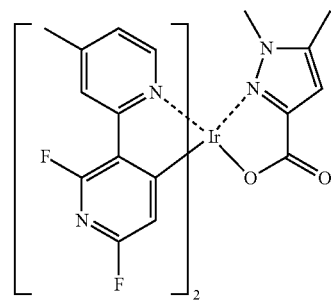
PD10
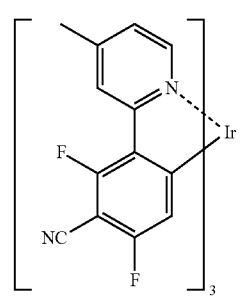
PD11
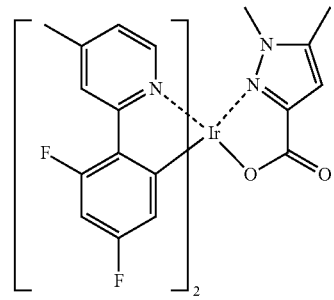

PD12 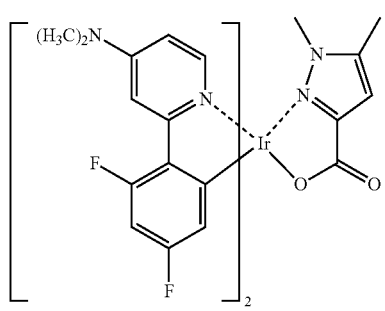
PD17 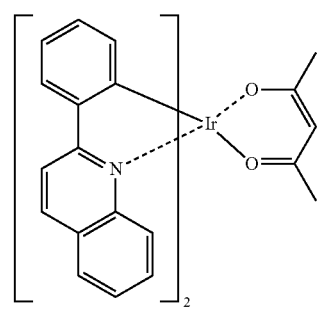
PD13 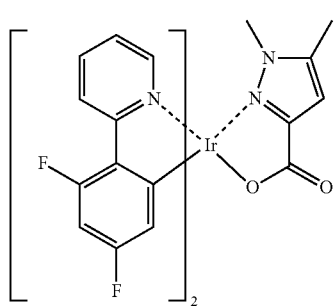
PD18 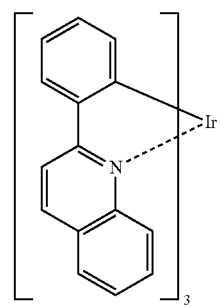
PD14 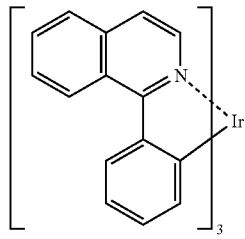
PD19 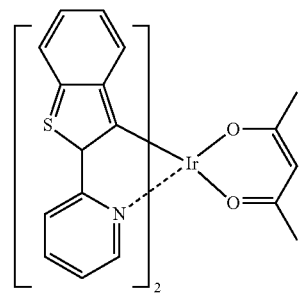
PD15 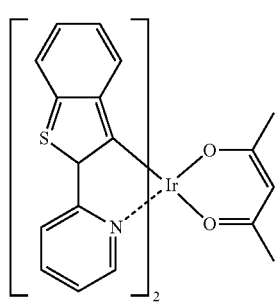
PD20 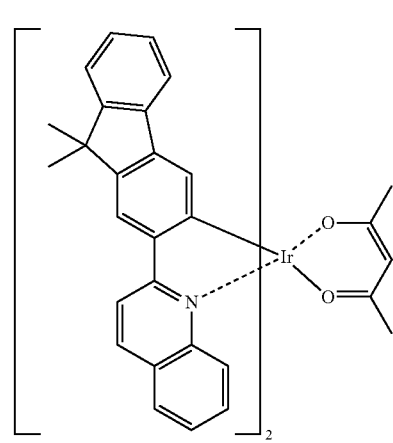
PD16 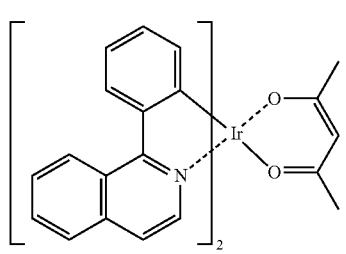

PD21 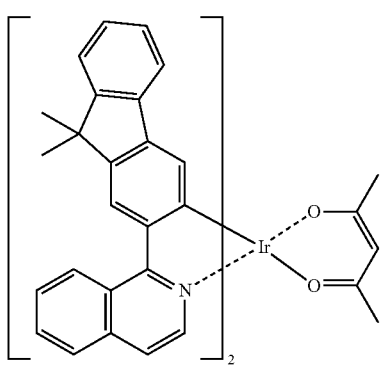
PD22 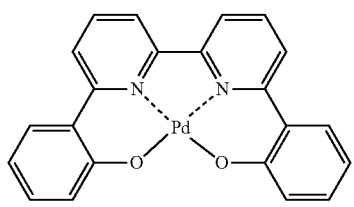
PD23 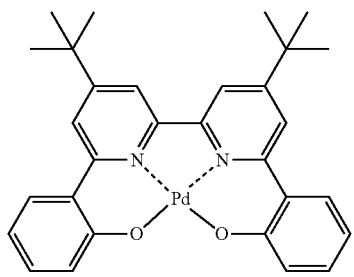
PD24 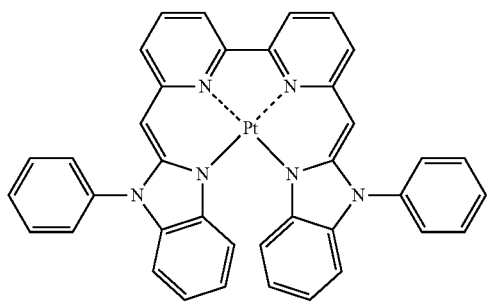
PD25 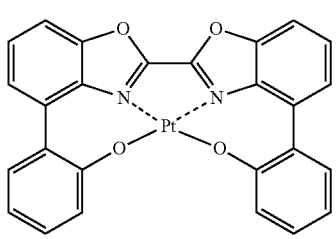
PD26 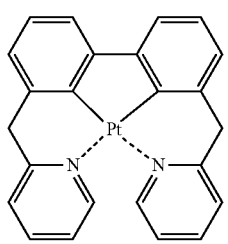
PD27 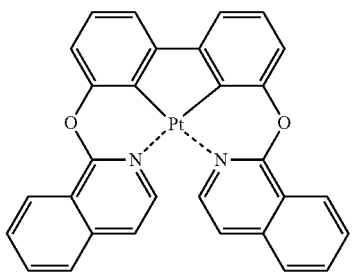
PD28 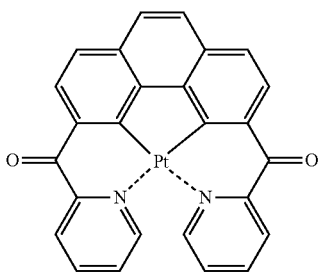
PD29 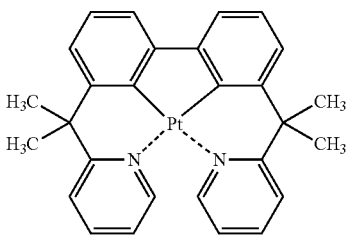
PD30 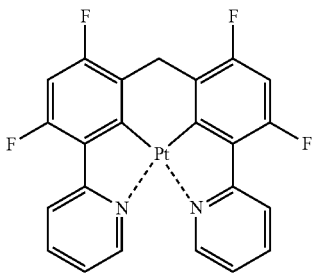
PD31 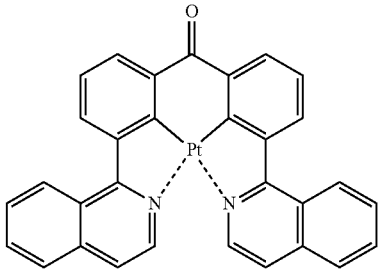
PD32 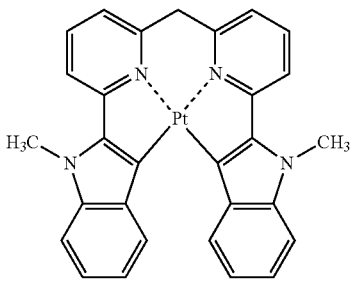

PD33 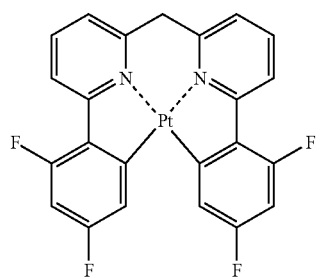
PD34 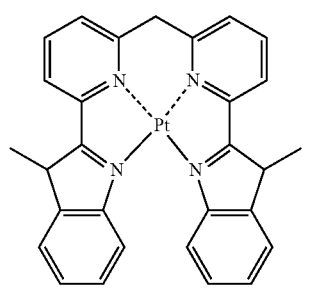
PD35 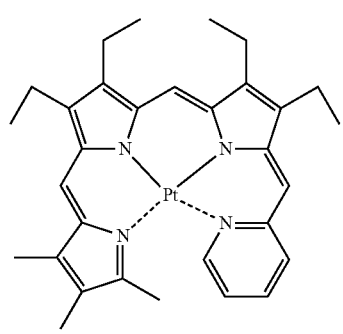
PD36 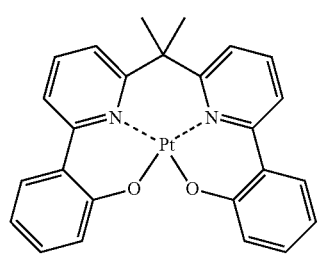
PD37 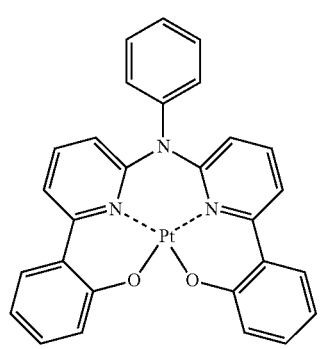
PD38 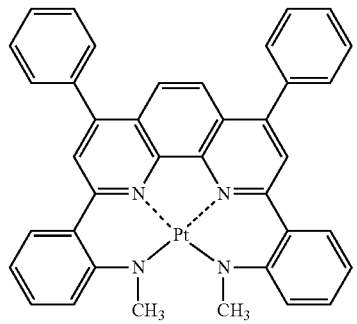
PD39 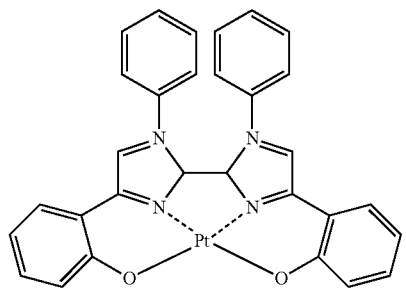
PD40 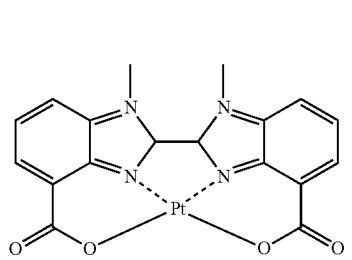
PD41 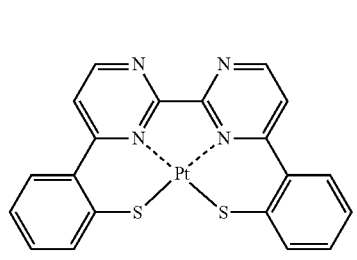
PD42 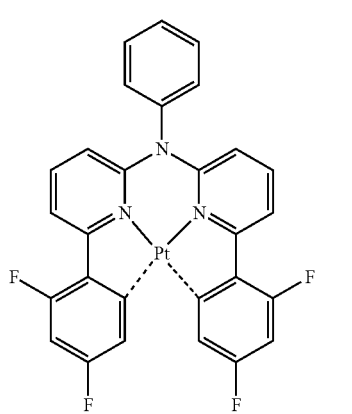

-continued
PD43
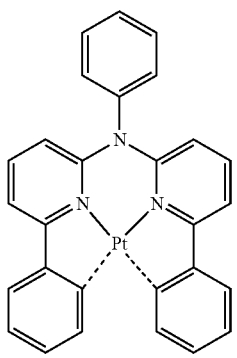
PD44
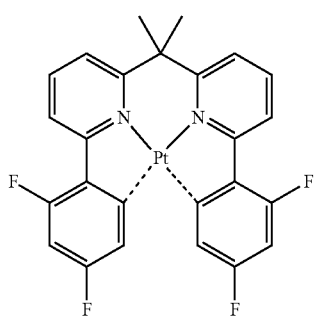
PD45
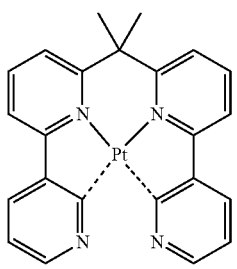
PD46
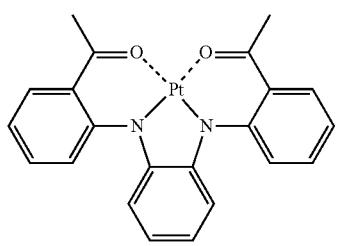
PD47
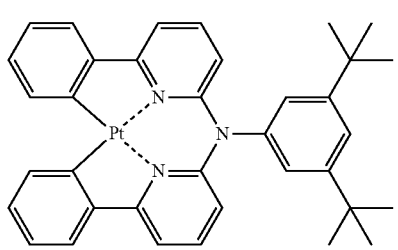
-continued
PD48
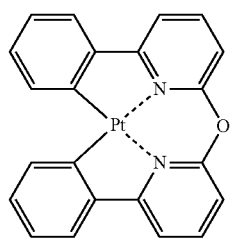
PD49
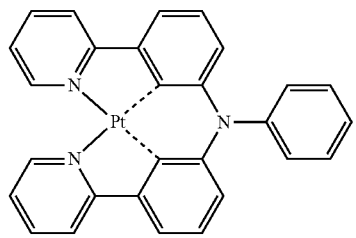
PD50
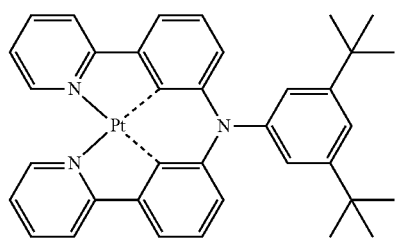
PD51
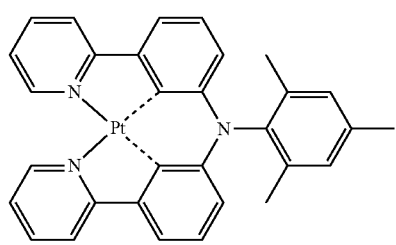
PD52
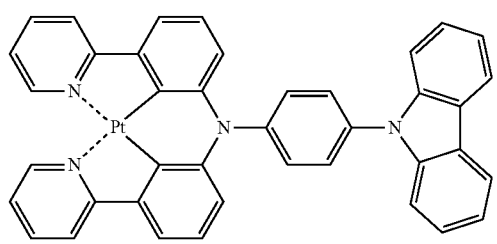
PD53
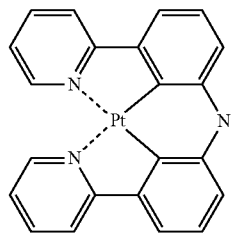

PD54 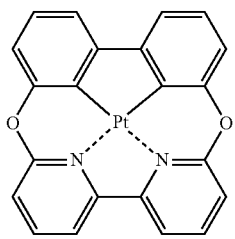
PD55 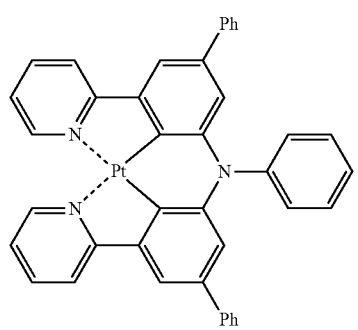
PD56 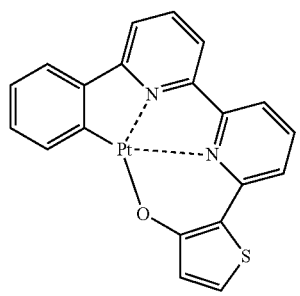
PD57 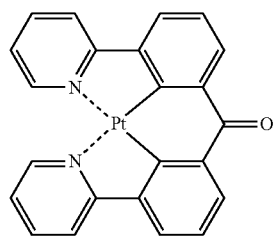
PD58 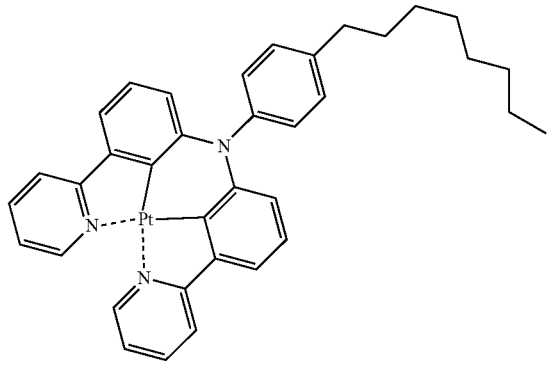
PD59 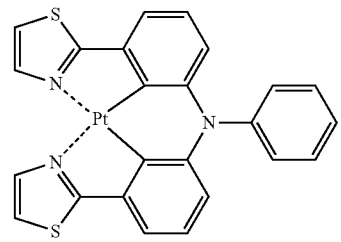
PD60 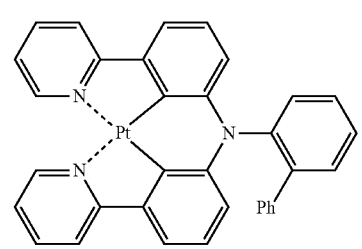
PD61 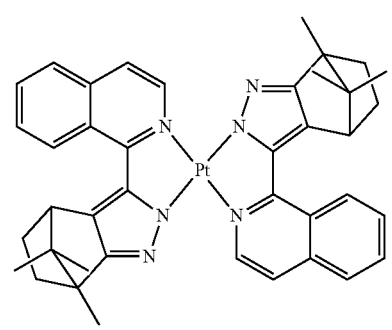
PD62 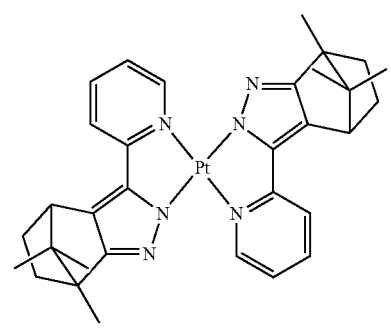
PD63 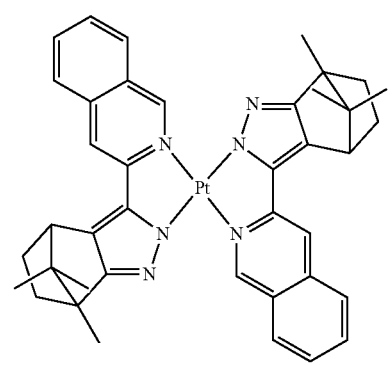

-continued
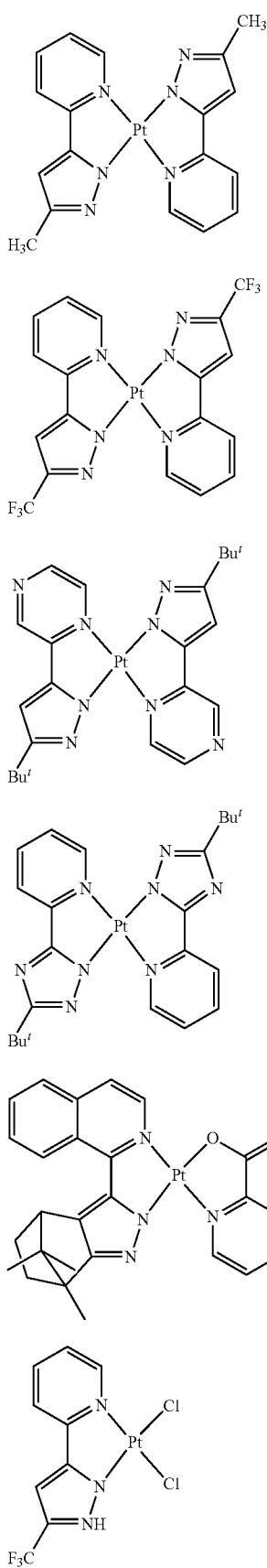
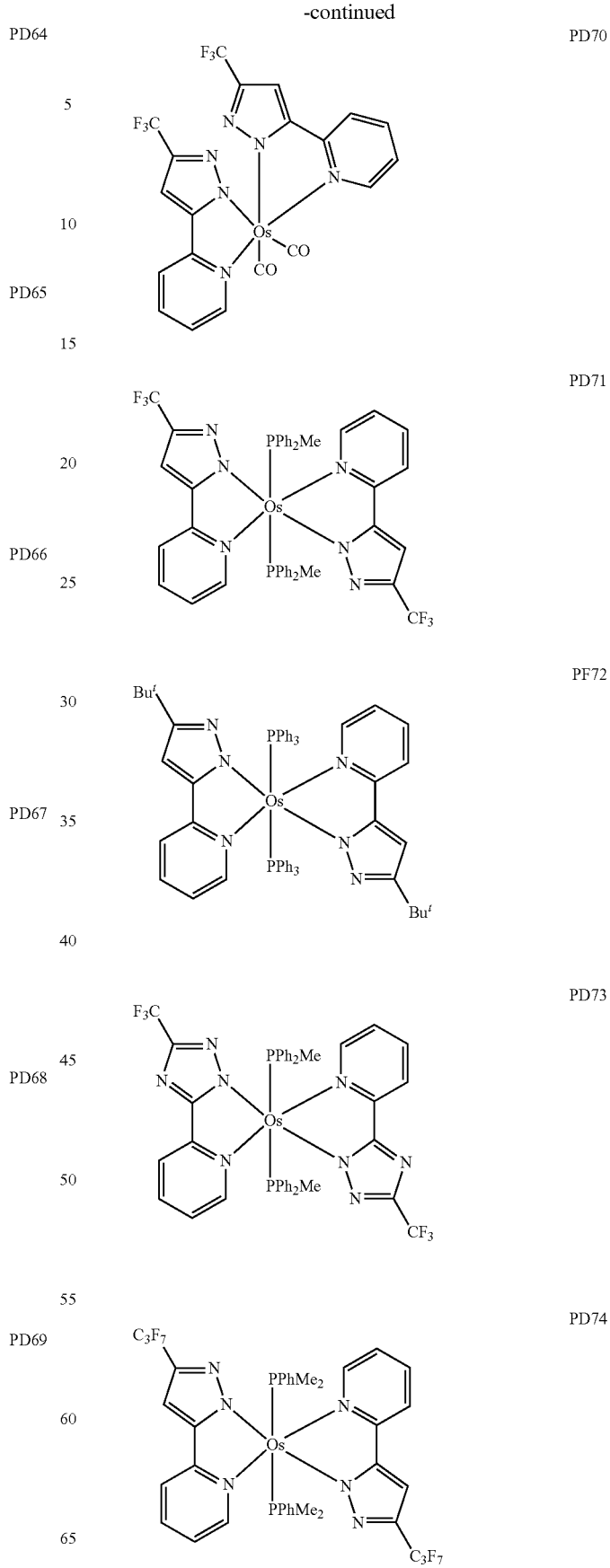

Alternatively, the phosphorescent dopant may include PtOEP below:
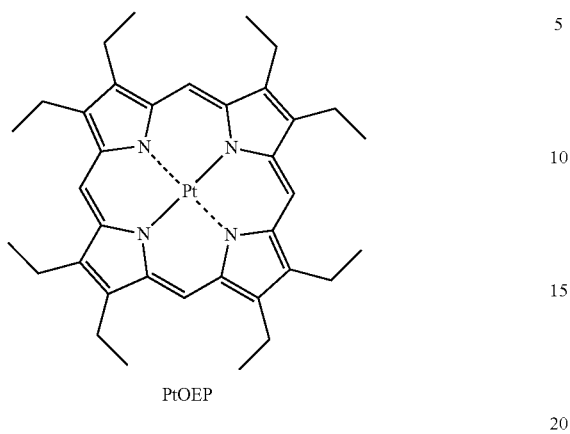
PtOEP
The fluorescent dopant may include at least one selected from DPAVBi, BDAVBi, TBPe, DCM, DCJTB, Coumarin 6, and C545T:
DPVBi
DPAVBi
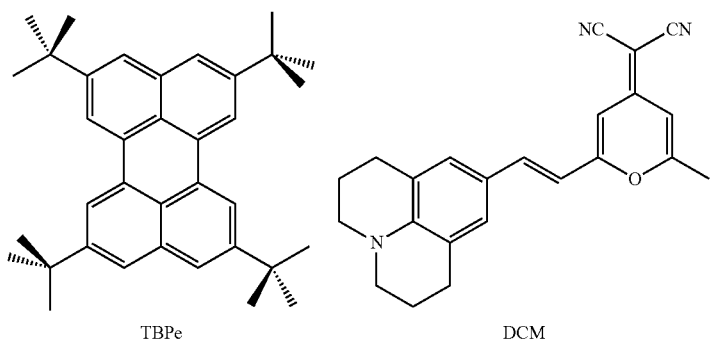
TBPe                    DCM

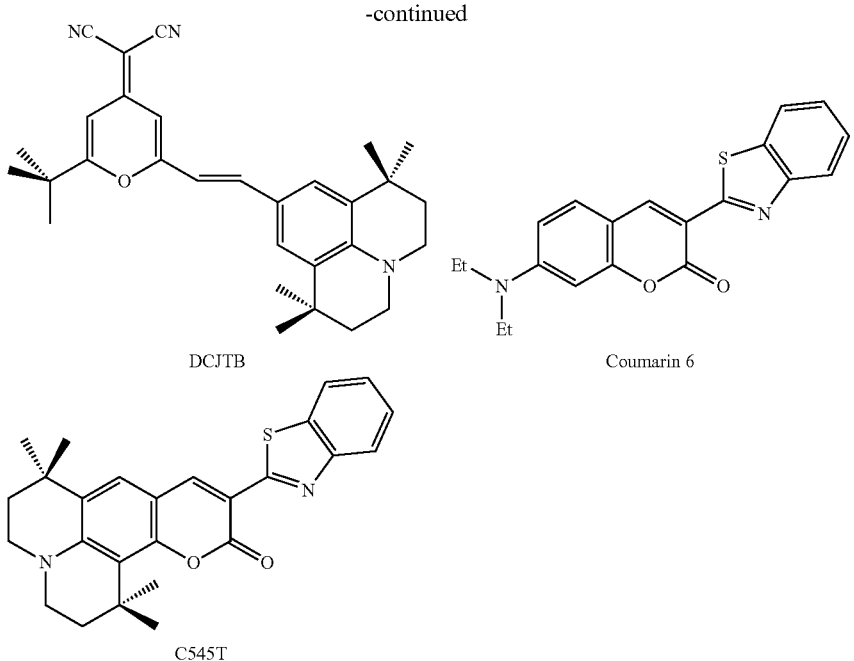

DCJTB  Coumarin 6

C545T

Alternatively, the fluorescent dopant may include a compound represented by Formula 501 below:

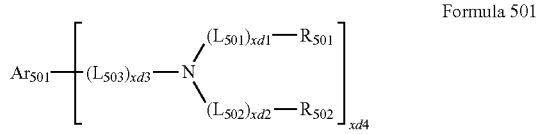

Formula 501

In Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group (e.g., a $C_2$-$C_{60}$ heteroaryl group), a non-aromatic condensed polycyclic group, and —$Si(Q_{501})(Q_{502})(Q_{503})$, where $Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{501}$ to $L_{503}$ are the same as defined in the description of $L_{201}$ in the present specification;

$R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group and a dibenzofuranyl group, and a dibenzothiophenyl group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may be each independently an integer selected from 0, 1, 2, and 3; and xd4 may be an integer selected from 1, 2, 3, and 4.

The fluorescent dopant may include at least one selected from Compounds FD1 to FD8 below:
FD1
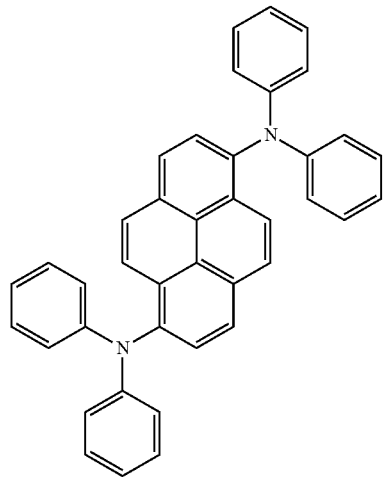
FD2
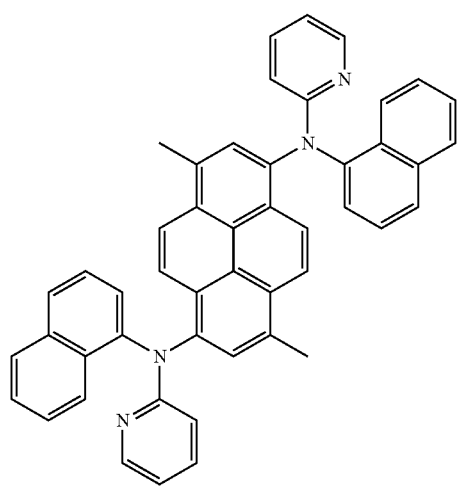
FD3
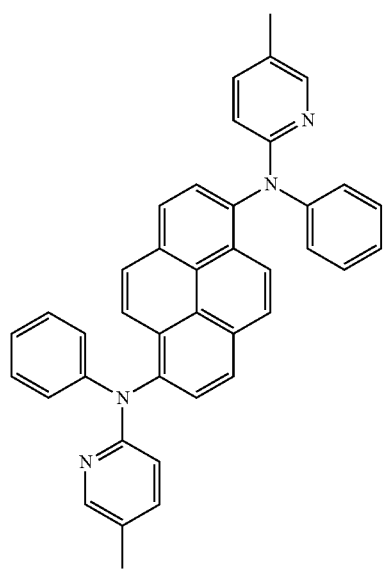
FD4
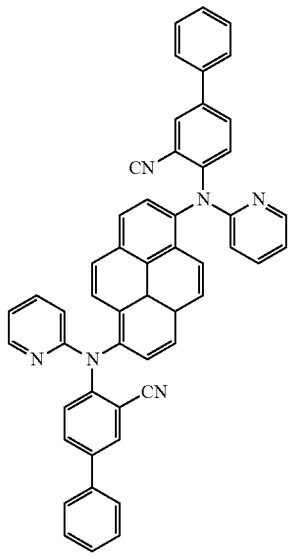
FD5
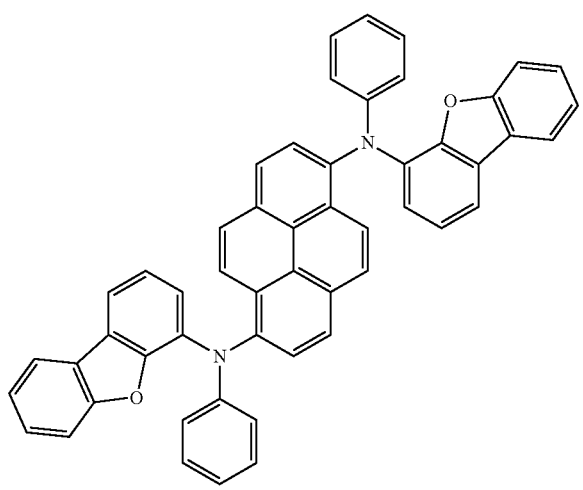
FD6
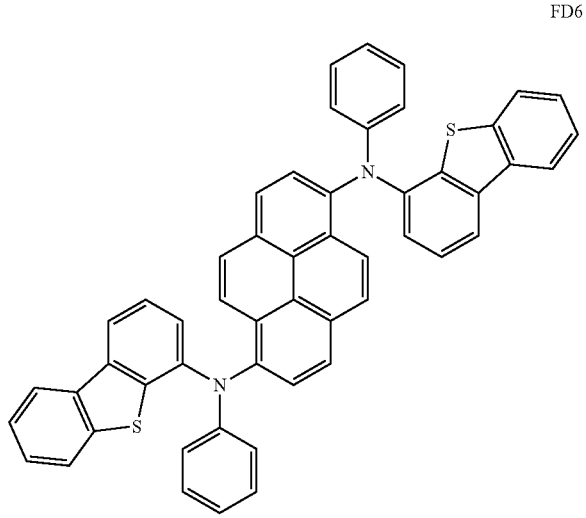

FD7

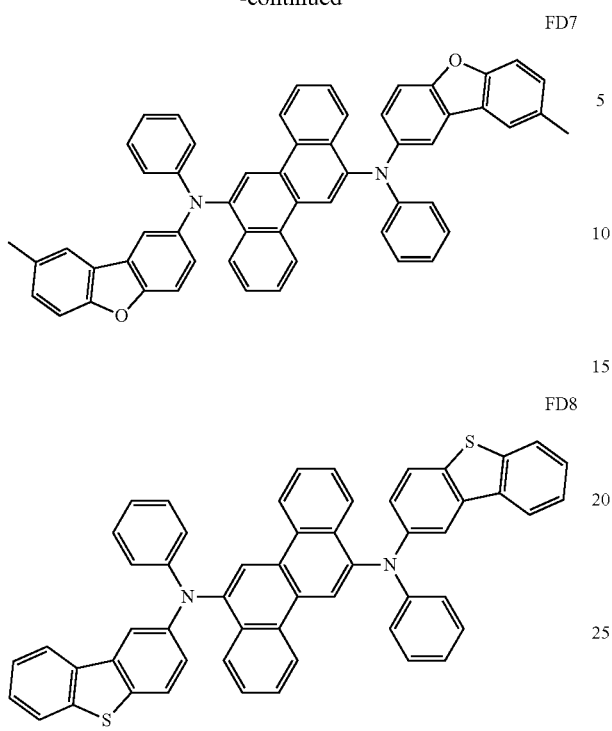

FD8

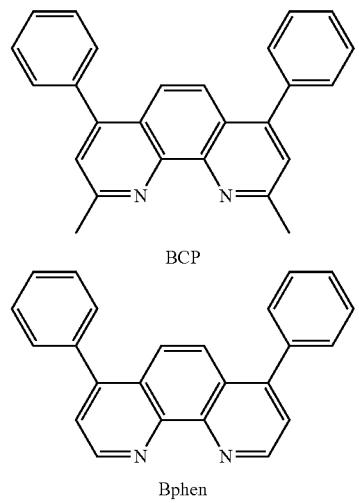

BCP

Bphen

An amount of dopant in the EML may be about 0.01 parts by weight to about 15 parts by weight based on 100 parts by weight of the dopant, but the dopant is not limited thereto.

A thickness of the EML may be about 100 Å to about 1000 Å, for example, about 200 Å to about 600 Å. When the thickness of the EML is in the range described above, the EML may have excellent light-emitting ability without a substantial increase in driving voltage.

Then, the electron transport region may be disposed on the EML.

The electron transport region may include at least one of the HBL, the ETL, and the EIL, but the electron transport region is not limited thereto.

For example, the electron transport region may have a structure in which the ETL/EIL or HBL/ETL/EIL are sequentially layered on the EML, but the electron transport region is not limited thereto.

The electron transport region may include the HBL. The HBL may be formed to (or configured to) prevent (or reduce) triplet excitons or holes from being diffused to the ETL when the EML uses a phosphorescent dopant.

When the electron transport region includes the HBL, the HBL may be formed on the EML by using various suitable methods such as vacuum deposition, spin coating, casting, LB deposition, inkjet printing, laser printing, or LITI. When the HBL is formed by as vacuum deposition and spin coating, the deposition conditions and the coating conditions of the HBL may be the same as the deposition conditions and the coating conditions described with respect to the HIL.

The HBL may include, for example, at least one of BCP and Bphen below, but the HBL is not limited thereto:

A thickness of the HBL may be in a range of about 20 Å to about 1,000 Å, for example, about 30 Å to about 300 Å. When a thickness of the EML is within any of the foregoing ranges, excellent hole blocking properties may be obtained without substantial increase in driving voltage.

The electron transport region may include the ETL. The ETL may be formed on the EML or the HBL by using various suitable methods such as vacuum deposition, spin coating, casting, LB deposition, inkjet printing, laser printing, or LITI. When ETL is formed by vacuum deposition and spin coating, the deposition conditions and the coating conditions of the ETL may be the same as the deposition conditions and the coating conditions described with respect to the HIL.

The ETL may further include at least one of BCP and Bphen above and Alq$_3$, Balq, TAZ, and NTAZ below:

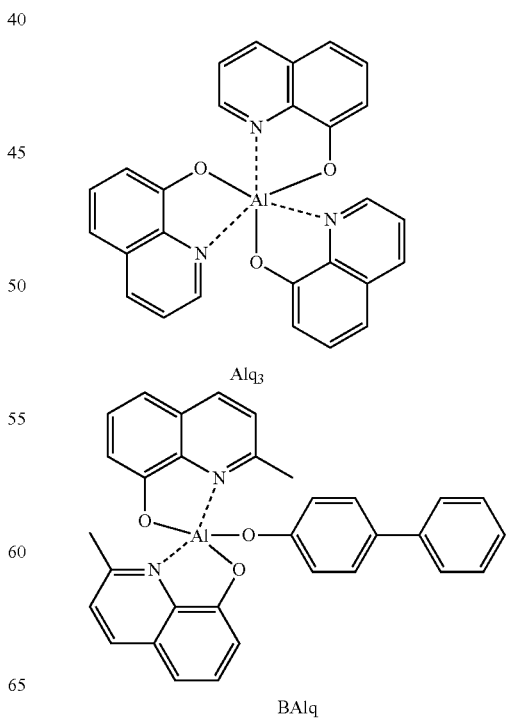

Alq$_3$

BAlq

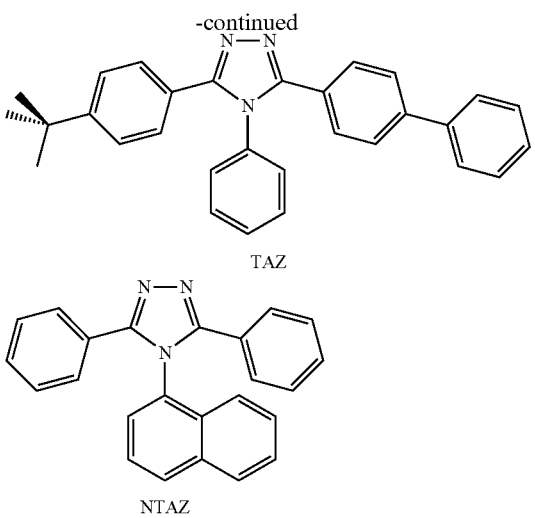

TAZ

NTAZ

Also, the ETL may include at least one compound represented by Formula 601:

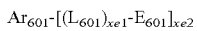

Formula 601

In Formula 601,
Ar$_{601}$ is selected from:

a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a non-aromatic condensed polycyclic group, and —Si(Q$_{301}$)(Q$_{302}$)(Q$_{303}$), where Q$_{301}$ to Q$_{303}$ are each independently selected from a hydrogen atom, a $C_1$-$C_{60}$ alkyl group, a $C_2$-$C_{60}$ alkenyl group, a $C_6$-$C_{60}$ aryl group, and a $C_1$-$C_{60}$ heteroaryl (e.g., a $C_2$-$C_{60}$ heteroaryl group);

L$_{601}$ may be as defined in the description of L$_{201}$;
E$_{601}$ is selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group;

xe1 is an integer selected from 0, 1, 2, and 3; and
xe2 is an integer selected from 1, 2, 3, and 4.

Also, the ETL may include at least one compound represented by Formula 602 in addition to the amine-based compound represented by Formula 1:

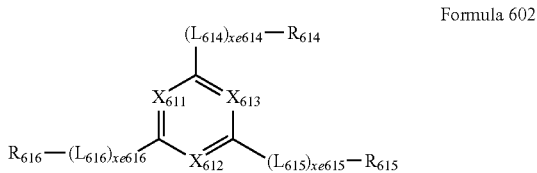

Formula 602

In Formula 602, $X_{611}$ is N or $C-(L_{611})_{xe611}-R_{611}$, $X_{612}$ is N or $C-(L_{612})_{xe612}-R_{612}$, $X_{613}$ is N or $C-(L_{613})_{xe613}-R_{613}$, and at least one of $X_{611}$ to $X_{613}$ is N;

$L_{611}$ to $L_{616}$ are each independently as defined in the description of $L_{201}$;

$R_{611}$ to $R_{616}$ are each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 are each independently an integer selected from 0, 1, 2, and 3.

The compound represented by Formula 601 and the compound represented by Formula 602 may include at least one selected from Compounds ET1 to ET15:

ET1

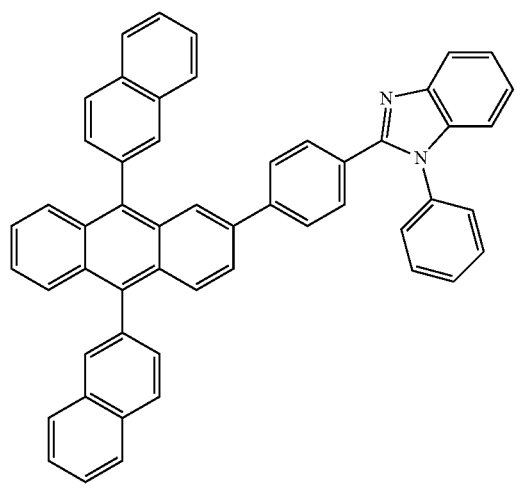

ET2

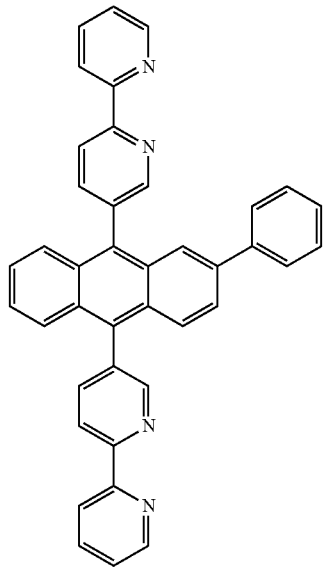

ET3

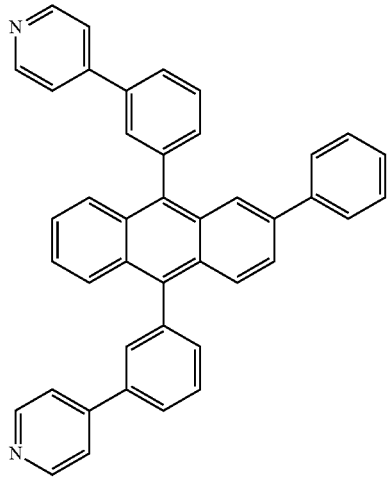

ET4

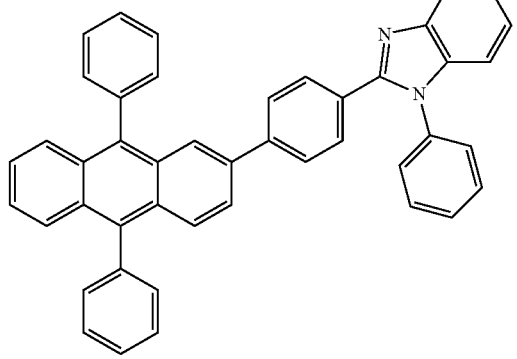

ET5
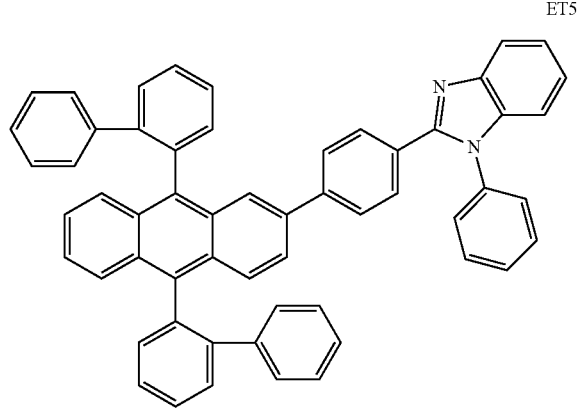
ET6
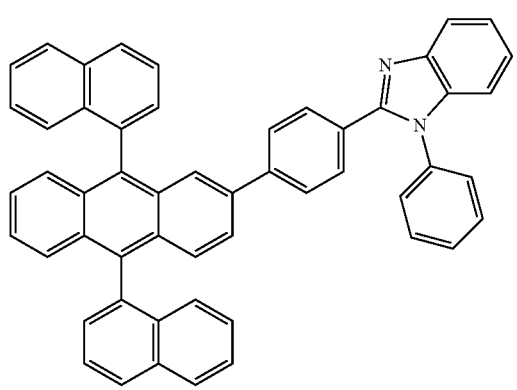
ET7
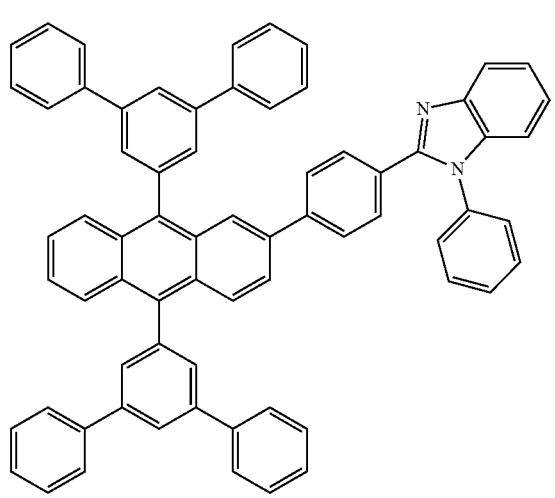
ET8
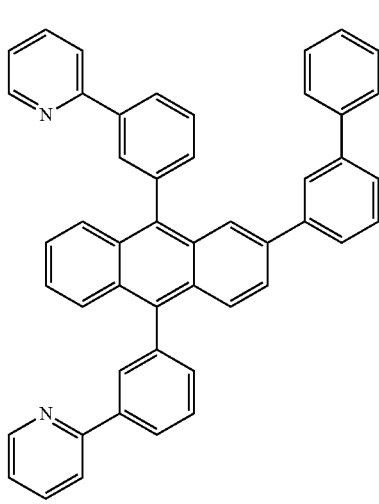
ET9
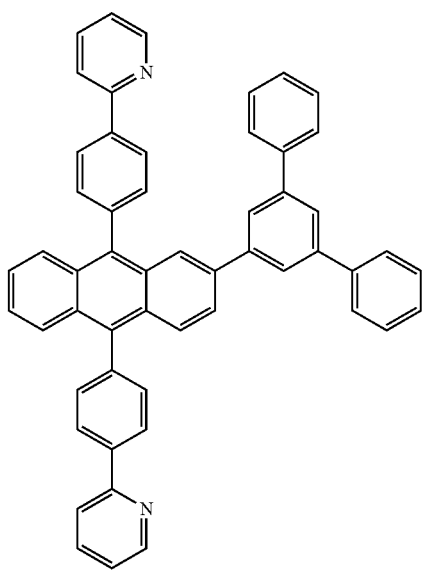
ET10
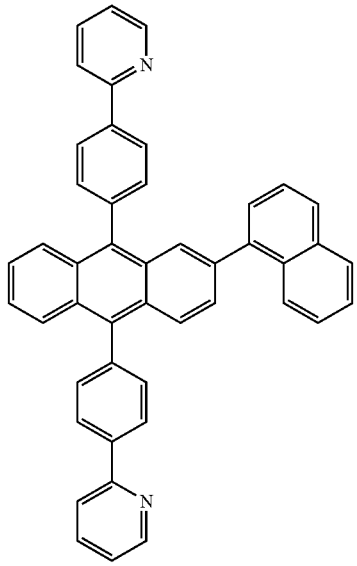

ET11

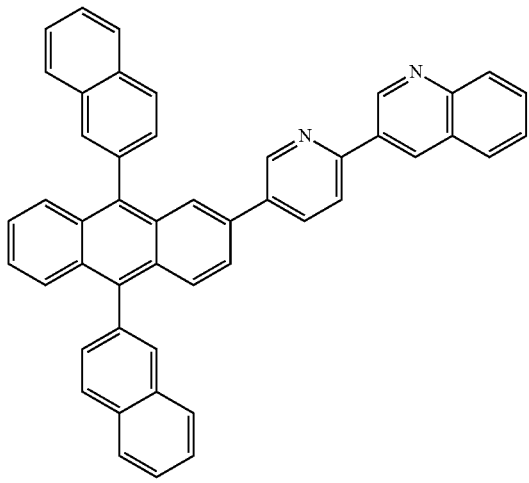

ET12

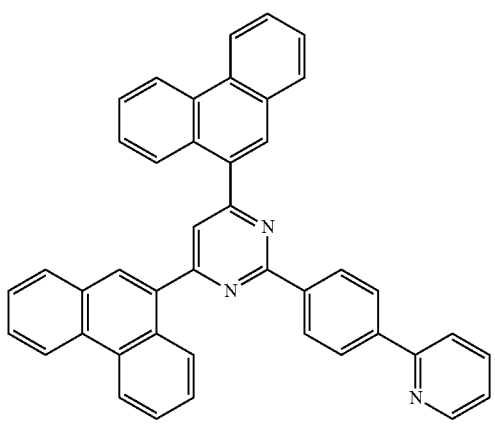

ET13

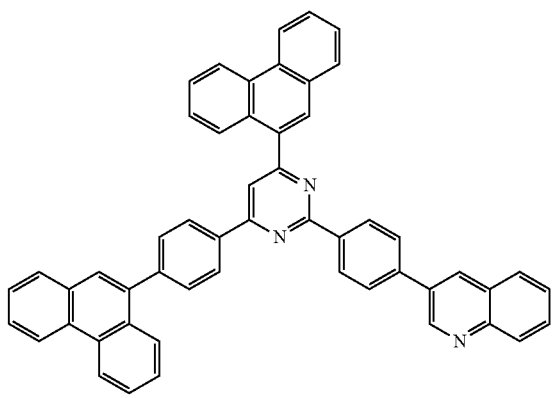

ET14

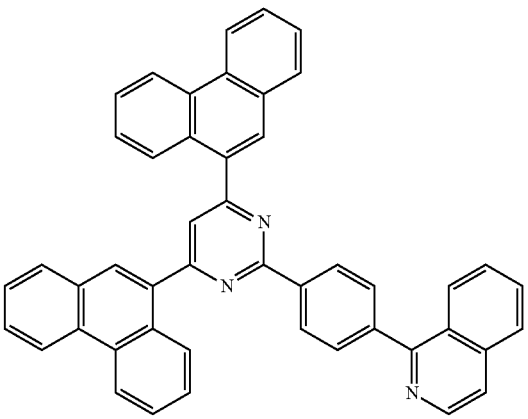

ET15

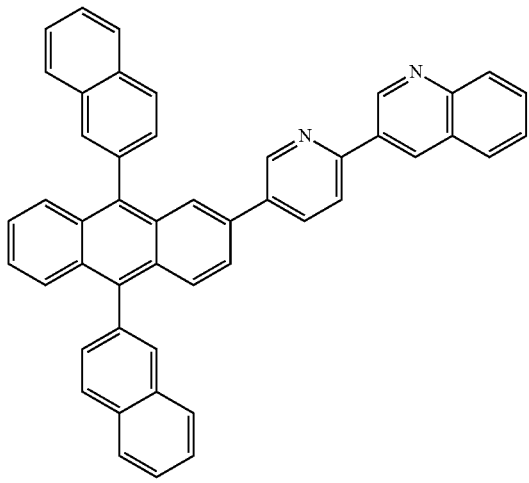

A thickness of the ETL may be in a range of about 100 Å to about 1,000 Å, for example, about 150 Å to about 500 Å. When a thickness of the ETL is within any of the foregoing ranges, excellent electron transporting properties may be obtained without substantial increase in driving voltage.

The ETL may further include a metal-containing material in addition to the materials above.

The metal-containing material may include a Li-complex. The Li-complex may include, for example, Compound ET-D1 (lithium quinolate (LiQ)) or ET-D2:

ET-D1

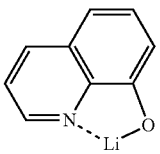

ET-D2

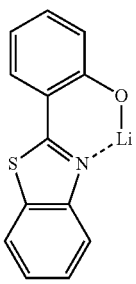

The electron transport region may include the EIL that facilitates injection of electrons from the second electrode 190.

The EIL may be formed on the ETL by using various suitable methods such as vacuum deposition, spin coating, casting, LB deposition, inkjet printing, laser printing, or LITI. When EIL is formed by vacuum deposition and spin coating, the deposition conditions and the coating conditions of the EIL may be the same as the deposition conditions and the coating conditions described with respect to the HIL.

The EIL may include at least one selected from LiF, NaCl, CsF, $Li_2O$, BaO, and LIQ.

A thickness of the EIL may be in a range of about 1 Å to about 100 Å, for example, about 3 Å to about 90 Å. When a thickness of the EIL is within any of the foregoing ranges, excellent electron injecting properties may be obtained without substantial increase in driving voltage.

The second electrode 190 is disposed on the organic layer 150. The second electrode 190 may be a cathode, which is an electron injection electrode. In this regard, a metal for forming the second electrode 190 may include a metal, an alloy, an electric conducting compound, and a mixture thereof having low work function. In particular, the second electrode 190 may be formed as a thin film by using lithium (Li), magnesium (Mg), aluminum (Al), aluminum-lithium (Al—Li), calcium (Ca), magnesium-indium (Mg—In), or magnesium-silver (Mg—Ag). Also, ITO or IZO may be used as metal for forming the second electrode 190. The second electrode 190 may be a reflective electrode or a transparent electrode.

The OLED 10 has been described by referring to the accompanying drawing, but the OLED is not limited thereto.

As used herein, examples of the $C_1$-$C_{60}$ alkyl group include a monovalent linear or branched aliphatic hydrocarbon group, such as a methyl group, an ethyl group, a propyl group, an isobutyl group, a sec-butyl group, a ter-butyl group, a pentyl group, an iso-amyl group, or a hexyl group. As used herein, the substituted $C_1$-$C_{60}$ alkylene group denotes a divalent group that has the same structure as the $C_1$-$C_{60}$ alkyl group.

As used herein, a $C_1$-$C_{60}$ alkoxy group denotes a monovalent group having a formula of —$OA_{101}$ (here, $A_{101}$ is the $C_1$-$C_{60}$ alkyl group), and examples of the $C_1$-$C_{60}$ alkoxy group include a methoxy group, an ethoxy group, and an isopropyloxy group.

As used herein, the $C_2$-$C_{60}$ alkenyl group has a structure including at least one carbon double bond at the main body (or middle) or at an end of the $C_2$-$C_{60}$ alkyl group, and examples of the $C_2$-$C_{60}$ alkenyl group include an ethenyl group, a propenyl group, and a butenyl group. As used herein, the $C_2$-$C_{60}$ alkenylene group denotes a divalent group that has the same structure as the $C_2$-$C_{60}$ alkenyl group.

As used herein, the $C_2$-$C_{60}$ alkynyl group has a structure including at least one carbon triple bond at the main body (or middle) or at an end of the $C_2$-$C_{60}$ alkyl group, and examples of the $C_2$-$C_{60}$ alkynyl group include an ethynyl group and a propynyl group. As used herein, the $C_2$-$C_{60}$ alkynylene group denotes a divalent group that has the same structure as the $C_2$-$C_{60}$ alkynyl group.

As used herein, the $C_3$-$C_{10}$ cycloalkyl group denotes a $C_3$-$C_{10}$ monovalent hydrocarbon monocyclic group, and examples of the $C_3$-$C_{10}$ cycloalkyl group include a cyclopropyl group, a cyclobutyl group, a cyclopentyl group, a cyclohexyl group, and a cycloheptyl group. As used herein, the $C_3$-$C_{10}$ cycloalkylene group denotes a divalent group that has the same structure as the $C_3$-$C_{10}$ cycloalkyl group.

As used herein, the $C_3$-$C_{10}$ heterocycloalkyl group denotes a $C_3$-$C_{10}$ monovalent monocyclic group including at least one hetero atom of N, O, P, and S as a ring-forming atom, and examples of the $C_3$-$C_{10}$ heterocycloalkyl group include a tetrahydrofuranyl group and a tetrahydrothiophenyl group. As used herein, the $C_3$-$C_{10}$ heterocycloalkylene group denotes a divalent group that has the same structure as the $C_3$-$C_{10}$ heterocycloalkyl group.

As used herein, the $C_3$-$C_{10}$ cycloalkenyl group denotes a $C_3$-$C_{10}$ monocyclic group having at least one double bond in the ring while not losing its aromaticity, and examples of the $C_3$-$C_{10}$ cycloalkenyl group include a cyclopentyl group, a cyclohexenyl group, and a cycloheptenyl group. As used herein, the $C_3$-$C_{10}$ cycloalkenylene group denotes a divalent group that has the same structure as the $C_3$-$C_{10}$ cycloalkenyl group.

As used herein, the $C_3$-$C_{10}$ heterocycloalkenyl group denotes a $C_3$-$C_{10}$ monovalent monocyclic group including at least one hetero atom of N, O, P, and S as a ring-forming atom and at least one double bond in the ring, and examples of the $C_3$-$C_{10}$ heterocycloalkenyl group include a 2,3-hydrofuranyl group and a 2,3-hydrothiophenyl group. As used herein, the $C_3$-$C_{10}$ heterocycloalkenylene group denotes a divalent group that has the same structure as the $C_3$-$C_{10}$ heterocycloalkenyl group.

As used herein, the $C_6$-$C_{60}$ aryl group denotes a monovalent group having a $C_6$-$C_{60}$ carbocyclic aromatic system, and the $C_6$-$C_{60}$ arylene group denotes a divalent group that has a $C_6$-$C_{60}$ carbocyclic aromatic system. Examples of the $C_6$-$C_{60}$ aryl group include a phenyl group, a naphthyl group, an anthracenyl group, a phenanthrenyl group, a pyrenyl group, and a chrysenyl group. As used herein, when the $C_6$-$C_{60}$ aryl group and the $C_6$-$C_{60}$ arylene group include at least two rings, the rings may be fused to each other (e.g., combined together).

As used herein, the $C_1$-$C_{60}$ heteroaryl group denotes a monovalent group including at least one hetero atom selected from N, O, P, and S as a ring-forming atom and having a $C_1$-$C_{60}$ carbocyclic aromatic system (e.g., a $C_2$-$C_{60}$ carbocyclic aromatic system), and the $C_1$-$C_{60}$ heteroarylene group denotes a divalent group including at least one hetero atom selected from N, O, P, and S as a ring-forming atom and having a $C_1$-$C_{60}$ carbocyclic aromatic system (e.g., a $C_2$-$C_{60}$ carbocyclic aromatic system). Examples of the $C_1$-$C_{60}$ heteroaryl group (or $C_2$-$C_{60}$ heteroaryl group) include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and/or the $C_1$-$C_{60}$ heteroarylene group each include at least two rings, the rings may be fused to each other (e.g., combined together).

As used herein, the $C_6$-$C_{60}$ aryloxy group denotes —$OA_{102}$ (here, $A_{102}$ is the $C_6$-$C_{60}$ aryl group), and the $C_6$-$C_{60}$ arylthio group denotes —$SA_{103}$ (here, $A_{103}$ is the $C_6$-$C_{60}$ aryl group).

As used herein, the non-aromatic condensed polycyclic group denotes a monovalent group having at least two rings that are condensed to each other, only carbon as a ring-forming atom (e.g., the number of carbon atoms may be 8 to 60), and non-aromaticity as a whole molecule. Examples of the non-aromatic condensed polycyclic group include a fluorenyl group. As used herein, the divalent non-aromatic condensed polycyclic group denotes a divalent group that has the same structure as the non-aromatic condensed polycyclic group.

As used herein, the non-aromatic heterocondensed polycyclic group denotes a monovalent group having at least two rings that are condensed to each other, one hetero atom selected from N, O, P, and S as a ring-forming atom in addition to carbon (e.g., the number of carbon atoms may be 2 to 60), and non-aromaticity as a whole molecule. Examples of the non-aromatic heterocondensed polycyclic group include a carbazolyl group. As used herein, the divalent non-aromatic heterocondensed polycyclic group denotes a divalent group that has the same structure as the non-aromatic heterocondensed polycyclic group.

As used herein, the term "Ph" denotes a phenyl group, the term "Me" denotes a methyl group, the term "Et" denotes an ethyl group, and the term "ter-Bu" or "Bu$^t$" denotes a tert-butyl group.

Hereinafter, an OLED according to an embodiment of the present disclosure will now be described with reference to the following examples. In the examples, the expression "B was used instead of A" indicates that an amount per mol of A and an amount per mol B are the same (or substantially the same).

EXAMPLE

Representative Synthesis Example 1

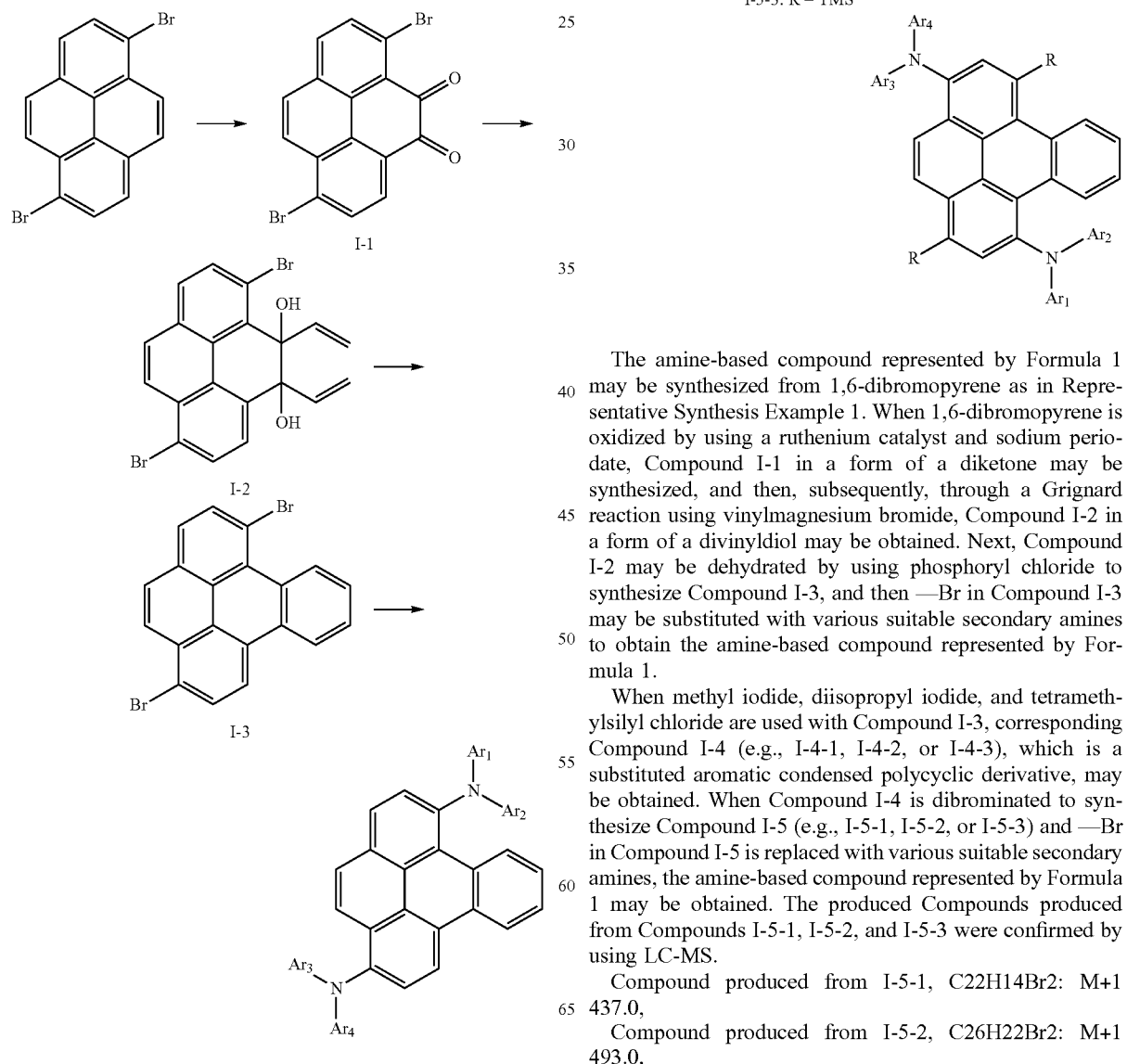

The amine-based compound represented by Formula 1 may be synthesized from 1,6-dibromopyrene as in Representative Synthesis Example 1. When 1,6-dibromopyrene is oxidized by using a ruthenium catalyst and sodium periodate, Compound I-1 in a form of a diketone may be synthesized, and then, subsequently, through a Grignard reaction using vinylmagnesium bromide, Compound I-2 in a form of a divinyldiol may be obtained. Next, Compound I-2 may be dehydrated by using phosphoryl chloride to synthesize Compound I-3, and then —Br in Compound I-3 may be substituted with various suitable secondary amines to obtain the amine-based compound represented by Formula 1.

When methyl iodide, diisopropyl iodide, and tetramethylsilyl chloride are used with Compound I-3, corresponding Compound I-4 (e.g., I-4-1, I-4-2, or I-4-3), which is a substituted aromatic condensed polycyclic derivative, may be obtained. When Compound I-4 is dibrominated to synthesize Compound I-5 (e.g., I-5-1, I-5-2, or I-5-3) and —Br in Compound I-5 is replaced with various suitable secondary amines, the amine-based compound represented by Formula 1 may be obtained. The produced Compounds produced from Compounds I-5-1, I-5-2, and I-5-3 were confirmed by using LC-MS.

Compound produced from I-5-1, C22H14Br2: M+1 437.0,

Compound produced from I-5-2, C26H22Br2: M+1 493.0,

Compound produced from I-5-3, C26H26Br2Si2: M+1 553.0.

Representative Synthesis Example 2

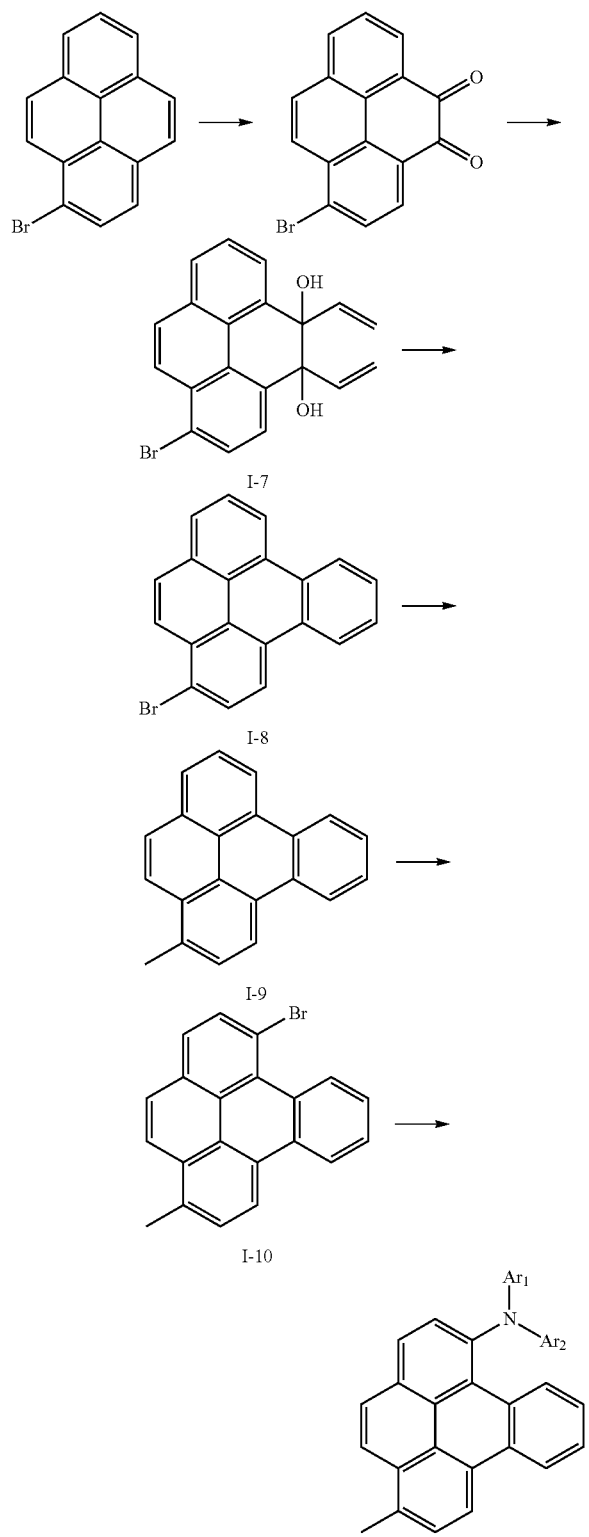

The amine-based compound represented by Formula 1 may be synthesized from 1-dibromopyrene as in Representative Synthesis Example 2. When 1-dibromopyrene is oxidized by using a ruthenium catalyst and sodium periodate, Compound I-6 in a form of a diketone may be synthesized, and then, subsequently, through a Grignard reaction using vinylmagnesium bromide, Compound I-7 in a form of a divinyldiol may be obtained. Next, Compound I-7 may be dehydrated by using phosphoryl chloride to synthesize Compound I-8, which is an aromatic condensed polycyclic compound, and then methyliodide may be used to obtain Compound I-9. When Compound I-9 is brominated to synthesize Compound I-10 and —Br in Compound 1-10 is substituted with various suitable secondary amines, the amine-based compound represented by Formula 1 may be obtained. The produced Compound produced from Compound I-10 was confirmed by using LC-MS.

C21H13Br: M+1 345.0.

Hereinafter, synthesis examples of some compounds synthesized according to an embodiment of the present disclosure will be described, and thus a compound having a structure of Formula 1 may be synthesized as described in the synthesis examples.

Synthesis Example 1: Synthesis of Compound 6

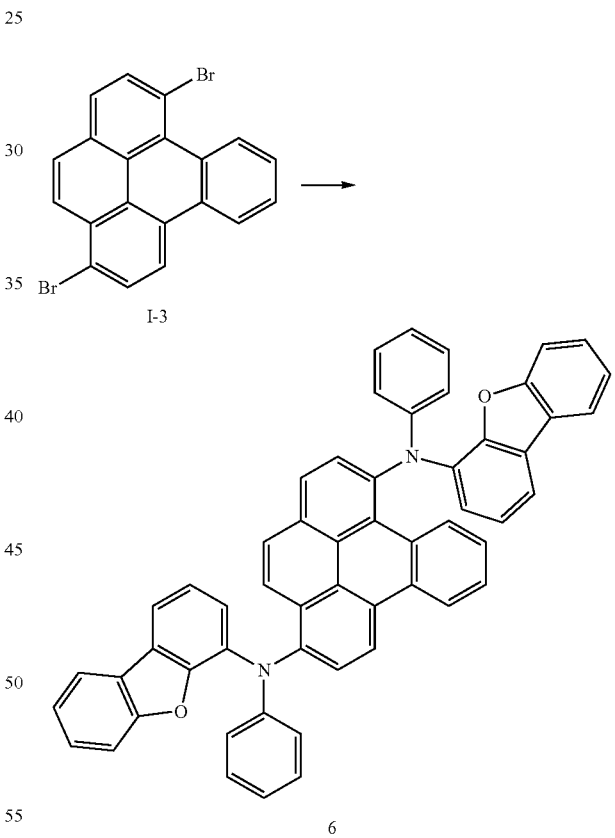

4.10 g of 1,6-dibromobenzopyrene (10.0 mmol), 5.45 g of N-phenyldibenzofuran-4-amine (21.0 mmol), 0.15 g of Pd$_2$(dba)$_3$ (0.17 mmol), 0.03 g of PtBu$_3$ (0.17 mmol), and 1.2 g of NaOtBu (12.5 mmol) were dissolved in 70 mL of toluene to prepare a solution, and the solution was stirred at a temperature of 120° C. for 5 hours. The reaction solution was cooled to room temperature and then extracted three times using salt water, water, and diethylether, respectively. An organic layer separated from the extraction was dried by using magnesium sulfate, the solvent was evaporated, and the residue thus obtained was separated and purified by using a silica gel chromatography to obtain 6.67 g of Compound 6 (yield: 87.0%). Identification of the product was confirmed by LC-MS and $^1$H NMR.

C56H34N2O2: M+1 767.3, $^1$H NMR (500 MHz, CDCl$_3$) δ=8.66 (d, 1H), 8.42 (d, 1H), 8.96-8.94 (m, 2H), 7.83-7.81 (m, 2H), 7.70-7.54 (m, 7H), 7.49-7.46 (m, 2H), 7.42-7.37 (m, 3H), 7.07-7.01 (m, 4H), 6.99-6.82 (m, 6H), 6.64-6.60 (m, 2H), 6.29-6.22 (m, 4H)

Synthesis Example 2: Synthesis of Compound 12

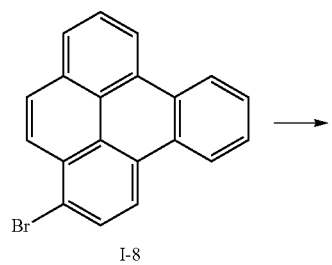
I-8

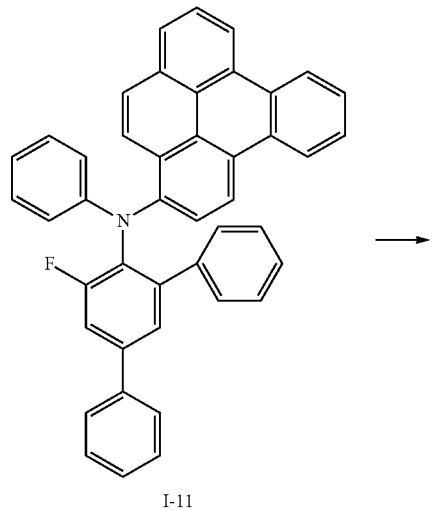
I-11

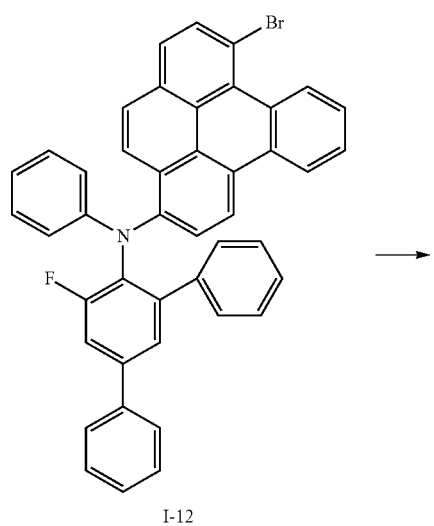
I-12

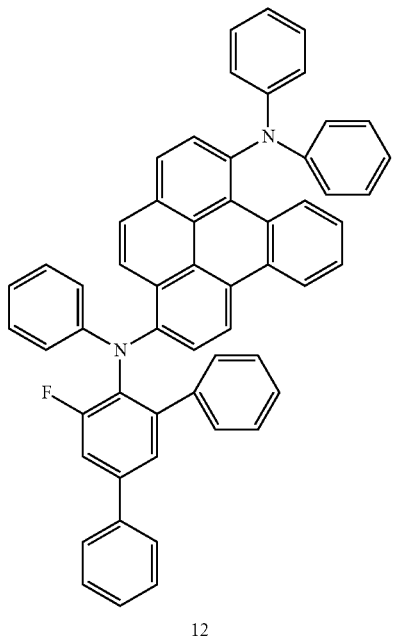
12

10.8 g of Compound I-11 (yield: 91.3%) was synthesized as described in Synthesis Example 1, except that 6.62 g of 3-bromobenzopyrene (Compound I-8, 20.0 mmol) was used instead of 1,6-dibromobenzopyrene, and 5'-fluoro-N-phenyl-[1,1':3',1''-terphenyl]-4'-amine was used instead of N-phenyldibenzofuran-4-amine. Then, Compound I-11 was reacted with bromine to synthesize 7.42 g of Compound I-12 (yield: 60.8%). Next, 6.51 g of Compound 12 (yield: 77.5%) was synthesized as described in Synthesis Example 1, except that Compound I-12 was used instead of 1,6-dibromobenzopyrene, and N,N-diphenyl amine was used instead of N-phenyldibenzofuran-4-amine. Identification of Compound 12 was confirmed by LC-MS and $^1$H NMR.

C56H37FN2: M+1 757.3, $^1$H NMR (500 MHz, CDCl$_3$) δ=8.66 (d, 1H), 8.36 (d, 1H), 8.28 (d, 1H), 7.74-7.49 (m, 14H), 7.40-7.34 (m, 4H), 7.70-7.01 (m, 7H), 6.64-6.58 (m, 3H), 6.18-6.08 (m, 6H)

Synthesis Example 3: Synthesis of Compound 24

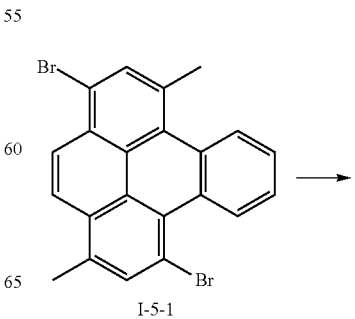
I-5-1

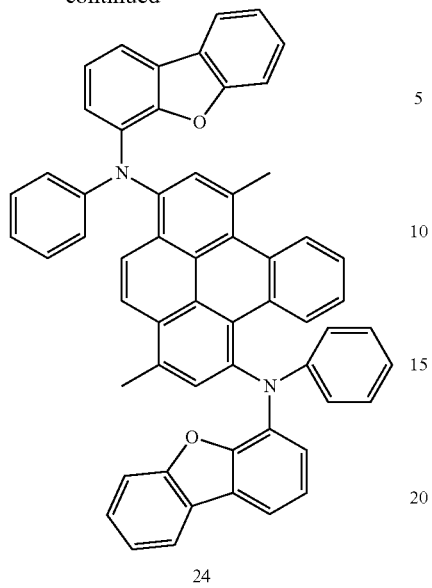

24

Compound 24 was synthesized as described in Synthesis Example 1, except that 1,6-dibromo-3,8-dimethylbenzopyrene (compound I-5-1) was used instead of 1,6-dibromobenzopyrene. Identification of Compound 24 was confirmed by LC-MS and $^1$H NMR.

C58H38N2O2: M+1 795.3, $^1$H NMR (500 MHz, CDCl$_3$) δ=8.72 (d, 1H), 8.22 (d, 1H), 8.04 (d, 1H), 7.97-7.80 (m, 3H), 7.67-7.63 (m, 4H), 7.56 (d, 1H), 7.49-7.46 (m, 3H), 7.39-7.41 (m, 2H), 7.32-7.30 (m, 2H), 7.05-6.94 (m, 8H), 6.63-6.61 (m, 2H), 2.77 (s, 3H), 2.56 (s, 3H)

Synthesis Example 4: Synthesis of Compound 25

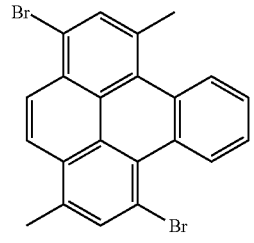

I-5-1

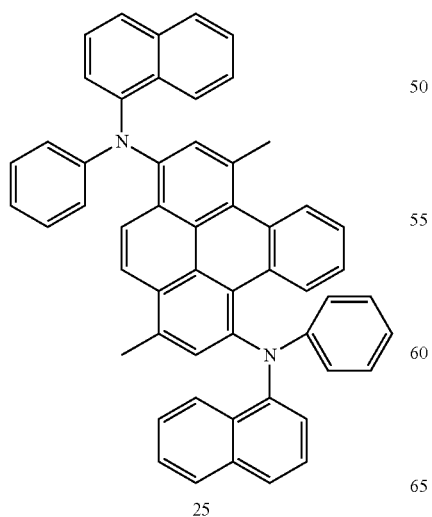

25

Compound 25 was synthesized as described in Synthesis Example 1, except that 1,6-dibromo-3,8-dimethylbenzopyrene was used instead of 1,6-dibromobenzopyrene, and N-phenylnaphthalene-1-amine was used instead of N-phenyldibenzofuran-4-amine. Identification of Compound 25 was confirmed by LC-MS and $^1$H NMR.

C54H38N2: M+1 715.3, $^1$H NMR (500 MHz, CDCl$_3$) δ=8.72 (d, 1H), 8.22 (d, 1H), 8.04-8.05 (m, 2H), 7.98 (d, 1H), 7.88-7.86 (m, 2H), 7.76 (d, 1H), 7.56-7.54 (m, 3H), 7.48-7.32 (m, 5H), 7.23-7.17 (m, 4H), 7.04-7.02 (m, 4H), 6.66-6.62 (m, 4H), 6.07-6.02 (m, 4H), 2.77 (s, 3H), 2.56 (s, 3H)

Synthesis Example 5: Synthesis of Compound 33

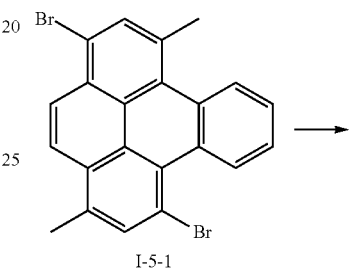

I-5-1

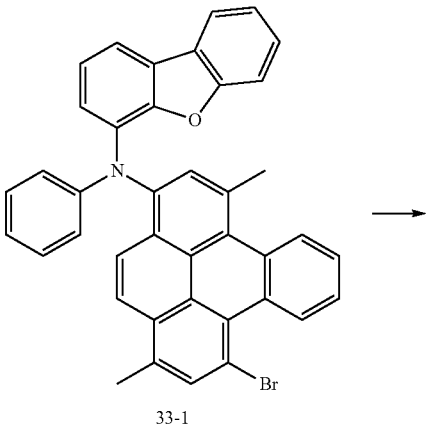

33-1

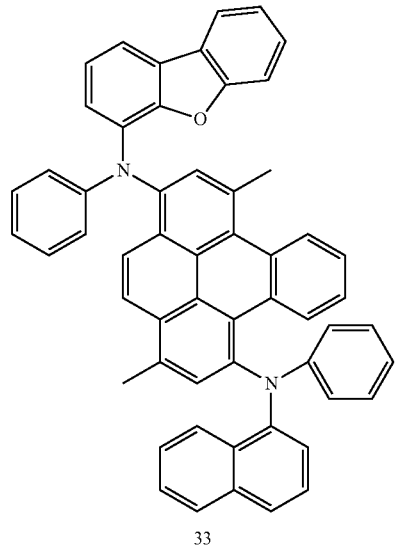

33

5.88 g of Compound 33-1 (yield: 47.7%) was synthesized as described in Synthesis Example 1, except that 8.76 g of 1,6-dibromo-3,8-dimethylbenzopyrene (Compound I-5-1, 20.0 mmol) was used instead of 1,6-dibromobenzopyrene. Then, 5.94 g of Compound 33 (yield: 82.5%) was synthesized as described in Synthesis Example 1, except that Compound 33-1 was used instead of 1,6-dibromobenzopyrene, and N-phenylnaphthalene-1-amine was used instead of N-phenyldibenzofuran-4-amine. Identification of Compound 33 was confirmed by LC-MS and $^1$H NMR.

C56H38N2O: M+1 755.3, $^1$H NMR (500 MHz, CDCl$_3$) δ=8.72 (d, 1H), 8.22 (d, 1H), 8.06-8.03 (m, 2H), 7.98 (d, 1H), 7.88-7.82 (m, 2H), 7.70-7.54 (m, 4H), 7.48-7.40 (m, 4H), 7.32-7.19 (m, 4H), 7.05-6.94 (m, 6H), 6.63-6.61 (m, 2H), 6.24-6.22 (m, 2H), 6.06-6.04 (m, 2H), 2.77 (s, 3H), 2.56 (s, 3H)

Synthesis Example 6: Synthesis of Compound 111

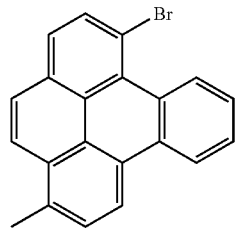

I-10

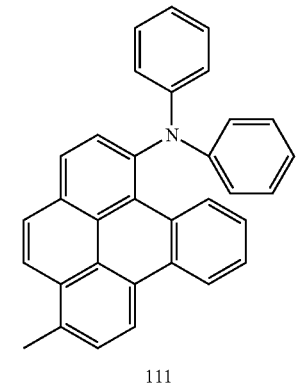

111

Compound 111 was synthesized as described in Synthesis Example 1, except that 1-bromo-6-methylbenzopyrene (i.e., Compound I-10) was used instead of 1,6-dibromobenzopyrene, and N,N-diphenylamine was used instead of N-phenyldibenzofuran-4-amine. Identification of Compound 111 was confirmed by LC-MS and $^1$H NMR.

C33H23N: M+1 434.2, $^1$H NMR (500 MHz, CDCl$_3$) δ=8.66 (d, 1H), 8.48 (d, 1H), 8.36 (t, 1H), 8.10 (t, 1H), 8.00 (d, 1H), 7.66-7.62 (m, 2H), 7.56-7.54 (m, 2H), 7.33 (t, 1H), 7.07-7.03 (m, 4H), 6.64-6.62 (m, 2H), 6.19-6.15 (m, 4H), 2.84 (s, 3H)

Synthesis Example 7: Synthesis of Compound 127

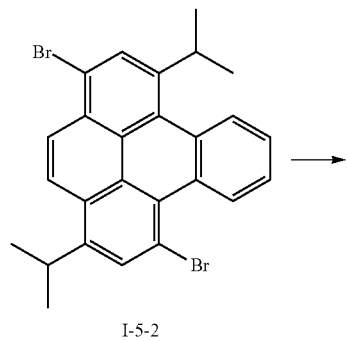

I-5-2

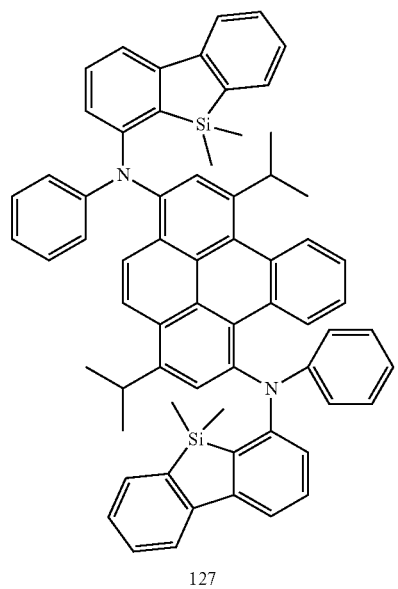

127

Compound 127 was synthesized as described in Synthesis Example 1, except that 1,6-dibromo-3,8-diisopropylbenzopyrene (i.e., Compound I-5-2) was used instead of 1,6-dibromobenzopyrene, and 5,5-dimethyl-N-phenyl-5H-dibenzosilole-4-amine was used instead of N-phenyldibenzofuran-4-amine. Identification of Compound 127 was confirmed by LC-MS and $^1$H NMR.

C66H58N2Si2: M+1 935.4, $^1$H NMR (500 MHz, CDCl$_3$) δ=8.56 (d, 1H), 8.36 (d, 1H), 8.08-8.01 (m, 3H), 7.96 (t, 1H), 7.59-7.49 (m, 6H), 7.33-7.32 (m, 2H), 7.26-7.21 (m, 6H), 7.03-7.00 (m, 4H), 6.62-6.59 (m, 4H), 6.09-6.07 (m, 4H), 4.38 (q, 1H), 4.14 (q, 1H), 1.44 (d, 6H), 1.37 (d, 6H), 0.36-0.30 (m, 12H)

Synthesis Example 8: Synthesis of Compound 129

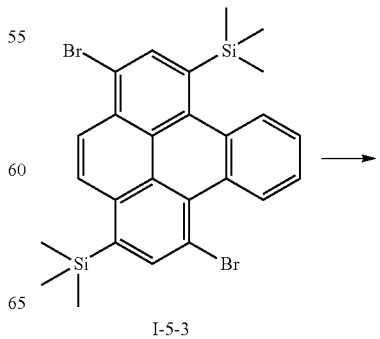

I-5-3

-continued

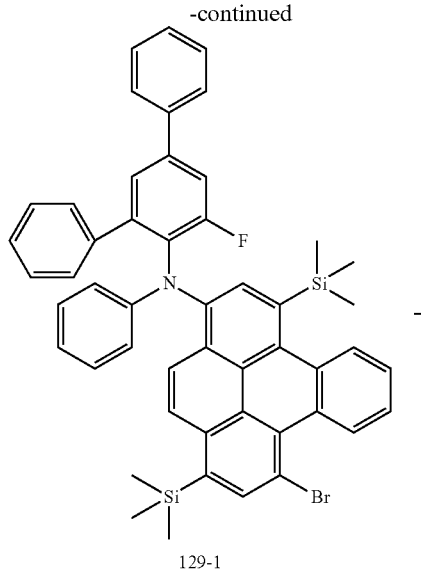
129-1

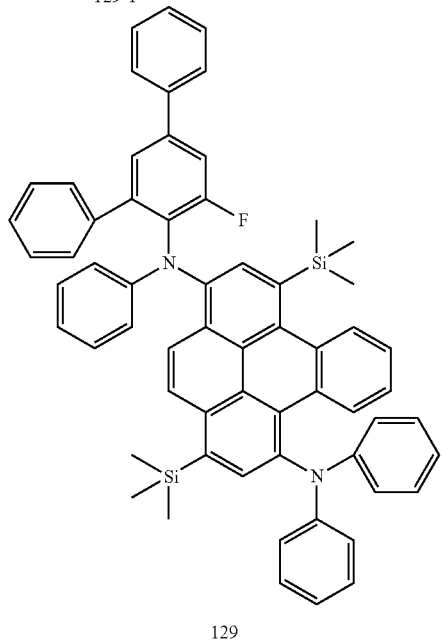
129

8.43 g of Compound 129-1 (yield: 31.9%) was synthesized as described in Synthesis Example 1, except that 18.0 g of 1,6-dibromo-3,8-trimethylsilylbenzopyrene (Compound I-5-3, 32.5 mmol) was used instead of 1,6-dibromobenzopyrene, and 5'-fluoro-N-phenyl-[1,1':3',1''-terphenyl]-4'-amine was used instead of N-phenyldibenzofuran-4-amine. Then, 7.42 g of Compound 129 (yield: 79.4%) was synthesized as described in Synthesis Example 1, except that Compound 129-1 was used instead of 1,6-dibromobenzopyrene, and N,N-diphenyl amine was used instead of N-phenyldibenzofuran-4-amine. Identification of Compound 129 was confirmed by LC-MS and $^1$H NMR.

C62H53FN2Si2: M+1 901.4, $^1$H NMR (500 MHz, CDCl$_3$) δ=8.57 (d, 1H), 8.37 (d, 1H), 8.19 (d, 1H), 7.99 (t, 1H), 7.68-7.50 (m, 11H), 7.41-7.38 (m, 1H), 7.34 (t, 1H), 7.31 (d, 1H), 7.09-7.04 (m, 7H), 7.63-7.60 (m, 3H), 6.13-6.11 (m, 4H), 6.06-6.04 (m, 2H), 0.47 (s, 9H), 0.41 (s, 9H)

Example 1

An ITO glass substrate (available from Corning Co.) including an ITO layer having a thickness of 1200 Å (sheet resistance of 15 Ω/cm$^2$), as an anode, was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was then mounted on a vacuum depositor.

2-TNATA was deposited on the ITO anode to form an HIL having a thickness of 600 Å, NPB was deposited on the HIL to form an HTL having a thickness of 300 Å, and then DNA (a host) and Compound 2 were co-deposited at a weight ratio of 98:2 on the HTL to form an EML having a thickness of 300 Å.

Then, Alq$_3$ was deposited on the EML to form an ETL having a thickness of 300 Å. LiF was deposited on the ETL to form an EIL having a thickness of 10 Å, and Al was vacuum-deposited on the EIL to form a cathode having a thickness of 3000 Å, thereby completing manufacture of an OLED.

Example 2

An OLED was manufactured as described in Example 1, except that Compound 3 was used instead of Compound 2 in the formation of the EML.

Example 3

An OLED was manufactured as described in Example 1, except that Compound 12 was used instead of Compound 2 in the formation of the EML.

Example 4

An OLED was manufactured as described in Example 1, except that Compound 20 was used instead of Compound 2 in the formation of the EML.

Comparative Example 1

An OLED was manufactured as described in Example 1, except that Compound A was used instead of Compound 2 in the formation of the ETL.

Compound A

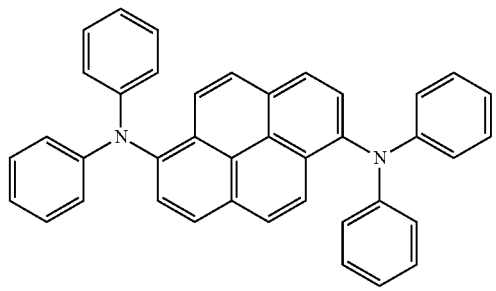

Evaluation Example 1

Driving voltages, current densities, brightnesses, efficiencies, and half-lives of the OLEDs prepared in Examples 1 to 4 and Comparative Example 1 were evaluated by using Keithley SMU 236 and PR650 Spectroscan Source Measurement Unit (PhotoResearch), and the results are shown in Table 1. The half-life was the time consumed (e.g., the time that elapsed) for an OLED to have 50% reduced brightness after driving the device compared to its initial brightness.

TABLE 1

|  | Dopant | Driving voltage (V) | Current density (mA/cm$^2$) | Brightness (cd/m$^2$) | Efficiency (cd/A) | Color of emitted light | Half-life (hr@ 100 mA/cm$^2$) |
| --- | --- | --- | --- | --- | --- | --- | --- |
| Example 1 | Compound 2 | 6.85 | 50 | 3290 | 6.94 | Blue | 335 |
| Example 2 | Compound 3 | 6.72 | 50 | 3210 | 7.13 | Blue | 320 |
| Example 3 | Compound 12 | 6.59 | 50 | 3340 | 7.35 | Blue | 360 |
| Example 4 | Compound 20 | 6.63 | 50 | 3270 | 7.29 | Blue | 345 |
| Comparative Example 1 | Compound A | 7.01 | 50 | 2645 | 5.29 | Blue | 258 |

Referring to Table 1, the OLEDs prepared in Examples 1 to 4 had better driving voltages, brightnesses, efficiencies, and half-lives than those of the OLED prepared in Comparative Example 1.

As described above, according to one or more of the above embodiments of the present disclosure, an OLED including the amine-based compound may have a low driving voltage, a high efficiency, a high brightness, a long lifespan, and a high color purity.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the accompanying drawing, it will be understood by those of ordinary skill in the art that various changes in form and details may be made herein without departing from the spirit and scope of the present invention as defined by the following claims, and equivalents thereof.

What is claimed is:
1. An amine-based compound represented by Formula 1:

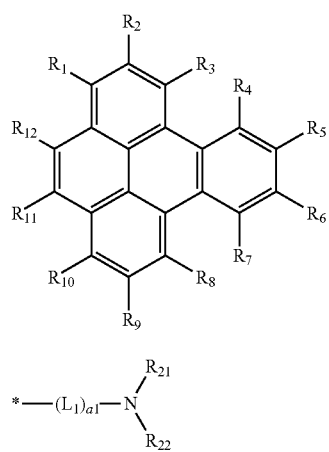

Formula 1

Formula 2 wherein, in Formulae 1 and 2,
$L_1$ is selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic hetero-condensed polycyclic group;
a1 is selected from 0, 1, 2 and 3;
$R_1$, $R_3$, $R_8$, and $R_{10}$ are each independently selected from a group represented by Formula 2, a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$);
at least one of $R_1$, $R_3$, $R_8$, and $R_{10}$ is a group represented by Formula 2;
$R_2$, $R_4$ to $R_7$, $R_9$, $R_{11}$, and $R_{12}$ are each independently selected from a hydrogen atom, a deuterium atom, a halogen atom, a hydroxyl group, a cyano group, a nitro group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$),
wherein $Q_3$ to $Q_5$ are each independently selected from a $C_1$-$C_{20}$ alkyl group, a phenyl group, and a naphthyl group;
$R_{21}$ and $R_{22}$ are each independently selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic hetero-condensed polycyclic group;

at least one substituent of the substituted $C_3$-$C_{10}$ cycloalkylene group, substituted $C_3$-$C_{10}$ heterocycloalkylene group, substituted $C_3$-$C_{10}$ cycloalkenylene group, substituted $C_3$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_3$-$C_{10}$ heterocycloalkyl group, substituted $C_3$-$C_{10}$ cycloalkenyl group, substituted $C_3$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic hetero-condensed polycyclic group is selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy;

a $C_1$-$C_{60}$ alkyl group, a $C_2$-$C_{60}$ alkenyl group, a $C_2$-$C_{60}$ alkynyl group, and a $C_1$-$C_{60}$ alkoxy, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy, a $C_6$-$C_{60}$ arylthio, a $C_1$-$C_{60}$ group, a monovalent non-aromatic condensed polycyclic group, a monovalent non-aromatic hetero-condensed polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ a alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic hetero-condensed polycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ are each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic hetero-condensed polycyclic group, and wherein:

$R_3$ and $R_{10}$ are each independently a group represented by Formula 2;

$R_3$ and $R_8$ are each independently a group represented by Formula 2;

$R_1$ and $R_{10}$ are each independently a group represented by Formula 2;

$R_1$ and $R_8$ are each independently a group represented by Formula 2;

$R_1$ and $R_3$ are each independently a group represented by Formula 2; or $R_8$ and $R_{10}$ are each independently a group represented by Formula 2.

2. The amine-based compound of claim 1, wherein, in Formula 2, $L_1$ is a group selected from Formulae 3-1 to 3-30:

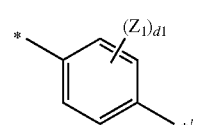

3-1

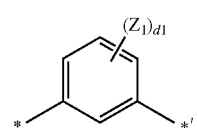

3-2

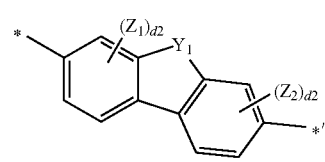

3-3

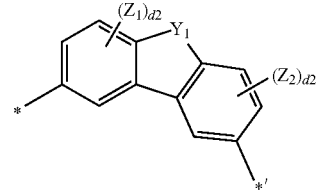

3-4

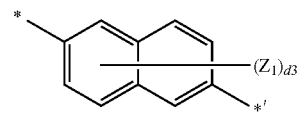

3-5

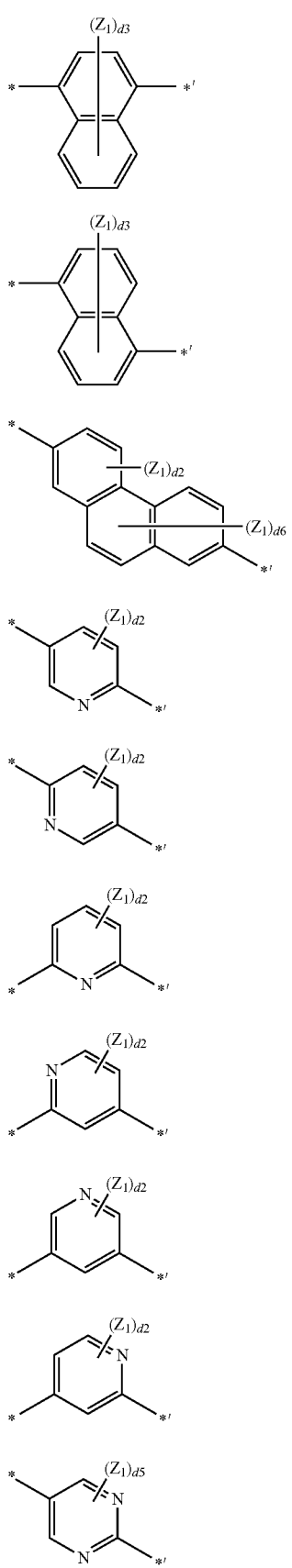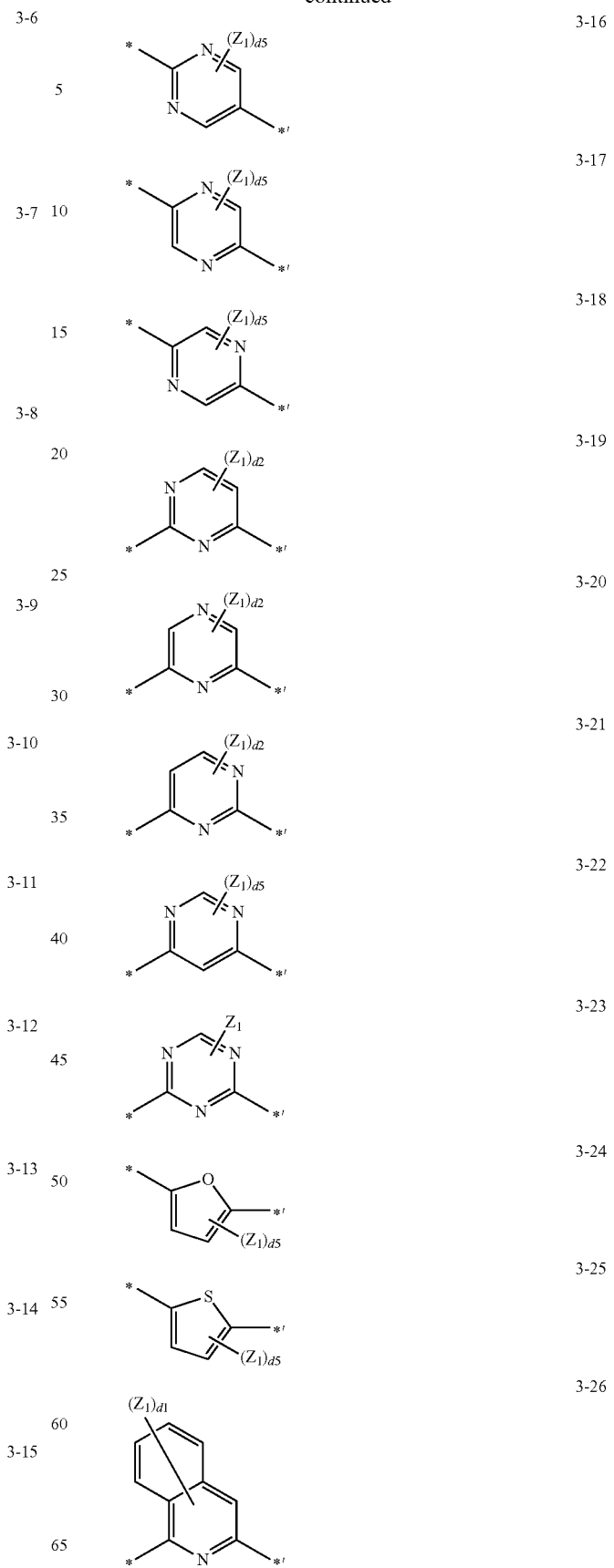

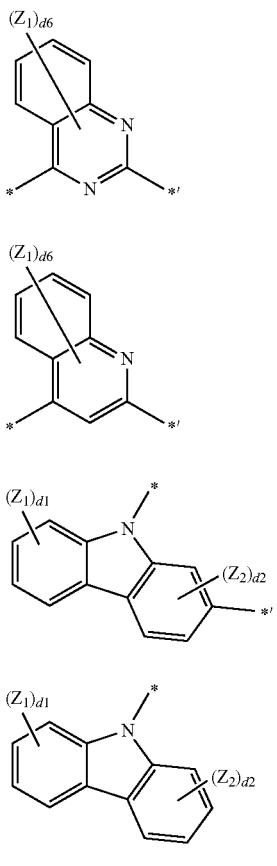

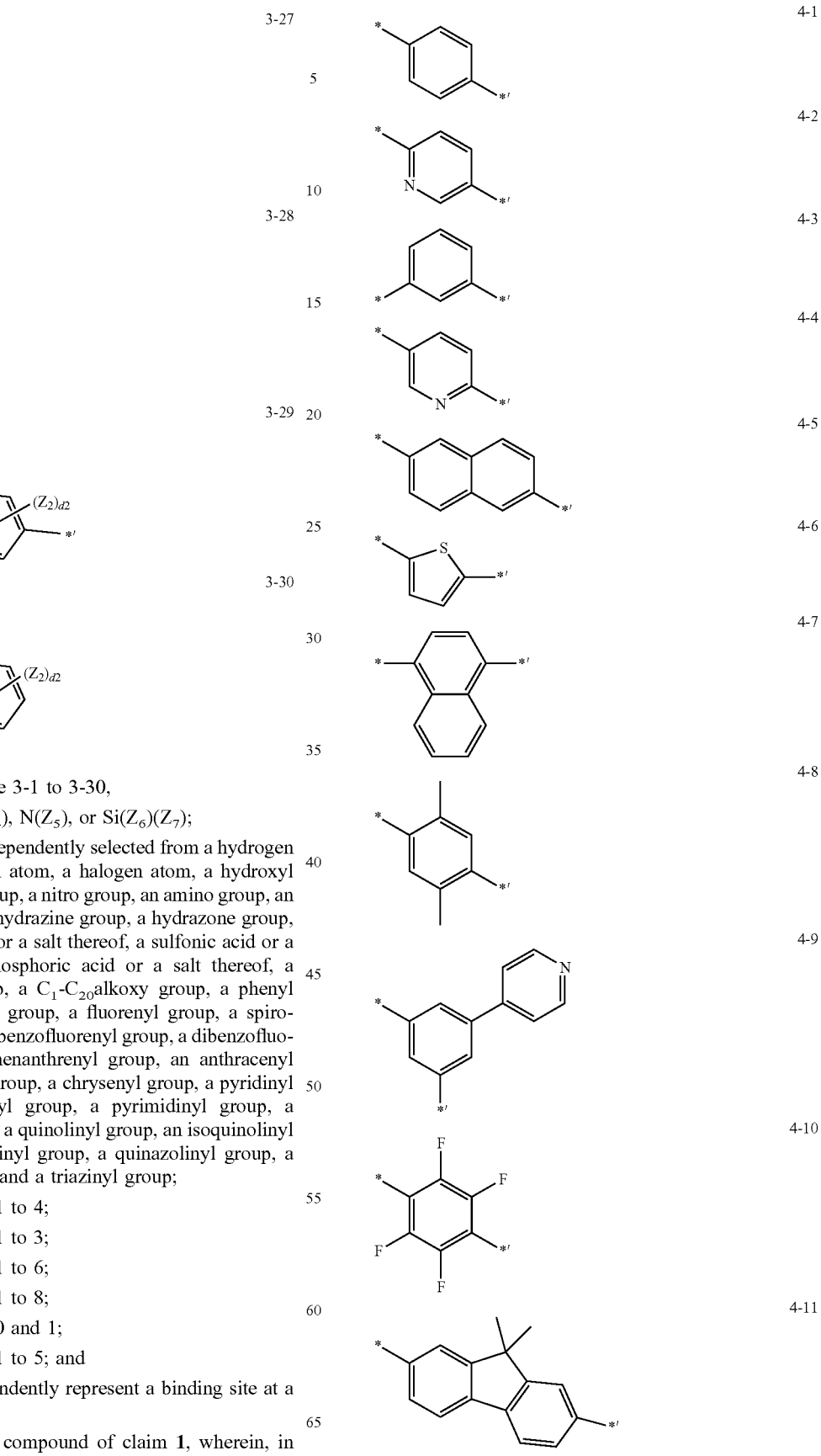

wherein, in Formulae 3-1 to 3-30, $Y_1$ is O, S, $C(Z_3)(Z_4)$, $N(Z_5)$, or $Si(Z_6)(Z_7)$;

$Z_1$ to $Z_7$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$alkyl group, a $C_1$-$C_{20}$alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 is selected from 1 to 4;

d2 is selected from 1 to 3;

d3 is selected from 1 to 6;

d4 is selected from 1 to 8;

d5 is selected from 0 and 1;

d6 is selected from 1 to 5; and

\* and \*' each independently represent a binding site at a neighboring atom.

3. The amine-based compound of claim 1, wherein, in Formula 2, $L_1$ is a group selected from Formulae 4-1 to 4-21:

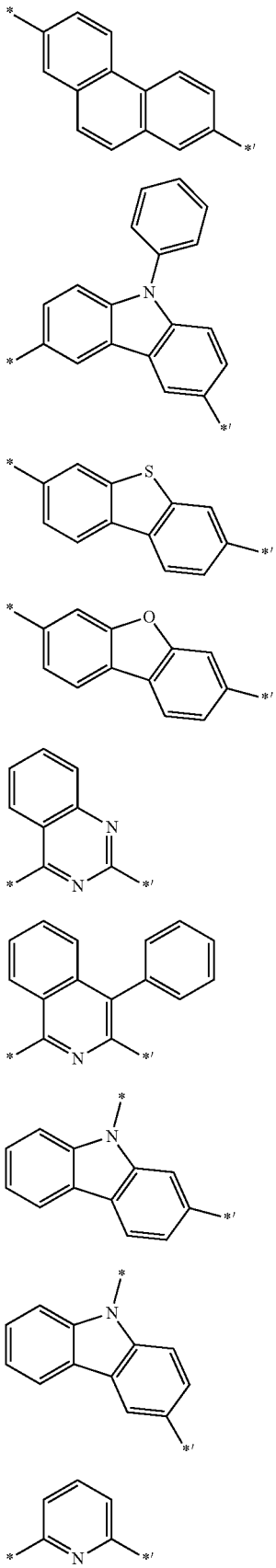

wherein, in Formulae 4-1 to 4-24,
and *' each independently represent a binding site at a neighboring atom.

4. The amine-based compound of claim 1, wherein $R_{21}$ and $R_{22}$ are each independently selected from:

a phenyl group, a naphthyl group, a fluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, a quinolinyl group, an isoquinolinyl group, a phenanthridinyl group, an acridinyl group, a phenanthrolinyl group, a benzimidazolyl group, a benzofuranyl group, a benzothiophenyl group, a benzoxazolyl group, a triazolyl group, a tetrazolyl group, a triazinyl group, a dibenzofuranyl group, a dibenzothiophenyl group, and a dibenzosilolyl group; and a phenyl group, a naphthyl group, a fluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, a quinolinyl group, an isoquinolinyl group, a phenanthridinyl group, an acridinyl group, a phenanthrolinyl group, a benzimidazolyl group, a benzofuranyl group, a benzothiophenyl group, a benzoxazolyl group, a triazolyl group, a tetrazolyl group, a triazinyl group, a dibenzofuranyl group, a dibenzothiophenyl group, and a dibenzosilolyl group, each substituted with at least one selected from a deuterium atom, a halogen atom, a cyano group, a nitro group, a methyl group, an ethyl group, an n-propyl group, a tert-butyl group, a methoxy group, an ethoxy group, a tert-butoxy group, —Si(CH$_3$)$_3$, —Si(Ph)$_3$, —CF$_3$, a phenyl group, a naphthyl group, a fluorenyl group, a phenanthrenyl group, an anthracenyl group, a triphenylenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a naphthyridinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, and a dibenzothiophenyl group.

5. The amine-based compound of claim 1, wherein $R_{21}$ and $R_{22}$ are each independently a group selected from Formulae 5-1 to 5-52:

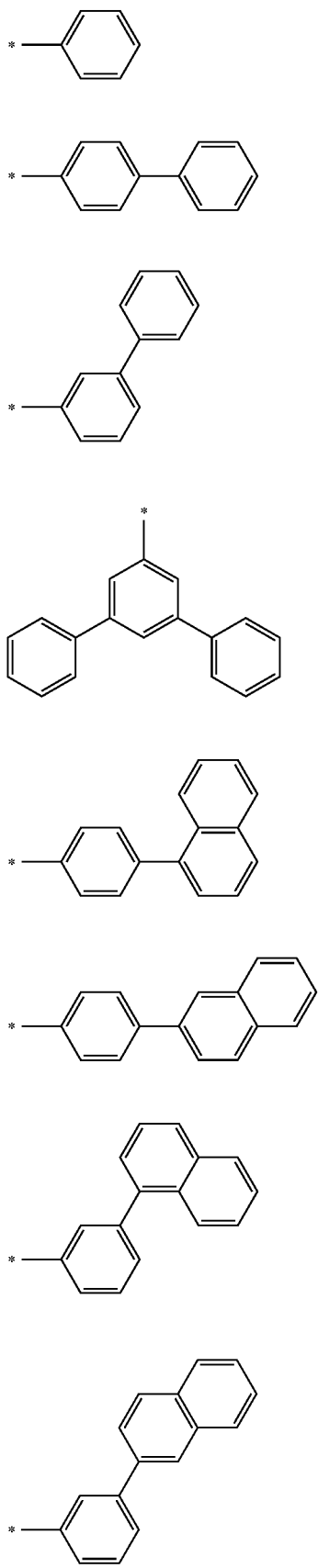
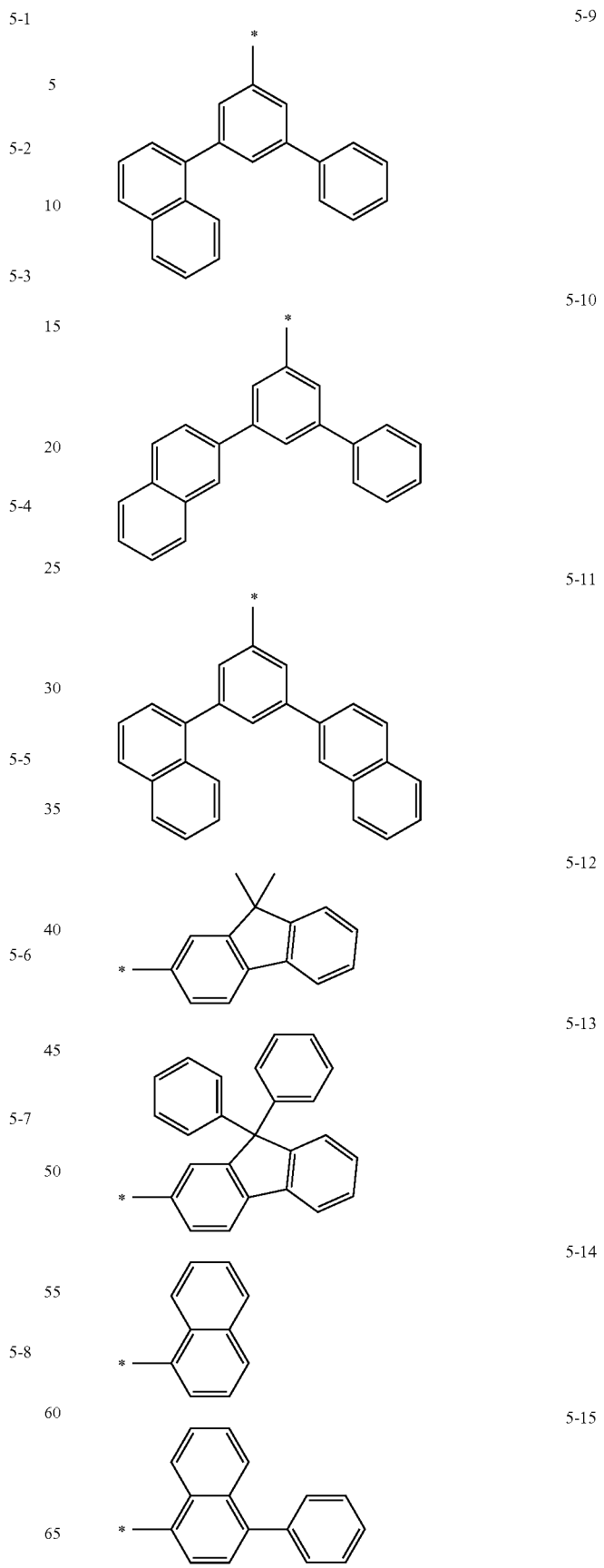

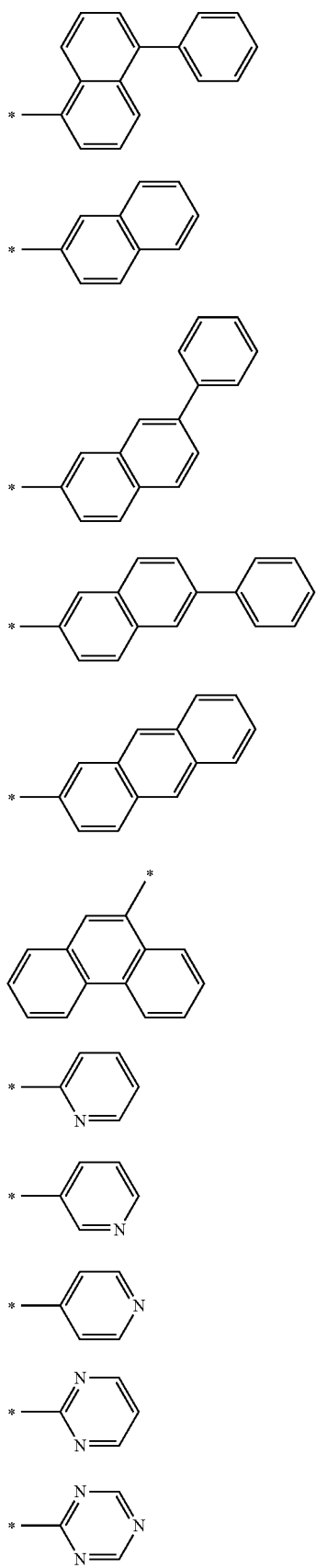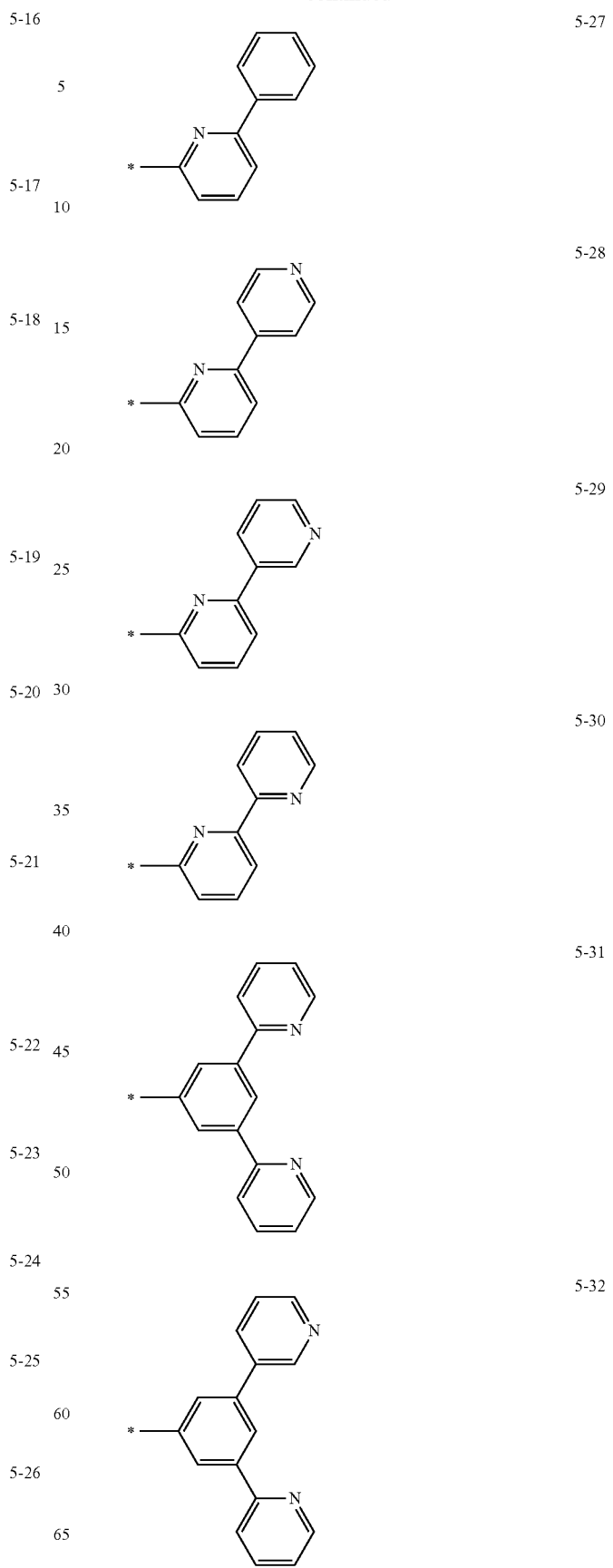

-continued
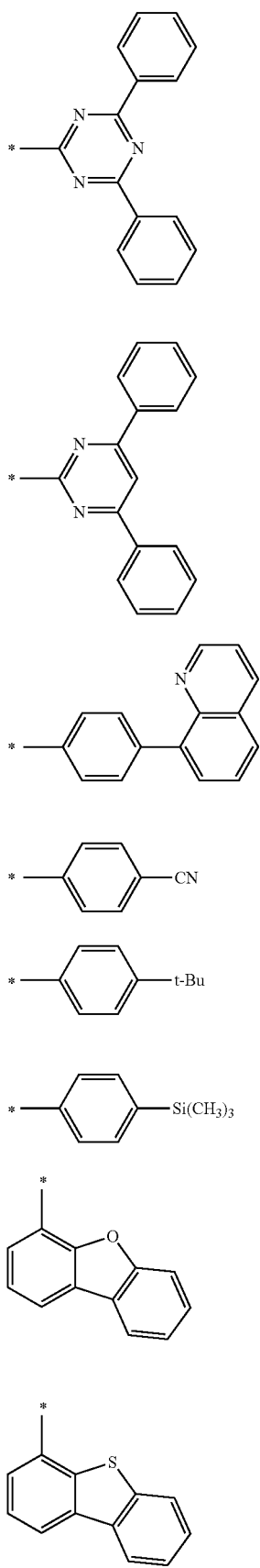
-continued
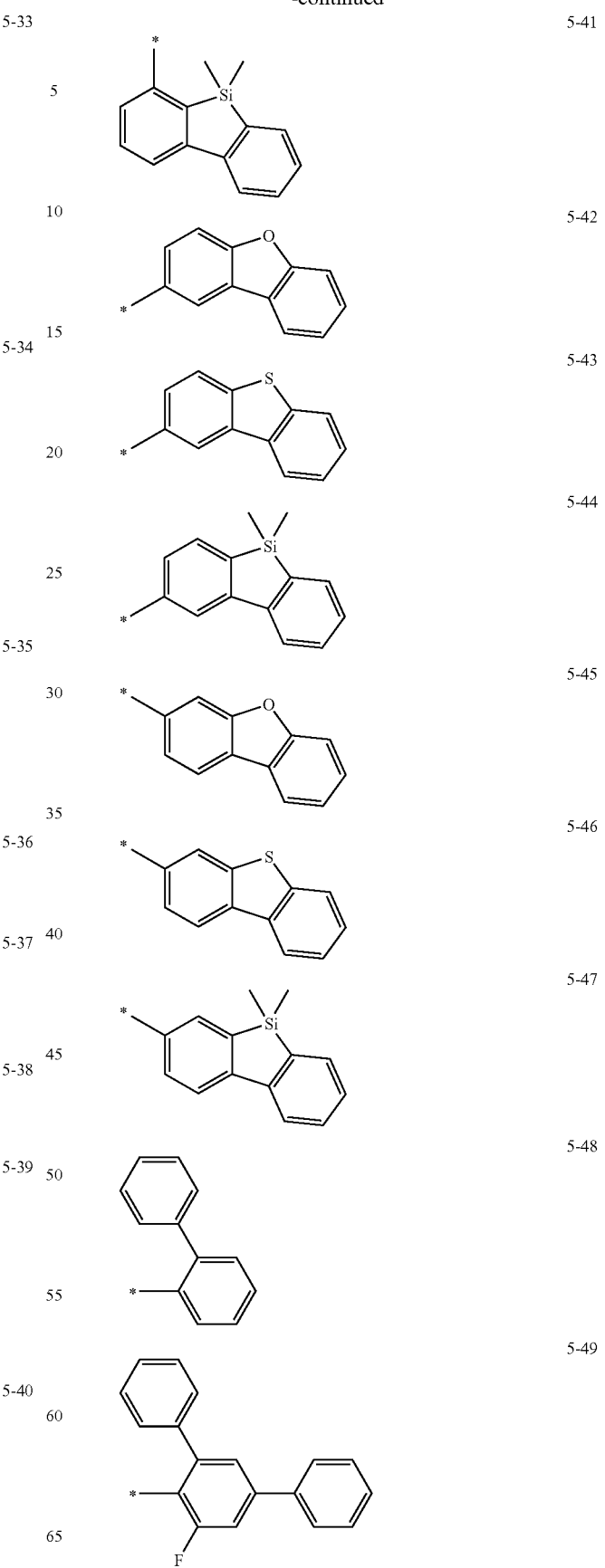

-continued

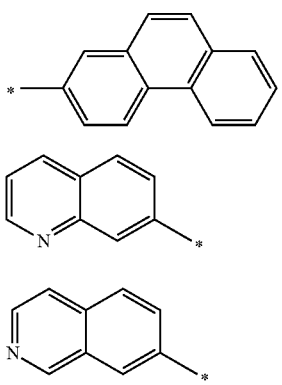

5-50

5-51

5-52 wherein, in Formulae 5-1 to 5-52,
* represents a binding site at a neighboring atom.

6. The amine-based compound of claim 1, wherein the amine-based compound is represented by Formula 1A:

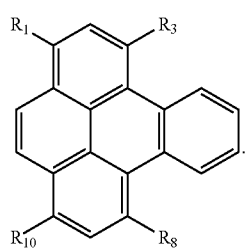

Formula 1A

7. The amine-based compound of claim 6, wherein in Formula 1A,
$R_1$ is a group represented by Formula 2;
one selected from $R_3$, $R_8$, and $R_{10}$ is a group represented by Formula 2; and
remaining ones of $R_3$, $R_8$, and $R_{10}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), and
wherein $Q_3$ to $Q_5$ are each independently selected from a $C_1$-$C_{20}$ alkyl group, a phenyl group, and a naphthyl group.

8. The amine-based compound of claim 6, wherein, in Formula 1A,
$R_1$ and $R_{10}$ are each independently a group represented by Formula 2; and
$R_3$ and $R_8$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), and
wherein $Q_3$ to $Q_5$ are each independently selected from a $C_1$-$C_{20}$ alkyl group, a phenyl group, and a naphthyl group.

9. The amine-based compound of claim 6, wherein, in Formula 1A,
$R_3$ is a group represented by Formula 2;
one selected from $R_1$, $R_8$, and $R_{10}$ is a group represented by Formula 2; and
remaining ones of $R_1$, $R_8$, and $R_{10}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), and
wherein $Q_3$ to $Q_5$ are each independently selected from a $C_1$-$C_{20}$ alkyl group, a phenyl group, and a naphthyl group.

10. The amine-based compound of claim 6, wherein, in Formula 1A,
$R_3$ and $R_8$ are each independently a group represented by Formula 2; and
$R_1$ and $R_{10}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_3$)($Q_4$)($Q_5$), and
wherein $Q_3$ to $Q_5$ are each independently selected from a $C_1$-$C_{20}$ alkyl group, a phenyl group, and a naphthyl group.

11. The amine-based compound of claim 6, wherein, in Formula 1,
$R_1$ and $R_5$ are each independently a group represented by Formula 2; and R$_3$ and R$_{10}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si(Q$_3$)(Q$_4$)(Q$_5$), and wherein Q$_3$ to Q$_5$ are each independently selected from a C$_1$-C$_{20}$ alkyl group, a phenyl group, and a naphthyl group.

12. The amine-based compound of claim 6, wherein, in Formula 1A,
R$_3$ and R$_{10}$ are each independently a group represented by Formula 2; and R$_1$ and R$_8$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si(Q$_3$)(Q$_4$)(Q$_5$), and wherein Q$_3$ to Q$_5$ are each independently selected from a C$_1$-C$_{20}$ alkyl group, a phenyl group, and a naphthyl group.

13. An amine-based compound selected from one of Compounds 1 to 153:

1

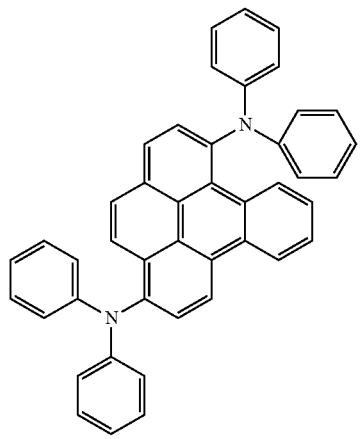

2

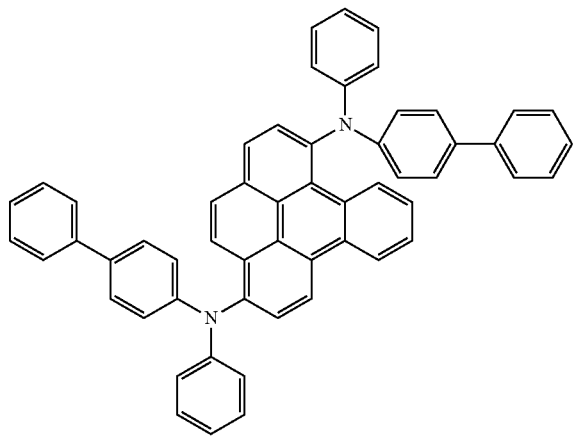

3

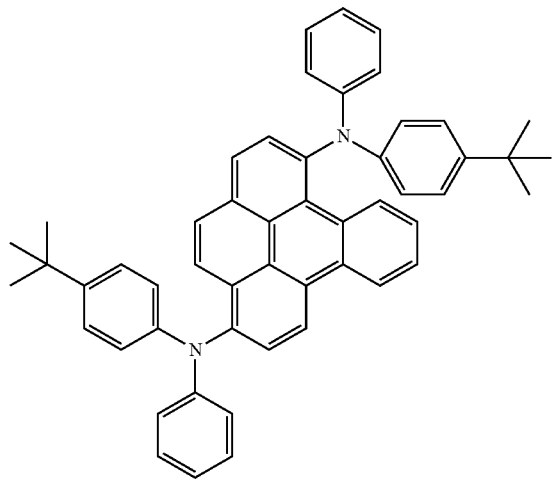

4

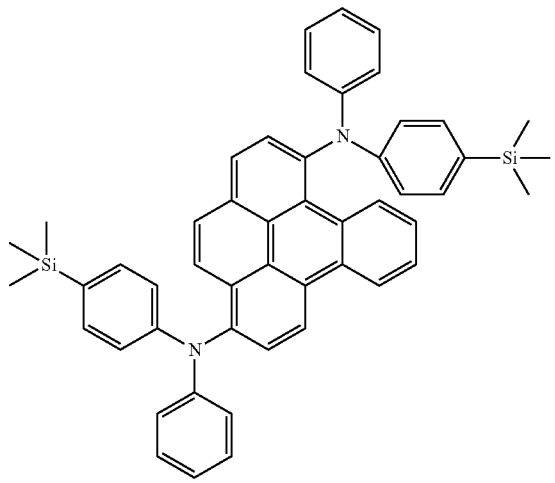

| 5 | 6 |
|---|---|
| 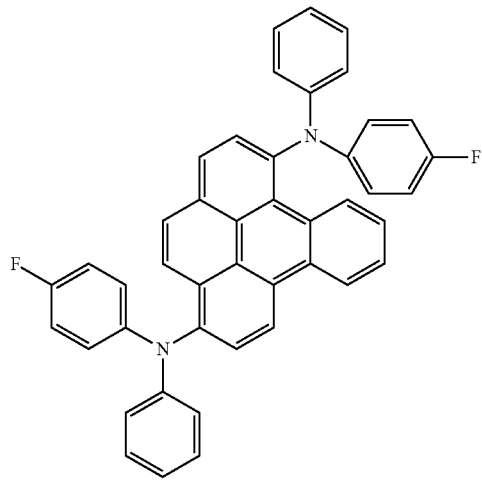 | 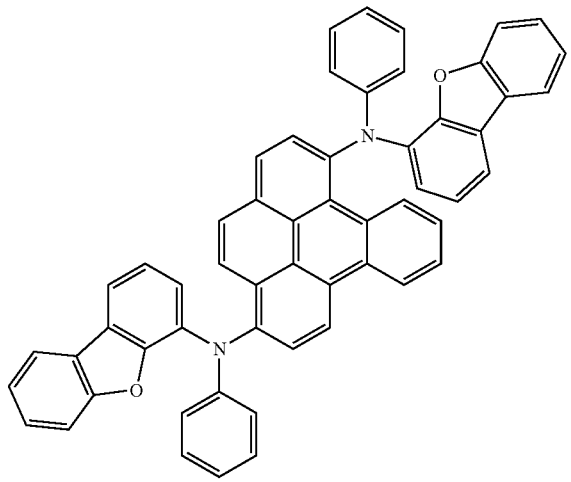 |
| 7 | 8 |
| 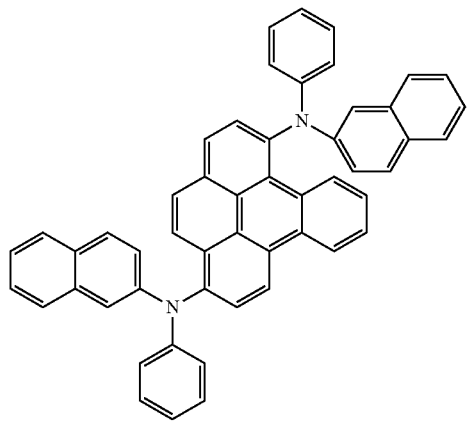 | 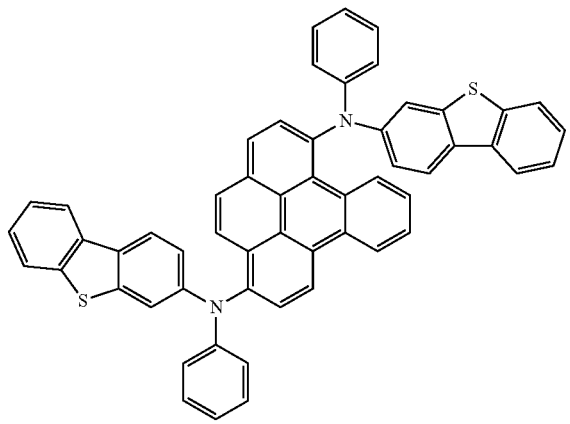 |
| 9 | 10 |
| 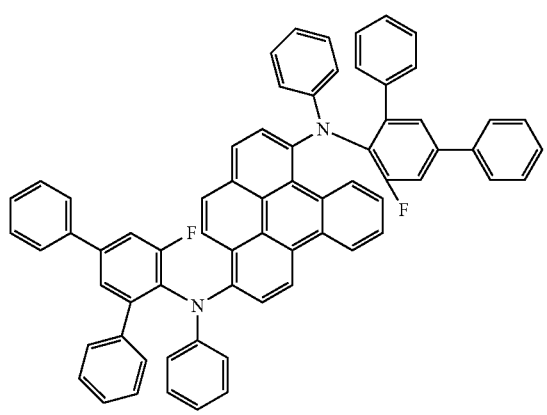 | 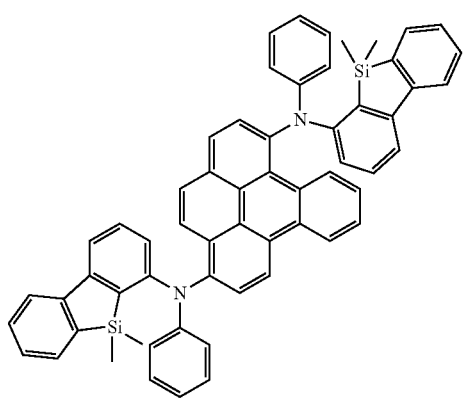 |

-continued
11
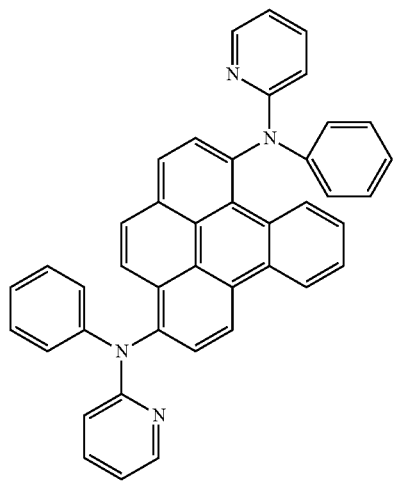
12
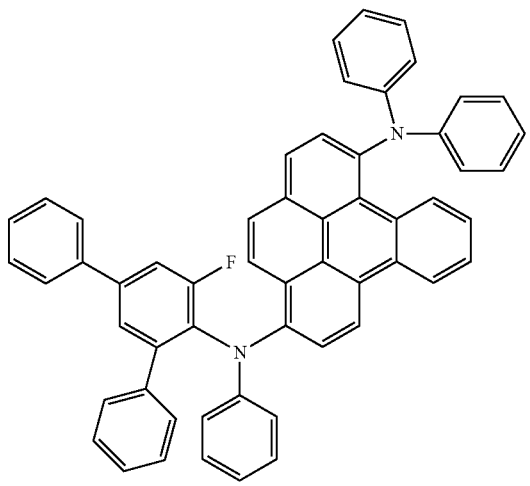
13
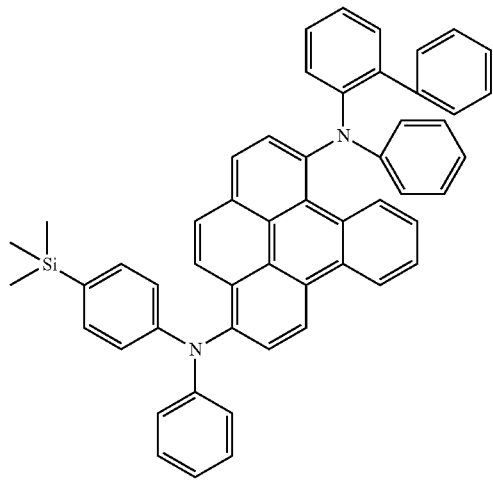
14
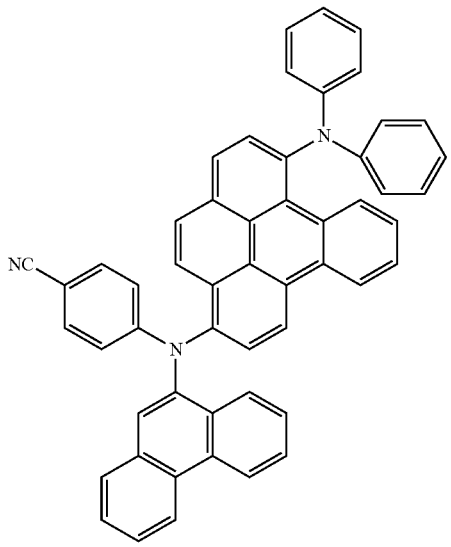
15
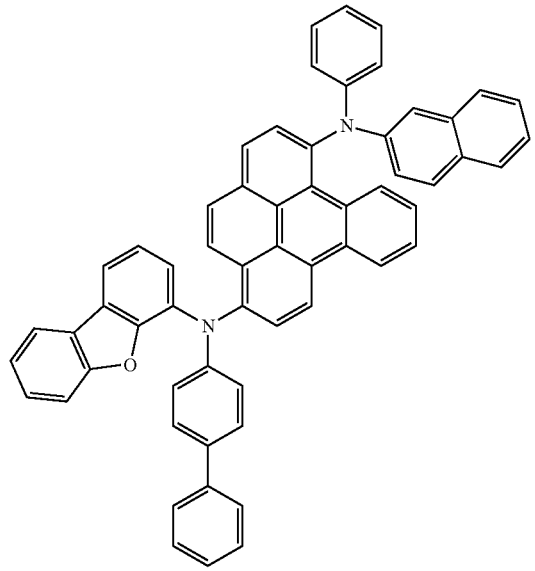
16
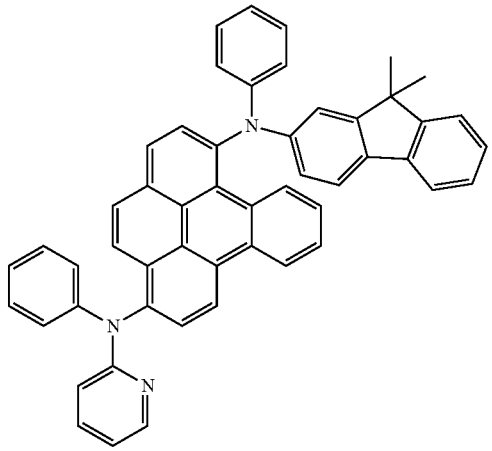

189
17
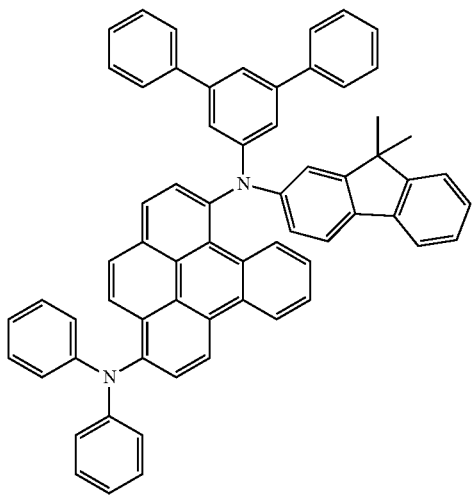
190
18
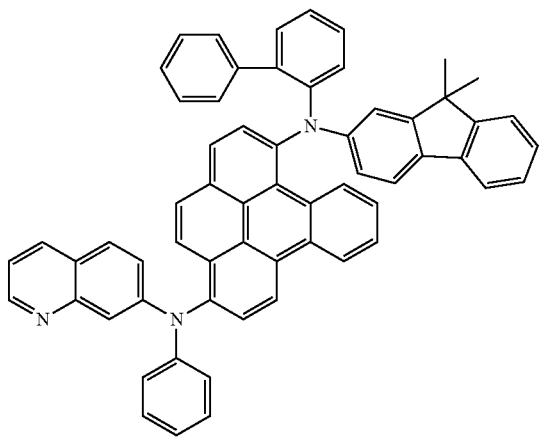
19
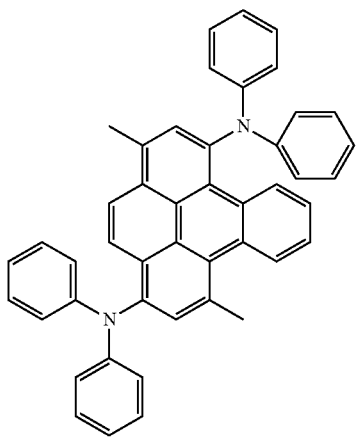
20
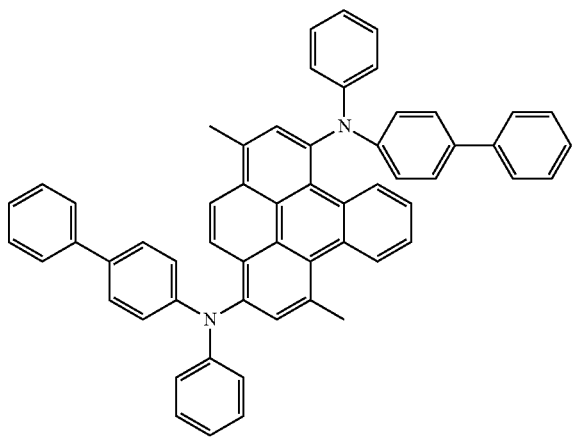
21
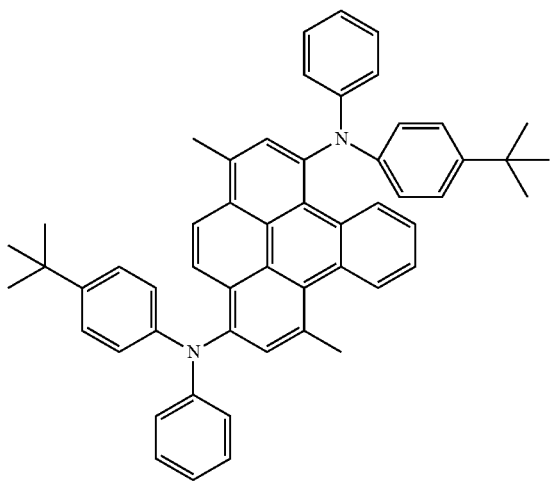
22
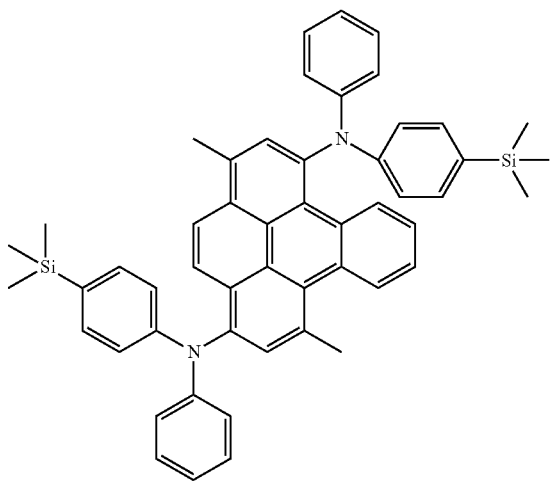

-continued
23
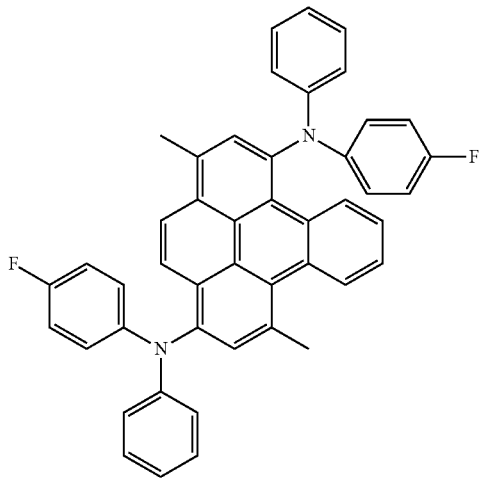
24
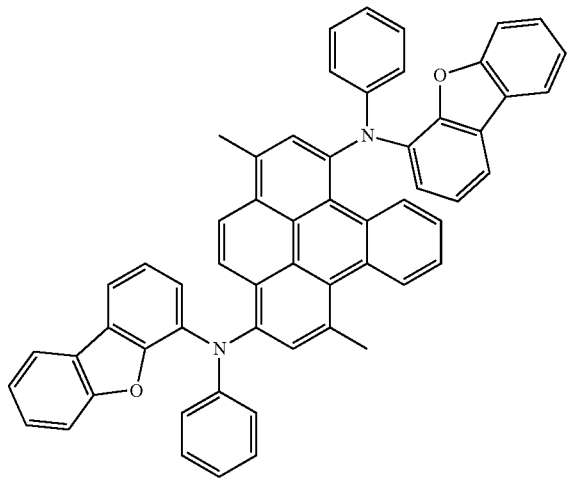
25
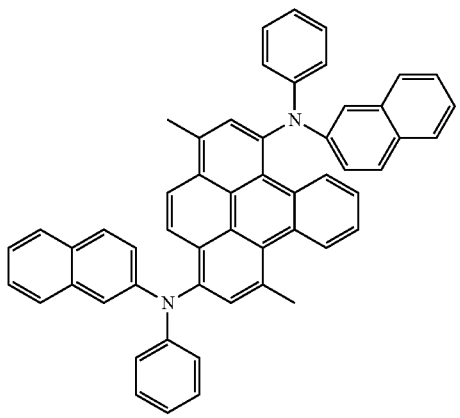
26
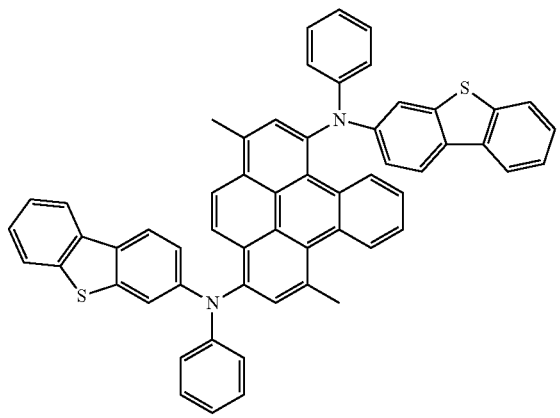
27
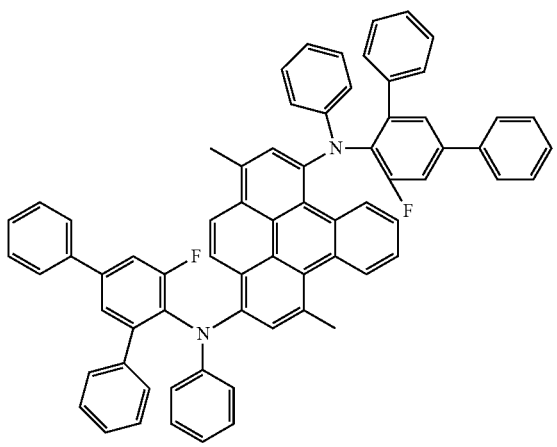
28
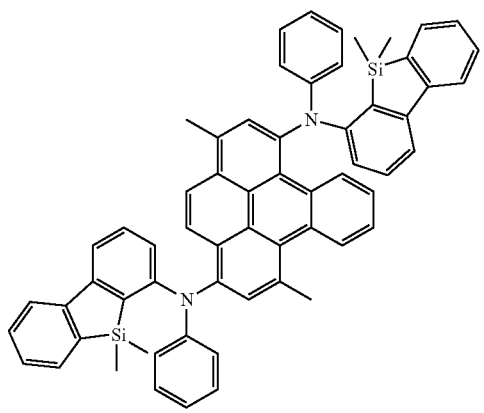

-continued
29
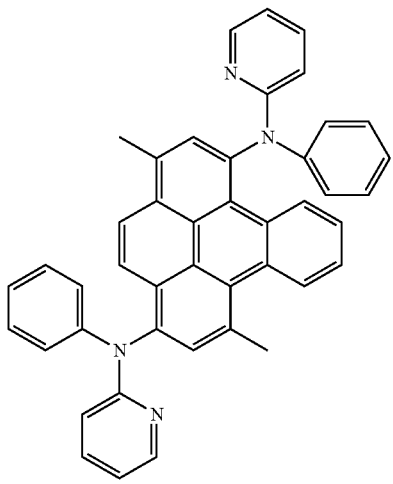
30
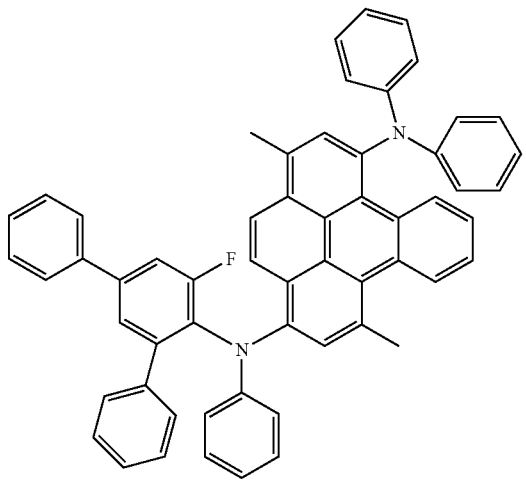
31
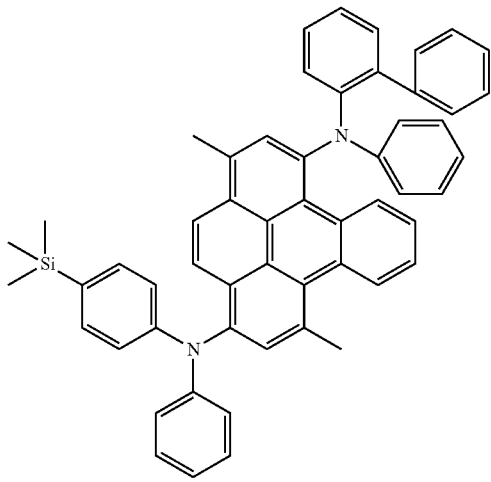
32
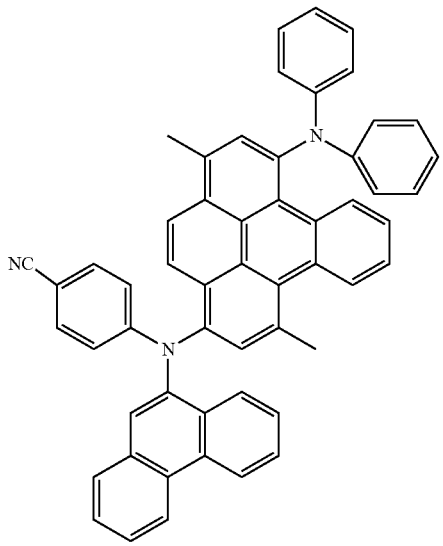
33
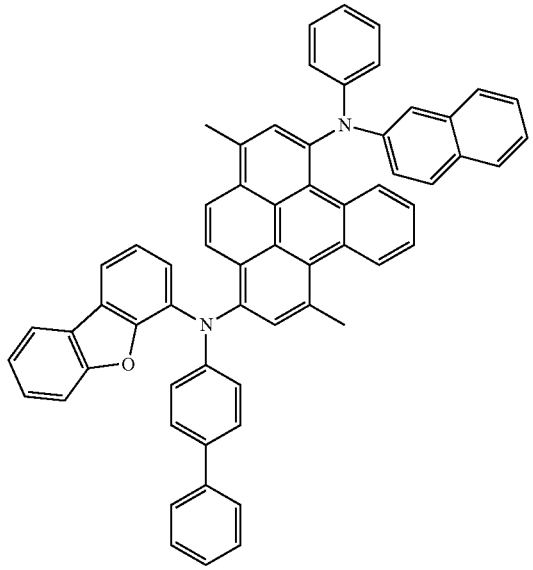
34
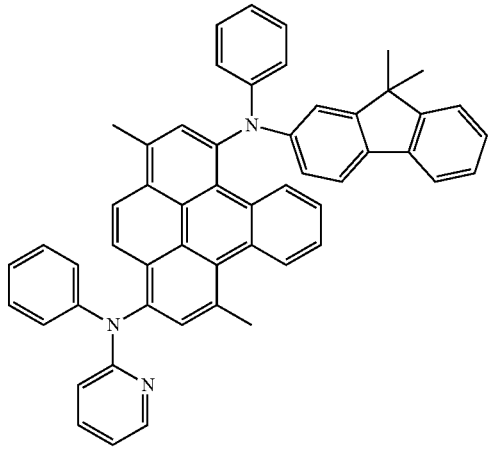

-continued
35
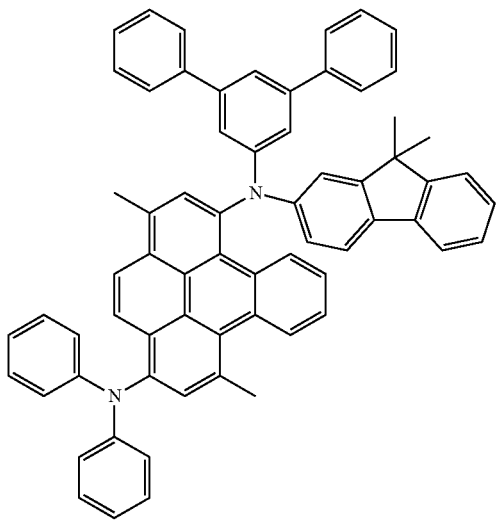
36
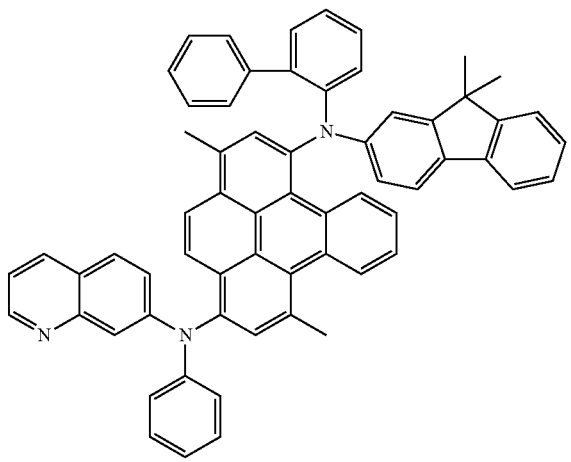
37
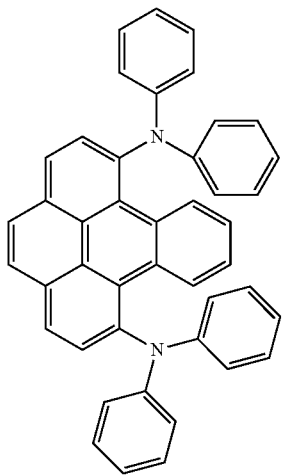
38
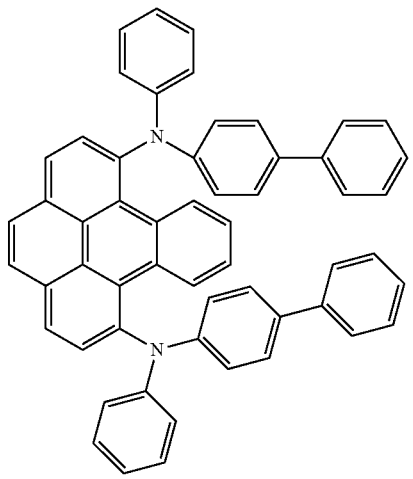
39
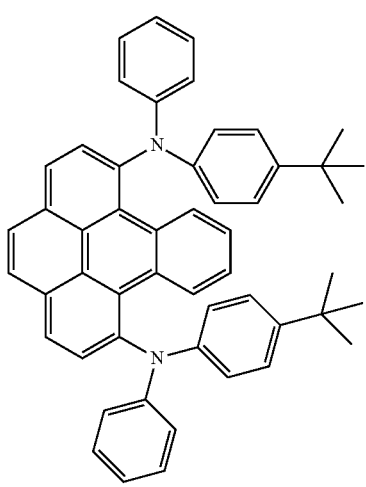
40
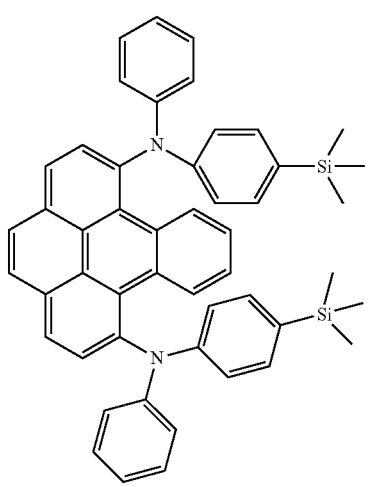

197 198
-continued
41 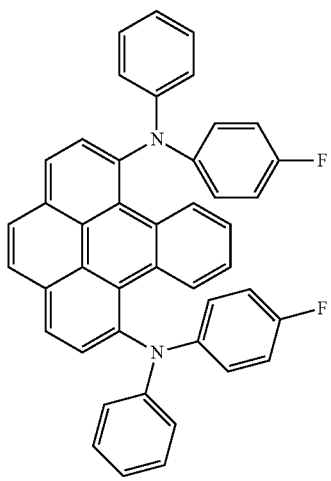 42 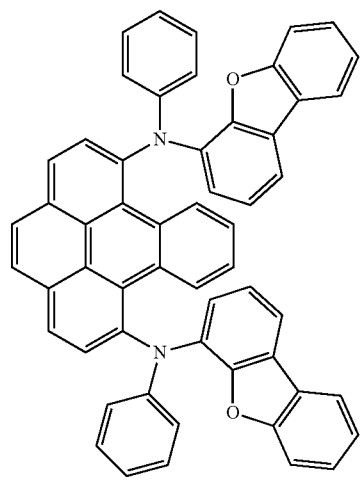
43 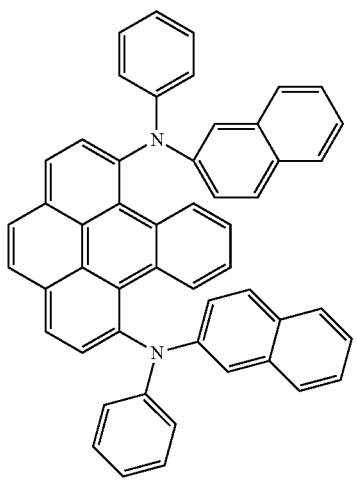 44 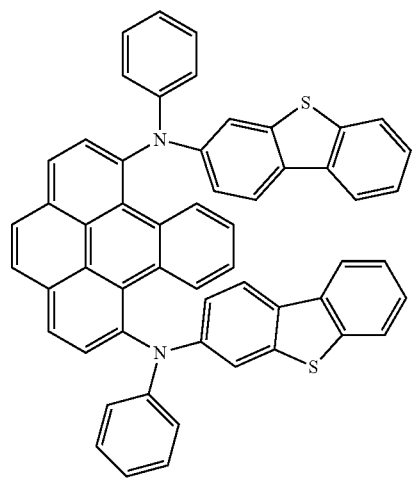
45 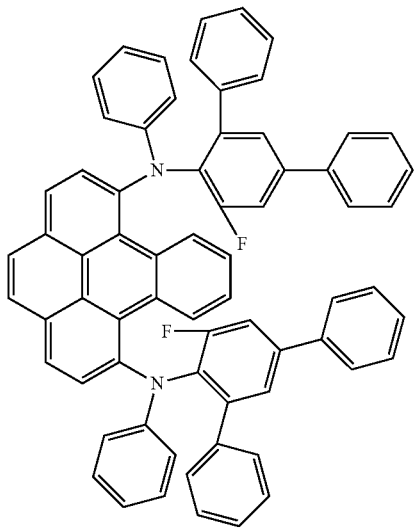 46 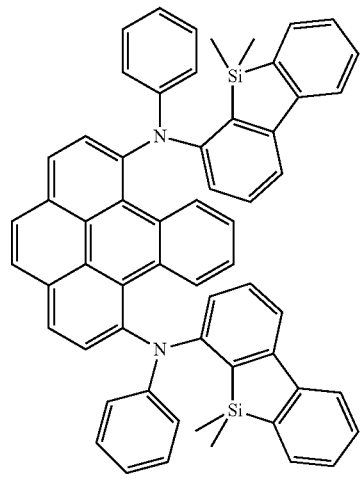

-continued
47
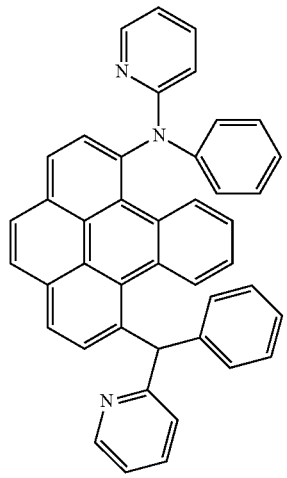
48
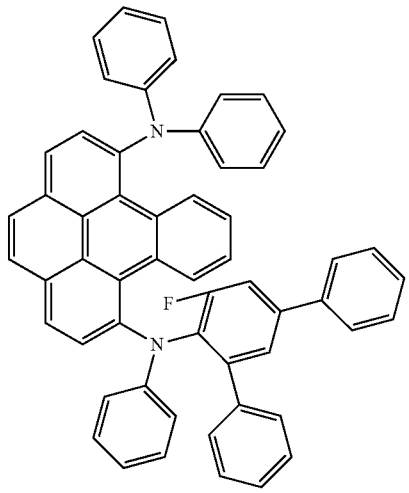
49
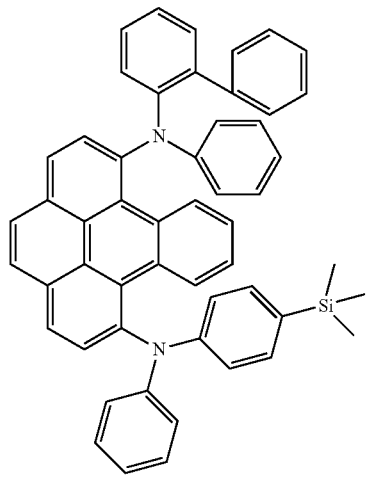
50
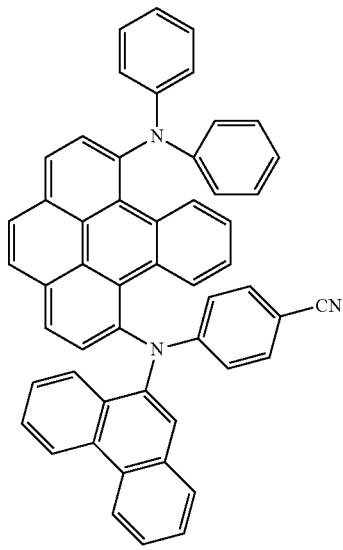
51
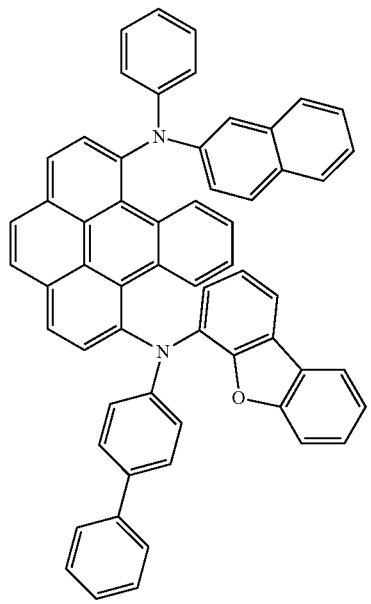
52
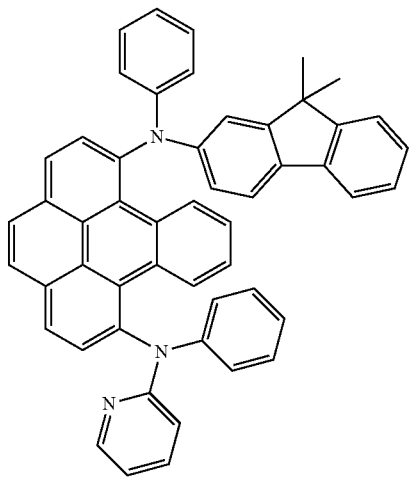

-continued
53
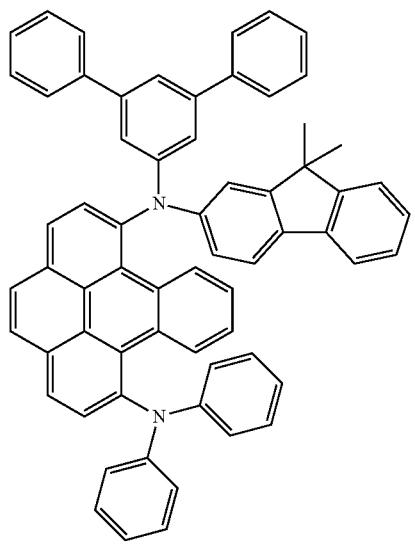
54
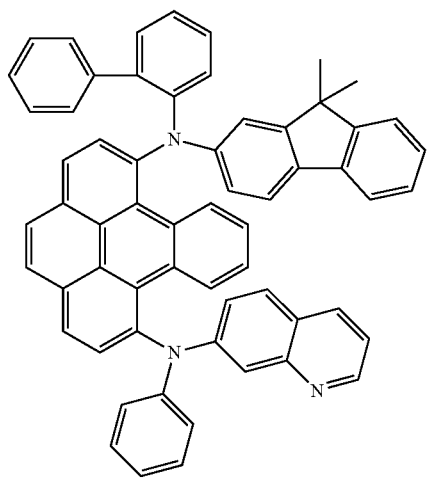
55
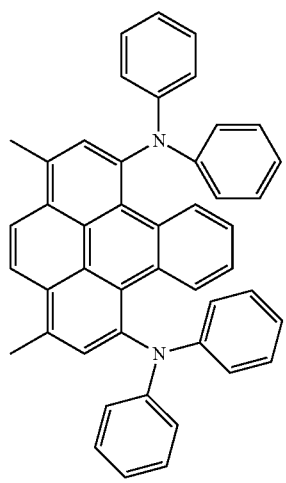
56
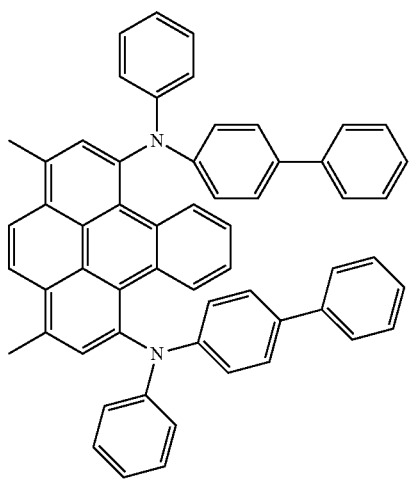
57
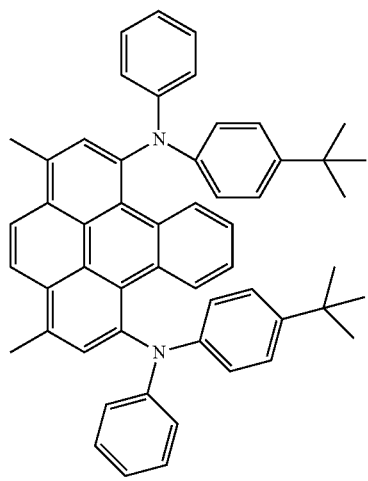
58
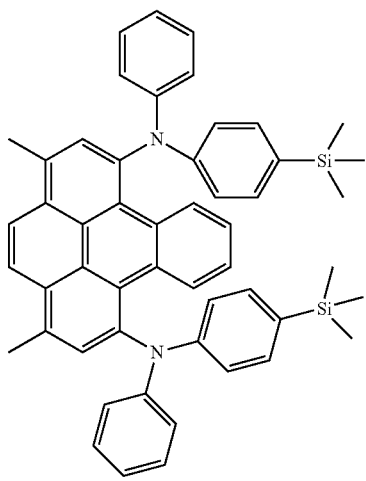

-continued
59
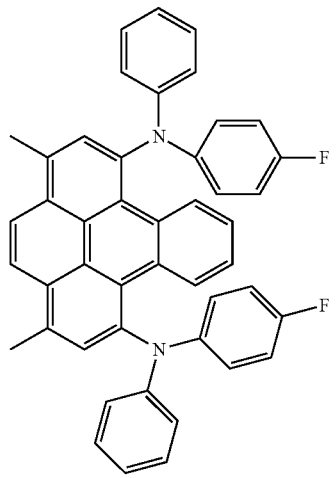
60
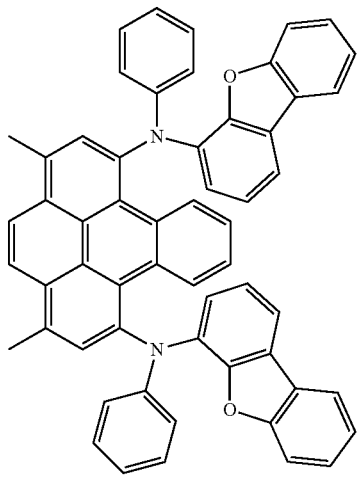
61
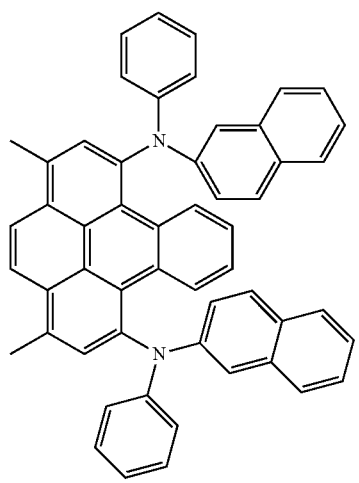
62
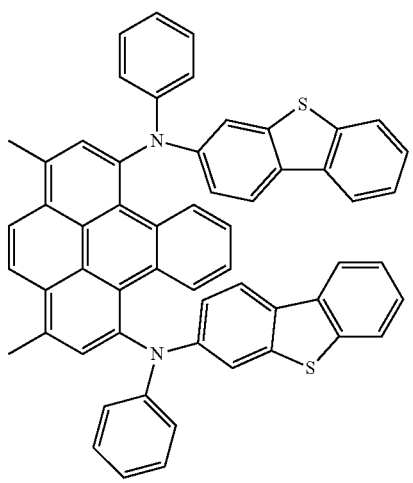
63
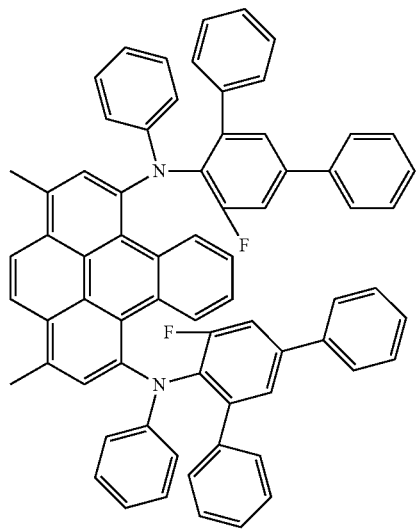
64
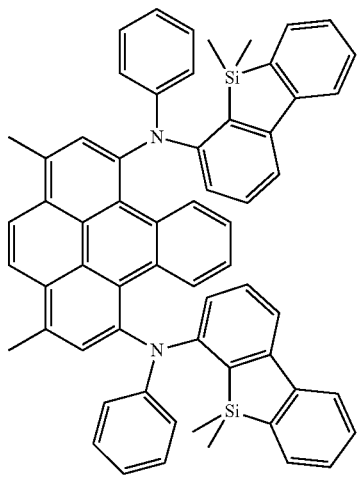

-continued
65
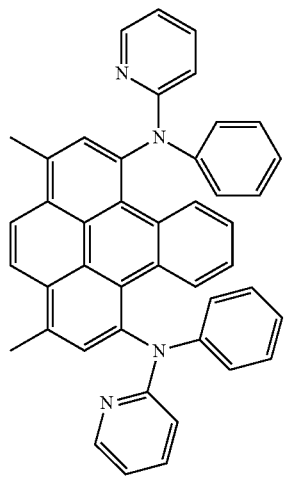
66
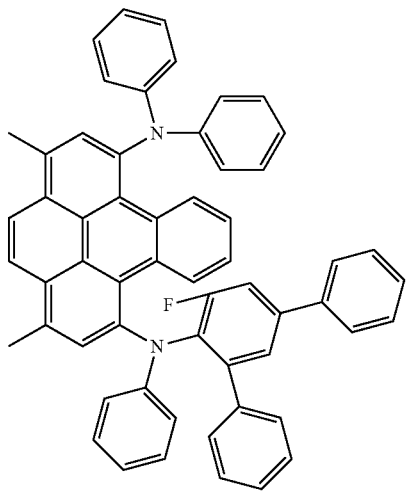
67
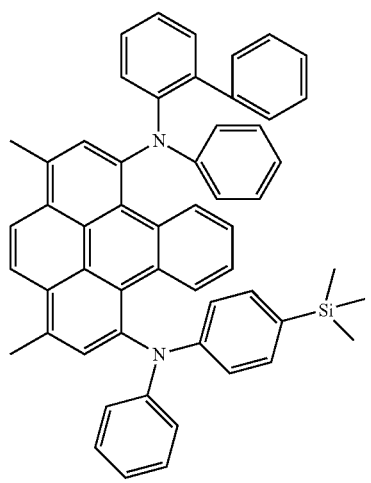
68
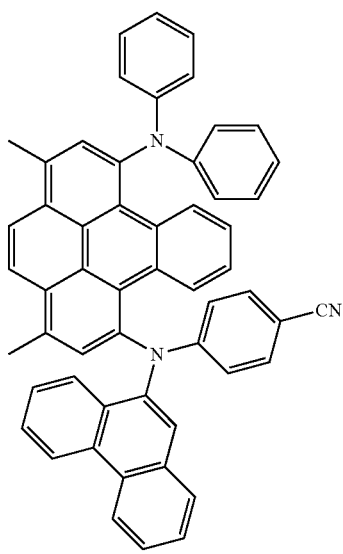
69
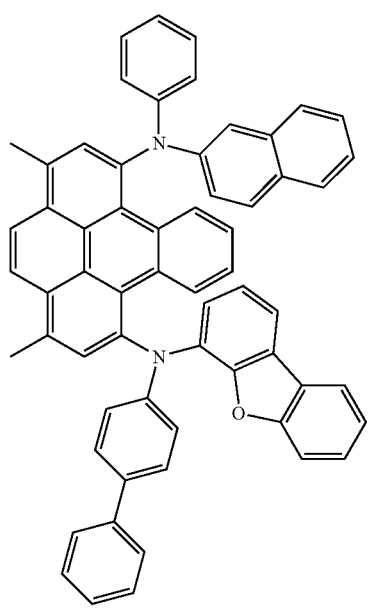
70
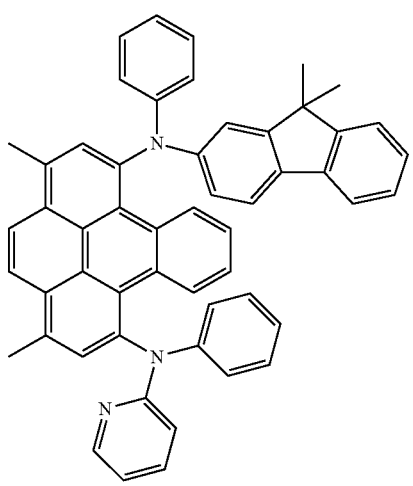

-continued
207
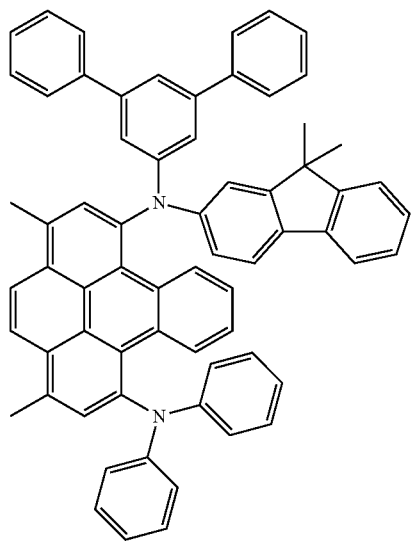
208
71
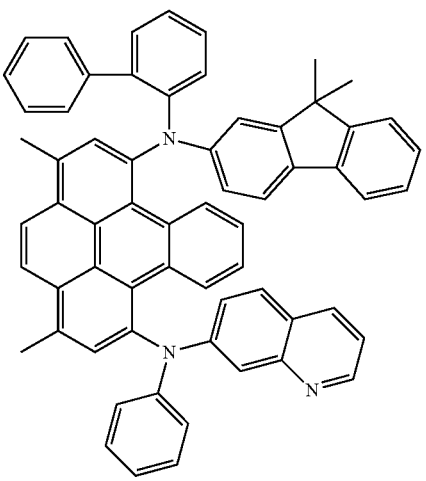
72
73
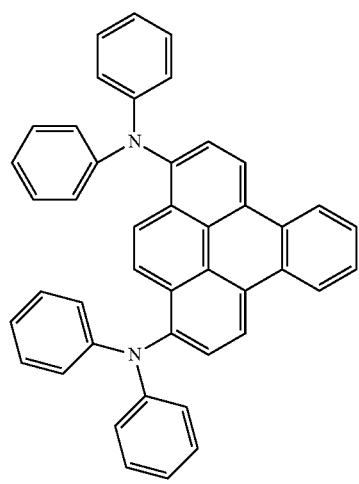
74
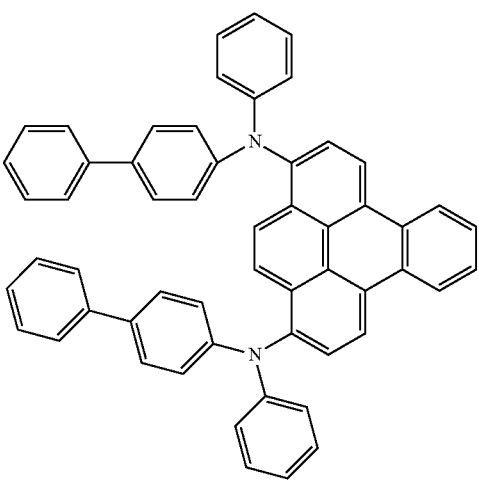
75
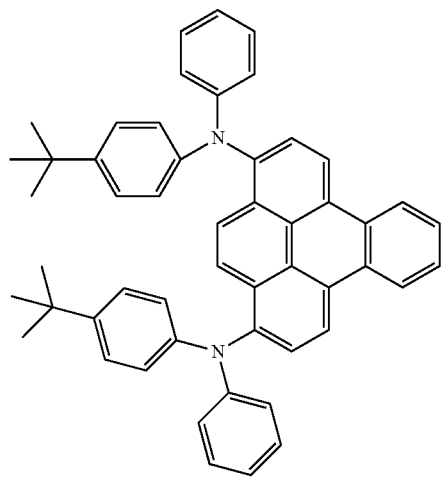
76
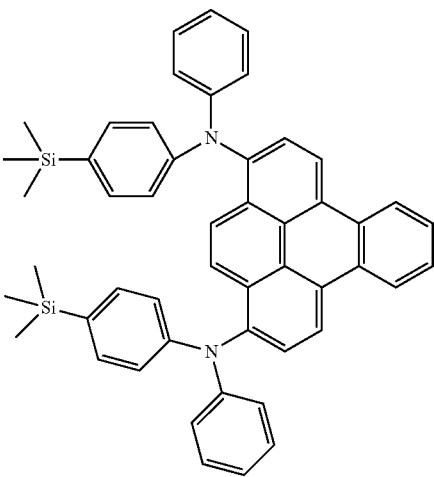

-continued
77
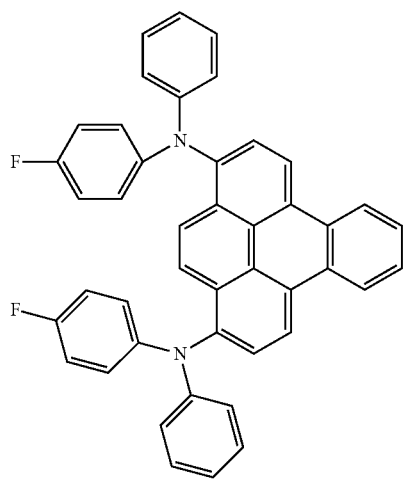
78
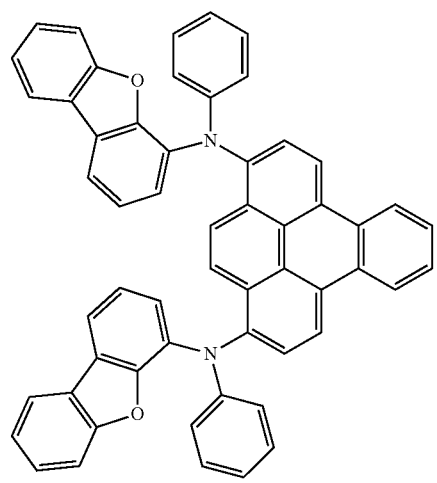
79
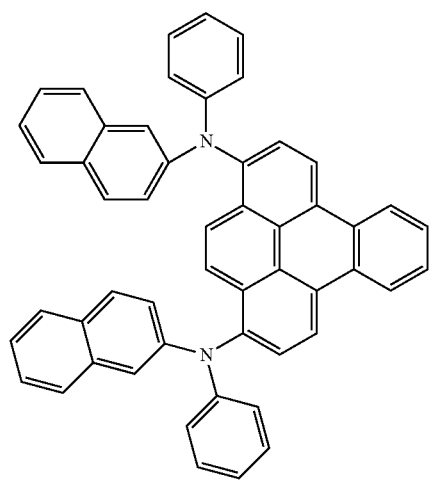
80
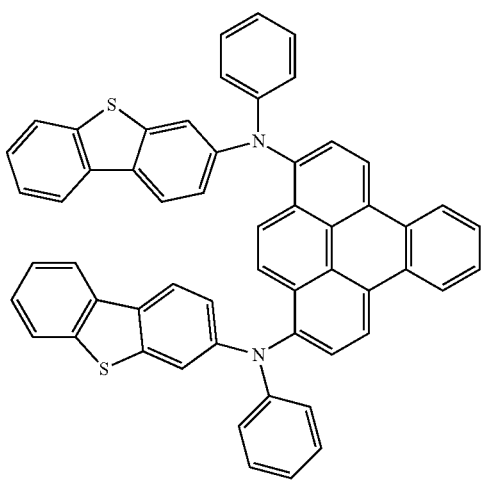
81
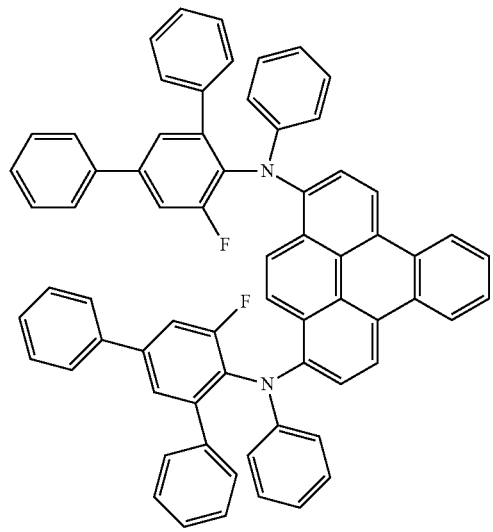
82
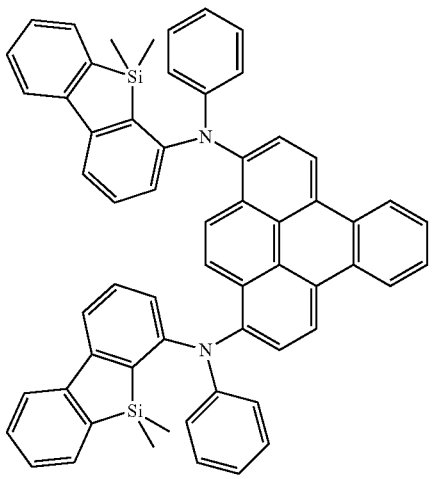

US 10,290,820 B2
211 212
-continued
83
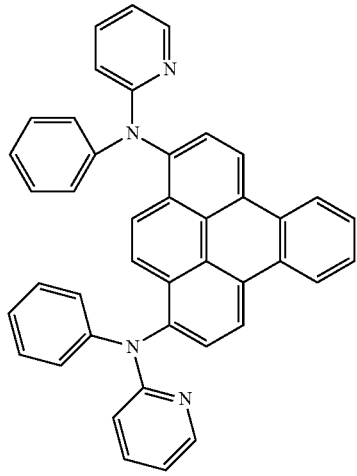
84
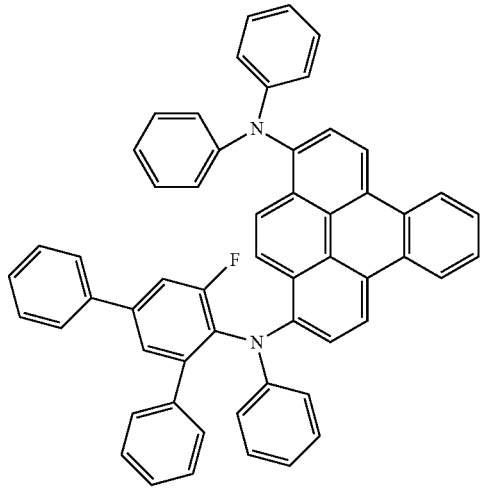
85
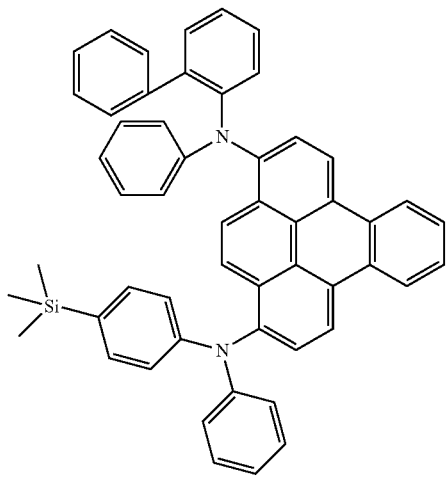
86
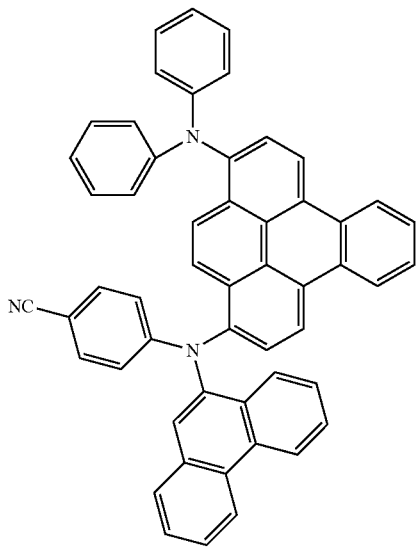
87
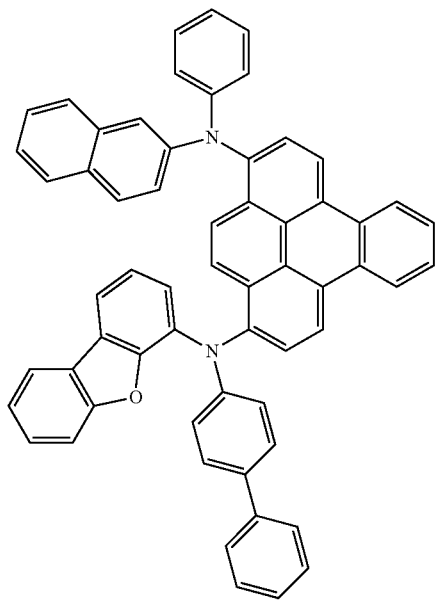
88
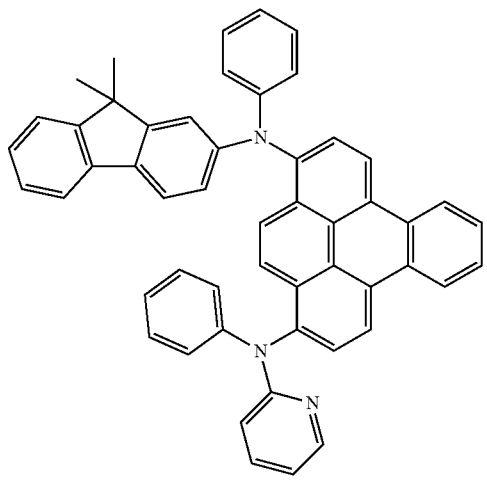

213
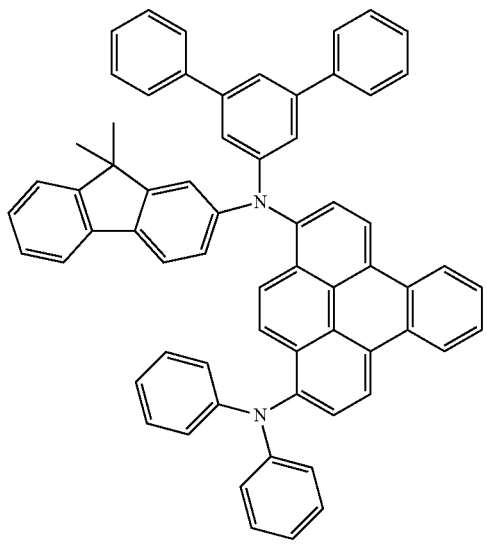
89
214
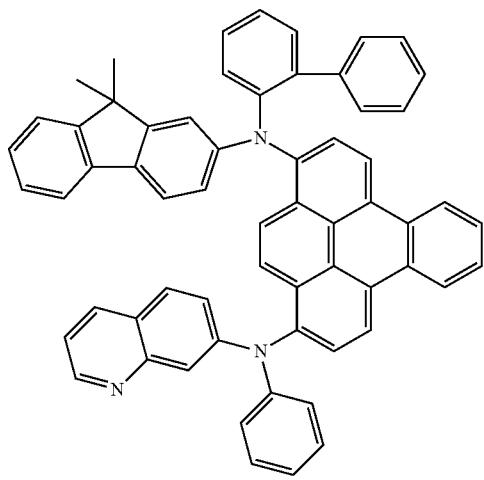
90
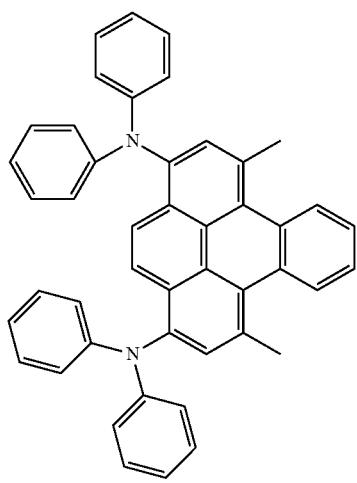
91
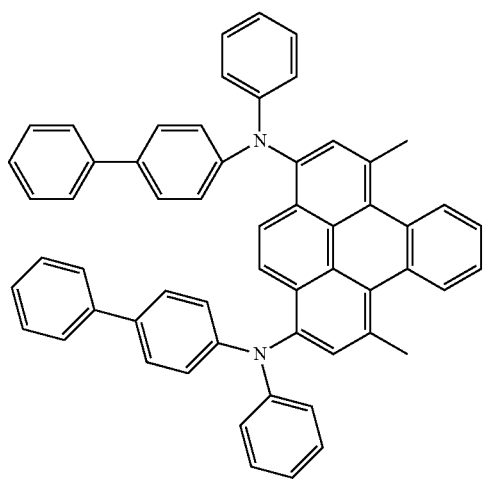
92
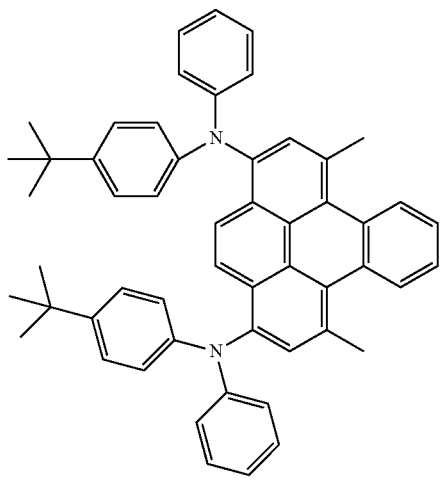
93
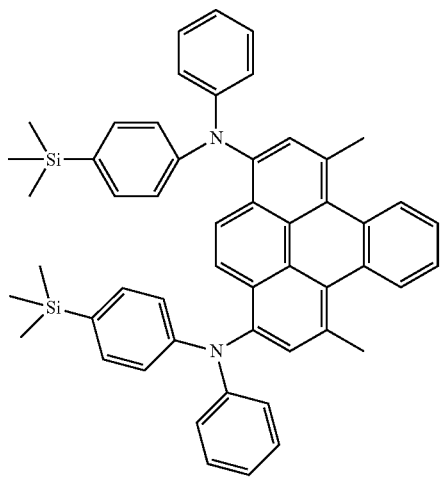
94

-continued
95
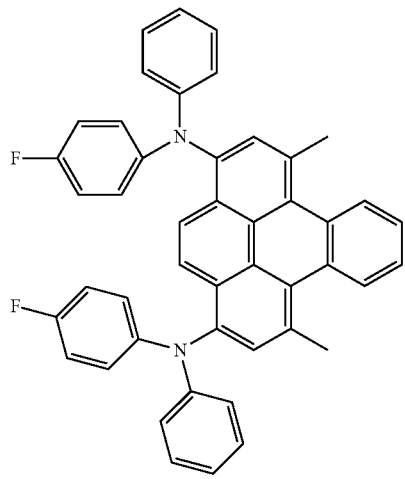
96
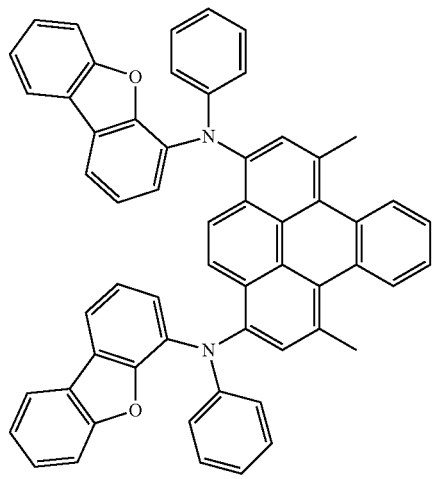
97
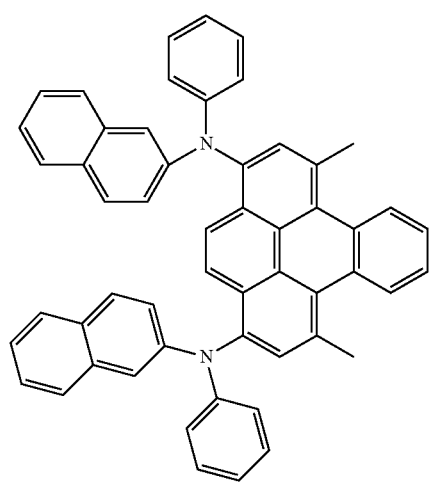
98
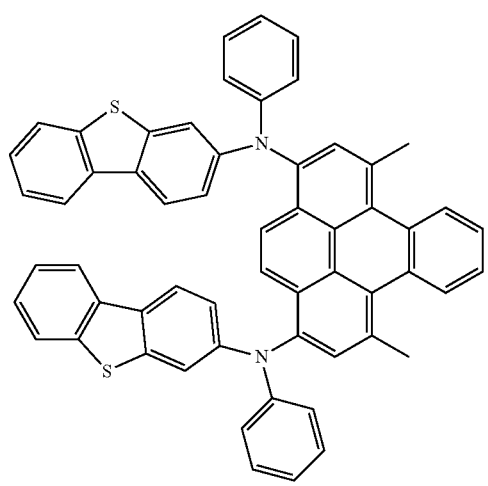
99
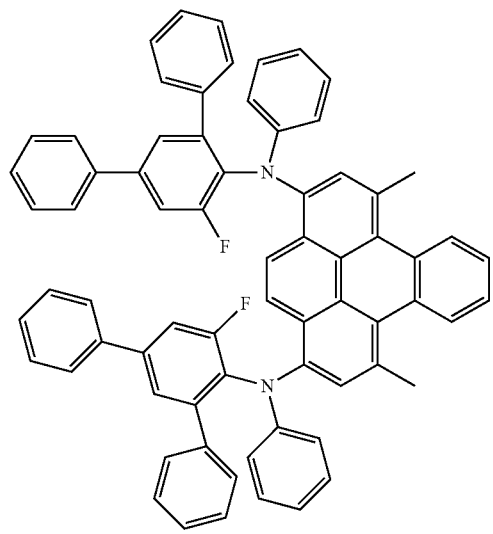
100
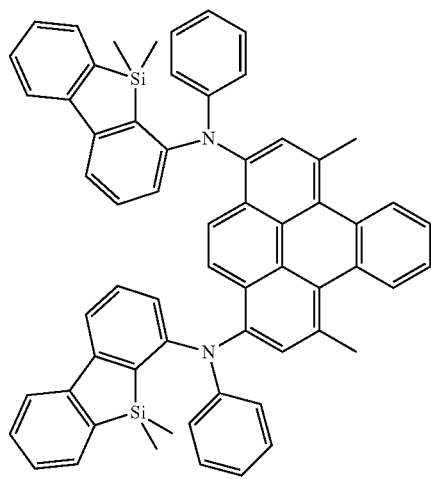

-continued
101
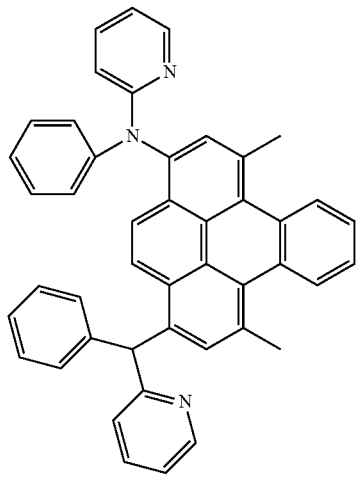
102
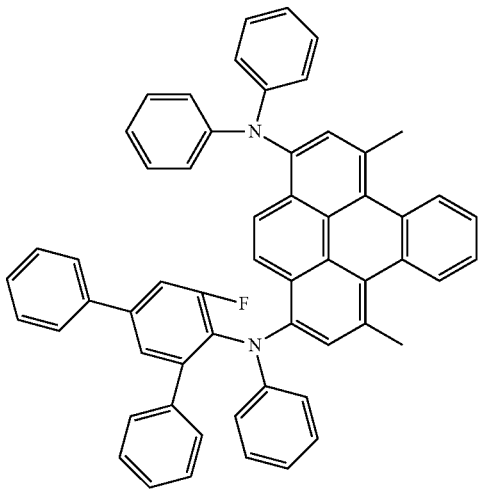
103
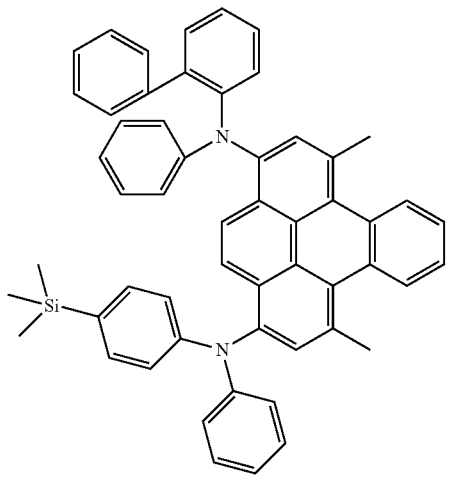
104
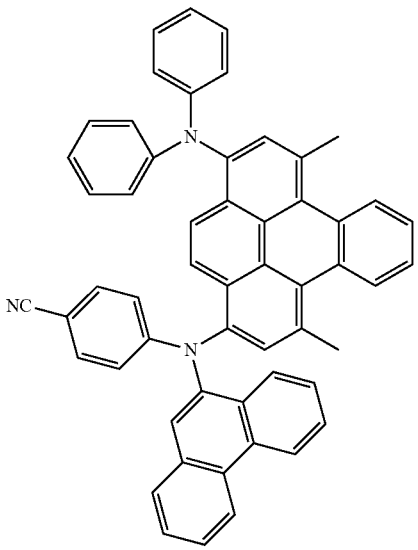
105
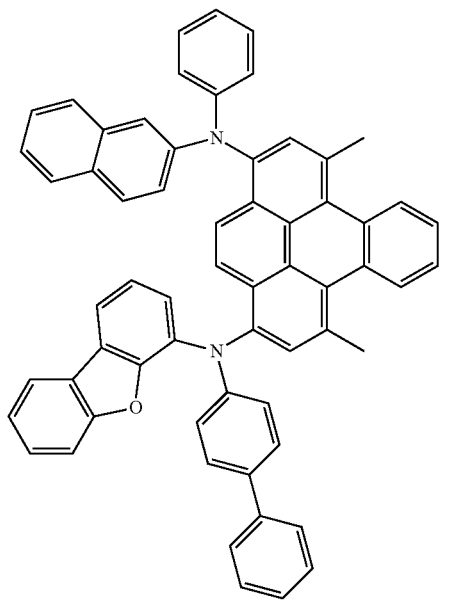
106
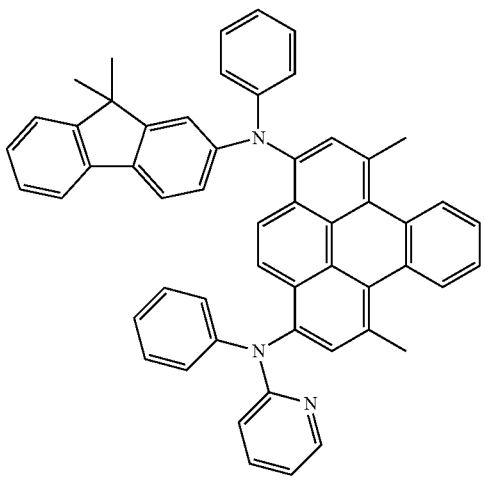

-continued
107
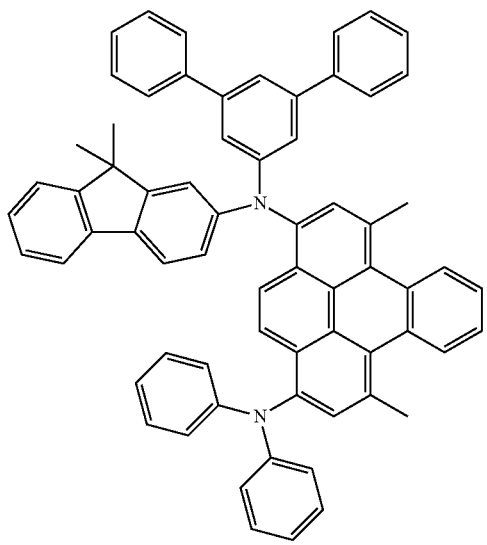
108
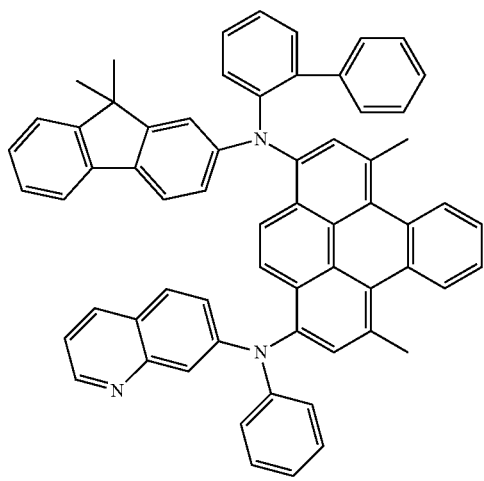
109
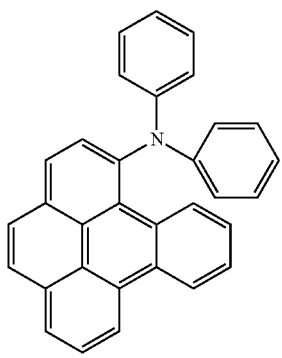
110
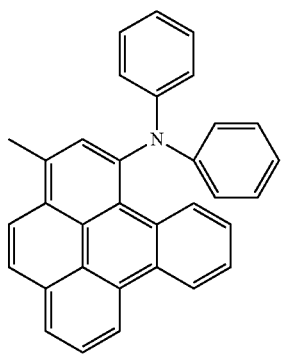
111
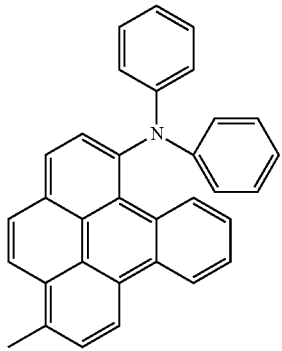
112
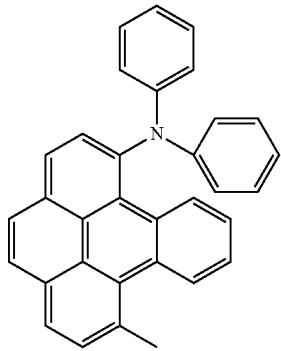
113
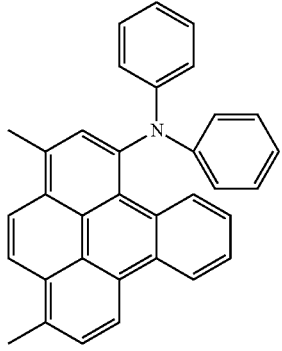
114
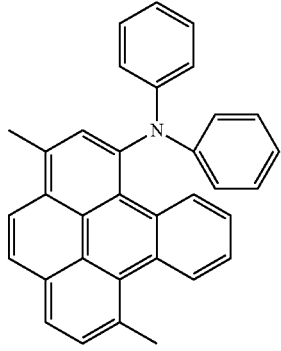

-continued
| 115 | 116 |
|---|---|
| 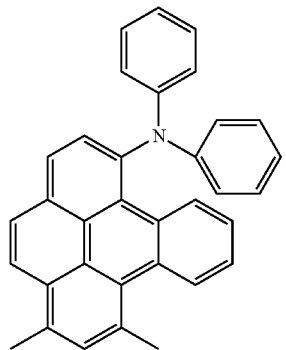 | 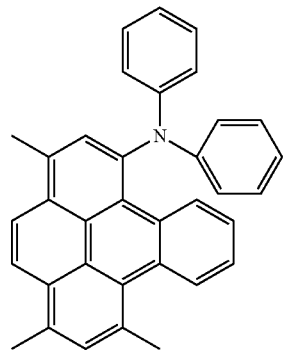 |
| 117 | 118 |
| 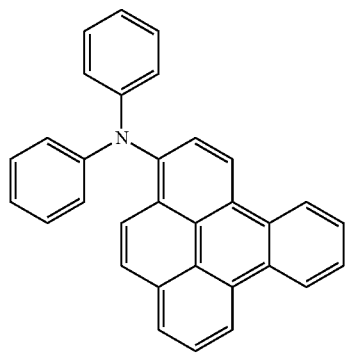 | 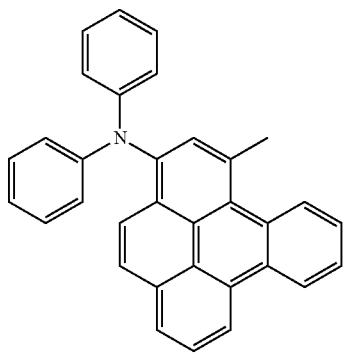 |
| 119 | 120 |
| 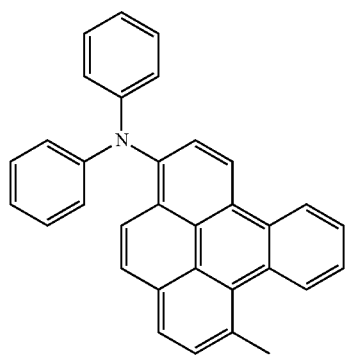 | 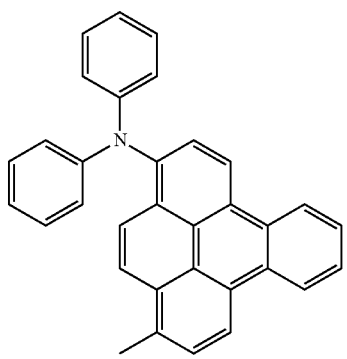 |
| 121 | 122 |
| 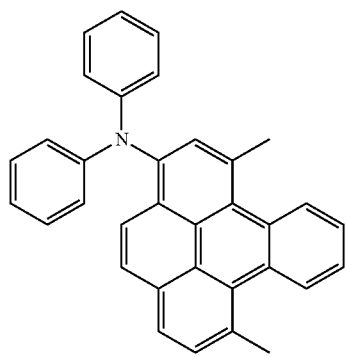 | 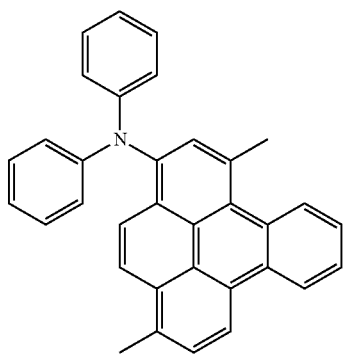 |

-continued
123
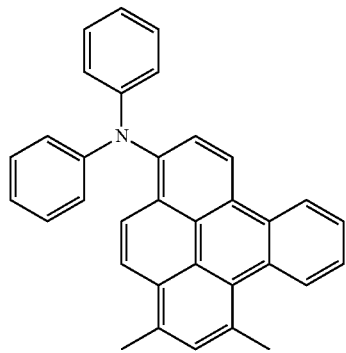
124
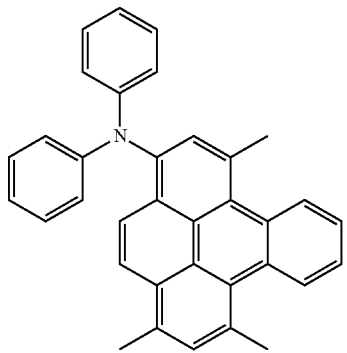
125
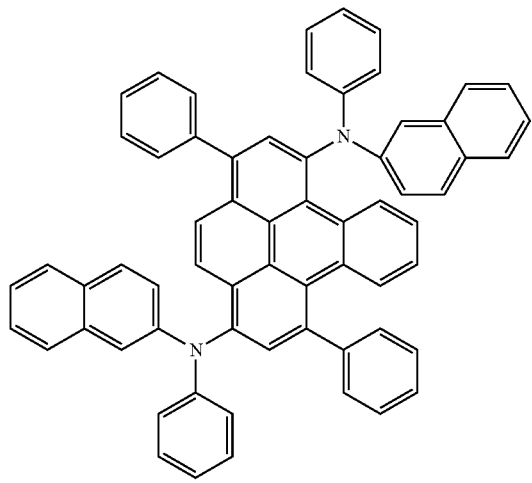
126
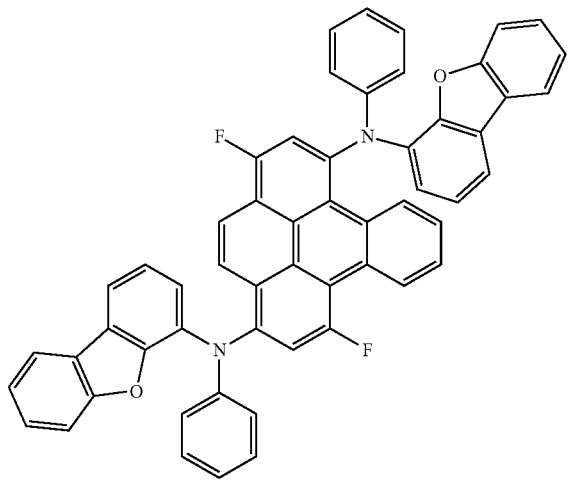
127
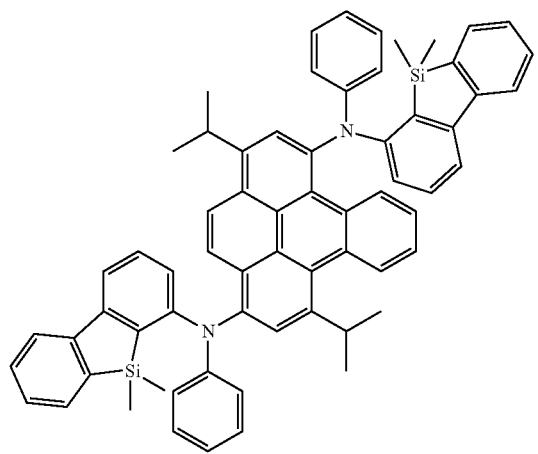
128
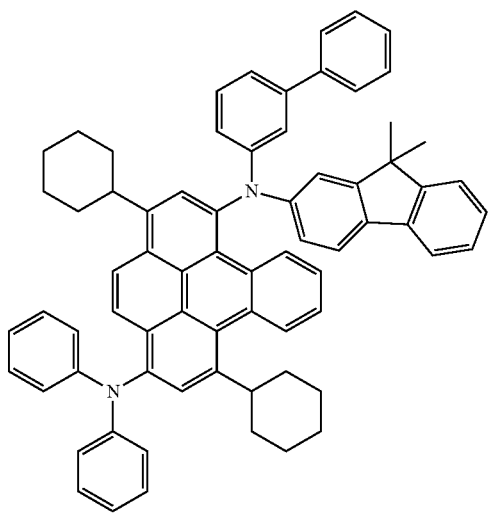

-continued
129
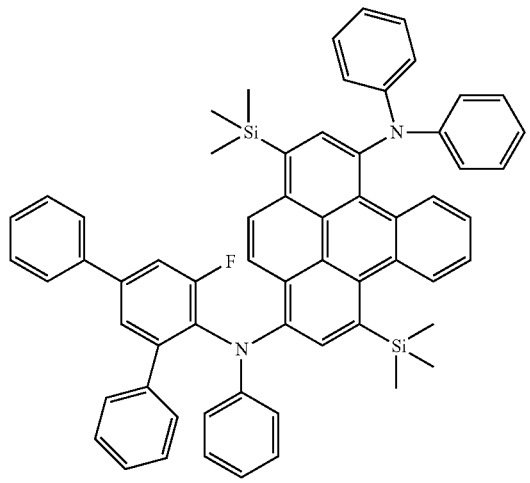
130
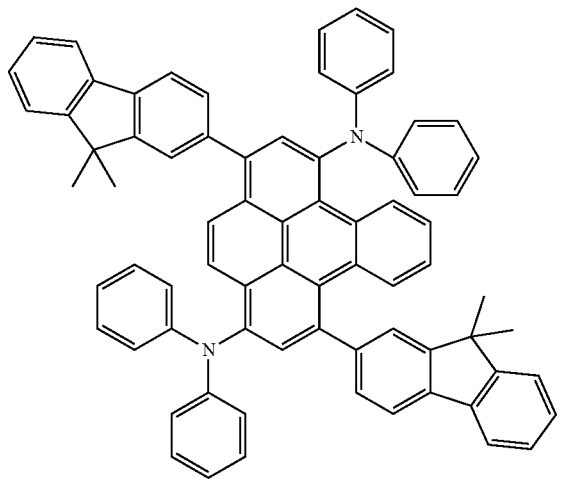
131
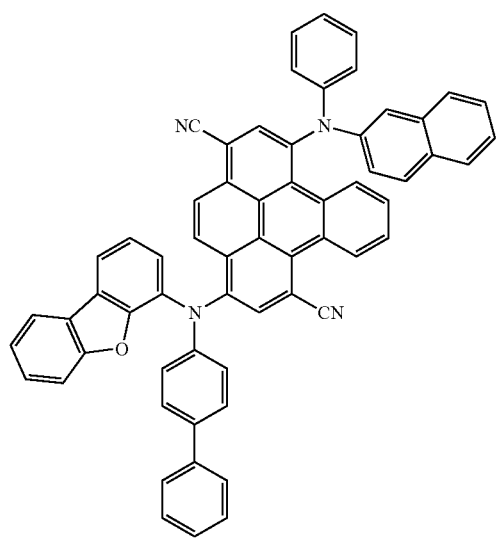
132
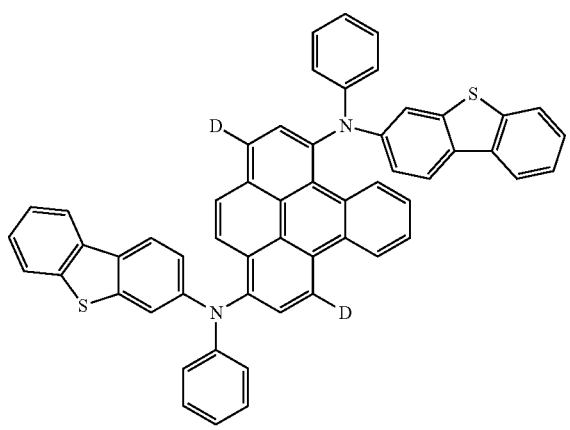
133
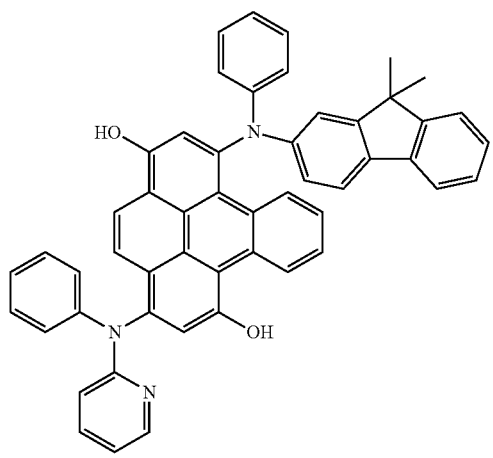
134
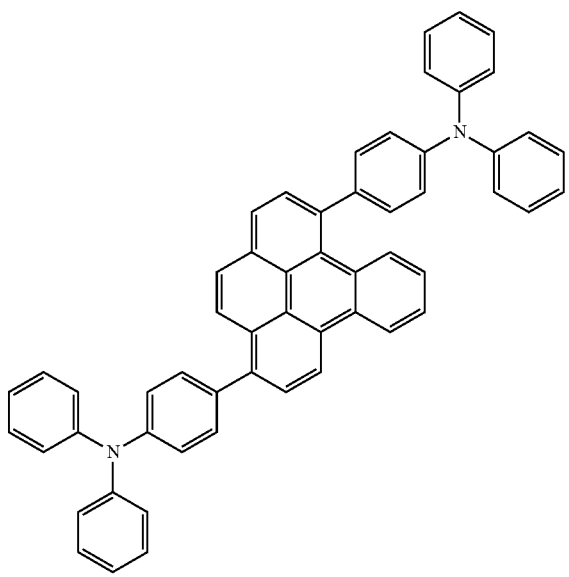

-continued
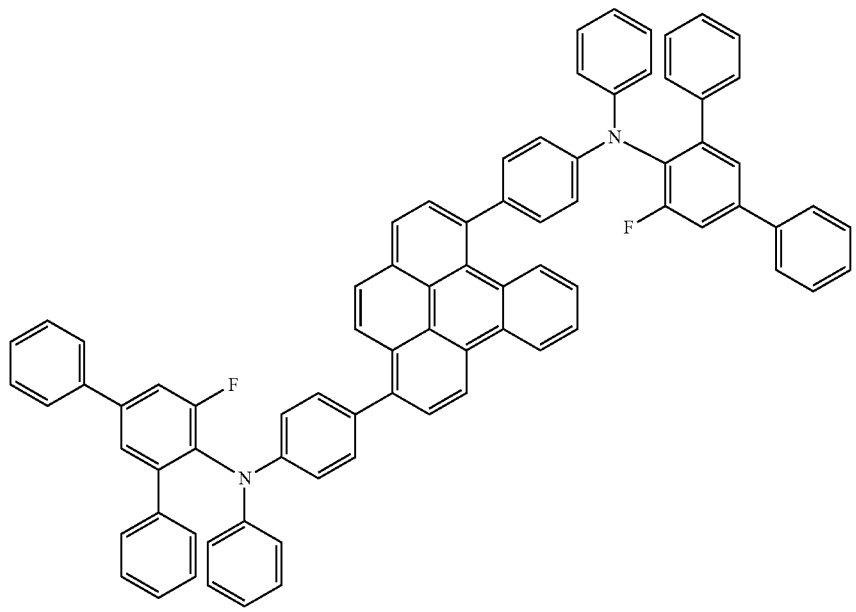
135
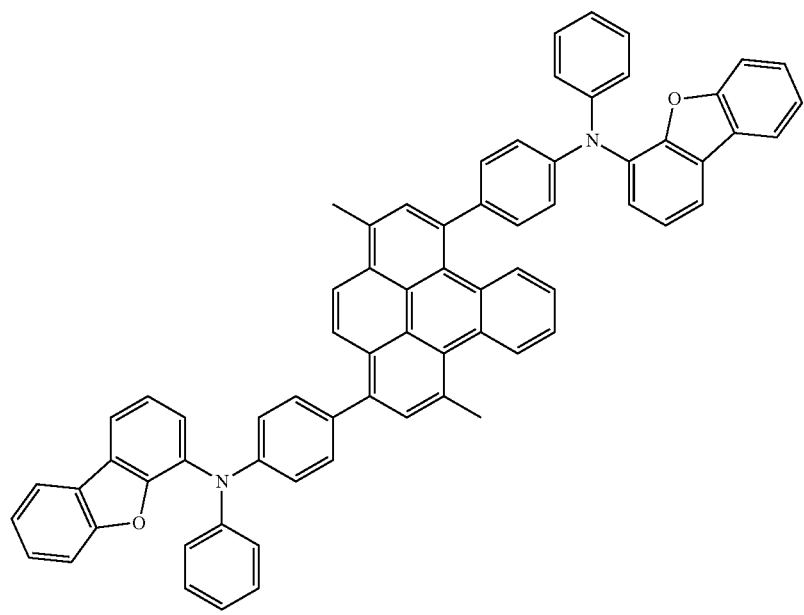
136

137
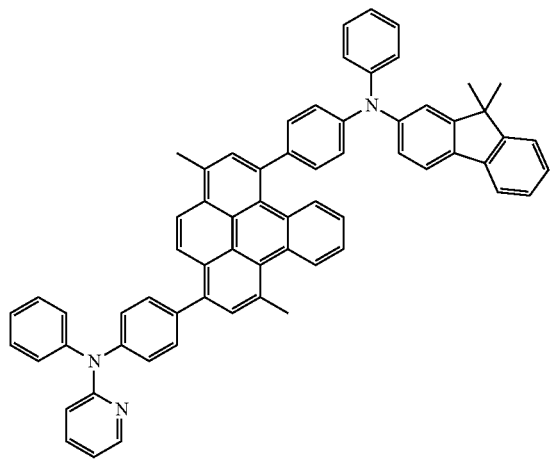
138
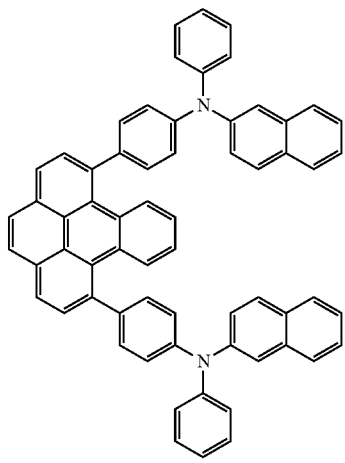
139
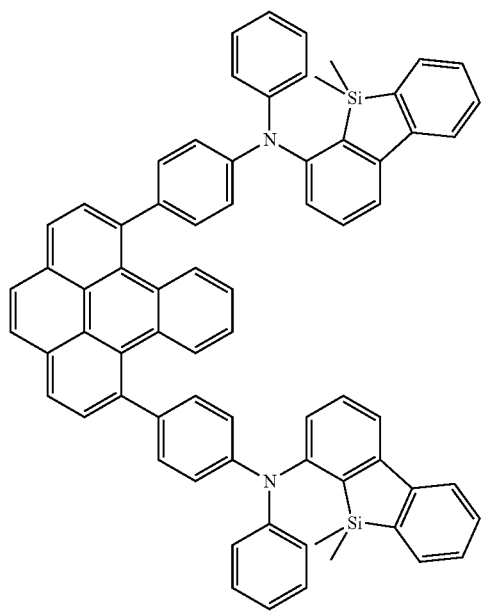
140
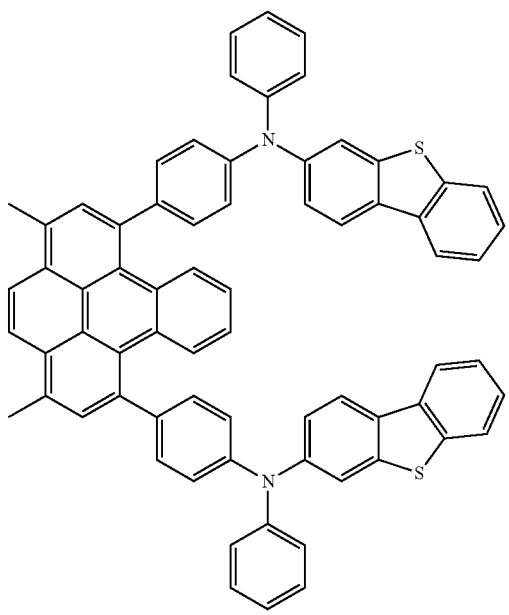

-continued
231
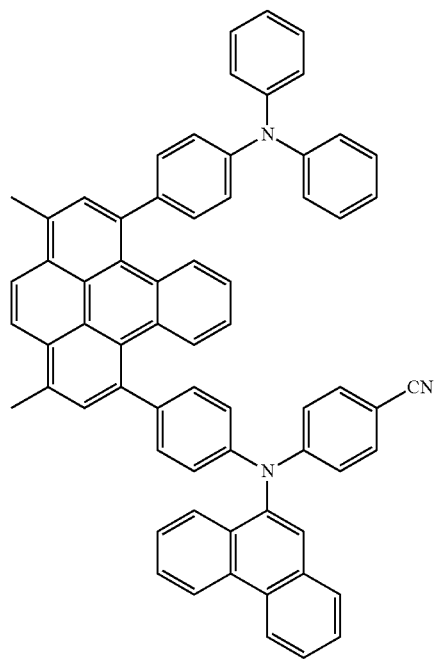
232
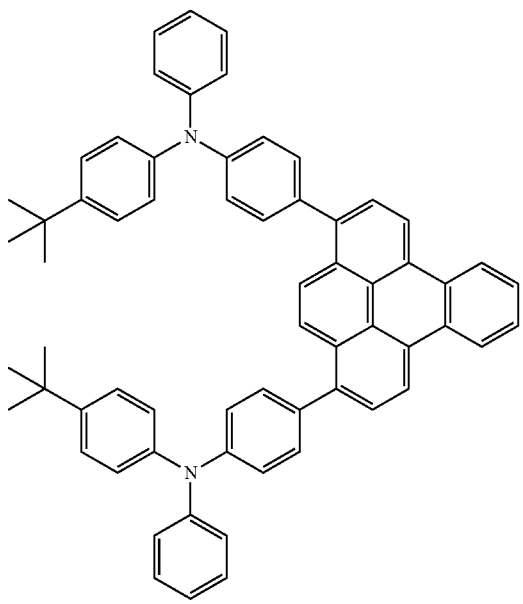
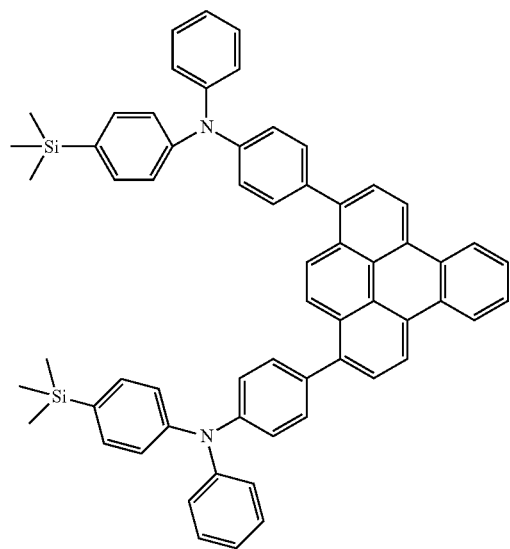
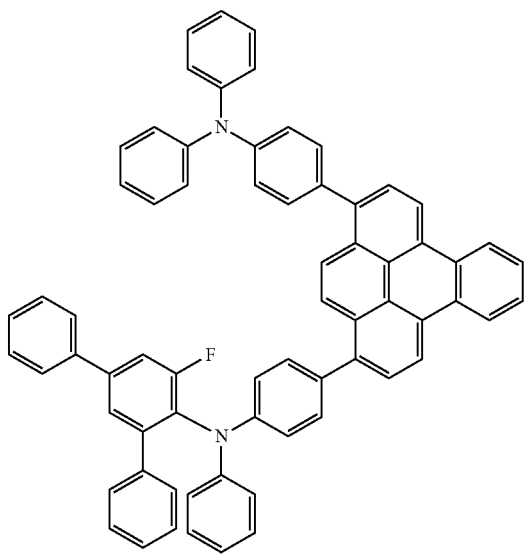

145
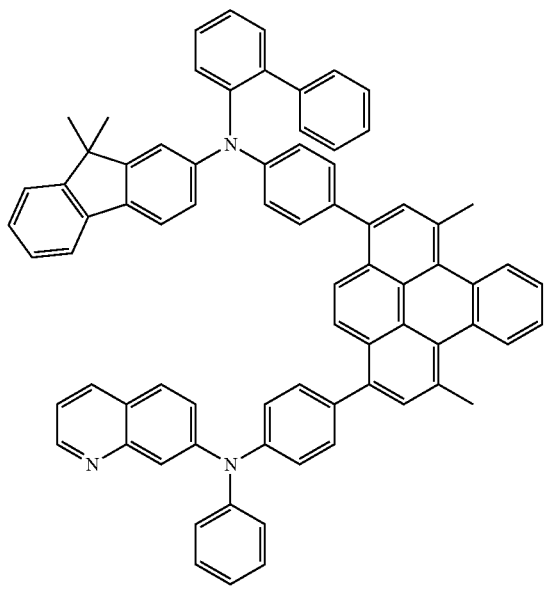
146
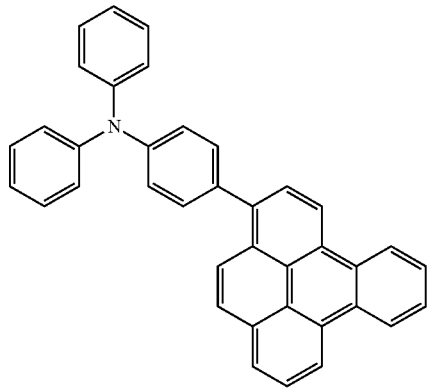
147
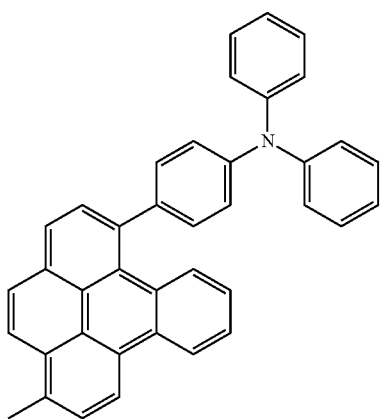
148
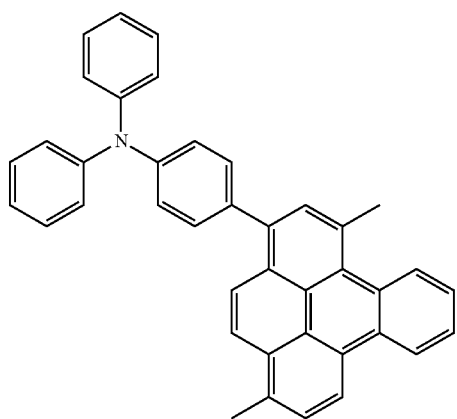
149
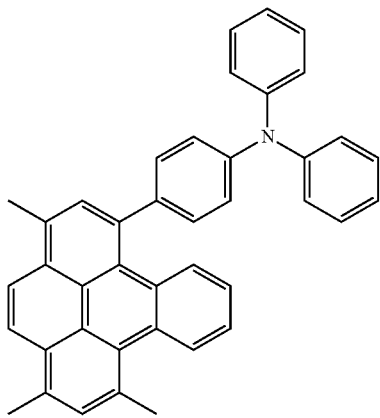

-continued
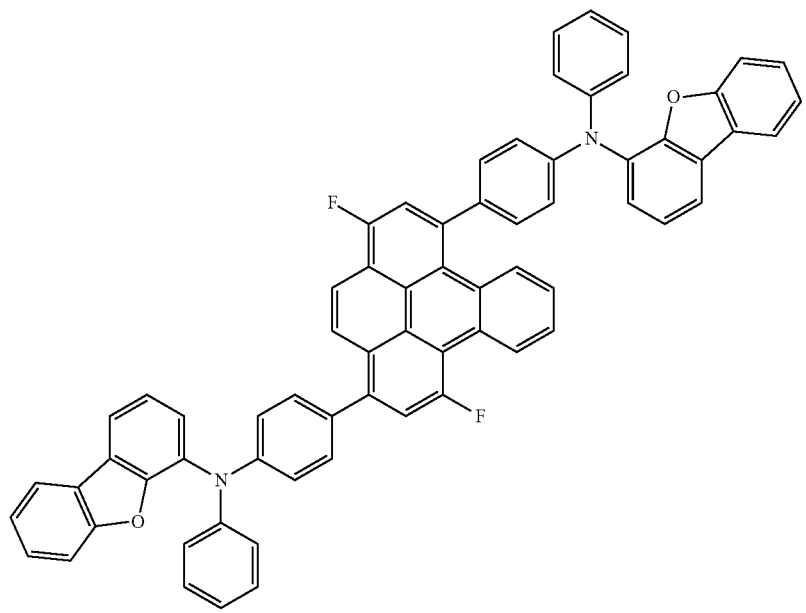
150
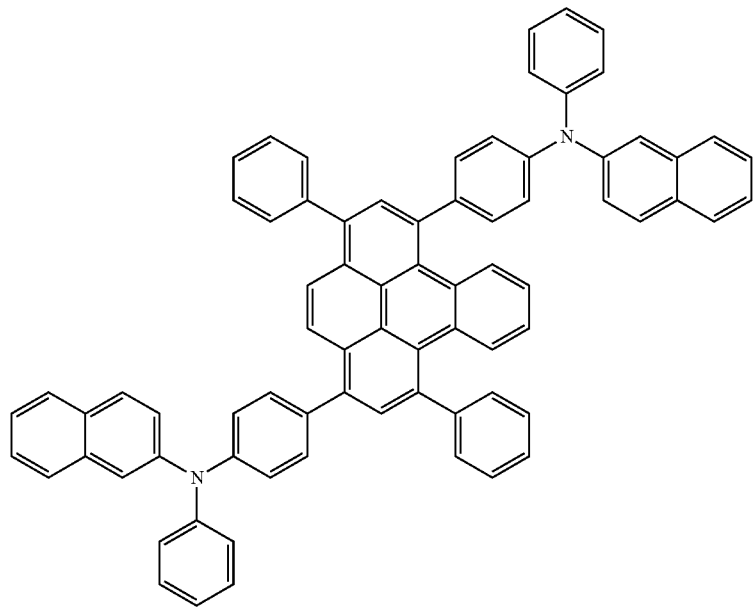
151

-continued

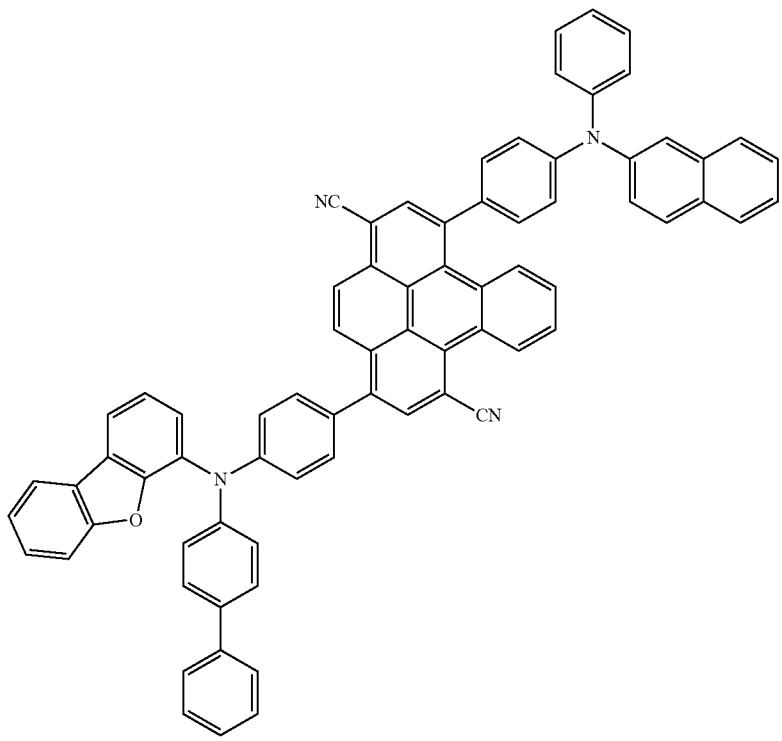

152

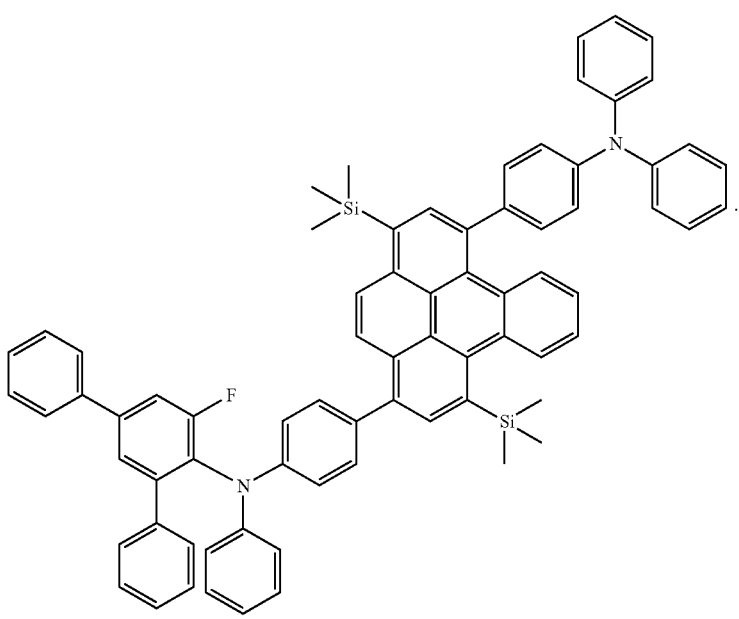

153

14. An organic light-emitting device (OLED) comprising:
a first electrode;
a second electrode facing the first electrode; and
an organic layer between the first electrode and the second electrode and comprising an emission layer,
wherein the organic layer comprises the amine-based compound of claim 1.

15. The OLED of claim 14, wherein the emission layer further comprises a host and the amine-based compound is a dopant.

* * * * *